(12) United States Patent
Bonutti

(10) Patent No.: US 7,749,229 B1
(45) Date of Patent: Jul. 6, 2010

(54) TOTAL KNEE ARTHROPLASTY THROUGH SHORTENED INCISION

(75) Inventor: Peter M. Bonutti, Effingham, IL (US)

(73) Assignee: Marctec, LLC, Effingham, IL (US)

( * ) Notice: Subject to any disclaimer, the term of this patent is extended or adjusted under 35 U.S.C. 154(b) by 559 days.

(21) Appl. No.: 11/170,969

(22) Filed: Jun. 30, 2005

Related U.S. Application Data

(63) Continuation of application No. 10/191,751, filed on Jul. 8, 2002, now Pat. No. 7,104,996, which is a continuation-in-part of application No. 09/976,396, filed on Oct. 11, 2001, now Pat. No. 6,770,078, and a continuation-in-part of application No. 09/941,185, filed on Aug. 28, 2001, now Pat. No. 6,702,821, and a continuation-in-part of application No. 09/566,070, filed on May 5, 2000, now Pat. No. 6,575,982, and a continuation-in-part of application No. 09/737,380, filed on Dec. 15, 2000, now Pat. No. 6,503,267, and a continuation-in-part of application No. 09/569,020, filed on May 11, 2000, now Pat. No. 6,423,063, and a continuation-in-part of application No. 09/483,676, filed on Jan. 14, 2000, now Pat. No. 6,468,289, and a continuation-in-part of application No. 09/798,870, filed on Mar. 1, 2001, now Pat. No. 6,503,277, and a continuation-in-part of application No. 09/526,949, filed on Mar. 16, 2000, now Pat. No. 6,620,181, and a continuation-in-part of application No. 09/789,621, filed on Feb. 21, 2001, now Pat. No. 6,635,073.

(51) Int. Cl.
*A61F 5/00* (2006.01)

(52) U.S. Cl. .......................... 606/86 R; 606/88; 606/87

(58) Field of Classification Search ............... 606/79, 606/80, 82, 86, 88, 87, 89, 86 R, 86 A; 128/898

See application file for complete search history.

(56) References Cited

U.S. PATENT DOCUMENTS 2,589,720 A 3/1952 Aubaoiac (Continued)

FOREIGN PATENT DOCUMENTS

EP 0520737 9/1992

(Continued)

OTHER PUBLICATIONS

Accuris Redefining the Uni Knee, Minimally Invasive Unicompartmental Knee System, Smith & Nephew, May 2003.

(Continued)

*Primary Examiner*—Pedro Philogene
(74) *Attorney, Agent, or Firm*—Fleit Gibbons Gutman Bongini & Bianco PL; Paul D. Bianco; Martin Fleit

(57) ABSTRACT

A method is provided for performing total knee arthroplasty. The method includes making a primary incision near the knee joint of a leg of a patient and cutting medial and lateral condyles of the femur of the leg to create at least one femoral cut surface. The method also includes moving a femoral component of a total knee implant through the primary incision and positioning the femoral component with respect to the at least one femoral cut surface. The primary incision has a length of less than thirteen (13) centimeters.

32 Claims, 37 Drawing Sheets

U.S. PATENT DOCUMENTS

| | | |
|---|---|---|
| 3,229,006 A | 1/1966 | Nobl |
| 3,624,747 A | 11/1971 | McKnight |
| 3,750,652 A | 8/1973 | Sherwin |
| 3,807,393 A | 4/1974 | McDonald |
| 3,811,449 A | 5/1974 | Gravlee et al. |
| 3,852,830 A | 12/1974 | Marmor |
| 3,869,731 A | 3/1975 | Waugh et al. |
| 3,903,549 A | 9/1975 | Deyerle |
| 3,911,923 A | 10/1975 | Yoon |
| 3,920,022 A | 11/1975 | Pastor |
| 3,967,625 A | 7/1976 | Yoon |
| 3,989,049 A | 11/1976 | Yoon |
| 3,991,426 A | 11/1976 | Flom |
| 3,994,287 A | 11/1976 | Turp |
| 4,000,525 A | 1/1977 | Klawitter |
| 4,053,953 A | 10/1977 | Flom |
| 4,085,466 A | 4/1978 | Goodfellow |
| 4,085,743 A | 4/1978 | Yoon |
| 4,103,680 A | 8/1978 | Yoon |
| RE29,757 E | 9/1978 | Helfet |
| 4,169,470 A | 10/1979 | Ender et al. |
| 4,203,444 A | 5/1980 | Bonnell et al. |
| 4,209,012 A | 6/1980 | Smucker |
| 4,209,861 A | 7/1980 | Walker |
| 4,213,209 A | 7/1980 | Insall |
| 4,224,696 A | 9/1980 | Murray et al. |
| 4,298,992 A | 11/1981 | Burstein et al. |
| 4,299,224 A | 11/1981 | Noiles |
| 4,311,145 A | 1/1982 | Esty |
| 4,344,193 A | 8/1982 | Kenny |
| 4,369,768 A | 1/1983 | Vukovic |
| 4,373,709 A | 2/1983 | Whitt |
| 4,374,523 A | 2/1983 | Yoon |
| 4,385,404 A | 5/1983 | Sully |
| 4,421,112 A | 12/1983 | Mains et al. |
| 4,457,302 A | 7/1984 | Caspari et al. |
| 4,474,177 A | 10/1984 | Whiteside |
| 4,509,518 A | 4/1985 | McGarry |
| 4,545,375 A | 10/1985 | Cline |
| 4,565,192 A | 1/1986 | Shapiro |
| 4,574,794 A | 3/1986 | Cooke et al. |
| 4,619,391 A | 10/1986 | Sharkany |
| 4,624,254 A | 11/1986 | McGarry |
| 4,641,648 A | 2/1987 | Shapiro |
| 4,646,738 A | 3/1987 | Trott |
| 4,662,372 A | 5/1987 | Sharkany |
| 4,682,598 A | 7/1987 | Beraha |
| 4,685,460 A | 8/1987 | Thornton |
| 4,719,908 A | 1/1988 | Averill |
| 4,721,104 A | 1/1988 | Kaufman |
| 4,739,751 A | 4/1988 | Sapega et al. |
| 4,759,350 A * | 7/1988 | Dunn et al. .................. 606/82 |
| 4,817,602 A | 4/1989 | Beraha |
| 4,825,857 A | 5/1989 | Kenna |
| 4,911,721 A | 3/1990 | Branemark |
| 4,936,852 A | 6/1990 | Kent |
| 4,944,760 A * | 7/1990 | Kenna ....................... 128/898 |
| 4,945,896 A | 8/1990 | Gade |
| 4,950,298 A | 8/1990 | Gustilo |
| 4,952,213 A | 8/1990 | Bowman et al. |
| 4,961,954 A | 10/1990 | Goldberg |
| 4,964,865 A | 10/1990 | Burkhead |
| 4,979,949 A | 12/1990 | Matsen, III et al. |
| 4,983,179 A | 1/1991 | Sjostrom |
| 4,985,038 A | 1/1991 | Lyell |
| 5,007,912 A | 4/1991 | Albrektsson et al. |
| 5,019,104 A | 5/1991 | Whiteside et al. |
| 5,021,056 A | 6/1991 | Hofmann et al. |
| 5,032,132 A | 7/1991 | Matsen |
| 5,035,699 A | 7/1991 | Coates |
| 5,037,423 A | 8/1991 | Kenna |
| 5,053,039 A | 10/1991 | Hofmann et al. |
| 5,060,678 A | 10/1991 | Bauman |
| 5,098,436 A | 3/1992 | Ferrante et al. |
| 5,098,437 A | 3/1992 | Kashuba |
| 5,099,859 A | 3/1992 | Bell |
| 5,100,409 A | 3/1992 | Coates |
| 5,100,689 A | 3/1992 | Goldberg |
| 5,108,441 A | 4/1992 | McDowell |
| 5,111,987 A | 5/1992 | Moeinzadeh |
| 5,123,906 A | 6/1992 | Kelman |
| 5,152,744 A | 10/1992 | Krause |
| 5,152,778 A | 10/1992 | Bales |
| 5,154,717 A | 10/1992 | Matsen, II et al. |
| 5,163,949 A | 11/1992 | Bonutti |
| 5,170,800 A | 12/1992 | Smith |
| 5,171,243 A | 12/1992 | Kashuba |
| 5,171,244 A | 12/1992 | Caspari et al. |
| 5,171,276 A | 12/1992 | Caspari |
| 5,174,300 A | 12/1992 | Bales |
| 5,176,684 A | 1/1993 | Ferrante et al. |
| 5,176,702 A | 1/1993 | Bales |
| 5,178,622 A | 1/1993 | Lehner |
| 5,183,053 A | 2/1993 | Yeh |
| 5,183,464 A | 2/1993 | Dubrul et al. |
| 5,186,178 A | 2/1993 | Yeh |
| 5,197,488 A | 3/1993 | Kovacevic |
| 5,197,968 A | 3/1993 | Clement |
| 5,197,971 A | 3/1993 | Bonutti |
| 5,197,987 A | 3/1993 | Koch |
| 5,207,692 A | 5/1993 | Kraus |
| 5,217,463 A | 6/1993 | Mikhail |
| 5,226,915 A | 7/1993 | Bertin |
| 5,228,459 A | 7/1993 | Caspari et al. |
| 5,234,433 A | 8/1993 | Bert et al. |
| 5,236,432 A | 8/1993 | Matsen, III et al. |
| 5,258,004 A | 11/1993 | Bales |
| 5,258,032 A | 11/1993 | Bertin |
| 5,263,498 A | 11/1993 | Caspari |
| 5,263,987 A * | 11/1993 | Shah ....................... 623/18.11 |
| 5,269,785 A | 12/1993 | Bonutti |
| 5,273,524 A | 12/1993 | Fox |
| 5,275,166 A | 1/1994 | Vaitekunas |
| 5,282,803 A | 2/1994 | Lackey |
| 5,282,866 A | 2/1994 | Cohen et al. |
| 5,285,773 A | 2/1994 | Bonutti |
| 5,293,878 A | 3/1994 | Bales |
| 5,295,994 A | 3/1994 | Bonutti |
| 5,304,181 A | 4/1994 | Caspari et al. |
| 5,306,311 A | 4/1994 | Stone |
| 5,308,349 A | 5/1994 | Mikhail |
| 5,312,411 A | 5/1994 | Steele |
| 5,314,482 A | 5/1994 | Goodfellow |
| 5,320,611 A | 6/1994 | Bonutti et al. |
| 5,322,505 A | 6/1994 | Krause |
| 5,326,361 A | 7/1994 | Hollister |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,358,530 A | 10/1994 | Hodorek |
| 5,360,016 A | 11/1994 | Kovacevic |
| 5,364,402 A | 11/1994 | Mumme et al. |
| 5,368,599 A | 11/1994 | Hirsch |
| 5,379,133 A | 1/1995 | Kirk |
| 5,395,376 A * | 3/1995 | Caspari et al. ................ 606/86 |
| 5,395,401 A | 3/1995 | Bahler |
| 5,403,319 A | 4/1995 | Matsen, III et al. |
| 5,405,395 A | 4/1995 | Coates |
| D358,647 S | 5/1995 | Cohen |
| 5,415,663 A | 5/1995 | Luckman |
| 5,417,695 A | 5/1995 | Axelson, Jr. |
| 5,425,355 A | 6/1995 | Kullick |
| 5,425,745 A | 6/1995 | Green |

| | | | | | |
|---|---|---|---|---|---|
| 5,425,775 A | 6/1995 | Kovacevic | 5,769,854 A | 6/1998 | Bastian et al. |
| 5,445,639 A | 8/1995 | Kuslich et al. | 5,769,855 A | 6/1998 | Bertin et al. |
| 5,454,365 A | 10/1995 | Bonutti | 5,769,899 A | 6/1998 | Schwartz |
| 5,454,815 A | 10/1995 | Geisser | 5,772,594 A | 6/1998 | Barrick |
| 5,454,816 A | 10/1995 | Ashby | 5,776,200 A | 7/1998 | Johnson |
| 5,456,268 A | 10/1995 | Bonutti | 5,776,201 A | 7/1998 | Colleran et al. |
| 5,456,720 A | 10/1995 | Schultz | 5,782,925 A | 7/1998 | Collazo et al. |
| 5,458,643 A | 10/1995 | Oka | 5,788,700 A | 8/1998 | Morawa et al. |
| 5,462,549 A | 10/1995 | Glock | 5,792,139 A | 8/1998 | Chambers |
| 5,464,406 A | 11/1995 | Ritter et al. | 5,806,518 A | 9/1998 | Mittelstadt |
| 5,470,354 A | 11/1995 | Hershberger | 5,810,827 A | 9/1998 | Haines |
| 5,472,415 A | 12/1995 | King | 5,817,109 A | 10/1998 | McGarry |
| 5,474,559 A | 12/1995 | Bertin et al. | 5,842,477 A | 12/1998 | Naughton et al. |
| 5,484,095 A | 1/1996 | Green | 5,846,237 A | 12/1998 | Nettekoven |
| 5,497,933 A | 3/1996 | DeFonzo | 5,846,931 A | 12/1998 | Hattersley |
| 5,514,139 A | 5/1996 | Goldstein | 5,851,183 A | 12/1998 | Bucholz |
| 5,514,141 A | 5/1996 | Prizzi | 5,853,415 A | 12/1998 | Bertin et al. |
| 5,514,143 A | 5/1996 | Bonutti et al. | 5,860,980 A | 1/1999 | Axelson |
| 5,514,153 A | 5/1996 | Bonutti | 5,860,981 A | 1/1999 | Bertin et al. |
| 5,520,692 A | 5/1996 | Ferrante | 5,866,415 A | 2/1999 | Villeneuve |
| 5,520,694 A | 5/1996 | Dance et al. | 5,871,018 A | 2/1999 | Delp |
| 5,520,695 A | 5/1996 | Luckman | 5,871,493 A | 2/1999 | Sjostrom |
| 5,522,897 A | 6/1996 | King | 5,871,541 A | 2/1999 | Gerber |
| 5,540,695 A | 7/1996 | Levy | 5,871,543 A | 2/1999 | Hofmann |
| 5,540,696 A | 7/1996 | Booth | 5,879,354 A | 3/1999 | Haines |
| 5,542,947 A | 8/1996 | Treacy | 5,880,976 A | 3/1999 | DiGioia et al. |
| 5,549,683 A | 8/1996 | Bonutti | 5,888,219 A | 3/1999 | Bonutti |
| 5,549,689 A | 8/1996 | Epstein et al. | 5,897,559 A | 4/1999 | Masini |
| 5,554,169 A | 9/1996 | Green | 5,899,914 A | 5/1999 | Zirps |
| 5,569,163 A | 10/1996 | Francis | 5,899,939 A | 5/1999 | Boyce et al. |
| 5,569,259 A | 10/1996 | Ferrante et al. | 5,908,424 A | 6/1999 | Bertin et al. |
| 5,570,700 A | 11/1996 | Vogeler | 5,911,723 A | 6/1999 | Ashby et al. |
| 5,571,196 A | 11/1996 | Stein | 5,913,874 A | 6/1999 | Berns |
| 5,578,039 A | 11/1996 | Vendrely et al. | 5,916,219 A | 6/1999 | Matsuno et al. |
| 5,593,448 A | 1/1997 | Dong | 5,916,220 A | 6/1999 | Masini |
| 5,597,379 A | 1/1997 | Haines | 5,916,221 A | 6/1999 | Hodorek |
| 5,601,565 A | 2/1997 | Huebner | 5,916,269 A | 6/1999 | Serbousek et al. |
| 5,609,603 A | 3/1997 | Linden | 5,921,990 A | 7/1999 | Webb |
| 5,609,644 A | 3/1997 | Ashby et al. | 5,944,722 A | 8/1999 | Masini |
| 5,624,463 A | 4/1997 | Stone | 5,947,973 A | 9/1999 | Masini |
| 5,632,745 A | 5/1997 | Schwartz | 5,957,926 A | 9/1999 | Masini |
| 5,643,272 A | 7/1997 | Haines et al. | 5,961,499 A | 10/1999 | Bonutti |
| 5,649,946 A | 7/1997 | Bramlet | 5,961,523 A | 10/1999 | Masini |
| 5,658,292 A | 8/1997 | Axelson | 5,971,989 A | 10/1999 | Masini |
| 5,662,710 A | 9/1997 | Bonutti | 5,980,526 A | 11/1999 | Johnson et al. |
| 5,667,069 A | 9/1997 | Williams | 5,995,738 A | 11/1999 | Di Gioia et al. |
| 5,667,512 A | 9/1997 | Johnson | 5,997,566 A | 12/1999 | Tobin |
| 5,667,520 A | 9/1997 | Bonutti | 5,997,577 A | 12/1999 | Herrington |
| 5,669,914 A | 9/1997 | Eckhoff | 6,001,106 A | 12/1999 | Ryan |
| 5,681,316 A | 10/1997 | DeOrio | 6,002,859 A | 12/1999 | Di Gioia et al. |
| 5,682,886 A | 11/1997 | Delp et al. | 6,007,537 A | 12/1999 | Burkinshaw |
| 5,683,397 A | 11/1997 | Vendrely et al. | 6,012,456 A | 1/2000 | Schuerch |
| 5,683,469 A | 11/1997 | Johnson | 6,013,103 A | 1/2000 | Kaufman et al. |
| 5,702,447 A | 12/1997 | Walch | 6,015,419 A | 1/2000 | Strome |
| 5,702,475 A | 12/1997 | Zahedi | 6,019,767 A | 2/2000 | Howell |
| 5,707,350 A | 1/1998 | Krause | 6,022,350 A | 2/2000 | Ganem |
| 5,712,543 A | 1/1998 | Sjostrom | 6,024,746 A | 2/2000 | Katz |
| 5,715,836 A | 2/1998 | Kliegis | 6,027,504 A | 2/2000 | McGuire |
| 5,716,360 A | 2/1998 | Baldwin et al. | 6,033,410 A | 3/2000 | McLean et al. |
| 5,718,708 A | 2/1998 | Webb | 6,034,296 A | 3/2000 | Elvin |
| 5,720,752 A | 2/1998 | Elliott | 6,056,754 A | 5/2000 | Haines |
| 5,722,978 A | 3/1998 | Jenkins | 6,059,788 A | 5/2000 | Katz |
| 5,723,016 A | 3/1998 | Minns et al. | 6,059,817 A | 5/2000 | Bonutti et al. |
| 5,723,331 A | 3/1998 | Tubo | 6,059,831 A * | 5/2000 | Braslow et al. ............. 128/898 |
| 5,733,292 A | 3/1998 | Gustilo et al. | 6,063,095 A | 5/2000 | Wang et al. |
| 5,735,904 A | 4/1998 | Pappas | 6,068,633 A | 5/2000 | Masini |
| 5,741,264 A | 4/1998 | Capolletti | 6,077,269 A | 6/2000 | Masini |
| 5,743,915 A | 4/1998 | Bertin et al. | 6,077,270 A | 6/2000 | Katz |
| 5,749,876 A | 5/1998 | Duvillier et al. | 6,077,287 A | 6/2000 | Taylor |
| 5,755,731 A | 5/1998 | Grinberg | 6,086,593 A | 7/2000 | Bonutti |
| 5,755,791 A | 5/1998 | Whitson et al. | 6,090,122 A | 7/2000 | Sjostrom |
| 5,755,803 A | 5/1998 | Haines | 6,099,531 A | 8/2000 | Bonutti |
| 5,763,416 A | 6/1998 | Bonadio | 6,099,532 A | 8/2000 | Florea |

| | | | | | | |
|---|---|---|---|---|---|---|
| 6,102,850 | A | 8/2000 | Wang et al. | 6,575,980 B1 | 6/2003 | Robie |
| 6,102,916 | A | 8/2000 | Masini | 6,589,248 B1 | 7/2003 | Hughes |
| 6,102,955 | A | 8/2000 | Mendes et al. | 6,589,281 B2 * | 7/2003 | Hyde, Jr. ................ 623/18.11 |
| 6,106,529 | A | 8/2000 | Techiera | 6,589,283 B1 | 7/2003 | Metzger |
| 6,110,188 | A | 8/2000 | Narciso | 6,616,696 B1 | 9/2003 | Merchant |
| 6,118,845 | A | 9/2000 | Simon et al. | 6,620,181 B1 | 9/2003 | Bonutti |
| 6,132,468 | A | 10/2000 | Mansmann | 6,623,526 B1 | 9/2003 | Lioyd |
| 6,146,385 | A | 11/2000 | Torrie | 6,629,997 B2 | 10/2003 | Mansmann |
| 6,159,246 | A | 12/2000 | Mendes et al. | 6,632,225 B2 | 10/2003 | Sanford et al. |
| 6,165,223 | A | 12/2000 | Metzger | 6,648,896 B2 | 11/2003 | Overes |
| 6,171,340 | B1 | 1/2001 | McDowell | 6,652,587 B2 | 11/2003 | Felt |
| 6,174,314 | B1 | 1/2001 | Waddell | 6,660,040 B2 | 12/2003 | Cahn et al. |
| 6,174,321 | B1 | 1/2001 | Webb | 6,695,848 B2 | 2/2004 | Haines |
| 6,176,880 | B1 | 1/2001 | Plouhar | 6,702,821 B2 * | 3/2004 | Bonutti ..................... 606/88 |
| 6,185,315 | B1 | 2/2001 | Schmucher et al. | 6,709,460 B2 | 3/2004 | Merchant |
| 6,187,010 | B1 | 2/2001 | Masini | 6,723,102 B2 | 4/2004 | Johnson et al. |
| 6,187,023 | B1 | 2/2001 | Bonutti | 6,743,258 B1 | 6/2004 | Keller |
| 6,195,168 | B1 | 2/2001 | De Lega et al. | 6,749,638 B1 | 6/2004 | Saladino |
| 6,197,064 | B1 | 3/2001 | Haines et al. | 6,755,865 B2 | 6/2004 | Tarabishy |
| 6,198,794 | B1 | 3/2001 | Peshkin et al. | 6,770,077 B2 | 8/2004 | Van Zile et al. |
| 6,205,411 | B1 | 3/2001 | DiGioia et al. | 6,770,078 B2 | 8/2004 | Bonutti |
| 6,206,927 | B1 | 3/2001 | Fell et al. | 6,793,676 B2 | 9/2004 | Plouhar |
| 6,211,976 | B1 | 4/2001 | Popovich et al. | 6,827,723 B2 | 12/2004 | Carson |
| 6,214,011 | B1 | 4/2001 | Masini | 6,858,032 B2 | 2/2005 | Chow et al. |
| 6,214,051 | B1 * | 4/2001 | Badorf et al. ............ 623/20.14 | 6,859,661 B2 | 2/2005 | Tuke |
| 6,228,090 | B1 | 5/2001 | Waddell | 6,916,341 B2 | 7/2005 | Rolston |
| 6,228,091 | B1 | 5/2001 | Lombardo et al. | 6,972,039 B2 | 12/2005 | Metzger |
| 6,228,121 | B1 | 5/2001 | Khalili | 6,986,791 B1 | 1/2006 | Metzger |
| 6,241,735 | B1 | 6/2001 | Marmulla | 7,048,741 B2 | 5/2006 | Swanson |
| 6,253,100 | B1 | 6/2001 | Zhdanov | 7,104,996 B2 | 9/2006 | Bonutti |
| 6,258,095 | B1 | 7/2001 | Lombardo | 7,105,027 B2 | 9/2006 | Lipman |
| 6,258,127 | B1 | 7/2001 | Schmotzer | 7,220,264 B1 | 5/2007 | Hershberger |
| 6,264,701 | B1 | 7/2001 | Brekke | 7,244,274 B2 | 7/2007 | Delfosse |
| 6,277,136 | B1 | 8/2001 | Bonutti | 7,422,605 B2 | 9/2008 | Burstein |
| 6,280,476 | B1 | 8/2001 | Metzger et al. | 7,510,557 B1 | 3/2009 | Bonutti |
| 6,290,703 | B1 | 9/2001 | Ganem | 2002/0055755 A1 | 5/2002 | Bonutti |
| 6,296,646 | B1 | 10/2001 | Williamson | 2002/0127264 A1 | 9/2002 | Felt |
| 6,299,645 | B1 | 10/2001 | Ogden et al. | 2002/0138150 A1 | 9/2002 | Leclercq |
| 6,306,169 | B1 | 10/2001 | Lee et al. | 2002/0198528 A1 | 12/2002 | Engh et al. |
| 6,306,172 | B1 | 10/2001 | O'Neil | 2003/0093079 A1 | 5/2003 | Masini |
| 6,325,806 | B1 | 12/2001 | Fox | 2003/0100906 A1 | 5/2003 | Rosa et al. |
| 6,325,828 | B1 | 12/2001 | Dennis | 2003/0100907 A1 | 5/2003 | Rosa et al. |
| 6,328,572 | B1 | 12/2001 | Higashida | 2003/0130665 A1 | 7/2003 | Pinczewski et al. |
| 6,338,730 | B1 | 1/2002 | Bonutti et al. | 2003/0153923 A1 | 8/2003 | Pinczewski |
| 6,338,737 | B1 | 1/2002 | Toledano | 2003/0158606 A1 | 8/2003 | Coon |
| 6,342,075 | B1 * | 1/2002 | MacArthur ............... 623/20.14 | 2003/0163137 A1 | 8/2003 | Smucker et al. |
| 6,352,558 | B1 | 3/2002 | Spector | 2003/0171757 A1 | 9/2003 | Coon et al. |
| 6,358,266 | B1 | 3/2002 | Bonutti | 2003/0181984 A1 | 9/2003 | Abendscein |
| 6,379,387 | B1 | 4/2002 | Tornier | 2003/0212403 A1 | 11/2003 | Swanson |
| 6,391,040 | B1 | 5/2002 | Christodias | 2003/0220697 A1 | 11/2003 | Justin |
| 6,398,815 | B1 | 6/2002 | Pope et al. | 2003/0225458 A1 | 12/2003 | Donkers |
| 6,406,495 | B1 | 6/2002 | Schoch | 2003/0236523 A1 | 12/2003 | Johnson et al. |
| 6,409,722 | B1 | 6/2002 | Hoey | 2004/0039395 A1 | 2/2004 | Coon et al. |
| 6,413,279 | B1 | 7/2002 | Metzger | 2004/0143338 A1 | 7/2004 | Burkinshaw |
| 6,423,096 | B1 | 7/2002 | Musset et al. | 2004/0204760 A1 | 10/2004 | Fitz |
| 6,431,743 | B1 | 8/2002 | Mizutani | 2004/0260301 A1 | 12/2004 | Lionberger |
| 6,440,444 | B2 | 8/2002 | Boyce et al. | 2005/0043807 A1 | 2/2005 | Wood |
| D462,767 | S | 9/2002 | Meyer | 2007/0173946 A1 | 7/2007 | Bonutti |
| 6,443,991 | B1 | 9/2002 | Running | 2008/0147075 A1 | 6/2008 | Bonutti |
| 6,478,799 | B1 | 11/2002 | Williamson | | | |
| 6,482,209 | B1 * | 11/2002 | Engh et al. .................... 606/79 | FOREIGN PATENT DOCUMENTS | | |
| 6,488,687 | B1 | 12/2002 | Masini | | | |
| 6,491,726 | B2 | 12/2002 | Pappas | EP | 1245204 | 10/2002 |
| 6,494,914 | B2 | 12/2002 | Brown et al. | EP | 1317911 | 6/2003 |
| 6,500,179 | B1 | 12/2002 | Masini | FR | 2682287 | 4/1993 |
| 6,500,181 | B1 | 12/2002 | Portney | JP | 291779 | 10/2007 |
| 6,514,259 | B2 | 2/2003 | Picard et al. | WO | WO 93/25157 | 6/1993 |
| 6,522,906 | B1 | 2/2003 | Salisbury | WO | WO 95/14444 | 6/1995 |
| 6,540,786 | B2 | 4/2003 | Chibrac | WO | WO 97/25006 | 7/1997 |
| 6,551,324 | B2 | 4/2003 | Muller | WO | WO 98/32384 | 7/1998 |
| 6,554,838 | B2 | 4/2003 | McGovern | WO | WO 99/13803 | 3/1999 |
| 6,558,391 | B2 | 5/2003 | Axelson | WO | WO 99/40864 | 8/1999 |
| 6,558,421 | B1 | 5/2003 | Fell | WO | WO 02/17821 | 8/2000 |

| | | |
|---|---|---|
| WO | WO 02/067783 | 9/2002 |

OTHER PUBLICATIONS

AVON™ Patello-Femoral Arthroplasty, Christopher E. Ackroyd, Stryker Howmedica Ostionics, © 2002.
Clinical Orthopaedics, Long-Term Results with the First Patellofemoral Prosthesis, Phillipe Cartier, pp. 46-54, Jul. 2005.
FxRx, Stryker Howmedia Osteonics, Indian Summer 2003.
ImmediateCare™ External Fixation Systems Sterile Ankle Kit, Stryker Howmedica Osteonics, © 2002.
ImmediateCare™ External Fixation Systems Sterile Wrist Fixator, Stryker Howmedica Osteonics, © 2002.
Insall/Burstein II Modular Knee System—Publication date unknown, but before Aug. 1, 2001.
The M/G Unicompartmental Knee—Minimally Invasive Surgical Technique—Publication date unknown, but before Aug. 1, 2001.
NexGen Complete Knee Solution—Design Rationale—Publication date unknown, but before Aug. 1, 2001.
NexGen Complete Knee Solution—Extramedullary/ Intramedullary Tibial Resector Surgical Technique—Publication date unknown, but before Aug. 1 2001.
NexGen Complete Knee Solution—Intramedully Instrumentation Technique—For the NexGen Cruciate Retaining & Legacy® Posterior Stabilized Knee—Publication date unknown, but before Aug. 1, 2001.
NexGen Complete Knee Solution—Multi-Reference Reference™ 4-in-1 Femoral Instrumentation—Anterior Reference Surgical Technique—Publication date unknown, but before Aug. 1, 2001.
NexGen Complete Knee Solution—Surgical Technique for the LPS-Flex Fixed Bearing Knee—Publication date unknown, but before Aug. 1, 2001.
Operative Arthroscopy—John B. McGinty M.D.—Department of Orthopedic Surgery, Medical University of South Carolina, Charleston, South Carolina—© 1991 by Raven Press, Ltd., p. 9.
Scorpio Single Axix Total Knee System—Passport Total Knee Instrumentation—Passport P.R Surgical Technique—Publication date unknown, but before Aug. 1, 2001.
Scorpio Single Axis Total Knee System—Stryker® Howmedica Osteonics- One Revolutionary Idea, Three great Potential Benefits, Mar. 2000.
Scorpio Total Stabilizer Revision Knee System Surgical Protocol, ScorpioTS Single Axis Total Knee System Stryker® Howmedica Osteonics, Jan. 2001.
The Series 7000 Total Knee System—Passport A.R. Total Knee Instruments—© Osteonics 1996.
Simplex Enhancement Systems, Howmedica Catalog, pp. 3-4, 1990.
Sterile Yellow Monotube® TRIAX™ Kit, Stryker Howmedica Osteonics, © 2001.
Sulzer Orthopedics TM Natural-Knee® U System Surgical Technique—© 1998 Sulzer Orthopedics Inc.

Surgical Navigation for Total Knee Arthroplasty—Believed to have been presented at the American Academy of Orthopedic Surgeons In Feb. 2001.
Surgical Protocol—Solar TM Total Shoulder System—© Osteonics Corp. 1998.
Surgical Technique—Stryker® Howmedica Osteonics—Restoration TM T3 Femoral Component Using the Command® Instrument System, Feb. 2000.
Total Joints Orthopedic, Richards Modular Knee, Richards Manufacturing Company, Publication date unknown, but before 2001.
Zimmer Catalog, Wilder Retractors, pp. 38-39, © 1972.
U.S. Appl. No. 10/681,526, filed Oct. 8, 2003, Bonutti.
U.S. Appl. No. 10/684,904, filed Oct. 14, 2003, Bonutti.
U.S. Appl. No. 10/722,102, filed Nov. 25, 2003, Bonutti.
U.S. Appl. No. 10/072,729, filed Dec. 3, 2003, Bonutti.
U.S. Appl. No. 10/888,783, filed Jul. 9, 2004, Bonutti.
U.S. Appl. No. 11/171,700, filed Jun. 30, 2005, Bonutti.
U.S. Appl. No. 11/684,178, filed Mar. 9, 2007, Bonutti.
U.S. Appl. No. 11/037,855, filed Jan. 18, 2005, Bonutti.
U.S. Appl. No. 11/171,902, filed Jun. 30, 2005, Bonutti.
U.S. Appl. No. 11/171,676, filed Jun. 30, 2005, Bonutti.
U.S. Appl. No. 10/795,887, filed Mar. 8, 2008, Bonutti.
U.S. Appl. No. 10/795,887, filed Mar. 8, 2004, Bonutti, application not published.
M. Bottlang, Ph.D, et al., A Mobile-bearing Knee Prosthesis Can Reduce Strain at the Proximal Tibia, Clinical Orthopaedics and Related Research, No. 447, pp. 105-111, Copyright © 2006, Lippincott Williams & Wilkins, retrieved Jan. 13, 2010.
Seo SS, et al., Effect of Posterior Condylar Offset on Cruciate-Retaining Mobile TKA, Pusan Paik Hospital, College of Medicine, www.ncbi.nlm.nih.gov, PubMed, p. 1, Copyright © 2009, retrieved Jan. 13, 2010.
ScienceDirect, -The Knee- Influence of Posterior Condylar Offset on Knee Flexion After Cruciate-Sacrificing Mobile-Bearing Total Knee Replacement: A prospective Analysis of 410 Consecutive Cases., Published by Elsevier B.V., www.sciencedirect.com, 3 pgs., Copyright © 2009, retrieved Jan. 13, 2010.
B.M. Hanratty et al., The Influence of Posterior Condylar Offset on Knee Flexion After Total Knee Replacement Using Cruciate-Sacrificing Mobile-Bearing Implant., Journal of Bone and Joint Surgery, British vol. 89-B, iSSUE 7, 915-918, Copyright © 2007, British Editorial Society of Bone and Joint Surgery—retrieved Jan. 12, 2010.
12ZCopending U.S. Appl. No. 11,684,178, Non-Final Rejection mailed Feb. 24, 2010.
12CONCopending U.S. Appl. No. 11/928,898, Non-Final Rejection mailed Mar. 11, 2010.
12KCopending U.S. Appl. No. 11/171,676, Response to Office Action filed Mar. 20, 2009.
12KCopending U.S. Appl. No.11/171,676, Response to Office Action filed Mar. 31, 2008.

* cited by examiner

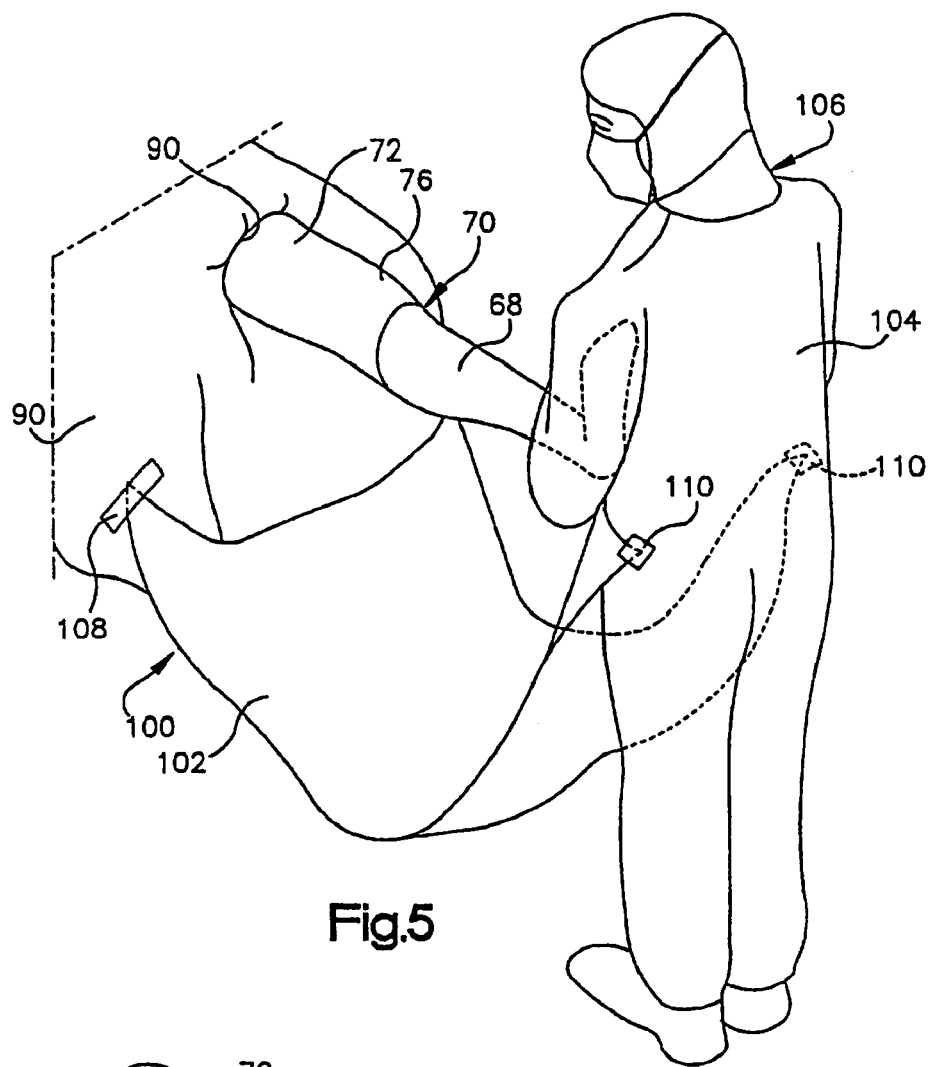
Fig.5
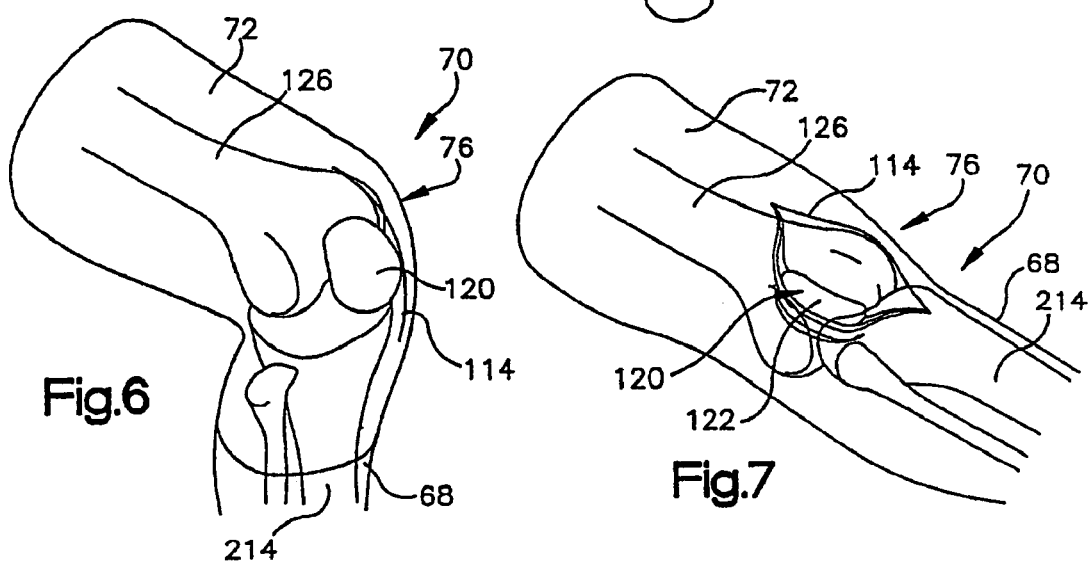
Fig.6
Fig.7

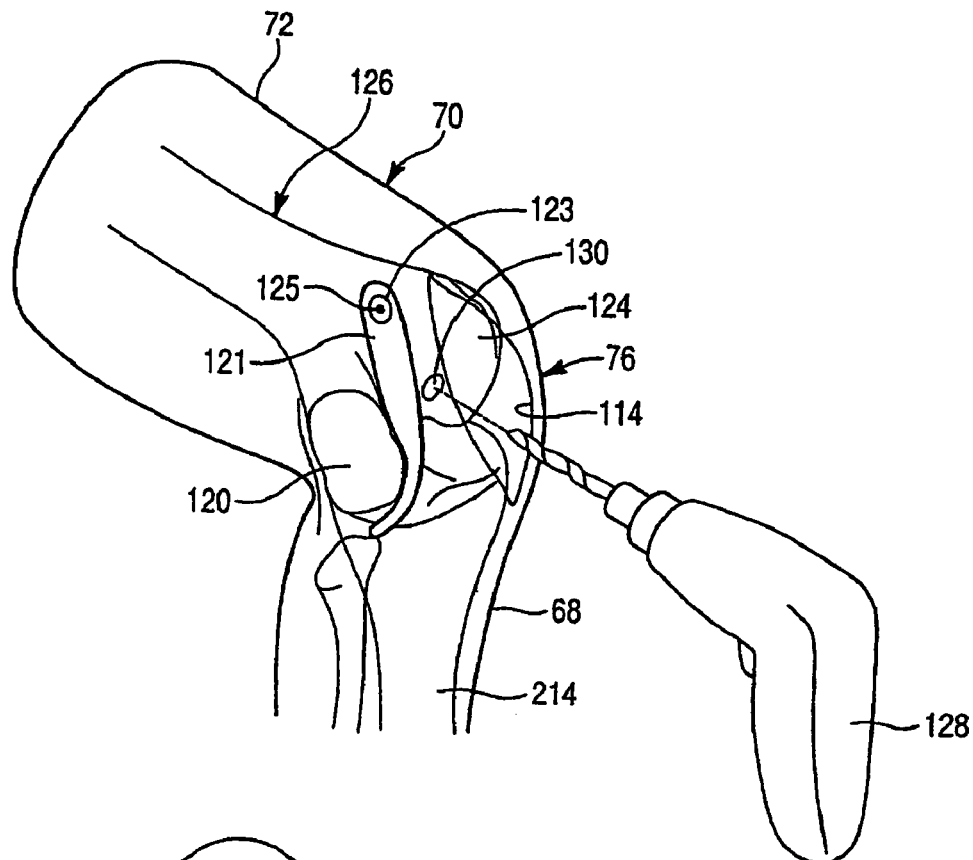
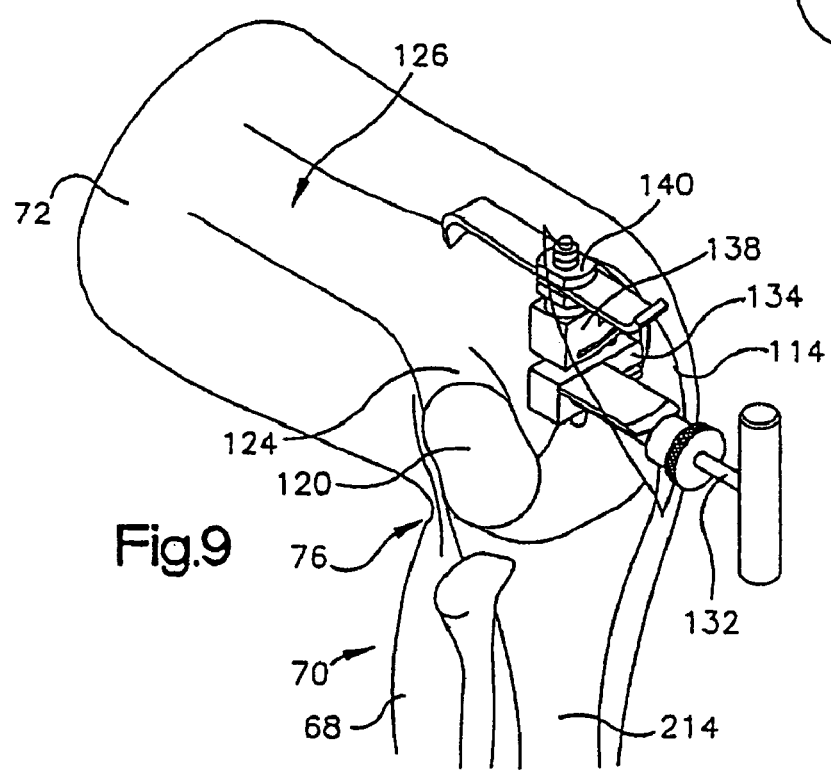

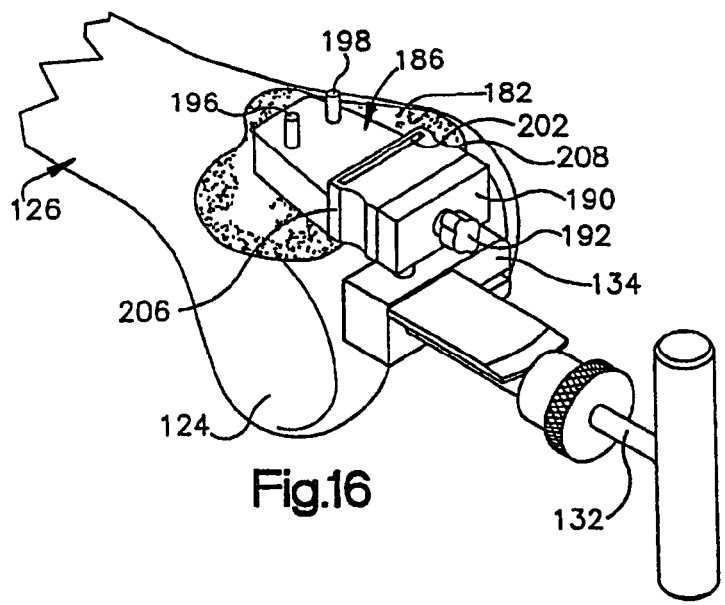
Fig.16
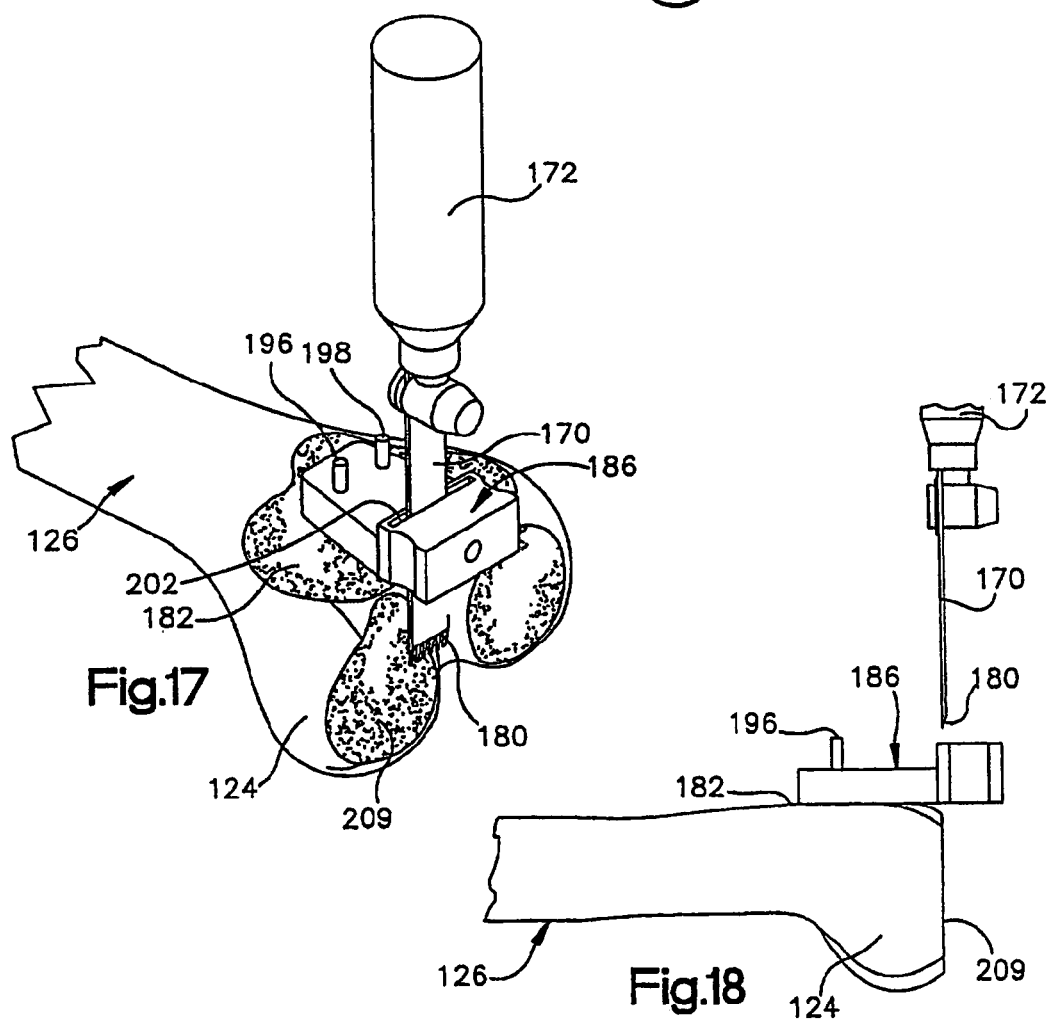
Fig.17
Fig.18

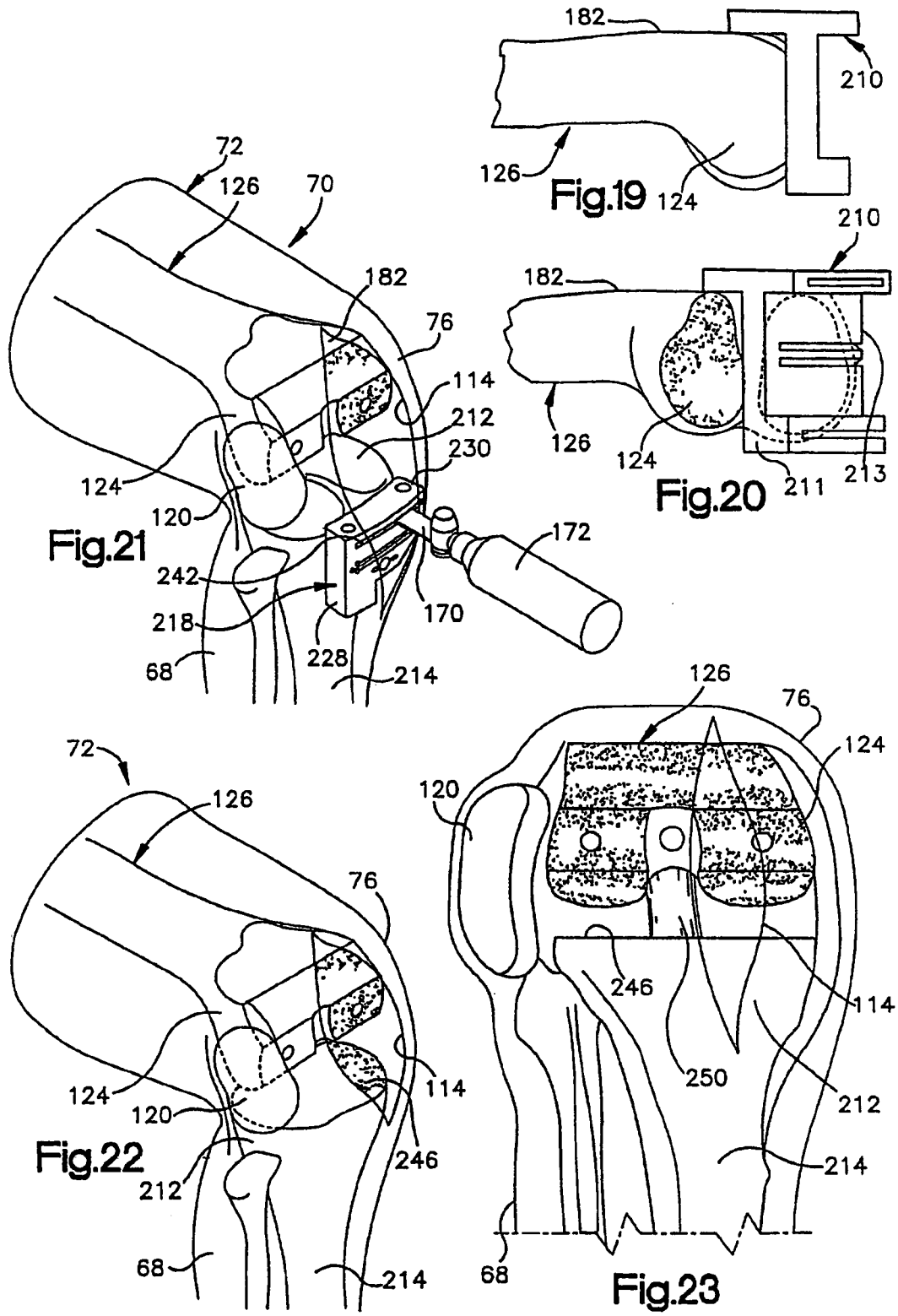

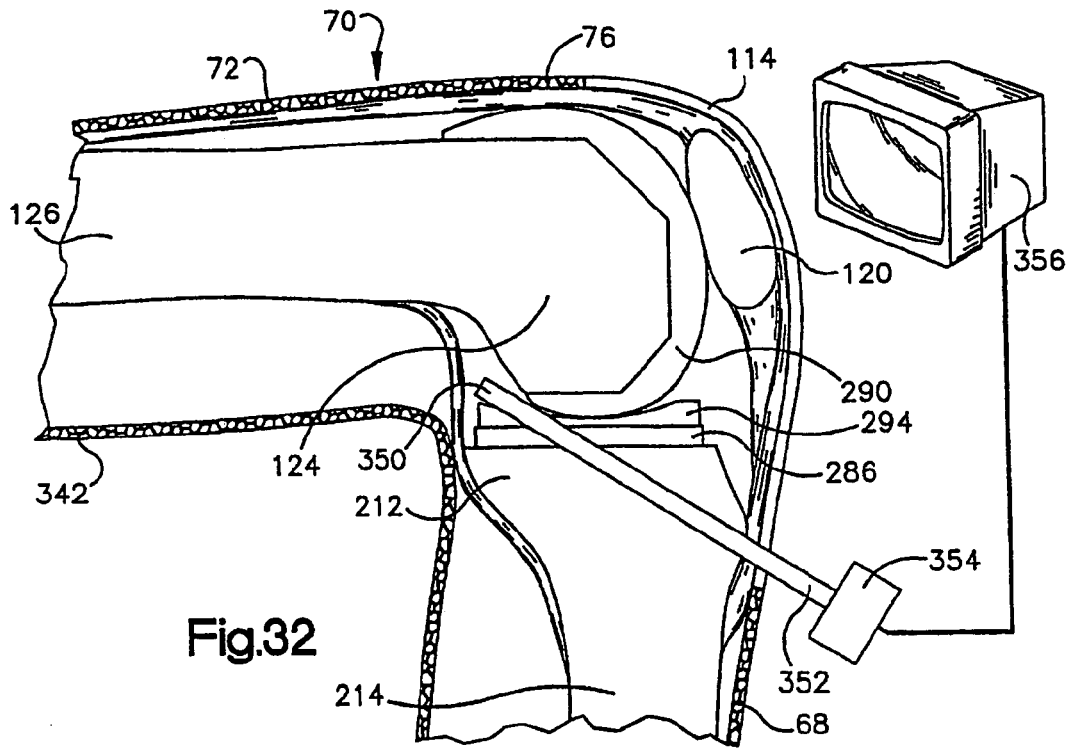
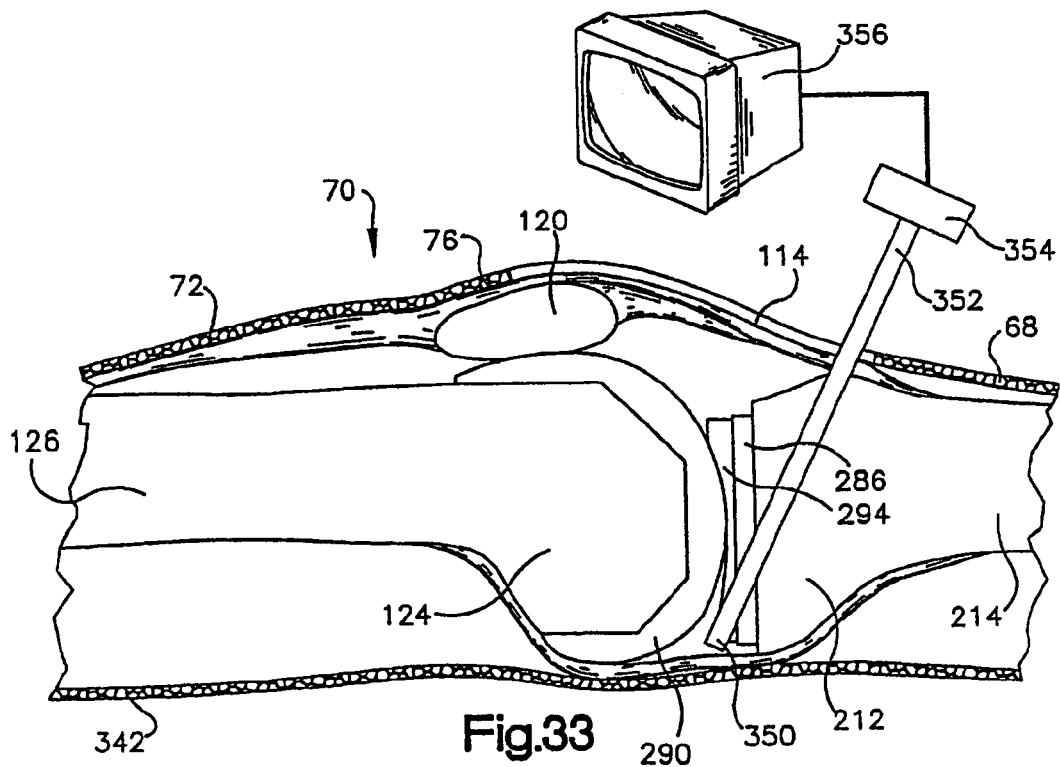

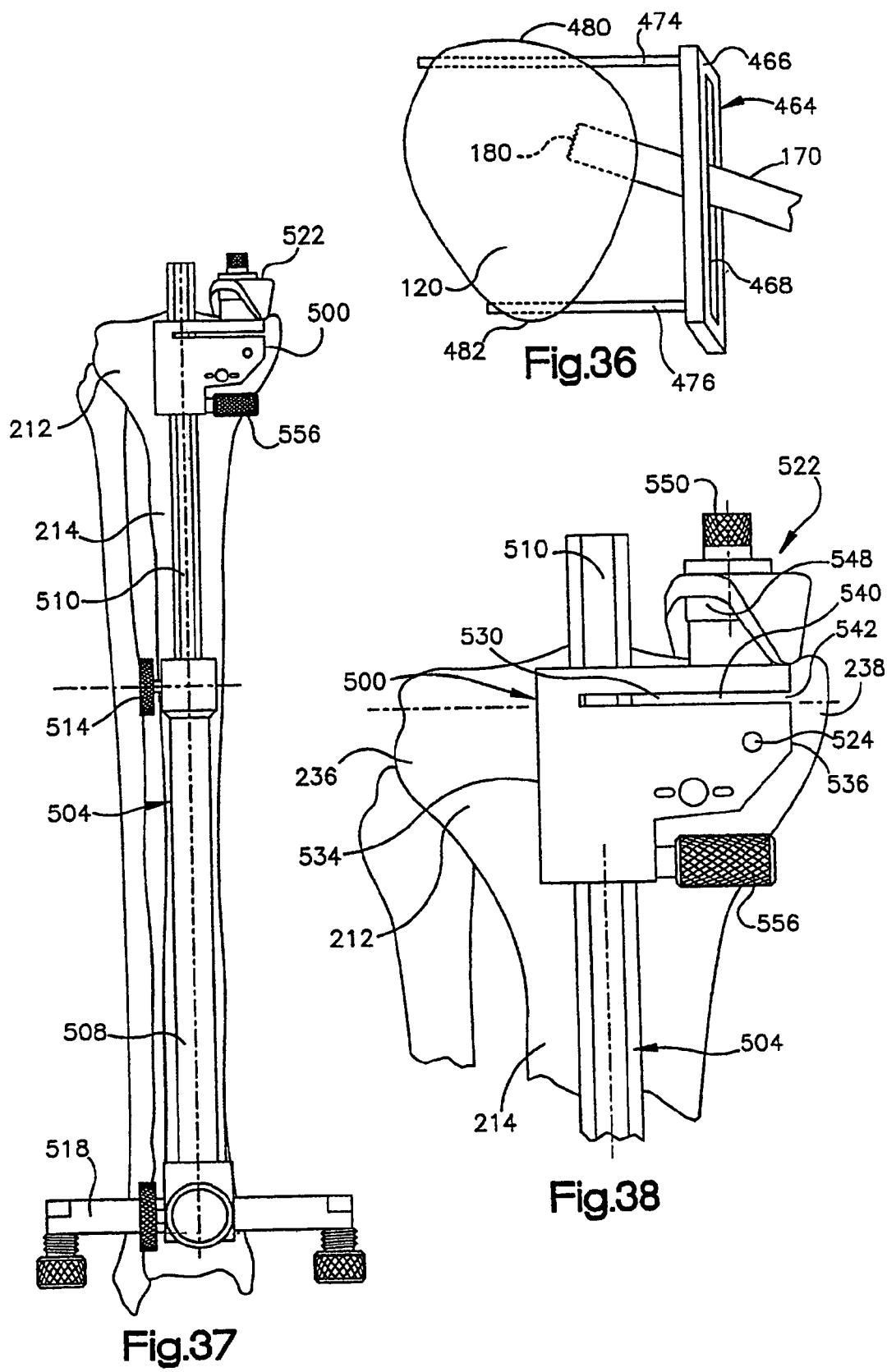

TOTAL KNEE ARTHROPLASTY THROUGH SHORTENED INCISION

CROSS-REFERENCE TO RELATED APPLICATION

This application is a continuation of U.S. patent application Ser. No. 10/191,751 filed Jul. 8, 2002 now U.S. Pat. No. 7,104,996. U.S. patent application Ser. No. 10/191,751 is a continuation-in-part of U.S. patent application Ser. No. 09/976,396 filed Oct. 11, 2001, now U.S. Pat. No. 6,770,078. U.S. patent application Ser. No. 10/191,751 is also continuation-in-part of U.S. patent application Ser. No. 09/941,185 filed Aug. 28, 2001, now U.S. Pat. No. 6,702,821. U.S. patent application Ser. No. 10/191,751 is also a continuation-in-part of U.S. patent application Ser. No. 09/566,070 filed May 5, 2000, now U.S. Pat. No. 6,575,982. U.S. patent application Ser. No. 10/191,751 is also a continuation-in-part of U.S. patent application Ser. No. 09/737,380 filed Dec. 15, 2000, now U.S. Pat. No. 6,503,267. U.S. patent application Ser. No. 10/191,751 is also a continuation-in-part of U.S. patent application Ser. No. 09/569,020 filed May 11, 2000, now U.S. Pat. No. 6,423,063. U.S. patent application Ser. No. 10/191,751 is also a continuation-in-part of U.S. patent application Ser. No. 09/483,676 filed Jan. 14, 2000, now U.S. Pat. No. 6,468,289. U.S. patent application Ser. No. 10/191,751 is also a continuation-in-part of U.S. patent application Ser. No. 09/798,870 filed Mar. 1, 2001, now U.S. Pat. No. 6,503,277. U.S. patent application Ser. No. 10/191,751 is also a continuation-in-part of U.S. patent application Ser. No. 09/526,949 tiled on Mar. 16, 2000, now U.S. Pat. No. 6,620,181. U.S. patent application Ser. No. 10/191,751 is also a continuation-in-part of U.S. patent application Ser. No. 09/789,621 filed Feb. 21, 2001, now U.S. Pat. No. 6,635,073.

BACKGROUND OF THE INVENTION

The present invention relates to a new and improved method of performing surgery, and instruments, implants, and other surgical implements that can be used in surgery. The surgery may be of any desired type. The surgery may be performed on joints in a patient's body. The surgery may be performed on any desired joint in a patient's body. Regardless of the type of surgery to be performed, a limited incision may advantageously be utilized.

In some embodiments, this specification relates to limited incision partial or total knee joint replacements and revisions and is the result of a continuation of work which was previously performed in conjunction with the subject matter of U.S. Pat. No. 5,514,143. This specification also contains subject matter which relates to U.S. Pat. Nos. 5,163,949; 5,269,785; 5,549,683; 5,662,710; 5,667,520; 5,961,499; 6,059,817; and 6,099,531. Although this specification refers to knee joints, it should be understood that the subject matter of this application is also applicable to joints in many different portions of a patient's body, for example a shoulder, spine, arm, hand, hip or foot of a patient.

During a total or partial knee replacement or revision, an incision is made in a knee portion of a leg of the patient to obtain access to the knee joint. The incision is relatively long to enable instrumentation, such as a femoral alignment guide, anterior resection guide, distal resection guide, femoral cutting guide, and femoral anterior, posterior and chamfer resection guide to be positioned relative to a distal end portion of the femur. In addition, the incision must be relatively large to enable a tibial resection guide to be positioned relative to the proximal end portion of the tibia.

With known procedures of total or partial knee replacement, the incision in the knee portion of the patient is made with the leg of the patient extended (straight) while the patient is lying on his or her back. At this time, the extended leg of the patient is disposed along and rests on a patient support surface. After the incision has been made in the knee portion of the leg of the patient, the leg is flexed and a foot connected with the leg moves along the patient support surface. The knee portion of the flexed leg of the patient is disposed above the patient support surface. This results in the soft tissue in the knee being compressed against the back of the knee joint. This makes it very difficult to access posterior soft tissue to remove bone spurs (ostified), meniscus, posterior capsule, ligaments in the back of the joint, and/or any residual soft tissue or connective tissue that is blocking further flexion.

After the incision has been made and while the leg is flexed with the foot above the patient support surface, the surgeon cannot view arteries, nerves and veins which are sitting just posterior to the knee capsule. Therefore, a surgeon may be very reluctant, or at least very careful, of inserting instruments into the back of the knee joint to remove tissue. This may result in osteophytes, bone spurs and similar types of posterior soft tissue being left in place.

With known techniques, the patella is commonly everted from its normal position. When the patella is everted, the inner side of the patella is exposed and faces outward away from end portions of the femur and tibia. The outer side of the everted patella faces inward toward the end portions of the femur and the tibia. Moving the everted patella to one side of end portions of the femur and tibia tends to increase the size of the incision which must be made in the knee portion of the patient's leg.

After implants have been positioned in the knee portion of the patient's leg, it is common to check for flexion and extension balancing of ligaments by flexing and extending the knee portion with the foot above the support surface. If the ligaments are too tight medially or laterally, they can be released to obtain the desired tension. However, the checking of ligament balance by flexing and extending the leg of the patient, ignores rotational balancing of ligaments. Since the femoral implant is movable relative to the tibial implant, the stability of the knee joint is dependent upon balancing of the ligaments in flexion, extension, and rotation.

SUMMARY OF THE INVENTION

The present invention relates to a new and improved method and apparatus for use in performing any desired type of surgery on a joint in a patient's body. The joint may advantageously be a knee joint. However, the method and apparatus may be used in association with surgery on other joints in a patient's body. There are many different features of the present invention which may used either together or separately in association with many different types of surgery. Although features of the present invention may be used with many different surgical procedures, the invention is described herein in conjunction with surgery on a joint in a patient's body.

One of the features of the present invention relates to the making of a limited incision. The limited incision may be in any desired portion of a patient's body. For example, the limited incision may be in a knee portion of a leg of a patient. The limited incision may be made while a lower portion of the leg of the patient is extending downward from the upper portion of the leg of the patient. At this time, a foot connected with the lower portion of the leg of the patient may be below a surface on which the patient is supported. The limited incision may be made while the lower portion of the leg of the patient is suspended from the upper portion of the leg or while the lower portion of the leg and/or the foot of the patient are held by a support device. After the incision has been made, any one of many surgical procedures may be undertaken.

It is believed that in certain circumstances, it may be desired to have a main incision of limited length and a secondary incision of even smaller length. The secondary incision may be a portal or stab wound. A cutting tool may be moved through the secondary incision. An implant may be moved through the main incision.

Once the incision has been made, a patella in a knee portion of the patient may be offset to one side of its normal position. When the patella is offset, an inner side of the patella faces inward toward the end portions of a femur and tibia. If desired, the patella can be cut and realigned in situ, with minimal or no subluxation. Additionally, the cutting and/or realignment can be done while the knee is in flexion, which is the natural position, rather than extension.

Although any one of many known surgical procedures may be undertaken through the limited incision, down sized instrumentation for use in the making of cuts in a femur and/or tibia may be moved through or part way through the incision. The down sized instrumentation may be smaller than implants to be positioned in the knee portion of the patient. The down sized instrumentation may have opposite ends which are spaced apart by a distance which is less than the distance between lateral and medial epicondyles on a femur or tibia in the leg of the patient.

It is contemplated that the down sized instrumentation may have cutting tool guide surfaces of reduced length. The length of the cutting tool guide surfaces may be less than the length of a cut to be made on a bone. A cut on a bone in the patient may be completed using previously cut surfaces as a guide for the cutting tool.

It is contemplated that at least some, if not all, cuts on a bone may be made using light or other electromagnetic radiation, such as infrared radiation, directed onto the bone as a guide. The light directed onto the bone may be in the form of a three dimensional image. The light directed onto the bone may be a beam along which a cutting or milling tool is moved into engagement with the bone.

There are several different orders in which cuts may be made on bones in the knee portion of the leg of the patient. It is believed that it may be advantageous to make the patellar and tibial cuts before making the femoral cuts.

There are many different reasons to check ligament balancing in a knee portion of the leg of a patient. Ligament balancing may be checked while the knee portion of the leg of the patient is flexed and the foot of the patient is below the support surface on which the patient is disposed. Flexion and extension balancing of ligaments may be checked by varying the extent of flexion of the knee portion of the leg of the patient. In addition, rotational stability of the ligaments may be checked by rotating the lower portion of the leg of the patient about its central axis. Balancing of ligaments may also be checked by moving the foot of the patient sideways, rotating the lower portion of the leg of the patient, and/or moving the foot anteriorly or posteriorly.

It is believed that it may be advantageous to utilize an endoscope or a similar apparatus to examine portions of the patient's body which are spaced from the incision. It is also contemplated that images of the knee portion of the patient's leg may be obtained by using any one of many known image generating devices other than an endoscope. The images may be obtained while the patient's leg is stationary or in motion. The images may be obtained to assist a surgeon in conducting any desired type of surgery.

Balancing of the ligaments in the knee portion of a patient's leg may be facilitated by the positioning of one or more transducers between tendons, ligaments, and/or bones in the knee portion. One transducer may be positioned relative to a medial side of a knee joint. Another transducer may be positioned relative to a lateral side of the knee joint. During bending of the knee joint, the output from the transducers will vary as a function of variations in tension forces in the ligaments. This enables the tension forces in ligaments in opposite sides of the knee portion to be compared to facilitate balancing of the ligaments.

Patellar tracking may be checked by the positioning of one or more transducers between the patella and the distal end portion of the femur. If desired, one transducer may be placed between a medial portion of the patella and the distal end portion of the femur. A second transducer may be placed between a lateral portion of the patella and the distal end portion of the femur. Output signals from a transducer will vary as a function of variations in force transmitted between the patella and femur during bending of the leg.

The articular surface on the patella may be repaired. The defective original articular surface on the patella may be removed by cutting the patella while an inner side of the patella faces toward a distal end portion of a femur. The step of cutting the patella may be performed while the patella is disposed in situ and is urged toward the distal end portion of the femur by connective tissue. An implant may then be positioned on the patella.

It is contemplated that the size of the incision in the knee or other portion of the patient may be minimized by conducting surgery through a cannula. The cannula may be expandable. To facilitate moving of an implant through the cannula, the implant may be formed in two or more portions. The portions of the implant may be interconnected when the portions of the implant have been positioned in the patient's body. Although the implants disclosed herein are associated with a patient's knee, it should be understood that the implants may be positioned at any desired location in a patient's body.

An implant may be positioned in a recess formed in a bone in a patient. The implant may contain biological resurfacing and/or bone growth promoting materials. The implant may contain mesenchymal cells and/or tissue inductive factors. Alternatively, the implant may be formed of one or more materials which do not enable bone to grow into the implant.

In accordance with one of the features of the present invention, body tissue may be moved or stretched by a device which is expandable. The expandable device may be biodegradable so that it can be left in a patient's body. The expandable device may be expanded to move and/or stretch body tissue and increase a range of motion of a joint. The expandable device may be used to stretch body tissue in which an incision is to be made.

An improved drape system is provided to maintain a sterile field between a surgeon and a patient during movement of the surgeon relative to the patient. The improved drape system includes a drape which extends between the surgeon and a drape for the patient. During surgery on a knee portion of a leg of a patient, the drape system extends beneath a foot portion of the leg of a patient. It is contemplated that the drape system will be utilized during many different types of operations other than surgery on a leg of a patient.

An implant may be movable relative to both a femur and a tibia in a leg of a patient during bending of the leg. The implant may include a single member which is disposed between and engaged by end portions of both the femur and tibia. Alternatively, the implant may include a plurality of members which are disposed in engagement with each other. If desired, one of the members of the plurality of members may be secured to a bone and engaged by a member which is not secured to a bone. The implant may be secured to soft tissue in the knee portion of the patient's leg.

There are many different features to the present invention. It is contemplated that these features may be used together or separately. It is also contemplated that the features may be utilized in association with joints in a patient's body other than a knee joint. For example, features of the present invention may be used in association with surgery on vertebral joints or glenoid joints. However, it is believed that many of the features may be advantageously utilized together during the performance of surgery on a patient's knee. However, the invention should not be limited to any particular combination of features or to surgery on any particular joint in a patient's body. It is contemplated that features of the present invention will be used in association with surgery which is not performed on a joint in a patient's body.

BRIEF DESCRIPTION OF THE DRAWINGS

The foregoing and other features of the invention will become more apparent upon a consideration of the following description taken in connection with the accompanying drawings wherein:

FIG. 5 is a schematic illustration depicting the manner in which the drape system of FIG. 4 maintains a sterile field during movement of the surgeon relative to the patient;

FIG. 6 is a schematic illustration depicting the manner in which an incision is made in the knee portion of the leg of the patient when the leg is in the position illustrated in FIGS. 2 and 3;

FIG. 7 is a schematic illustration depicting the manner in which the incision is expanded and a patella is everted with the leg of the patient extended;

FIG. 8 is a schematic illustration depicting the manner in which a drill is utilized to form a passage in a femur in the upper portion of the leg of the patient with the leg in the position illustrated in FIGS. 2 and 3 and the patella offset from its normal position;

FIG. 9 is a schematic illustration of the positioning of a femoral alignment guide in the hole formed by the drill of FIG. 8 with the leg of the patient in the position illustrated in FIGS. 2 and 3;

FIG. 16 is a schematic illustration depicting the manner in which the femoral alignment guide is utilized to position a distal resection guide relative to the distal end portion of the femur after making of the anterior femur cut and with the leg of the patient in the position illustrated in FIGS. 2 and 3;

FIG. 17 is a schematic illustration depicting the manner in which a distal femur cut is made with a cutting tool after the femoral alignment guide has been removed, the leg of the patient being in the position illustrated in FIGS. 2 and 3;

FIG. 18 is a schematic illustration depicting the relationship of the cutting tool and distal resection guide of FIG. 17 to the femur;

FIG. 19 is a schematic illustration depicting the manner in which a femoral cutting guide is positioned on the distal end portion of the femur with the leg of the patient in the position illustrated in FIGS. 2 and 3;

FIG. 20 is a schematic illustration further depicting the relationship of the femoral cutting guide to the distal end portion of the femur;

FIG. 21 is a schematic illustration depicting the relationship of a tibial resection guide to the proximal end portion of a tibia in the lower portion of the patient's leg after making the femoral cuts and with the leg of the patient in the position illustrated in FIGS. 2 and 3;

FIG. 22 is a schematic illustration of the distal end portion of the femur and the proximal end portion of the tibia after making the femoral and tibial cuts with the leg of the patient in the position illustrated in FIGS. 2 and 3 and the patella offset to one side of the incision;

FIG. 23 is a schematic illustration further depicting the femoral and tibial cuts of FIG. 22;

FIG. 32 is a schematic illustration depicting the manner in which an endoscope may be inserted through an incision in a patient's knee to inspect portions of the patient's knee which are remote from the incision with the leg of the patient in the position illustrated in FIGS. 2 and 3;

FIG. 33 is a schematic illustration similar to FIG. 32, depicting the manner in which the endoscope may be inserted through the incision in the patient's knee with the leg of the patient extended;

FIG. 36 is a schematic illustration depicting the manner in which a cutting tool is moved relative to a guide member to cut the patella of FIG. 35 while the patella is disposed in situ;

FIG. 37 is a schematic illustration depicting the manner in which a tibial alignment shaft and a tibial resection guide are positioned relative to a tibia in a lower portion of a leg of the patient with the leg of the patient in the position illustrated in FIGS. 2 and 3;

FIG. 38 is an enlarged fragmentary view of a portion of FIG. 37 and illustrating the construction of the tibial resection guide;

DESCRIPTION OF SPECIFIC PREFERRED EMBODIMENTS OF THE INVENTION

Known Method of Performing Surgery on a Patient's Knee

Figure 1:
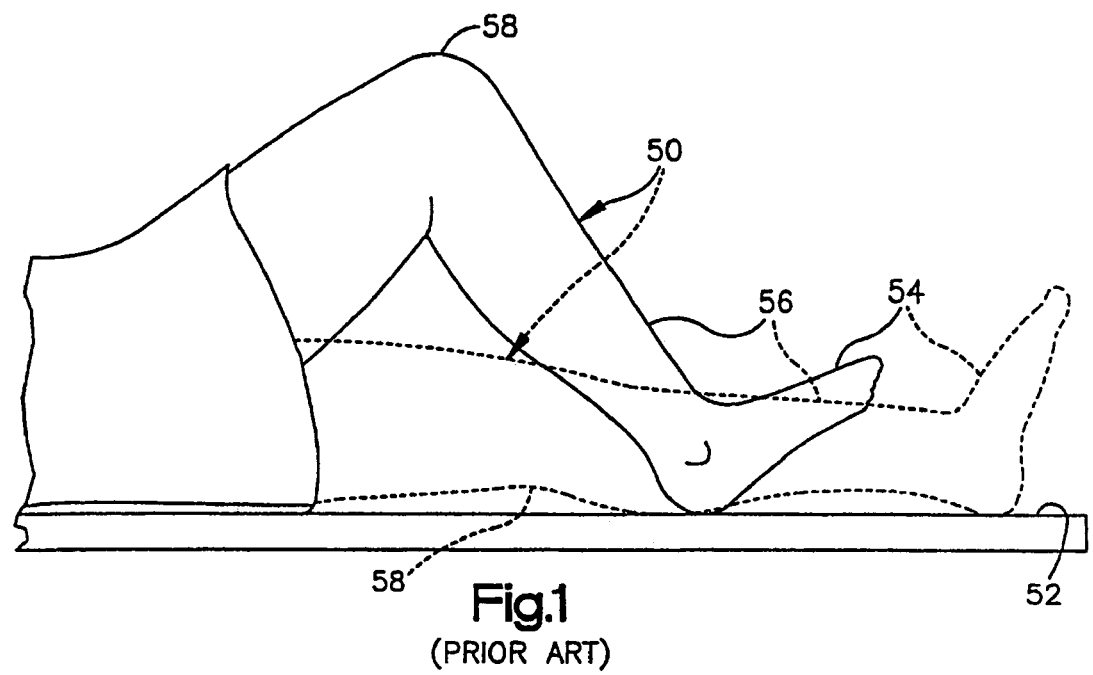
FIG. 1 is a schematic illustration depicting extended and flexed positions of a patient's leg during performance of knee surgery in a known manner.

During the performance of surgery using known methods, a patient is supported on an operating table or other support surface 52 (FIG. 1). When a leg 50 of the patient is in the extended position illustrated in dashed lines in FIG. 1, a foot 54 connected with a lower portion 56 of the leg 50 is disposed above the support surface 52. During an operation on a knee portion 58 of the leg 50, the knee portion is raised and lowered relative to the support surface as the leg 50 is flexed and extended. However, the foot 54 is always disposed above the support surface 54 and may be supported by the support surface throughout the operation.

During this known operating procedure, an incision is made in the knee portion 58 of the leg 50 when the leg is in the extended position illustrated in dashed lines in FIG. 1. At this time, the foot 54 of the patient may rest on the support surface 52 or be disposed in a foot support located above the support surface. Once an incision has been formed in the knee portion 58, the leg 50 may be flexed or bent to the position illustrated in solid lines in FIG. 1.

As the knee portion 58 is bent, the leg 50 is flexed and compresses the soft tissue of the knee portion 58 against the back of the knee joint. This makes it very difficult to access the posterior of the knee portion 58 to remove bone spurs (osteophytes), the meniscus, the posterior capsule, and/or any residual soft tissue or bone that is blocking further flexion. The catching or pinching of soft tissue in the posterior aspect of the knee portion 58 may prevent further flexion and limits the range of motion. In addition, arteries, nerves and veins are sitting just posterior of the knee joint.

Due to the lack of access to the posterior of the knee portion 58, a surgeon may be very reluctant or, at least, very careful about inserting instruments blindly into the back of the knee joint to remove tissue. This may result in osteophytes, bone spurs and similar types of posterior soft tissue being left in place.

Cuts are made on a femur and tibia with the leg 50 in the bent or flexed condition, illustrated in FIG. 1. This results in the distal end portion of the femur and the proximal end portion of the tibia in the leg 50 being pressed together adjacent to the cuts. This interferes with ligament balancing. The relatively large incision which is necessary to accommodate known instrumentation systems increases time required for the patient to recover from the operation.

Preparation for Operation

It is contemplated that various features and/or combinations of features of the present invention will be utilized during surgery on different portions of a patient's body, such as a head, trunk or limbs of a patient. Although at least some of the features of the present invention are believed particularly advantageous when utilized in association with surgery on any one of the many joints in a patient's body, it is believed that the various features and/or combination of the features of the present invention are particularly advantageous when utilized in conjunction with surgery on a knee portion of a leg of a patient. It should be understood that the various features of the present invention may be use separately or in any desired combination of features.

Surgery on the knee portion of the patient may relate to any one of many different aspects of the knee portion, such as ligaments, tendons, articular surfaces, and/or total or partial knee replacements or revisions. Although the disclosure herein frequently refers to one particular type of knee operation, that is, a total knee replacement, features of the invention may be utilized with any desired type of surgery. It is believed that it will be apparent to a person having a knowledge of knee surgery how various features of the invention may be utilized with either a full or partial knee replacement. Therefore, there has been only minimal mention herein of how the features of the invention are applicable to partial knee replacements.

When knee surgery is to be performed in accordance with one of the features of the present invention, the patient 62 (FIG. 2) is disposed on a support surface 64 of an operating table 66. If desired, a patient support surface 64 other than an operating table could be used to support the patient. A lower portion 68 of a leg 70 extends downward from an upper portion 72 of the leg 70. A foot 74 connected with the lower portion 68 of the leg 70 is disposed below the support surface 64. The leg 70 is flexed so that a knee portion 76 of the leg is bent.

Figure 2:
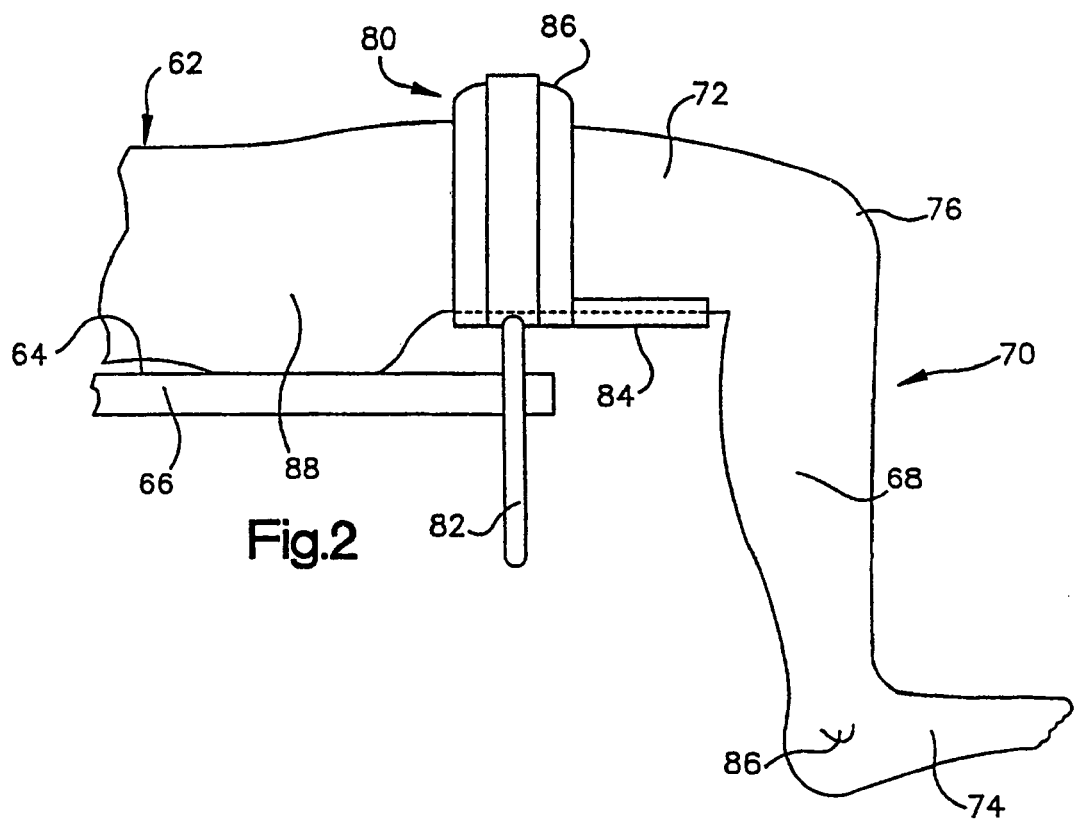
FIG. 2 is a schematic illustration depicting the manner in which a leg support is used to support an upper portion of a leg of a patient above a support surface on which the patient is disposed in a supine orientation during performance of knee surgery.

In accordance with another of the features of the present invention, the upper portion 72 of the leg 70 can be supported above the support surface 64 by a leg support 80 (FIG. 2). The leg support 80 includes a stand or base section 82 which is connected with the operating table 66. The leg support 80 includes a base 84 which is connected with an upper end portion of the stand 82. The base 84 is engaged by and supports the upper portion 72 of the leg 70.

A generally annular thigh holder 86 extends around the upper portion 72 of the leg 70 of the patient and is connected with the base 84 and stand 82. The base 84 has a portion which extends along the posterior side of the upper portion 72 of the leg 70 of the patient. The base 84 supports the upper portion 72 of the leg 70 above and spaced from the support surface 64. However, the upper portion 72 of the leg 70 could be disposed in engagement with the support surface 64 if desired.

The leg support 80 supports the leg 70 of the patient with a hip 88 of the patient hyperflexed at an angle of twenty to thirty degrees throughout the operation on the knee portion 76. The leg support 80 may have a known commercial construction or may have a construction similar to that disclosed in U.S. Pat. No. 4,373,709 or U.S. Pat. No. 6,012,456. If desired, a tourniquet may be combined with the leg support 80 in a manner similar to that provided in known leg supports or in a manner similar to that disclosed in U.S. Pat. No. 4,457,302.

In accordance with another feature of the invention, the lower portion 68 (FIG. 3) of the leg 70 is suspended from the upper portion 72 of the leg. This enables the foot 74 and ankle portion 86 of the leg 70 of the patient to be freely moved in any direction or a combination of directions. Thus, the foot 74 and ankle portion 86 of the leg 70 of the patient can be moved anteriorly or upward (as viewed in FIG. 3) to decrease the extent of flexion of the knee portion 72 or even to extend or straighten the leg 70.

Figure 3:
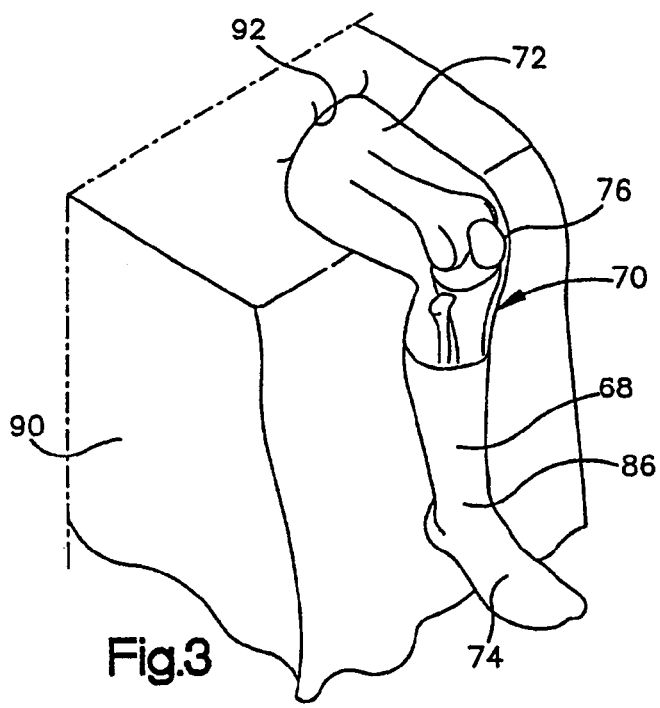
FIG. 3 is a schematic illustration depicting the patient's leg after a portion of a drape system has been positioned over the patient, the leg being shown in a flexed condition with the foot below the patient support surface and with an upper portion of the leg supported by the leg support of FIG. 2.

Alternatively, the foot 74 and ankle portion 86 may be moved posteriorly toward the operating table 66, from the position illustrated in FIG. 3, to hyperflex the knee portion 72 of the leg of a patient. The foot 74 may be moved sidewardly, that is in either a lateral or medial direction. In addition, the foot 74 may be rotated about the longitudinal central axis of the lower portion 68 of the leg 70.

It is contemplated that the foot 74 and ankle portion 86 may be simultaneously moved in a plurality of the directions previously mentioned. If desired, the upper portion 72 of the leg 70 of the patient may be supported on a separate section of the operating table 66, in a manner similar to the disclosure in U.S. Pat. No. 5,007,912.

After a drape 90 has been positioned over the patient 62 and the operating table 66, in the manner illustrated in FIG. 3, the leg 70 extends out of the drape. The drape 90 may be connected with the leg support 80 and have an opening 92 (FIGS. 3 and 4) through which the leg of the patient extends. This enables the leg 70 of a patient to be moved between the extended position illustrated in FIG. 4 and a hyperflexed position in which the foot 74 is disposed posteriorly from the position illustrated in FIG. 3.

When the leg 70 is in a hyperflexed condition, the included angle between the upper and lower portions 72 and 68 of the leg 70 is less than ninety degrees. The leg 70 may be flexed from the extended position of FIG. 4 to a hyperflexed position by manually moving the foot 74 and an ankle portion 96 of the leg 70 relative to the operating table 66 (FIG. 2) while the upper portion 72 of the leg is held by the leg support 80. When the leg 70 is hyperflexed, a portion of the foot 74 may be disposed beneath the operating table 66 (FIG. 2).

An improved drapery system 100 (FIG. 4) includes the drape 90 and a drape 102 connected with a gown 104 on a surgeon 106. The illustrated drape 102 is formed separately from the drape 90 and gown 104. However, the drape 102 may be integrally formed as one piece with the drape 90. Alternatively, the drape 102 may be integrally formed as one piece with the gown 104. If formed integral, drape 90, drape 102, and/or gown 104 can be provided with a quick release mechanism, such as serrated edges, to allow surgeon 106 to rapidly tear away. Thus, drapery system 100 allows the patient to be a sterile field directly or modularly attached to the surgeon and/or an assistant.

Regardless of whether separate or integral, drape 90 and/or drape 102 can include attachments for surgical instruments such as suction, Bovie, arthroscopic equipment, etc. Drape 102 can have a large pouch to collect all fluid, body parts, blood, etc. so they do not drain all over the floor and are collected in an easily disposable fashion. In this regard, drape 102 can include a drain, with or without active suction, to remove fluid and other debris.

Drape 90 could be adhesive drape with a Betadine adhesive or a clear plastic adhesive, either with or without antimicrobial agents impregnated, which covers the skin surrounding the operative field. Drape 90 could be a two layer drape with a larger drape below which sticks to the patient or is loosely attached to the patient and a narrower surgical field drape above for two layer draping.

Figure 4:
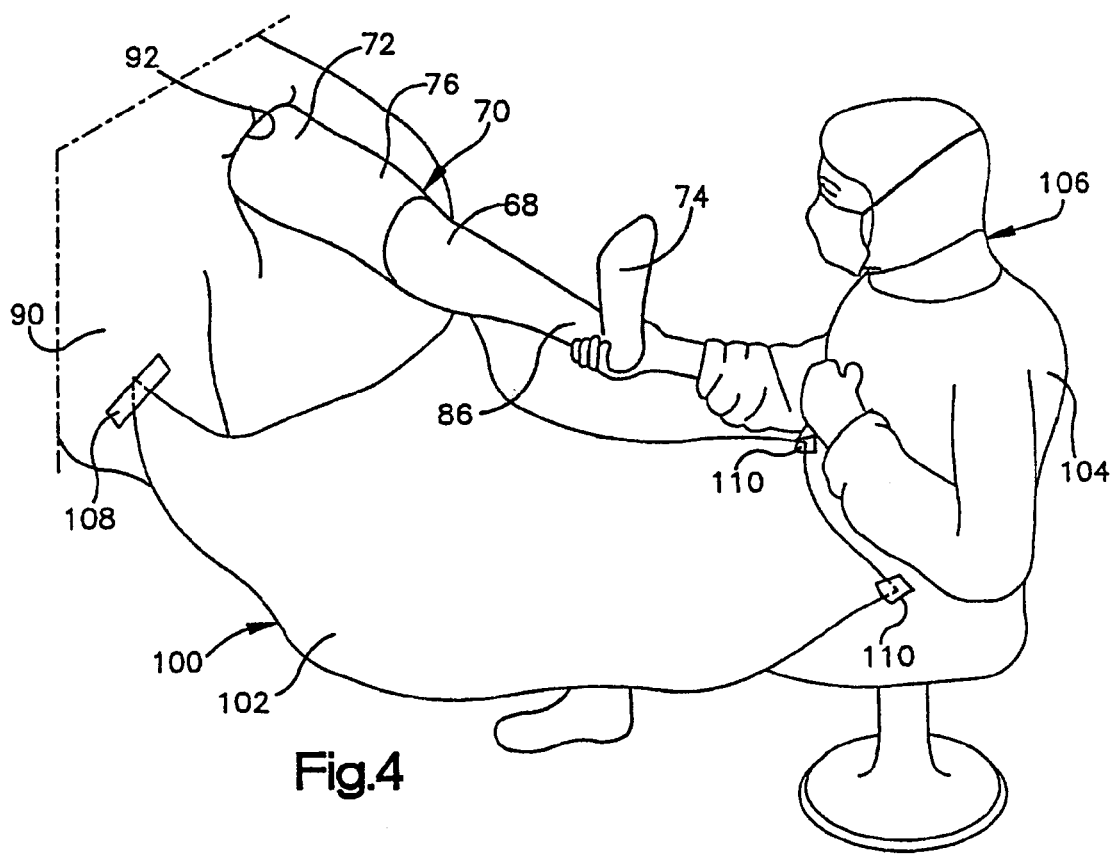
FIG. 4 is a schematic illustration of the patient's leg of FIGS. 2 and 3 in an extended condition and of the drape system which extends between a surgeon and the patient.

In the embodiment illustrated in FIG. 4, the drape 102 is formed separately from the gown 104 and the drape 90. The drape 102 is connected to the drape 90 by suitable clamps 108. The drape 102 is connected with the waist of the surgeon 106 by clamps 110 to the gown 104. Rather than utilizing clamps 108 to interconnect the drapes 90 and 102, the drapes could be interconnected by VELCRO, ties, or other known devices. Of course, similar devices could be utilized to connect the drape 102 with the gown 104 of the surgeon 106. The connection mechanism can be chosen such that, if surgeon 106 needs to change position with respect to the patient, the connection mechanism allows re-attachment of gown 104 to various locations of drape 102.

The improved drapery system 100 maintains a sterile field between the leg 70 and the surgeon 106 during movement of the surgeon relative to the patient 62. Thus, when the surgeon is in a seated position (FIG. 4) the drapery system 100 provides a sterile field which extends from the surgeon to the space beneath and adjacent to the leg 70. When the surgeon stands (FIG. 5) the drapery system 100 continues to maintain a sterile field between the surgeon and the patient. This enables the surgeon 106 to move the leg 70 of a patient during an operation without contaminating the sterile field. The draping system 100 enables the sterile field to be maintained when the patient's leg is moved between the extended position of FIGS. 4 and 5 and a hyperflexed position in which the foot 74 of the patient is disposed beneath the operating table 66.

During movement of the surgeon 106 relative to the patient, for example, between the seated position of FIG. 4 and the standing position of FIG. 5, the drape 102 moves with the surgeon and maintains a sterile field. Thus, when the surgeon 106 moves toward and away from the patient, the end portion of the drape 102 connected with the surgeon also moves toward and away from the patient. As the surgeon moves toward the patient, a portion of the drape 102 between the surgeon 106 and patient is lowered. As the surgeon moves away from the patient, the portion of the drape 102 between the surgeon and patient is raised. The foot 74 connected with the leg 70 of the patient is always above the drape 102 during movement of the surgeon 106.

Drape 102 and/or drape 90 has flexibility and could be provided with flexed sections or may have a large redundant area which would go down to the surgeon's knees or to the floor to maintain the sterile field. By typical sterile technique, anything below the waist level of the surgeon or the support surface is considered un-sterile. However, with drapery system 100, if drape 102 happens to drop down to the floor, it creates a contiguous sterile field and therefore, the surgeon could retrieve dropped objects from the floor if it is contained within drape 102 or drape 90. This could save a significant amount of money by eliminating the need to dispose of (or re-sterilize) fallen surgical instruments or implants.

Although the drapery system 100 has been illustrated in FIGS. 3-5 in association with a patient's leg 70, the drapery system may be used in association with surgery on any desired portion of a patient's body. For example, the drapery system 100 could be used to maintain a sterile field between a surgeon and patient during surgery on a trunk portion of a patient's body. Alternatively, the drapery system 100 could be used to maintain a sterile field during surgery on a head or arm portion of a patient's body.

Drapery system 100 can use disposable drapes or can be re-sterilizable, either in its entirety or portions thereof. Additionally, known current drape technology can be incorporated into drapery system 100. This includes the use of disposable independent drapes, ¾ sheet, disposable adherent drapes, U-drapes, disposable adhesive drapes, Betadine drapes, VELCRO attached drapes, snap, plastic snap drapes, single piece drapes, multi-drapes, two layer drapes, clear plastic drapes, independent or attached to drapes, one piece drapes with stretchable segment for extremities, arthroscopic drapes, shoulder drapes which incorporate U-drapes, square drapes, etc.

In another embodiment, drapes 90, 102 could be configured to create a mobile field. Specifically, the drapes can be made to have a surgeon's helmet attached to it and part of gown 104 attached to it so that the surgeon would literally walk into the drape system, his hands and his face would go into the drape to create a mobile surgical field attached to the patient to create even more of a sterile field. The drapery system could have laminar flow system connected to it to create sterile air coming in and then a suction coming out so it could have unidirectional airflow to further sterilize the field.

The drape system could have a tent, a cover over the top of this to create a mobile surgical field so that this could be done in emergency setting such as a military field or otherwise outdoors. Because the drape system can be provided with an attachment for flowing air in and out, maintaining extremely sterile air, the drape system could also be used for organ or tissue harvesting, such as bone harvesting under an emergency situation. The drape system could have the surgeon's gown, face mask, sterilizable hood all attached as part of it. It could be unrolled as one sterile pack adhering to the patient and rolling outward and the surgeon simply walks into the drape as does the assistant. When the procedure is complete, simply roll up the drape and throw it away, thereby maintaining all potential biohazards.

The drape could have a sterile flap where instruments could be passed through and/or a simple opening where the assistant could deliver instruments required through this field or the drape could be a flat open sheet where the assistant could bring the instruments on top of the sterile surgical field. There also may be a separate attachment for the circulating nurse.

As previously noted, drape 90 and/or drape 102 may also include an abbreviated gown 104 simply with the arms, front portion of the gown. This abbreviated gown could be a portion of drape 90, 102 so the draping system need not extend fully down to the floor. Rather, the abbreviated gown would have arm holes so that the surgeon can put his arms through the holes and the nurse would put gloves on him once they are sterilized. A provision can be made so that at least one person has an independently moveable surgical gown.

Incision

In accordance with another feature of the present invention, a limited incision 114 (FIG. 6) is formed in the knee portion 76 of the leg 70. The incision 114 is made just medial to the patella 120. However, the incision 114 could be disposed laterally of the patella 120. Although the length of the incision 114 may vary depending upon the circumstances, the incision 114 will usually have a length of between about seven (7) and about thirteen (13) centimeters. However, even smaller incisions may be made when circumstances permit.

In one embodiment, the incision is made when the knee portion 76 of the leg is flexed and the lower portion 68 of the leg extends downward from the upper portion 72 of the leg in the manner illustrated in FIGS. 2 and 3. At this time, the upper portion 72 of the leg 70 is supported above the support surface 64 by the leg support 80 (FIG. 2). The lower portion 68 of the leg 70 is suspended from the upper portion 72 of the leg (FIGS. 2 and 3).

When the knee portion 76 of the leg 70 is flexed so that the lower portion 68 of the leg is suspended at an angle of approximately ninety degrees relative to the upper portion 72 (FIGS. 2 and 3), the incision 114 (FIG. 6) may have a length of approximately ten (10) centimeters. When the leg 70 is straightened from the flexed condition of FIGS. 2 and 3 to the extended condition of FIGS. 4 and 5, the length of the incision 114 may decrease by between ten and thirty percent. Thus, in one specific instance, an incision 114 had a length of approximately eleven (11) centimeters when the leg 70 was in the flexed condition of FIGS. 2, 3 and 6 and a length of slightly less than ten (10) centimeters when the leg was in the extended condition of FIG. 5. By making the incision 114 with the leg in a flexed condition (FIGS. 2, 3, and 6) and operating on the leg 70 with the leg in a flexed condition, the overall length of the incision can be reduced from the length of incisions which have previously been made in the leg when it is in the extended condition.

The benefits of having a smaller incision include improved cosmetic results, improved rehab, less dissection of muscle and soft tissue, and preservation of the quadriceps mechanism.

It is preferred to have the incision 114 located adjacent to the medial edge of the patella 120, in the manner illustrated schematically in FIG. 6. However, the incision 114 could be located adjacent to the lateral edge of the patella 120 if desired. Alternatively, the incision 114 could be disposed midway between lateral and medial edges of the patella 120. By moving the incision 114 laterally or medially away from the midline of the knee, less stress is placed on incision 114 compared to a midline incision.

Although it is desired to minimize the length of the incision 114, it is contemplated that the incision may have a length of approximately twice the length of the patella. It may be desired to have the incision 114 extend from a proximal end of the tibia in the leg 70 to the epicondylar notch on the distal end portion of the femur in the leg 70. The length and location of the incision 114 may vary depending on the size of the implants to be positioned in the knee portion 76 and the location at which the implants are to be positioned. It is believed that it may be desired to have the incision 114 be smaller than the implants even though the implants must move through the incision. The visoelastic nature of the body tissue and mobility of the incision 114 enables the implants to be larger than the incision and still move through the incision.

A straight incision 114 has been illustrated in FIG. 6. However, the incision 114 could have a different configuration if desired. For example, the incision 114 could have an L-shaped configuration. The incision 114 could be skewed at an acute angle to a longitudinal central axis of the patella 120. If desired, the incision 114 could have a configuration matching the configuration of either the lateral or medial edge of the patella 120.

Immediately after the incision 114 is formed, the leg 70 may be moved from the flexed condition of FIGS. 2 and 3 to the extended condition of FIG. 5. While the leg 70 is in the extended condition, the incision 114 (FIG. 7) is elastically expanded using suitable retractors. The incision 114 can also be expanded while the leg is in the flexed condition. The retractors apply force against the visoelastic body tissue of the knee portion 76. The retractors have a construction similar to that disclosed in U.S. Pat. No. 5,308,349. Alternatively, a pneumatic retractor, such as is disclosed in U.S. patent application Ser. No. 09/526,949 filed on Mar. 16, 2000 by Peter M. Bonutti may be utilized to expand the incision.

After the incision 114 has been elastically expanded, a patella 120 and tissue on the lateral side of the incision may be everted in a manner illustrated in FIG. 7. Thus, the patella 120 is moved from the normal orientation of FIG. 6 to the everted or flipped orientation of FIG. 7, preferably while the leg 70 of the patient is in the extended orientation of FIG. 7. At this time, the inner side 122 of the patella 120 is facing outward away from other bones in the knee portion 76. The outer side of the everted patella 120 is facing inward toward other bones in the knee portion 76. This enables the inner side 122 of the patella 120 to be examined.

In order to enable a relatively small incision 114 to be used for operating on bones in the knee portion 76 of the leg 70 of the patient, the patella 120 is returned back to its normal position with the inner side 122 of the patella facing inward and the outer side of the patella facing outward. As this occurs, the opening at the incision 114 contracts. The retractors are then utilized to apply force against opposite sides of the incision 114. As this occurs, the visoelastic body tissue is extended, the opening at the incision 114 is again expanded, and the patella 120 is pushed to the lateral side of the knee portion 76. This moves the patella 120 to a location offset to one side of the incision 114 in a manner illustrated in FIG. 8. The leg 70 is then flexed to the orientation shown in FIGS. 2 and 3.

If desired, the foregoing step of inverting the patella 120 may be omitted. The patella 120 may be left in orientations in which the inner side 122 of the patella faces inward throughout the operation. If this is done, the inner side 122 of the patella 120 may be inspected by tilting the patella from its normal orientation and/or using viewing devices, such as an endoscope. Regardless of how the inner side 122 of the patella 120 is inspected, moving the patella to the offset position of FIG. 8, with the inner side 122 facing inward, facilitates utilization of an incision 114 having a limited length. It is contemplated that many different surgical procedures could be conducted on the knee portion 76 with the patella 120 in the offset position of FIG. 8. Furthermore, avoiding eversion of the patella 120 significantly reduces stress on the quadriceps/tendon complex. Applicant has found that the stress on the complex is at least 20% less compared to a procedure with eversion, thereby decreasing the risks of tearing, damage, and strain.

As shown in FIG. 8, a retractor 121 can be used to offset patella 120 and/or maintain patella 120 in the offset position. In an exemplary embodiment, retractor 121 is approximately 2-3 mm thick. Retractor 121 also holds soft tissue away to expose the bone. Accordingly, retractor 121 can include at least one hole 123 for receiving a pin 125 to secure retractor 121 to bone or other body tissue. Alternatively, a suture or wire can be threaded through hole 123 to secure retractor 121 to tissue. In another embodiment, retractor 121 includes a sharp end to hold retractor 121 to the tissue.

Retractor 121 can be made out of any suitable material, such as metallic materials typically used for surgical instruments. If retractor 121 is made of a polymer, it is contemplated that retractor 121 could be disposable. If this is done, retractor 121 may be partially or entirely formed of relatively inexpensive polymeric materials. As previously disclosed, the disposable retractors could be sharpened at one end like a Homan. Such a disposable retractor could be made of a polymer such as polyethylene, which may be malleable to a degree. Thus, the disposable retractor could be deformed to a desired shape to expose the joint as required and possibly pin the tissue directly through the malleable portion of the retractor to hold the soft tissue out of the way while one is working on the bone. This would allow enhanced exposure through a smaller incision, visualizing it through flexion and extension.

The retractors could also be a composite with some metal and some plastic with a portion of the device, flexible, malleable and locking into bone to keep the tissue out of the way while one is working on the bone. Additionally, it is contemplated that the retractors could also be heated and malleable intraoperatively. The retractors could be made of a biodegradable material and be left in position to maintain a soft tissue sleeve or exposure so as to minimize scarring the joint. Regardless of the material, the retractors could have ribs or a roughened surface to grip the tissue. The retractors could also be coupled with a balloon retractor (discussed below).

Femoral Procedure

Expansion of the incision 114 with the retractors exposes a distal end portion 124 (FIG. 8) of a femur 126 in the upper portion 72 of the leg 70. The incision 114 is movable relative to the distal end portion 124 of the femur 126 to maximize exposure of the femur through the limited length of the incision. The femur 126 is then cut to receive an implant. Although either intramedullary or extramedullary instrumentation can be utilized, intramedullary instrumentation is used in an exemplary embodiment during cutting of the femur 126. Therefore, a drill 128 is utilized to access the intramedullary canal or marrow cavity in the femur 126.

The drill 128 is utilized to form a hole 130 in the center of the intercondylar notch in the distal end portion 124 of the femur 126 in a known manner. The drill 128 is used to form the hole 130 while the leg 70 is in the orientation illustrated in FIGS. 2 and 3. The patella 120 is in the offset position illustrated in FIG. 8. At this time, the inner side 122 (FIG. 7) of the patella faces toward the femur 126.

An epicondylar reference guide (not shown) engages the hole in the distal end portion 124 of the femur 126 to enable a line parallel to an epicondylar axis peaks of the medial and lateral condyles to be inscribed on the distal end portion 124 of the femur 126. At this time, the leg 70 is in the orientation illustrated in FIGS. 2, 3, 8 and 9. A shaft 132 (FIGS. 9, 10, 11 and 12) of a femoral alignment guide 134 is then inserted into the intermedullary opening 130.

Figure 10:
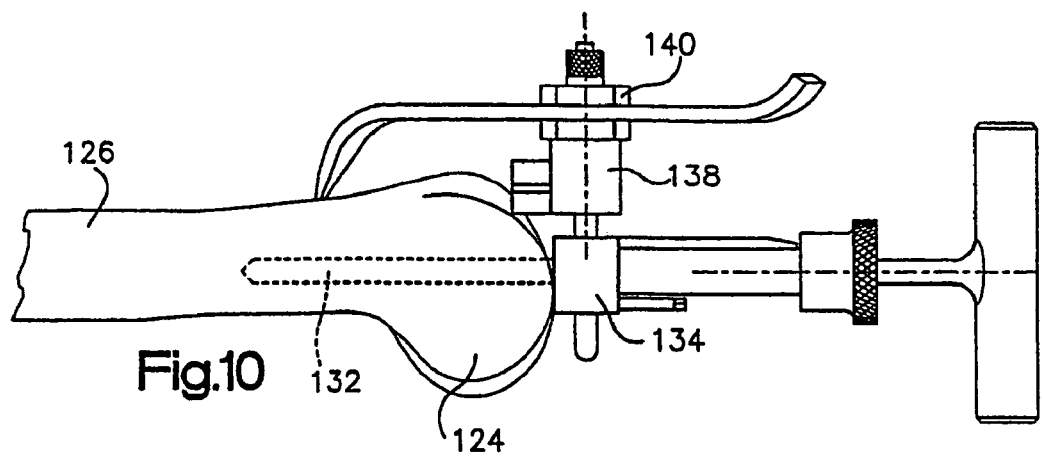
FIG. 10 is a schematic illustration depicting the position of an anterior resection guide and a stylus relative to the femoral alignment guide of FIG. 9 before an anterior femur cut has been made with the leg of the patient in the position illustrated in FIGS. 2 and 3.
Figure 11:
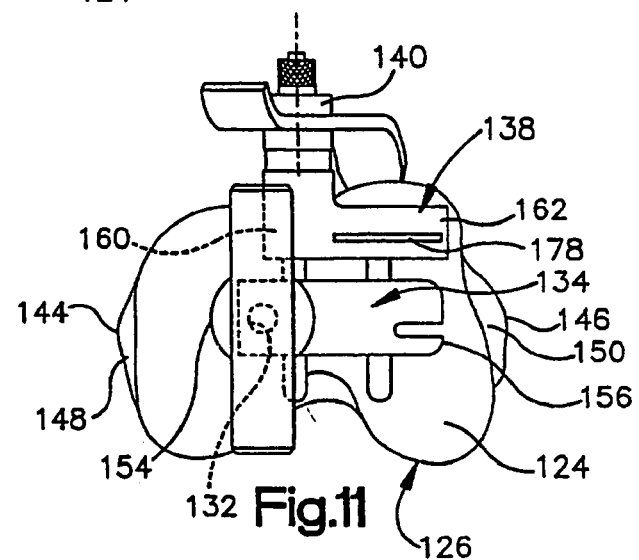
FIG. 11 is a schematic illustration, taken generally along the line 11-11 of FIG. 10, further illustrating the relationship of the anterior resection guide and stylus to the distal end portion of the femur.
Figure 12:
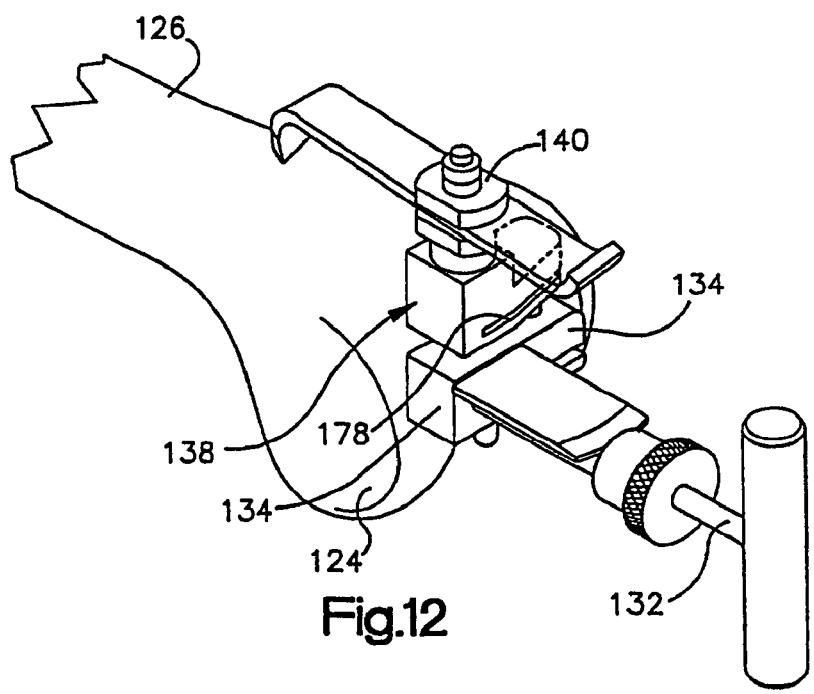
FIG. 12 is a schematic illustration further illustrating the relationship of the anterior resection guide and stylus to the distal end portion of the femur.

The femoral alignment guide 134 is then aligned with the epicondylar line which extends parallel to the epicondylar axis through the peaks of the lateral and medial condyles on the distal end portion 124 of the femur 126. The femoral alignment guide 134 is utilized to support an anterior resection guide 138 and stylus 140 (FIGS. 10, 11 and 12) on the distal end portion 124 of the femur 126 in the upper portion 72 of the leg 70 of the patient. Although only the femur 126 is illustrated in FIGS. 10, 11 and 12, it should be understood that the leg 70 is in the orientation illustrated in FIGS. 2 and 3. The upper portion 72 of the leg 70 us supported by the leg support 80.

In accordance with one of the features of the present invention, the instrumentation is down sized to enable the size of the incision 114 (FIG. 9) to be minimized. The downsized instrumentation has a transverse dimension which is smaller than a transverse dimension of an implant to be placed in the knee portion 76 (FIG. 9). Thus, the femoral alignment guide 134 and anterior resection guide 138 have transverse dimensions, perpendicular to a longitudinal central axis of the femur 126, which are smaller than transverse dimensions of a femoral implant 290, tibial bearing insert 294, and a tibial tray 286 (FIG. 29) in a direction perpendicular to the longitudinal central axis of the femur 126 (FIG. 9).

The instrumentation extends from a center portion of the femur 126 toward one side of the femur (FIG. 11). In the particular operation illustrated schematically in FIGS. 7-12, the incision 114 is offset to the medial side of the patella 120. Therefore, the instrumentation is offset to the medial side of the femur 126. However, if the incision 114 were offset to the lateral side of the patella 120, the instrumentation would be offset to the lateral side of the femur 126. If the incision 114 were centrally disposed relative to the femur 126, the instrumentation would be centrally disposed relative to the femur. Thus, the instrumentation is in general alignment with the incision 114 and extends only part way across the distal end portion 124 of the femur 126.

The femoral alignment guide 134 (FIGS. 10, 11 and 12) and anterior resection guide 138 have opposite ends which are spaced apart by distance which is less than a distance between epicondyles 148 and 150 on the distal end portion 124 of the femur 126. The distance between opposite ends 154 and 156 of the femoral alignment guide 134 is less than two thirds (⅔) of the distance between tips 144 and 146 of the lateral and medial epicondyles 148 and 150. Similarly, a distance between an end 160 and an opposite end 162 of the anterior resection guide 138 is less than two thirds (⅔) of the distance between the tips 144 and 146 of the lateral and medial epicondyles 148 and 150.

Figure 29:
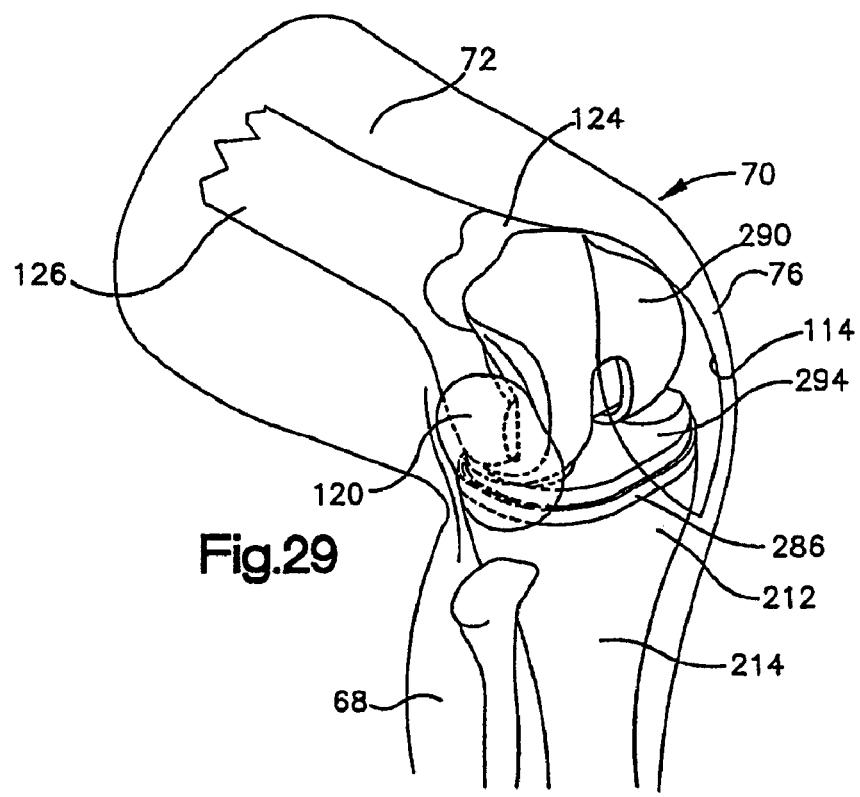
FIG. 29 is a schematic illustration depicting femoral and tibial implants with the leg of the patient in the position illustrated in FIGS. 2 and 3.

The distance between opposite ends of a known femoral alignment guide and the distance between opposite ends of a known anterior resection guide are approximately the same as or greater than the distance between the tips 144 and 146 of the lateral and medial condyles 148 and 150. The distance between opposite ends of the known femoral alignment guide and the distance between opposite ends of the known anterior resection guide are greater than the transverse dimensions of the femoral and tibial implants 286, 290 and 294 (FIG. 29). This known anterior resection guide and femoral alignment guide are commercially available from Howmedica Osteonics of 359 Veterans Boulevard, Rutherford, N.J. under the designation "Scorpio" (trademark) Single Axis Total Knee System.

The incision 114 must be large enough to enable the femoral alignment guide 134 and the anterior resection guide 138 to pass through the incision. By reducing the size of the femoral alignment guide 134 and anterior resection guide 138, the size of the incision 114 can be reduced. Of course, reducing the size of the incision 118 reduces damage to body tissue of the patient 62. The femoral alignment guide 134 and the anterior resection guide 138 may be larger than the incision 114. This is because the incision 114 can be resiliently stretched and/or moved relative to the femur 126 to enable the femoral alignment guide 134 and anterior resection guide 138 to move through the incision.

The distance between opposite ends 154 and 156 of the femoral alignment guide 134 is less than the distance which a femoral implant extends across the distal end portion 124 of the femur 126. Similarly, the distance between opposite ends 160 and 162 of the anterior resection guide 138 is less than the distance which the femoral implant extends across the distal end portion 124 of the femur 126. The femoral alignment guide 134 and the anterior resection guide 138 both extend medially from a center portion of the femur 126. However, if the incision 114 were offset laterally of the patella 120, the femoral alignment guide 134 and the anterior resection guide 138 would extend laterally from the center portion of the femur 126. Similarly, if the incision 114 was centered relative to the patella 120, the femoral alignment guide 134 and anterior resection guide 138 would be centered relative to the femur 126.

If leg 70 is positioned as shown in FIGS. 2 and 3, positioning of the femoral alignment guide 134 and anterior resection guide 138 on the distal end portion 124 of the femur 126 is facilitated by distracting the knee joint under the influence of the weight of the lower portion 68 of the patient's leg and the foot 74. Thus, when the femoral alignment guide 134 and anterior resection guide 138 are positioned on the distal end portion 124 of the femur 126, the lower portion 68 of the leg 70 can be suspended from the upper portion 72 of the leg. At this time, the foot 74 is below the level of the support surface 64 (FIG. 2) on which the patient is disposed in a supine orientation. The upper portion 72 of the patient's leg 70 is supported above the support surface 64 by the leg support 80 (FIG. 2).

By distracting the knee joint under the influence of the weight of the lower portion 68 of the leg of the patient, the distal end portion 124 of the femur 126 is exposed through the relatively small incision 114 (FIG. 9). Exposure of the distal end portion 124 of the femur 126 at the limited incision 114 is promoted by moving the lower portion 68 of the leg 70 and the incision relative to the femur. In addition, exposure of the distal end portion 124 of the femur 126 is promoted by having the patella 120 offset to the lateral side of its normal position. The inner side 122 of the patella 120 faces inward toward the distal end portion 124 of the femur 126 so that the skin on the knee portion 76 is not excessively stretched by everting the patella.

In accordance with another feature of the present invention, the instrumentation is at least partially positioned between the distal end portion 124 of the femur 126 and body tissue of the knee portion 76 (FIG. 9). To enable the size of the incision 114 to be minimized, the instrumentation is moved laterally of the incision so that a portion of the instrumentation moves between the knee capsule and the end portion 124 of the femur 126. This results in a portion of the instrumentation being exposed at the incision 114 and a laterally extending portion of the instrumentation being concealed by body tissue. For example, the end 154 (FIG. 11) of the femoral alignment guide 134 and/or the end 160 of the anterior resection guide 138 are overlaid by body tissue adjacent to the lateral edge portion of the incision 114. The body tissue which overlies portions of the instrumentation may include skin, the knee capsule, and connective and soft tissues.

With prior art instrumentation, the soft tissue must be completely dissected so that the distal end portion 124 of the femur 126 is fully exposed. In contrast, the instrumentation of the present invention can be at least partially positioned between the distal end portion 124 of the femur 126 and body tissue of the knee portion 76 (FIG. 9). As discussed in more detail below, the soft tissue can be lifted or otherwise retracted. This minimizes the need for dissection.

When the femoral alignment guide 134 and anterior resection guide 138 are connected with the femur 126, central axis of the femoral alignment guide and anterior resection guide are medially offset from the central axis of the femur. Thus, the central axis of the femur 216 extends through a lateral portion, that is, left portion as viewed in FIG. 11, of the femoral alignment guide 134. The anterior resection guide 138 is almost entirely offset to the right (as viewed in FIG. 11) of the central axis of the femur 126. The incision 114 is disposed along a medial edge, that is, a right edge as viewed in FIG. 6, of the patella 120 when the patella is in its normal or initial position.

By having both the incision 114 and the instrumentation medially offset relative to the femur 126, the central portion of the instrumentation is exposed at the incision. Thus, the medial edge of the incision overlaps the medial end 156 of the femoral alignment guide 134 and the medial end 162 of the anterior resection guide 138. Similarly, the lateral edge of the incision 114 overlaps the lateral end 154 of the femoral alignment guide 134 and the lateral end 160 of the anterior resection guide 138.

In view of the foregoing, it can be seen that the leg 70 (FIG. 3) of the patient 62 (FIG. 2) is maintained in the position illustrated in FIGS. 2 and 3 with the foot 74 of the patient below the support surface 64 upon which the patient is supported in a supine position during forming of the incision 114 in the knee portion 76 of the leg 70. The upper portion 72 of the patient's leg 70 is supported above the support surface 64 by the leg support 80 (FIG. 2). In addition, the leg of the patient is maintained in the position illustrated in FIGS. 2 and 3 during connection of the femoral alignment guide 134 and anterior resection guide 138 with the distal end portion 124 of the femur 126.

Figure 13:
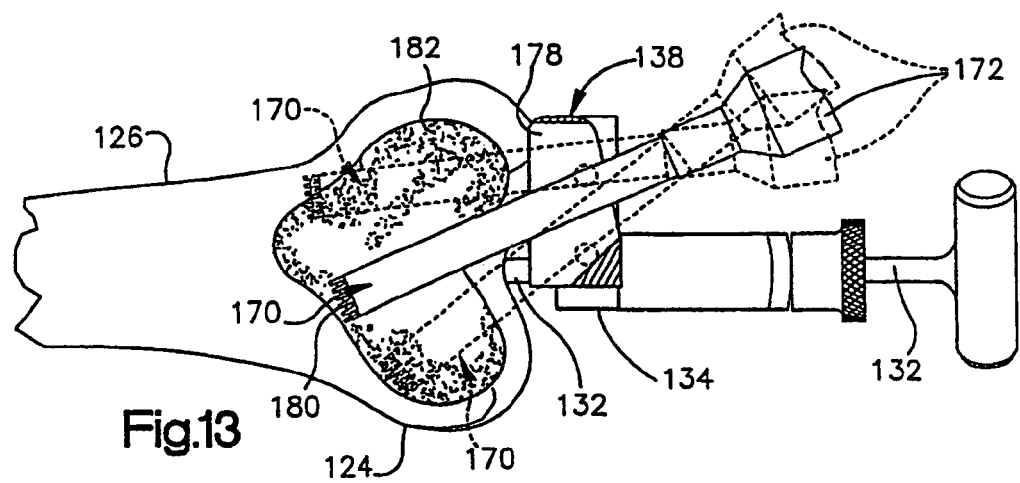
FIG. 13 is a schematic illustration depicting the manner in which a cutting tool is moved along a guide surface on the anterior resection guide during making of an anterior femur cut with the leg of the patient in the position illustrated in FIGS. 2 and 3.

Once the femoral alignment guide 134 and anterior resection guide 138 have been mounted on the distal end portion 124 of the femur 126, an anterior cut is made in the manner illustrated in FIG. 13. During the anterior cut, a blade 170 of a saw 172 is utilized to make a cut across anterior portions of the lateral and medial condyles. The saw blade 170 is moved along guide surface 178 (FIGS. 11 and 12) on the anterior resection guide 138.

The guide surface 178 extends only part way across of the end portion 124 of the femur 126 (FIGS. 11 and 13). The guide surface 178 does not extend across the lateral portion of the end portion 124 of the femur 126. This at least partially results from the fact that the incision 114 (FIG. 6) is offset in a medial direction from the center of the knee portion 76. The incision 114 extends along the medial edge portion of the patella 120 when the patella is in its normal, that is, initial, position. In addition, the large majority of the anterior resection guide 138 extends medially from the central axis of the shaft 132 of the femoral alignment guide 134 (FIG. 11). By having the anterior resection guide disposed in an overlying relationship with the medial portion of the end portion 124 of the femur 126 (FIGS. 11 and 13), the size of the incision 114 can be reduced.

When anterior portions of the lateral and medial condyles 148 and 150 (FIGS. 10, 11 and 12) on the distal end portion 124 of the femur 126 are to be cut with the saw 172, the blade 170 is pivoted sideways (FIG. 13) so that the cutting end of the blade has an arcuate component of movement. The cutting end of the blade 170 will move along a straight path during part of the movement of the blade along the guide surface 178. However, when the blade 170 reaches the ends of the guide surface 178, the saw 172 is pivoted to pivot the blade and move the cutting end of the blade along a path having an arcuate configuration. This results in a generally fan shaped cut which extends only part way across the anterior side of the lateral and medial condyles on the end portion 124 of the femur.

The saw blade may have teeth along opposite longitudinally extending edges. The saw blade 170 and saw 172 are of the oscillating type. However, a reciprocating type saw and blade may be utilized if desired. Additionally and as later described, a milling device and associated guides can be used.

Due to the limited length of the anterior resection guide 138, the saw blade 170 is moved along the guide surface 178 to only partially complete the anterior skim cut on the end portion 124 of the femur 126. The guide surface 178 is offset to the medial side of the central axis of femur 126 (FIG. 11). Therefore, the saw blade can only partially form the lateral portion of the anterior skim cut while the saw blade engages the guide surface 178. The anterior resection guide 138 can then disconnected from the femoral alignment guide 134 (FIGS. 14 and 15) and the anterior femur cut is completed.

During completion of the anterior femur (skim) cut, previously cut surfaces on the end portion 124 of the femur 126 can be used to guide the saw blade 170 (FIG. 13). Thus, an initial portion of the anterior skim cut is made on the distal end portion 124 of the femur 126 while the saw blade 170 is moved along one or more guide surfaces on the anterior resection guide 138. After the anterior resection guide 138 has been disconnected from the femoral alignment guide 134, the saw blade 170 is positioned in engagement with the cut surfaces on the distal end portion 124 of the femur 126. This is accomplished by inserting the saw blade 170 into a slot or saw kerf formed in the distal end portion 124 of the femur during the initial portion of the anterior skim cut.

The saw blade 170 is then moved along the previously cut surfaces on the distal end portion of the femur 126 to guide the saw blade during completion of the anterior skim cut. Utilizing cut surfaces formed during an initial portion of the anterior skim cut to guide the saw blade 170 enables the size of the anterior resection guide 138 to be minimized. Although the illustrated saw blade 170 has teeth 180 at only one end, the saw blade could also have teeth along opposite longitudinally extending edges.

By utilizing the anterior resection guide 138 to guide movement of the saw blade 170 during only an initial portion of forming the anterior skim cut on the distal end portion 124 of the femur 126, the overall length of the anterior resection guide, that is, the distance between the ends 160 and 162 (FIG. 11) of the anterior resection guide can be limited to a distance which is less than the distance between the epicondyles 148 and 150. Specifically, the distance between the ends 160 and 162 of the anterior resection guide 138 is less than two thirds (⅔) of the distance between the tips 144 and 146 of lateral and medial epicondyles 148 and 150 on the distal end portion 124 of the femur 126. By limiting the length of the anterior resection guide 138, the size of the incision 114 can be minimized.

It is contemplated that the initial portion of the anterior skim cut could be made with a first cutting tool and the anterior skim cut completed with a second cutting tool. The initial portion of the anterior skim cut may be made with relatively small oscillating saw blade. The final portion of the anterior skim cut may be made with a larger reciprocating saw blade. Alternatively, a small milling cutter could be used to make the initial portion of the anterior skim cut. The final portion of the skim cut could be made with a relatively long milling cutter or saw blade. It may be desired to make the initial portion of the anterior skim cut with a chisel and to complete the anterior skim cut with either a saw blade or a milling cutter.

The illustrated anterior resection guide 138 has a slot which forms the guide surface 178. This results in the saw blade 170 being captured so that the saw blade is restrained against both up and down movement (as viewed in FIG. 11) relative to the anterior resection guide 138. However, in order to reduce the size of the anterior resection guide 138, the slot could be eliminated and the saw blade 170 moved along a flat outer side of the anterior resection guide.

During making of the anterior skim cut, with and without the anterior resection guide 138, body tissue (FIG. 9) overlies at least portions of the lateral and medial condyles being cut. This is due to the relatively short extent of the incision 114. Thus, the saw blade 170 and the portion of the femur 126 being cut by the saw blade are both at least partially enclosed by body tissue overlying the femur during making of the anterior skim cut. During making of the anterior skim cut, the incision 114 is moved relative to the femur 126 to provide clearance for the saw blade.

Figure 14:
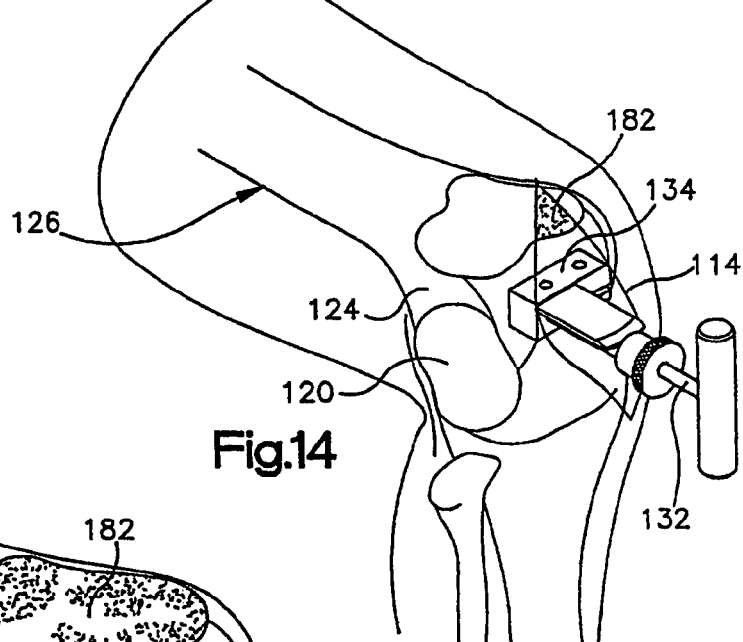
FIG. 14 is a schematic illustration depicting the relationship of the femoral alignment guide to the femur after making of the anterior femur cut of FIG. 13, the anterior resection guide and stylus being removed from the femoral alignment guide, and the leg of the patient being in the position illustrated in FIGS. 2 and 3.
Figure 15:
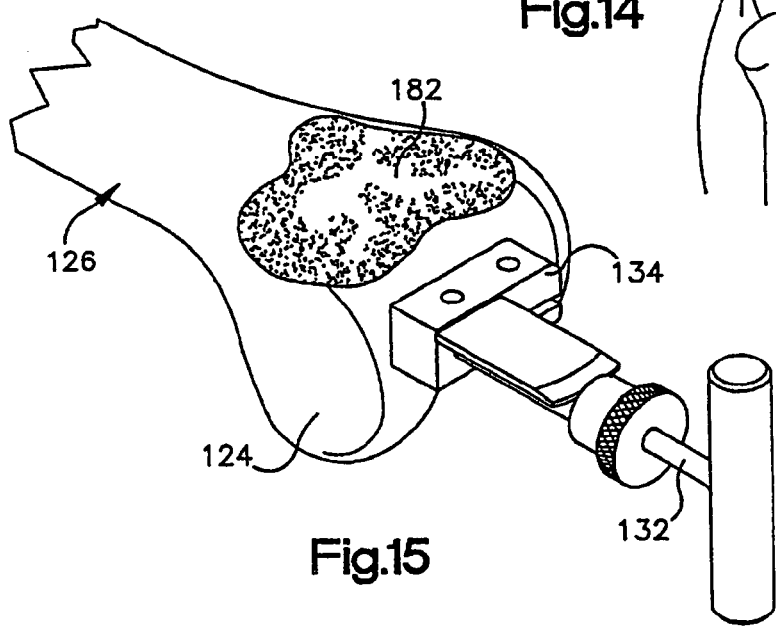
FIG. 15 is a schematic illustration of the anterior femur cut and femoral alignment guide of FIG. 14.

After the anterior portion of the lateral and medial epicondyles have been cut away and the anterior resection guide 138 removed, a flat anterior cut surface 182 (FIGS. 14 and 15) is disposed on the distal end portion 124 of the femur 126. The anterior skim cut is made on the distal end portion 124 of the femur 126 with the patella 120 offset to one side of the incision 118 (FIG. 14). The inner side of the patella 120 faces toward the distal end portion 124 of the femur 126 when the patella is in the offset position of FIGS. 9 and 14.

The flat anterior cut surface 182 (FIG. 15) extends parallel to the epicondylar axis. The maximum width of the anterior cut surface 182, as measured parallel to the epicondylar axis, is greater than the distance between opposite ends 154 and 156 (FIG. 11) of the femoral alignment guide 134. Similarly, the maximum width of the anterior cut surface 182 (FIG. 15), as measured parallel to the epicondylar axis, is greater than the distance between opposite ends 160 and 162 (FIG. 11) of the anterior resection guide 138. The anterior cut surface 182 is at least partially covered by body tissue which encloses the distal end portion of the femur 126 (FIG. 14).

During making of the anterior skim cut, the patient 62 (FIG. 2) is supported in a supine position on the support surface 64. The upper portion 72 of the leg 70 is disposed above the support surface on the leg support 80. The lower portion 68 of the leg 70 extends downward from the support surface 64. The foot 74 (FIG. 3) of the patient is disposed below the support surface.

Throughout the making of the anterior skim cut and the formation of the flat anterior cut surface 182 (FIGS. 14 and 15) on the distal end portion 124 of the femur 126, the lower portion 68 of the leg 70 can be suspended from the upper portion 72 of the leg in the manner illustrated in FIG. 3. This results in the knee portion 76 of the leg 70 being distracted by the combined weight of the lower portion 68 of the leg and the foot 74. At this time, the lower portion 68 of the leg 70 dangles from the upper portion 72 of the leg. If desired, a holder could be provided to engage either the foot 74 and/or the lower portion 68 of the leg 70 to maintain the foot 74 and lower portion 68 of the leg in a desired position relative to the support surface 64.

Once the anterior skim cut has been completed, a distal resection guide 186 is positioned relative to the flat anterior skim cut surface 182 (FIG. 16). To position the distal resection guide 186 relative to the cut surface 182, a resection guide stand 190 is mounted on the femoral alignment guide 134 in the manner illustrated in FIG. 16. The distal resection guide 186 is connected with the resection guide stand 190 by rotating a locking knob 192. The distal resection guide 186 and resection guide stand 190 may be magnetized to assure correct assembly. Since the femoral alignment guide 134 is medially offset relative to the distal end portion 124 of the femur 126, the distal resection guide 186 is also medially offset relative to the distal end portion of the femur.

When the distal resection guide 186 is to be connected with the resection guide stand 190, the distal resection guide is moved between the anterior skim cut surface 182 and body tissue overlying the anterior skim cut surface (FIG. 14). Thus, due to the limited extent of the incision 114, skin and other body tissues are disposed over the anterior skim cut surface 182. The distal resection guide 186 slides between the anterior skim cut surface 182 and the body tissue overlying the anterior skim cut surface. A lower (as viewed in FIGS. 16, 17 and 18) major side of the distal resection guide 186 engages the anterior skim cut surface 182. The opposite or upper (as viewed in FIGS. 16, 17 and 18) major side of the distal resection guide 186 is engaged by the body tissue overlying the anterior skim cut surface 182 (FIG. 14). The surgeon moves the incision 114 and/or the lower portion 68 of the leg 70 relative to the distal end portion of the femur 126 to facilitate movement of the distal resection guide 186 onto the anterior skim cut surface 182.

Once the distal resection guide 186 has been positioned in the desired location on the flat anterior cut surface 182, the distal resection guide 186 is secured in place with pins 196 and 198 (FIG. 16). At this time, body tissue overlies the portion of the distal resection guide 186 spaced from the distal end of the femur. The distal resection guide 186 is medially offset from a central portion of the femur 126 and is aligned with the incision 114. The incision 114 (FIG. 14) is moved relative to the distal end portion 124 of the femur 216 to enable the pins 196 and 198 to be forced into the distal end portion of the femur.

The femoral alignment guide 134 and resection guide stand 190 are then separated from the distal end portion 124 of the femur 126 (FIGS. 17 and 18). As this is done, the resection guide stand 190 (FIG. 16) is separated from the distal resection guide 186. Separation of the resection guide stand 190 from the distal resection guide 186 is accomplished by rotating the knob 192 and moving the resection guide stand 190 upward (as viewed in FIG. 16) to disconnect the guide stand 190 from the femoral alignment guide 134. The intramedullary rod 132 and femoral alignment guide 134 are then removed from the femur 126. The distance between opposite ends 206 and 208 of the distal resection guide 186 is less than two thirds (⅔) of the distance between tips 144 and 146 (FIG. 11) of the lateral and medial epicondyles 148 and 150.

The distal resection guide 186, like the anterior resection guide 138, is down sized to enable the distal resection guide to move into the knee portion 76 of the patient's leg 70 through a relatively small incision 114. To enable the distal resection guide 186 to move into the incision through a relatively small incision 114, opposite ends 206 and 208 (FIG. 16) of the distal resection guide 186 are spaced apart by a distance which is less than the distance between the lateral and medial epicondyles 148 and 150 (FIG. 11) on the distal end portion 124 of the femur 126. The distance between opposite ends 206 and 208 of the distal resection guide 186 is less than the distance which a femoral implant extends across the distal end portion 124 of the femur 126.

The distal resection guide 186 is offset medially relative to the distal end portion 124 of the femur 126. The incision 114 is also medially offset relative to the distal end portion 124 of the femur 126. This results in the central portion of the guide surface 202 being exposed through the incision 114. The lateral and medial edges of the incision 114 overlap opposite ends 206 and 208 of the distal resection guide 186. The incision 114 also overlaps the anterior side, that is, the upper side as viewed in FIG. 16, of the distal resection guide. During cutting with the saw blade 170 (FIGS. 17 and 18), the incision 114 is elastically expanded with suitable retractors.

During making of the distal femoral cut, the saw blade 170 moves along the guide surface 202 (FIG. 17) on the distal resection guide 186. The guide surface 202 on the down sized distal resection guide 186 has a length which is less than a transverse dimension of a cut to be made in the distal end portion 124 of the femur 126. The saw 172 may be pivoted, in a manner illustrated schematically in FIG. 13, adjacent to opposite ends of the guide surface 202. This moves the cutting end of the saw blade 170 along an arcuate path to form a generally fan shaped distal femoral cut. The saw 172 may be either a reciprocating or oscillating saw.

Due to the reduced size of the distal resection guide 186, the saw blade 170 (FIGS. 17 and 18) is ineffective to complete the distal femoral cut while the saw blade is in engagement with the guide surface 202 (FIGS. 16 and 17). Therefore, after an initial portion of the distal cut has been made by moving the saw blade 170 along the guide surface 202, the distal resection guide 186 is disconnected from the distal end portion 124 of the femur 126 and the distal femoral cut is completed.

During completion of the distal femoral cut, surfaces formed during the initial portion of the distal femoral cut are effective to guide the saw blade 170. The saw blade 170 (FIGS. 17 and 18) is moved into the saw kerf or slot formed during the initial portion of the distal femoral cut. As the saw blade 170 extends the initial portion of the distal femoral cut, the saw blade slides along cut surfaces formed during the initial portion of the distal femoral cut. Thus, cut surfaces formed during movement of the saw blade 170 along the guide surface 202 are utilized to guide movement of the saw blade during completion of the distal femoral cut.

The initial portion of the distal femoral cut may be made with a first cutting tool and the final portion of the distal femoral cut may be made with a second cutting. For example, the initial portion of the distal femoral cut may be made with a relatively small oscillating saw blade which can be readily inserted through the incision 114 into engagement with the distal resection guide 186. The final portion of the distal femoral cut may be made with a larger saw blade which may be of the reciprocating type. It is contemplated that the initial and/or final portion of the distal femoral cut may be made with a milling cutter. It is also contemplated that a chisel may be used to make the initial and/or final portion of the distal femoral cut.

When the distal femoral cut is completed, a flat distal end surface 209 extends across the distal end of the femur 126 (FIG. 17). The distal end surface 209 extends perpendicular to the anterior cut surface 182. The maximum width of the distal end surface 209, as measured parallel to the anterior cur surface 182 and epicondylar axis, is greater than the distance between opposite ends 206 and 208 of the distal resection guide 186. The trochlear groove of the femur extends through the distal end surface 209.

The distal femoral cut can be formed with the patella 120 (FIG. 14) offset to one side of the incision 114 and with the inner side 122 of the patella facing toward the distal end portion 124 of the femur 126. In addition, the leg 70 of the patient can be in the orientation illustrated in FIGS. 2 and 3 with the foot 74 and lower portion 68 of the leg suspended from the upper portion 72 of the leg. The upper portion 72 of the leg is supported above the support surface 64 by the leg support 80.

A femoral cutting guide 210 (FIGS. 19 and 20) is then positioned on the distal end portion 124 of the femur 126 and utilized to make femoral anterior, posterior and chamfer cuts in a known manner. The femoral cutting guide 210 is connected with the distal end portion 124 of the femur 126 by two pins (not shown) in a known manner. The femoral cutting guide 210 is down sized so that it has opposite ends which are spaced apart by distance which is less than a distance between the lateral and medial epicondyles 148 and 150 (FIG. 11) on the distal end portion 124 of the femur 126. The femoral cutting guide 210 is offset in a medial direction from the center of the femur 126 (FIG. 20). The medially offset position of the femoral cutting guide 210 is the result of the medially offset position of the incision 114 (FIG. 6).

The initial portion of the femoral anterior, posterior and chamfer cuts are made by moving the saw blade 170 or other cutting tool along guide surfaces on the femoral cutting guide. Due to the relatively small size of the femoral cutting guide, the cuts cannot be completed while moving the saw blade 170 or other cutting tool along guide surfaces on the femoral cutting guide. Therefore, the femoral cutting guide 210 is separated from the distal end portion 124 of the femur 126 and the cuts are completed while guiding movement of the saw blade 170 or other cutting tool with cut surfaces formed during the making of the initial portions of the femoral anterior, posterior and chamfer cuts. When the femoral anterior, posterior and chamfer cuts are completed, the distal end portion 124 of the femur 126 will have the known configuration illustrated in FIGS. 22 and 23.

The femoral cutting guide 210 (FIGS. 19 and 20) may have the same construction as a femoral cutting guide which is commercially available from Howmedica Osteonics of 359 Veterans Boulevard, Rutherford, N.J. The femoral cutting guide may have the construction disclosed in U.S. Pat. No. 5,282,803 or 5,749,876. However, it is preferred to down size the known femoral cutting guides to have a distance between opposite ends which is less than two thirds (⅔) of the distance between tips 144 and 146 (FIG. 11) of medial and lateral condyles 148 and 150 on the distal end portion 124 of the femur 126. This enables the femoral cutting guide 210 to move through the incision 114.

Since the femoral cutting guide 210 is down sized, initial portions of the femoral anterior, posterior and chamfer cuts are made while guiding a saw blade or other cutting tool with the femoral cutting guide. These cuts are subsequently completed utilizing previously cut surfaces to guide the saw blade 170. To complete a cut in this manner, the saw blade 170 or other cutting tool is moved along the previously cut surfaces to guide the saw blade as the cuts are extended.

During the making of the initial portions of the anterior, posterior and chamfer cuts with the femoral cutting guide 210 and the subsequent completion of the cuts without the femoral cutting guide, the knee portion 76 of the leg 70 of the patient can be distracted by the weight of the lower portion 68 and foot 74 of the leg. Thus, the lower portion 68 and foot 74 of the leg 70 are suspended from the upper portion 72 of the leg in a manner illustrated in FIGS. 2 and 3 during the making of the femoral anterior, posterior and chamfer resections. The upper portion 72 of the patient's leg 70 is supported above the support surface 64 by the leg support 80 (FIG. 2).

By distracting the knee joint during the making of the femoral anterior, posterior and chamfer cuts, access to the distal end portion 124 of the femur 126 is promoted and the making of the cuts is facilitated. Access to the distal end portion 124 of the femur 126 is also promoted by moving the suspended lower portion 68 of the leg 70 relative to the distal end portion of the femur. The incision 114 may be moved relative to the distal end portion 124 of the femur 126 by applying force to body tissue adjacent to the incision.

Tibial Procedure

As was the case for femoral preparation, the tibial procedure can be performed with the leg 70 in the position shown in FIGS. 2 and 3. Since the knee portion 76 of the leg 70 is distracted, a proximal end portion 212 (FIG. 21) of a tibia 214 is separated from the distal end portion 124 of the femur 126. The foot 74 (FIG. 3) may be moved posteriorly to hyperflex the knee portion 76. This facilitates viewing of the proximal end portion 212 of the tibia 214 through the relatively small incision 114.

When the knee portion 76 (FIG. 2) is hyperflexed, the angle between the upper portion 72 and the lower portion 68 of the patient's leg 70 is less than ninety (90) degrees. At this time, the foot 74 is disposed posteriorly of the position illustrated in FIG. 2. This results in the proximal end portion 212 (FIG. 21) of the tibia 214 being moved anteriorly relative to the distal end portion 124 of the femur 126. The distal end portion 212 of the tibia 214 can then be viewed through limited incision 114. Even though the incision 114 has a relatively short length, it is possible to move the incision relative to the proximal end portion 212 of the tibia 214. Therefore, the entire or at least almost the entire, proximal end surface of the tibia 214 can be viewed through the incision 214.

It is contemplated that an external tibial alignment guide (not shown) will be utilized to align a tibial resection guide 218 (FIG. 21) with the proximal end portion 212 of the tibia 214. The tibial alignment guide has a known construction and may be similar or the same as is commercially available from Howmedica Osteonics of 359 Veterans Boulevard, Rutherford, N.J. Alternatively, the tibial alignment guide may have the construction disclosed in U.S. Pat. No. 5,578,039; or 5,282,803.

Once the tibial resection guide 218 (FIG. 21) has been aligned with and secured to the proximal end portion 212 of the tibia 214, the external tibial alignment guide (not shown) is disconnected from the tibial resection guide 218. The tibial resection guide 218 is secured to the proximal end portion 212 of the tibia 214 by suitable pins.

In accordance with one of the features of the present invention, the tibial resection guide 218 is relatively small so that it can be moved through a relatively small incision 114 into engagement with the proximal end portion 212 of the tibia 214. To facilitate moving of the tibial resection guide 218 through a relatively small incision 114, the tibial resection guide 218 is smaller than implants 286 (FIG. 27) and 294 (FIG. 28) to be positioned on the proximal end portion 212 of the tibia 214. The tibial resection guide 218 has a distance between opposite ends 228 and 230 (FIG. 21) which is less than two thirds (⅔) of the distance between tips of lateral and medial epicondyles on the tibia 214. Similarly, the distance between the ends 228 and 230 of the tibial resection guide 218 is less than two thirds (⅔) of the distance between tips 144 and 146 (FIG. 11) of the lateral and medial condyles 148 and 150 on the femur 126.

During positioning of the external tibial alignment guide and the tibial resection guide 218 (FIG. 21) relative to the tibia 214 in the leg 70 of the patient, the leg 70 can be supported in the manner illustrated in FIGS. 2 and 3. Thus, the upper portion 72 (FIG. 2) of the leg 70 is supported above the support surface 64 by the leg support 80. The lower portion 68 of the leg 70 is suspended from the upper portion 72 of the leg. The foot 74 (FIG. 3) connected with the lower portion 68 of the leg 70 is disposed below to support surface 64 (FIG. 2).

During positioning of the tibial resection guide 218 on the proximal end portion 212 of the tibia 214, the tibial resection guide is moved between the proximal end portion of the tibia and body tissue overlying the proximal end portion of the tibia. The tibial resection guide 218 is positioned relative to the proximal end portion 212 of the tibia 214 while the incision 114 is resiliently expanded. The incision 114 is expanded by applying force against opposite sides of the incision with suitable retractors. The retractors may have a construction similar to the construction disclosed in U.S. Pat. No. 5,308,349. Alternatively, a pneumatic retractor, such as is disclosed in U.S. patent application Ser. No. 09/526,949 filed Mar. 16, 2000 by Peter M. Bonutti may be used to expand the incision 114.

The tibial resection guide 218 is slid inferiorly, that is, downward (as viewed in FIG. 21) between the proximal end portion 212 of the tibia 214 and body tissue adjacent to the proximal end of the tibia. The tibial resection guide 218 is then connected to the proximal end portion 212 of the tibia 214 with suitable pins. Once the resection guide 218 has been connected with the tibia 214, the force applied against opposite sides of the incision 114 by retractors is interrupted and the incision contracts. As this occurs, the body tissue moves over the lower (as viewed in FIG. 21) portion of the tibial resection guide 218 to further enclose the tibial resection guide.

The tibial resection guide 218 is medially offset relative to the proximal end portion 212 of the tibia 214. This is because the incision 114 is medially offset relative to the proximal end portion 212 of the tibia 214. The incision 114 extends from the proximal end portion 212 of the tibia 214 to the superior portion of the trochlear groove in the distal end portion 124 of the femur 126. As was previously mentioned, the incision 114 and the instrumentation may be laterally offset relative to the femur 126 and the tibia 214.

Once the tibial resection guide 218 (FIG. 21) has been mounted on a proximal end portion 212 of the tibia 214, a proximal tibial cut is made. The proximal tibial cut is made by moving the blade 170 of the saw 172 along a guide surface 242 on the tibial resection guide 218 (FIG. 21). When the saw blade reaches an end portion of the tibial guide surface 242, the saw 172 is pivoted to move the saw blade 170 in the manner illustrated schematically in FIG. 16. This pivotal movement results in the cutting end portion of the saw blade 170 having an arcuate component of movement. This results in a generally fan shaped cut being formed in the proximal end portion 212 of the tibia 214.

Due to the reduced size of the tibial resection guide 218 to facilitate movement of the tibial resection guide through the incision 114, the saw 172 can only form an initial portion of the proximal tibial cut as the saw blade 170 moves along the guide surface 242 of the tibial resection guide 218. To complete the proximal tibial resection cut, the tibial resection guide 218 is disconnected from the tibia 214.

Once the tibial resection guide 218 has been separated from the tibia 214, the saw blade 170 is inserted into the slit or kerf made by the saw blade during the initial portion of the proximal tibial cut. The cut surfaces which were formed during an initial portion of making the proximal tibial cut on the tibia 214 are then used to guide the saw blade 170 during completion of the proximal tibial cut. Thus, the saw blade 170 is moved along surfaces formed during the making of the initial portion of the proximal tibial cut to guide movement of the saw blade during completion of the proximal tibial cut.

It is contemplated that different cutting tools may be utilized to make the initial and final portions of the proximal tibial cut. Thus, the saw blade 170 used to make the initial portion of the tibial cut may be a relatively small oscillating blade and the saw blade used to make the final portion of the tibial cut may be a relatively long reciprocating blade. Alternatively, the initial and/or final portion of the tibial cut may be made with a milling cutter. If desired, a chisel could be utilized to make the initial portion of the tibial cut. The incision 114 may be expanded with suitable retractors during making of the tibial cut. The retractors may have any desired construction, including the construction disclosed in U.S. Pat. No. 5,308,349. Ligaments and other body tissue adjacent to the proximal end portion 212 of the tibia 214 may be shielded with suitable surgical instruments during making of the tibial cut.

Upon completion of the proximal tibial cut on the proximal end portion 212 of the tibia 214, a flat proximal tibia cut surface 246 (FIG. 22) is exposed on the proximal end portion 212 of the tibia 214 through the incision 114. The flat cut surface 246 has a maximum width, as measured along an axis extending parallel to an axis extending through central axes of the collateral ligaments, which is greater than the distance between opposite ends 228 and 230 of the tibial resection guide 218. The distal end portion 124 of the femur 126 is also exposed through the incision 118.

In order to increase exposure of the proximal end portion 212 of the tibia 214 at the incision 218, the foot 74 and lower portion 68 of the leg 70 (FIG. 24) can be moved posteriorly toward the operating table 66 (FIG. 2) to hyperflex the knee portion 76 of the patient's leg 70 during the making of the proximal tibial cut. When the knee portion 76 of the leg 70 is hyperflexed, the ankle 86 is moved from a position either extending through or anterior of a vertical plane extending perpendicular to a longitudinal central axis of the upper portion 72 of the patient's leg 70 to a position disposed posteriorly of the vertical plane. Thus, as viewed in FIGS. 2 and 24, the ankle 86 is moved toward the left. As this occurs, an angle between a longitudinal central axis of the upper portion 72 of the patient's leg and the longitudinal central axis of the lower portion 68 of the patient's leg is decreased to an angle of less than ninety degrees.

Hyperflexing the patient's leg 70 moves the proximal end portion 212 (FIGS. 22 and 23) of the tibia 214 anteriorly away from the distal end portion 124 of the femur 126. At this time, the knee portion 76 of the patient's leg is distracted under the influence of the weight of the lower portion 68 of the patient's leg and the foot 74 connected with the lower portion of the patient's leg. If desired, a force pulling the lower portion of the patient's leg downward (as viewed in FIG. 3) may be applied to the patient's leg to further increase the distraction of the knee portion 76 of the leg and the extent of exposure of the proximal end portion 212 of the tibia 214.

Figure 24:
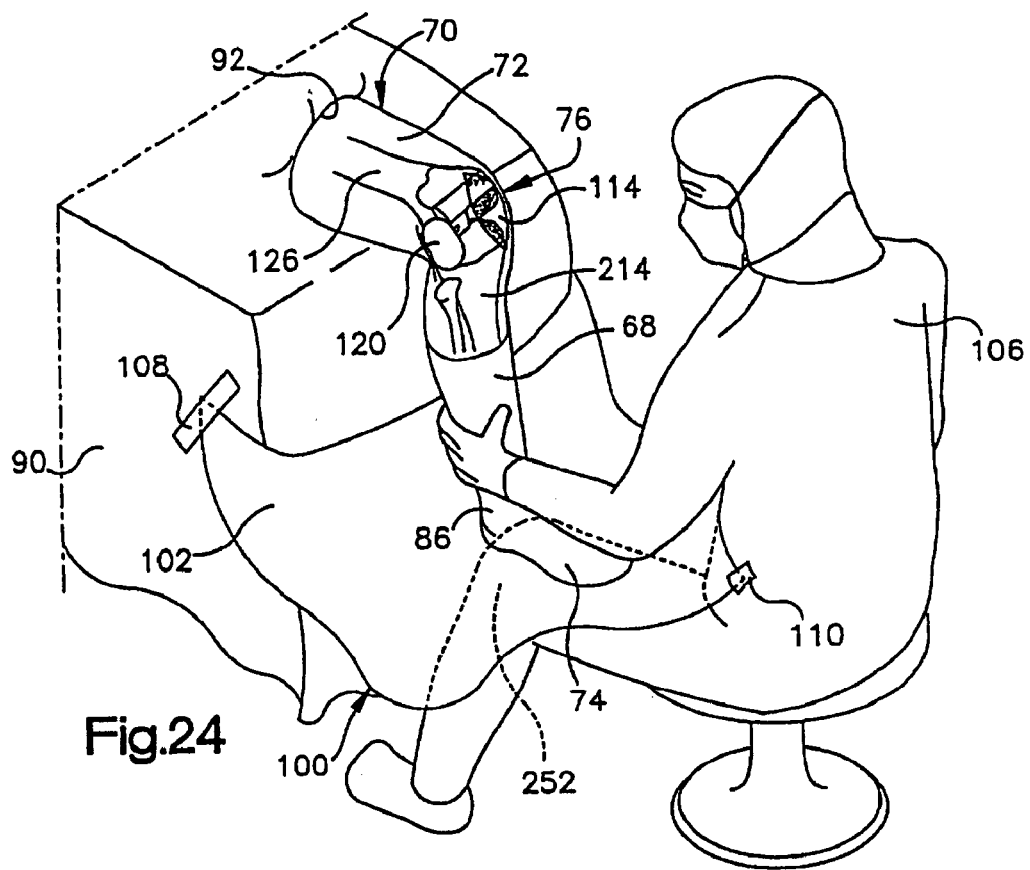
FIG. 24 is a schematic illustration depicting the manner in which force is applied against the bottom of the patient's foot by a surgeon's knee with the leg of the patient in the position illustrated in FIGS. 2 and 3.

By hyperflexing the knee portion 76 of the patient's leg 70 and applying a downward (as viewed in FIG. 3) force against the lower portion 68 of the patient's leg, the proximal end portion 212 of the tibia 214 is delivered anteriorly that is, toward the surgeon 106 (FIG. 24). Application of a downward force against the lower portion 68 of the patient's leg is effective to open the space between the proximal end portion 212 of the tibia 214 and the distal end portion 124 of the femur 126 to the maximum extent permitted by the tendons and ligaments, that is, fibrous connective tissue, interconnecting the femur and tibia.

This enables the posterior cruciate ligament 250 (FIG. 23) to be checked. In addition, access is provided to the posterior side of the knee portion 76 of the leg 70. The surgeon 106 (FIG. 24) can manually feel the posterior portion of the knee joint. There is sufficient space between the distal end portion 124 of the femur 126 and the proximal end portion 212 of the tibia 214 to enable the surgeon 106 to visually and tactilely check the posterior of the knee portion 76 of the patient's leg 70.

Access to the posterior portion of the knee enables osteophytes, bone spurs and similar types of posterior soft tissue to be removed. This enables tissue which could block further flexion of the knee portion 76 to be removed. In addition, it is possible to check the collateral ligaments and other fibrous connective tissue associated with the knee.

At this time, the lower portion 68 of the leg 70 (FIGS. 23 and 24) is suspended from the upper portion 72 of the leg. Therefore, the lower portion 68 of the leg 70 hangs from the upper portion 72. The foot 74 may be supported on the surgeon's knee 252 (FIG. 24) or other surface. The foot 74 is free to move in any direction relative to the knee portion 76. By raising or lowering his or her knee 252, the surgeon 106 can move the tibia 214 relative to the femur 126 and vary the space between the distal end of the femur and the proximal end of the tibia.

By varying force indicated by arrows 256 (FIG. 25), the vertical extent of space between the proximal end portion 212 of the tibia 214 and the distal end portion 124 of the femur 126 (FIGS. 22 and 23) can be either increased or decreased. The force 256 is varied by raising and lowering the surgeon's knee 252. Increasing the space between the proximal end portion 212 of the tibia 214 and the distal end portion 124 the femur 126 maximizes access to the posterior of the knee portion 76.

By moving the lower portion 68 of the leg 70 upward, the ligaments and other connective tissue between the tibia 214 and femur 126 are relaxed. This enables the lower portion 68 of the leg 70 to be rotated about its longitudinal central axis, in a manner indicated by arrows 258 in FIG. 25. Rotational movement of the lower portion 68 of the leg 70 about its central axis enables the surgeon to check the collateral ligaments and the resistance encountered to rotation of the lower portion 68 of the leg relative to the upper portion 72.

Figure 25:
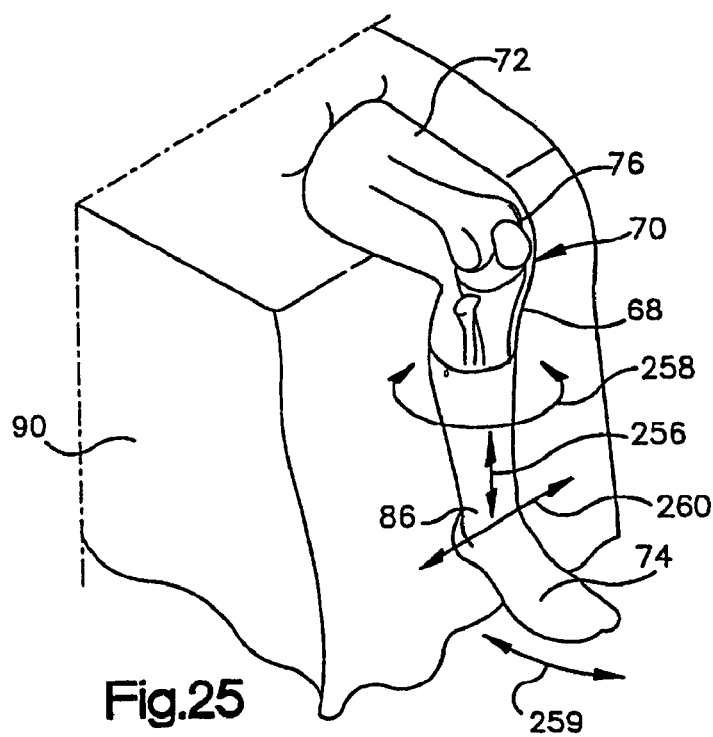
FIG. 25 is a schematic illustration depicting the various directions in which the lower portion of the patient's leg can be moved relative to the upper portion of the patient's leg to expose portions of the bone at the incision in the knee portion of the patient's leg and to check ligament balancing.

In addition, the foot 74 can be pivoted in a clockwise direction (as viewed in FIG. 25) about the knee portion 76, in the manner indicated by arrow 259 in FIG. 25, to increase the extent of flexion of the knee portion 76. Alternatively, the foot 74 can be pivoted in a counterclockwise direction about the knee portion 76 to decrease the extent of flexion of the leg 70.

The lower portion 68 of the leg 70 can also be moved sidewise, in the manner indicated by the arrow 260 in FIG. 25. When the lower portion 68 of the leg 70 is moved in the manner indicated by the arrow 260, the lower portion of the leg is moved along a path extending through lateral and medial surfaces of the foot 74 and the lower portion 68 of the leg 70. This enables the ligaments and other fibrous connective tissue in the leg to be checked for a range of movement. Although the incision 114 has not been shown in FIG. 25, it should be understood that the lower portion 68 of the leg 70 can be moved in the directions indicated by the arrows in FIG. 25 when the knee portion 76 is in the condition illustrated in FIGS. 22 and 23.

The illustrated instrumentation can be formed of a metal which enables the instrumentation to be sterilized and reused. For example, the instrumentation could be formed of stainless steel. However, known metal instruments are relatively heavy and bulky. This substantially increases transportation expense.

It is contemplated that it may be desired to use the instrumentation once and then dispose of the instrumentation. If this is done, the instrumentation may be partially or entirely formed of relatively inexpensive polymeric materials. Thus, the femoral resection guide 134, anterior resection guide 138, distal resection guide 186, femoral cutting guide 210, and/or tibial resection guide 218 could be formed of inexpensive polymeric materials. If this was done, the guides could be used once and disposed of without being sterilized. In addition, the polymeric guides would weigh substantially less than metal guides.

Implants

After the distal end portion 124 of the femur 126 has been prepared and the proximal end portion 212 of the tibia 214 is prepared to receive implants (FIGS. 22 and 23) and prior to insertion of the implants, any necessary work on the patella 120 may be undertaken. During work on the patella, the leg 70 of the patient may be extended and the patella 120 may be everted or flipped to the position illustrated in FIG. 7. The inner side or articular surface 122 of the patella 120 faces outward and is exposed. Known surgical techniques are then utilized to cut the patella 120 and position an implant on the patella in a known manner. This may be accomplished utilizing any one of many known devices and procedures, such as the devices and procedures disclosed in U.S. Pat. Nos. 4,565,192; 5,520,692; 5,667,512; 5,716,360; and/or 6,159,246. If desired any necessary work on the patella 120 may be undertaken after the femoral and tibial implants have been installed.

As an alternative to the above-described procedure in which patella 120 is everted or flipped to the position illustrated in FIG. 7, patella 120 can be resurfaced or otherwise worked upon while maintained in a substantially non-everted, anatomic position. U.S. Pat. No. 6,174,314 B1, the contents of which are incorporated herein by reference, discloses instrumentation and methods for in situ resurfacing of a patella.

Additionally, U.S. Pat. No. 5,163,949 and progeny, such as U.S. Pat. Nos. 6,358,266 B1, 6,277,136 B1, and 6,187,023 B1, discloses various embodiments of retractors and method of dissecting tissue. These embodiments include fluid operated retractors, mechanical retractors, and combinations thereof. The retractors and methods disclosed in this line of patents, which is incorporated herein by reference, can be used for patella procedures and/or visualization while the patella is maintained in a substantially non-everted, anatomic position.

Once the femoral and tibial cuts have been made and the patella repaired, femoral and tibial implants are installed in the knee portion of the leg 70. Prior to permanently mounting of the implants in the knee portion 76 of the leg 70, trials are conducted, in a known manner, with provisional femoral and tibial implants. The provisional femoral and tibial implants are releasably positioned relative to the distal end portion 124 of the femur 126 and the proximal end portion 212 of the tibia 214. As discussed in more detail below, the provisional implants (and/or instrumentation) can be made disposable and can be combined with the cutting guides or other instrumentation so that separate, dedicated provisional implants are not required.

The provisional implants are intended to aid the surgeon 106 in assessment of the function and balance of the various ligaments. The trials enable the surgeon 106 to observe the relationship of the provisional femoral and tibial implants relative to each other during flexion and extension of the knee portion 76 of the leg 70. In one embodiment, the lower portion 68 of the leg 70 is suspended from the upper portion 72 of the leg (FIGS. 2 and 3) during the trials with the provisional implants. Therefore, the lower portion of the leg 68 can be freely moved relative to the upper portion of the leg to check ligament balancing with the provisional implants. Since the lower portion of the leg 68 is suspended, it is possible to check for flexion and extension balancing of the ligaments and to check for rotational stability and rotational balancing of the ligaments during the trials with provisional implants. The lower portion 68 of the leg 70 can be moved with a combination of flexion or extension, rotation and sidewise movement.

The trials also enable the surgeon to check the manner in which the provisional implants interact with each other during flexion, extension, rotation, and sidewise movement. The manner in which the provisional femoral and tibial implants move relative to each other during combined bending and rotational movement of a patient's leg 70 enables a surgeon to check for the occurrence of excessive space or other undesirable situations between the provisional implants. During trials with provisional implants, the range of motion of the knee joint can be checked in both flexion/extension and rotation.

Utilizing known surgical techniques, it is very difficult, if not impossible, to check for both flexion/extension balancing, rotational balancing, and sidewise balancing during trials with provisional implants. With rotational balancing, the ligaments are balanced through multiple planes. When both flexion/extension and rotation are being checked, the surgeon can locate defects and improve the stability of the knee joint. The surgeon can assess the posterior cruciate ligament, collateral ligament balancing, and posterior capsule balancing. The surgeon can proceed with flexion/extension balancing of ligaments and rotational balancing of the ligaments. This enables the leg 70 to be examined throughout its range of motion during trials with provisional implants.

During an operation on the patient's leg 70, the surgeon can apply upward force against the foot of the patient by resting the foot 74 on the surgeon's knee 252 (FIG. 24) and raising the knee of the surgeon. Of course, when the foot 74 is to be lowered, the surgeon can lower the knee 252 upon which the foot 74 of the patient is resting. Alternatively, a pneumatic piston can be utilized to raise and lower the foot 74 of the patient.

Throughout the operation on the patient's knee 76, the upper portion 72 of the patient's leg 70 is supported above the support surface 64 by the leg support 80. This causes the hip of the patient to be hyperflexed by between 20 degrees and 40 degrees. Flexing of the hip by 20 degrees to 40 degrees improves rotational positioning and alignment. It also enhances the ability of the surgeon to hyperflex the knee portion 76 or to extend the knee portion during surgery. In addition, having the upper portion 72 of the patient's leg supported above the support surface 64 by the leg support 80 improves suspension of the lower portion 68 of the leg from the upper portion 72 of the leg. It is believed that the combination of suspending the lower portion 68 of the leg 70 and having the upper portion 72 of the leg supported above the support surface 64 by the leg support 80 will enhance the ability of a surgeon to check ligament balancing in flexion/extension, and rotation during trials during which provisional femoral and tibial components are temporarily connected with the distal end portion 124 of the femur 126 and with the proximal end portion 212 of the tibia 214.

During a portion of the trials, the patella 120 may be in the normal position relative to the distal end portion 124 of the femur 126 and the proximal end portion 212 of the tibia 214. Therefore, during trials, it is possible to check tracking of the patella relative to the provisional femoral implant. This is done in order to prevent any possible interference of the patella 120 with the movement of the knee through its range of motion.

Figure 26:
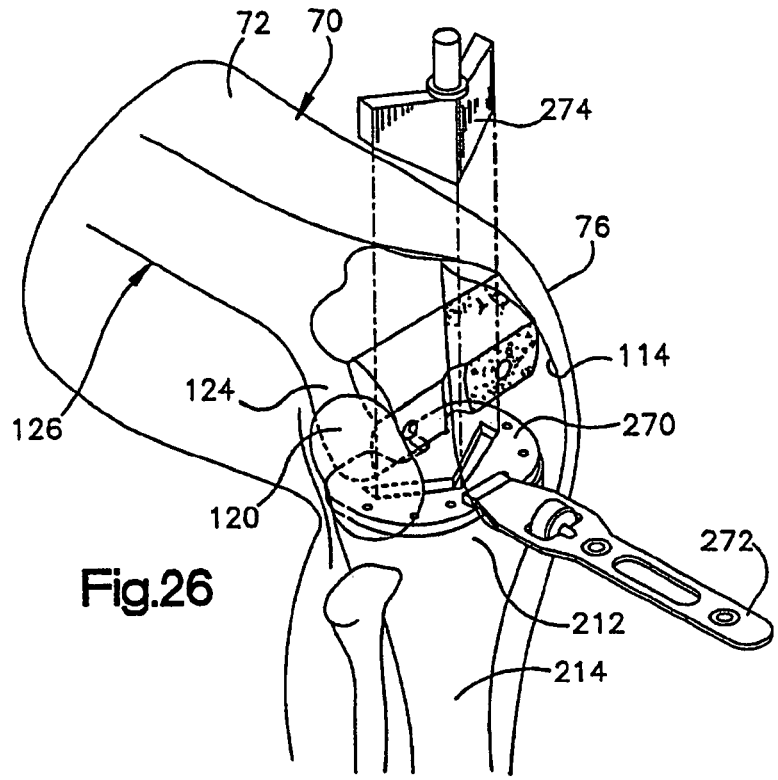
FIG. 26 is a schematic illustration depicting the manner in which a tibial punch is positioned relative to a tibial base plate with the leg of the patient in the position illustrated in FIGS. 2 and 3.

To install the trial femoral and tibial components, the proximal end portion 212 of the tibia 214 is prepared to receive the trial tibial implant. This is accomplished by positioning a tibial trial base plate 270 on the proximal end portion 212 of the tibia 214 (FIG. 26). An alignment handle 272 is connected with the tibial trial base plate 270 to facilitate positioning of the tibial trial base plate relative to the proximal end portion 214 of the tibia.

The trial femoral implant (not shown) is then placed on the distal end portion 124 of the femur 126. This may be done in a known manner using a femoral impactor/extractor. A trial tibial bearing insert (not shown) is then mounted on the tibial trial base plate 270 in a known manner. Once this has been done, the trial provisional implants are used during conducting of trials with flexion/extension and rotational movements of the lower portion 68 of the patient's leg. When the trials are completed, the trial provisional implants are removed in a known manner.

After completion of the trials, the tibial trial base plate 270 is pinned to the proximal end portion 214 of the tibia. A tibial punch 274 (FIG. 26) is positioned in a tibial punch tower (not shown) which is assembled onto the tibial trial base plate 270. The tibial punch 274 is advanced relative to the tibial punch tower by impacting a mallet against the tibial punch. The foot 74 rests against the knee 252 of the surgeon during pounding of the tibial punch 274 into the tibia 214. This results in the impaction forces being transmitted to the surgeon's knee 252 rather than to ligaments interconnecting the femur 126 and tibia 214.

Once the tibial punch 274 has been advanced until it is fully seated on the base plate, the punch is removed. The tibial trial base plate 270 is then removed from the proximal end portion 214 of the tibia. Once the tibial trial base plate 270 has been removed, an opening 282 (FIG. 27) formed in the proximal end portion 212 of the tibia 214 is exposed. The opening 282 has a configuration corresponding to the configuration of the tibial punch 274.

A tibial tray 286 (FIG. 27) forms a base portion of a tibial implant. The tibial tray 286 has a keel 288 with a configuration corresponding to the configuration of the tibial punch 274 (FIG. 26) and the opening 282 (FIG. 27) formed in the tibia 214. The keel 288 (FIG. 27) of the tibial tray 286 is covered with a suitable cement prior to being inserted into the opening 282. If desired, the cement may be omitted.

A tibial component impactor/extractor may be used to insert the tibial tray 286 into the opening 282. Once the tibial tray 286 has been mounted on the proximal end portion 212 (FIG. 28) of the tibia 214, a femoral component 290 (FIG. 29) is mounted on the distal end portion 124 of the femur 126. A known femoral impactor/extractor may be used to position the femoral component 290 on the distal end portion of the femur. The femoral component 290 may be provided with or without an intramedullary stem. Cement may or may not be used in association with the femoral component 290. Once the femoral component 290 has been mounted on the distal end portion 124 of the femur 126, a tibial bearing insert 294 (FIGS. 28 and 29) is positioned in the tibial tray.

The femoral and tibial implants 286, 290, and 294 may have any one of many known constructions. For example, the femoral and tibial implants could have the construction of a knee replacement which is commercially available from Howmedica Osteonics of 359 Veterans Boulevard, Rutherford, N.J. under the designation of "Scorpio" (trademark) total knee. Rather than being a total replacement, the femoral and tibial implants could be for a partial knee replacement. Thus, the femoral and tibial implants 286, 290 and 294 could have a construction which is the same as is illustrated in U.S. Pat. No. 5,514,143. The femoral and tibial implants 286, 290 and 294 may be of either the cemented type or the cementless types.

Once the femoral component 290 has been positioned on the femur 126 and the tibial tray 286 and bearing insert 294 positioned on the tibia 214, ligament balancing is again conducted. The ligament balancing includes a check of stability of the joint in flexion, extension, and rotation. The ligament balancing check is performed with the lower portion 68 of the leg 70 suspended from the upper portion 72 of the leg. The upper portion 72 of the leg 70 is held above the support surface 64 (FIG. 2) by the leg support 80 during the ligament balancing.

Since the lower portion 68 of the leg 70 is suspended from the upper portion 72, in the manner illustrated in FIGS. 2, 3 and 25, the surgeon has a more natural feel of the true ligamentous structure. This is because tissues are not squashed or bunched in the back of the knee portion 76. Since the lower portion 68 of the leg 70 is suspended from the upper portion 72 of the leg, the joint 76 is distracted without having the lower portion 68 of the leg jammed back against the upper portion 72 of the leg. With the leg suspended, a surgeon can view the tibial bearing insert 294 (FIG. 29) and the femoral component 290 to determine how the femoral and the tibial implants cooperate with each other and the ligaments, tendons, joint capsule and other tissues.

The knee portion 76 may be flexed and extended, by moving the lower portion of the leg 70 along the path indicated by arrow 259 in FIG. 25. In addition, the lower portion 68 of the leg 70 may be moved sideways, that is, laterally and/or medially, as indicated by arrow 260 in FIG. 25, to check for the occurrence of slight openings between the tibial bearing insert 294 (FIG. 29) and femoral component 290. The lower portion 68 of the leg can also be rotated about its longitudinal central axis, in the manner indicated by the arrow 258 in FIG. 25. By simultaneously applying a combination of rotational, sideward, and flexion or extension motion to the lower portion 68 of the leg 70, the surgeon can view the interaction between the tibial bearing insert 294 (FIG. 29) and femoral component 290 through the entire range of movement of the leg 70, including movement having rotational components.

By manually feeling resistance to flexion, rotational and/or sideward movement of the lower portion 68 of the patient's leg 70 (FIG. 25), the surgeon can check the balancing of ligaments and other tissues in the knee portion 76 of the leg. In addition, the surgeon can check the manner in which relative movement occurs between the tibial bearing insert 294 and femoral component 290 (FIG. 29). If a check of the rotational alignment of the femoral and tibial implants indicates that they are misaligned, the surgeon can change the rotational positions of the implants. If the ligaments are too tight medially or laterally, the surgeon can release the ligaments to the extent necessary. Ligaments which are too loose can be tightened. Since the lower portion 68 of the leg 70 is suspended, the surgeon can feel the effects of any ligamentous imbalance and take corrective action.

In contrast to the present invention, the majority of knee arthroplasties are done with the leg in a fixed position. Surgeons do not flex and extend through progressive intervals. As the above discussion illustrates, one aspect of the present invention involves controlling the position of the joint so that when the surgeon wants to work on the quadriceps mechanism the knee is in full extension. Similarly, when the surgeon wants to work on the tibia then he may be in more flexion, more toward 90-100°. The controlled positioning can be done in a leg alignment jig which allows reproducible holding positions that can be adjusted as desired. As previously noted, this can be achieved with electric motor, pneumatics, mechanical, or simple ratchets built on to a table, but allow precise positioning of the leg while surgeon goes from flexion to extension. There are existing leg holders, but these are very crude. Most surgeons simply use a sandbag and hold the leg in one position. This position is not precisely controlled, and therefore, somewhat variable. The soft tissue sleeve and relaxation is critical as one goes from flexion to extension, is more relaxed depending on which portion of the joint you want to expose, varying from flexion to extension. Certainly, quadriceps mechanism is the most relaxed in full extension, tighter against the femur in flexion. The tibia exposure may be improved in flexion, but controlling the specific amount of flexion/extension, locking this into position while the cuts are being performed sequentially and precisely is of significant value.

A portion of the foregoing check of ligamentous balancing may be performed with the patella 120 offset to one side of the incision 114, in the manner illustrated in FIG. 29. This enables the surgeon to have a clear view of the tibial bearing insert 294 and femoral component 290 through the open incision 114. After conducting a complete check of the ligamentous balancing with the patella 120 offset to one side of its natural position, the patella can be moved back to its natural position.

When the patella 120 is moved back to its natural position, the incision 114 closes so that there is little or no exposure of the tibial bearing insert 294 and femoral component 290 to the view of the surgeon. However, the surgeon 106 can move the lower portion 68 of the leg 70 with flexion/extension motion, indicated by the arrow 259 in FIG. 25, and/or rotational motion, indicated by the arrows 258, or sideways motion indicated by arrows 260. During this motion of the lower portion 68 of the leg 70, the surgeon can check the manner in which the patella 120 interacts with the tibial and femoral implants and other tissues in the knee portion 76 of the patient's leg. By providing combinations of the foregoing rotational and flexion/extension motion of the lower portion of the leg 70, the manner in which the patella 120, with or without an implant thereon, tracks relative to the tibial and femoral implants can be readily checked.

In the foregoing description, the patella 120 was repaired after making the femoral and tibial cuts and before trials. However, it is contemplated that the patella 120 may be repaired after trials and after installation of the implants 286, 290 and 294. Of course, the patella 120 may not need to be repaired and will be maintained in its original condition.

It is contemplated that fluid operated devices may be utilized to release ligaments or other tissue. The fluid operated devices may be utilized to apply force to tissue to move tissue relative to a bone, to expand the tissue, or to lengthen the tissue. For example, a balloon or bladder may be placed between tissue at the posterior of the knee portion 76 prior to mounting of the implants 286, 290 and 294. The balloon may be inflated with gas or the bladder filled with liquid to move tissue relative to the distal end portion 124 of the femur 126 and relative to the proximal end portion 212 of the tibia 214. The balloon or bladder may be used to move tissue before or after making of the femoral and/or tibial cuts. The balloon or bladder may be used to move tissue before or after the trial implants are positioned in the knee portion 76. The balloon or bladder may be used to move tissue before or after the implants 286, 290 and 294 are positioned in the knee portion 76.

The balloon or bladder may be formed of biodegradable or non-biodegradable material. If the balloon or bladder is formed of biodegradable material, it may be left in the knee portion during and after closing of the incision 114. Of course, the biodegradable balloon or bladder will eventually be absorbed by the patient's body. In this regard, a narcotic or other medicament may be incorporated in the material in the balloon or the fluid used to expand the balloon. This provides a gradual time release of the medicament as the balloon degrades. Regardless of whether the device is biodegradable, capsular tightening and capsular tissue can be expanded or stretched. In the device is left in postoperatively, the balloon or bladder provides for hemostasis and maintenance of the soft tissue sleeve to improve flexion/extension.

It is contemplated that fluid operated retractors, expanders, and/or dissectors may be used to retract, expand or dissect body tissue. For example, retractors having a construction similar to any one of the constructions disclosed in U.S. Pat. No. 5,197,971 may be utilized to release tissue at locations spaced from the incision 114. When tissue is to be released at locations where there is limited accessibility from the incision 114, a device similar to any one of the devices disclosed in U.S. Pat. No. 5,295,994 may be utilized. It is believed that devices similar to those disclosed in U.S. patent application Ser. No. 09/526,949 filed Mar. 16, 2000 may be used in ways similar to those disclosed therein to move and/or release body tissue.

While the lower portion 68 of the leg 70 is suspended from the upper portion 72 of the leg and while the upper portion of the leg is held above the support surface 64 by the leg support 80, the incision 114 in the knee portion 76 of the leg 70 is closed. Prior to closing of the incision 114, the incision is thoroughly drained. Tissues in the knee portion 78 are then interconnected using a suture or other suitable devices. The soft tissues are closed in a normal layered fashion.

Review

With the exception of the procedure on the patella 120 (FIG. 7), all of the foregoing procedures may be performed with the leg 70 of the patient in the orientation illustrated in FIGS. 2, 3 and 25. Thus, with the exception of procedures on the patella 120, all of the foregoing procedures may be conducted with the lower portion 68 of the leg 70 suspended from the upper portion 72 of the leg.

The incision 114 (FIG. 7) was made in the knee portion 76 of the leg 70 with the lower portion 68 of the leg suspended. Similarly, the incision 114 in the knee portion of the leg 70 was closed with the lower portion 68 of the leg suspended from the upper portion 72 of the leg. Thus, from the making of the incision 114 in the knee portion 76 of the leg 70 through the closing of the incision, the lower portion 68 of the leg is almost continuously extended downward from the upper portion 72 of the leg and the foot 74 was below the support surface 64. In addition, the upper portion 72 of the leg was supported above the support surface 64 by the leg support 80. Only during everting of the patella 120 (FIG. 7) and resecting of the patella to receive an implant was the leg 70 of the patient in an extended or straightened orientation. However, the leg 70 of the patient could be extended or straightened at any time the surgeon desires during the foregoing procedure.

Throughout the entire procedure, the drapery system 100 (FIGS. 4 and 5) maintained a sterile field between the surgeon 106 and the patient. As the surgeon moved between seated and standing positions and moved toward or away from the patient, the drape 102 would rise or fall. Thus, when the surgeon 106 moves from the seated position of FIG. 4 to the standing position of FIG. 5, the drape 102 tends to rise upward with the surgeon. Similarly, when the surgeon moves from the standing position of FIG. 5 back to the seated position of FIG. 4, the drape 102 tends to move downward. The drape 102 will tend to move upward as the surgeon moves away from the leg 70 of the patient and will tend to move downward as the surgeon moves toward the leg 70 of the patient. Although it is preferred to use the drapery system 100 illustrated in FIGS. 4 and 5 and the various other embodiments described in connection with these figures, it is contemplated that a different drapery system could be utilized if desired.

It is believed that it will be particularly advantageous to utilize down sized instrumentation in performing the foregoing procedures on the knee portion 76 of the patient. The femoral alignment guide 134 (FIGS. 10-15), anterior resection guide 138 (FIGS. 10-13), resection guide stand 190 (FIG. 16), distal resection guide 186 (FIGS. 16-18), and tibial resection guide 218 (FIG. 21) all have sizes which are two thirds (⅔) of their normal sizes or smaller. However, the various down sized instrumentation components of FIGS. 9-21 can be utilized in their normal manner and have generally known constructions. Thus, the instrumentation of FIGS. 9-21, with the exception of being down sized, is generally similar to known instrumentation which is commercially available from Howmedica Osteonics Corp. of Rutherford, N.J. under the trademark "Scorpio" single access total knee system.

As was previously mentioned, it is contemplated that extramedullary and/or intramedullary instrumentation could be utilized if desired. Although it is believed that it may be preferred to use instrumentation which is anteriorly based, it is contemplated that posteriorly based instrumentation systems could be used if desired. Additionally and as described below, lateral or medial based instrumentation could be used if desired. The present invention also envisions combinations of these various instrumentations.

In the foregoing description, the saw 172 and blade 170 (FIG. 15) were utilized to make cuts in various bones in the knee portion 76 of the leg 70 of the patient. The saw 172 and blade 170 may be of either the oscillating or reciprocating type. However, it is contemplated that other known cutting instruments could be utilized. For example, a milling device could be utilized to form at least some of the cuts. Alternatively, a laser or ultrasonic cutter could be utilized in making some of the cuts. It is believed that it may be particularly advantageous to utilize a laser or ultrasonic cutter to initiate the formation of a cut and then to utilize a saw or other device to complete the cut.

It is contemplated that either extramedullary or intramedullary instrumentation having a construction which is different than the illustrated construction could be utilized. For example, the anterior resection guide 138 FIGS. 10, 11 and 12 has a guide surface 178 which is formed by a slot through which the saw blade extends. If desired, the guide surface 178 could be provided on an end face without providing for capturing or holding of the saw blade 170 in a slot.

The instrumentation may be entirely or partially formed of light weight polymeric materials which are relatively inexpensive. A femoral cutting guide 210 has a size which corresponds to the size of the specific femoral component 290 which is to be installed on the distal end portion 124 of a femur 126. An inexpensive femoral cutting guide 210, formed of polymeric material, may be packaged along with a femoral component 290 of the same size. After the femoral component 290 is installed, the femoral cutting guide 210 may be discarded. This would minimize investment in instrumentation and would tend to reduce the cost of handling and/or sterilizing cutting guides. The result would be a reduction in cost to the patient.

It is contemplated that the use of guide members, corresponding to the anterior resection guide 138 of FIG. 11, the distal resection guide 186 of FIG. 16, and the tibial resection guide 218 of FIG. 21 could be eliminated if desired. If this was done, positioning of a saw blade or other cutting device could be provided in a different manner. For example, light forming a three dimensional image, such as a hologram, could be projected onto the distal end portion 124 of the femur 126. The three dimensional image would have lines which would be visible on the surface of the end portion 124 of the femur 126. The saw cut would be formed along these lines. Alternatively, robot type devices having computer controls could be utilized to form the cuts without using guide members.

It is contemplated that emitters, receivers, and/or reflectors of computer navigation systems could be pinned or otherwise attached onto the femur 126 and tibia 214 to provide cutting positions and to facilitate ligament balancing through relatively small incisions. The computer navigation system may utilize three or four separate registers which have optical feedback to a central unit. The computer navigation system may utilize electromagnetic or photo-optical feedback.

It is contemplated that various known structures could be utilized in association with the leg 70 of the patient during performing of one or more of the procedures described herein. For example, the apparatus disclosed in U.S. Pat. No. 5,514,143 could be connected with the leg 70 of the patient and used to control flexion and extension of the leg. Since the apparatus disclosed in U.S. Pat. No. 5,514,143 includes separate femoral and tibial sections, it is believed that this apparatus may be particularly well adapted for use with the leg of the patient in the orientation illustrated in FIGS. 2, 3 and 25. This apparatus does not interfere with distraction of the knee portion 76 and can accommodate flexion and extension of the leg 70 of the patient.

The foregoing description has primarily referred to a full knee replacement. However, it is contemplated that the apparatus and procedures disclosed herein may be utilized in association with a revision or partial knee replacement. For example, the method and apparatus disclosed herein could be utilized in association with a unicompartmental knee replacement of the type disclosed in the aforementioned U.S. Pat. No. 5,514,143. The method and apparatus disclosed herein could be utilized in association with a revision of a previously installed full or partial knee replacement. It is also contemplated that the procedures disclosed herein and apparatus similar to the apparatus disclosed herein may be utilized with many different types of joints. For example, the procedures and apparatus may be utilized in association with a joint in an arm, shoulder, spine or hip of a patient.

Support Assembly

Figure 30:
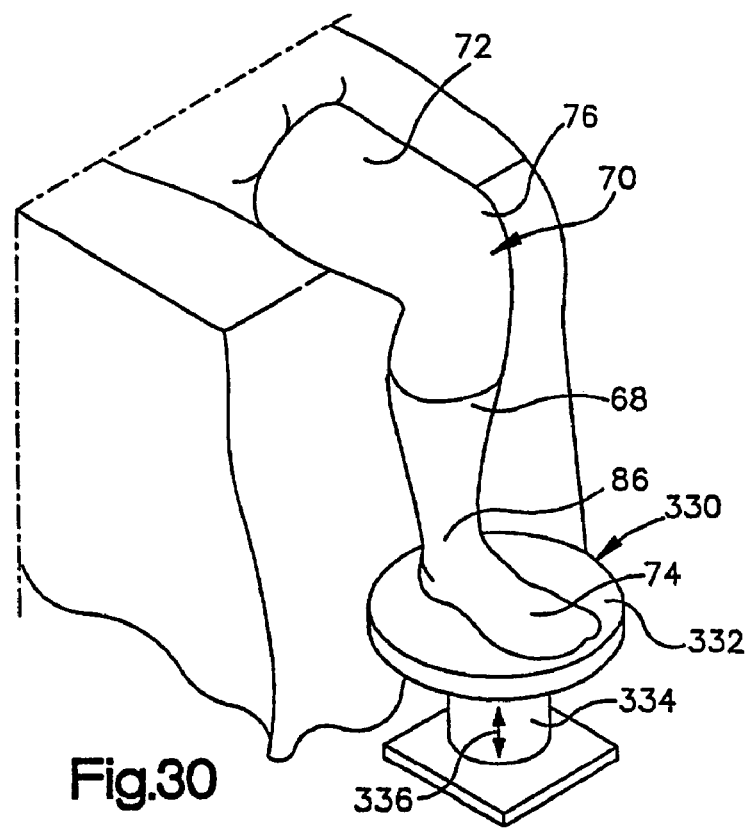
FIG. 30 is a schematic illustration of an apparatus which may be utilized to move the lower portion of a patient's leg relative to the upper portion of a patient's leg when the patient's leg is in the position illustrated in FIGS. 2 and 3.

In accordance with one of the features of the invention, a support assembly 330 (FIG. 30) is provided for the lower portion 68 of the leg 70 of the patient. Rather than support the foot 74 of the patient on the knee 252 of the surgeon (FIG. 24), as previously described herein, the support assembly 330 may be utilized. The support assembly 330 includes a flat surface 332 which engages the foot of the patient. A pneumatically actuated piston and cylinder assembly 334 is operable to raise and lower the foot 74 of the patient in the manner indicated schematically by an arrow 336 in FIG. 31. Mechanisms other than pneumatics, such as a motor, could be used to control piston and cylinder assembly 334.

When the knee portion 76 of the leg 70 is to be distracted, the piston and cylinder assembly is operated to lower the surface 332 and foot 74 of the patient. As this occurs, the weight transferred from the foot 74 of the patient to the support surface decreases until the support surface 332 is below and spaced from the foot 74. Similarly, when the extent of distraction of the knee portion 76 is to be decreased, the piston and cylinder assembly 334 is operated to raise the support surface 332 and foot 74 of the patient.

By providing a flat support surface 332, the lower portion 68 of the leg of the patient may be rotated about its longitudinal central axis relative to the upper portion 72 of the leg of the patient when the support assembly 330 is being utilized to at least partially support the lower portion 68 of the leg of the patient. However, it is contemplated that a foot holder could be provided in place of the flat surface 332. The foot holder would have the advantage of being able to hold the foot 74 of the patient in a desired orientation relative to the upper portion 72 of the leg 70 of the patient. The foot holder could be constructed so as to have a pneumatically (or other) actuated drive to rotate the foot 74 about the longitudinal central axis of the leg 70 and/or lower portion 68 of the leg 70 of the patient.

The support surface 332 is raised and lowered by operation of the piston and cylinder assembly 334. Therefore, operation of the piston and cylinder assembly 334 is effective to move the lower portion 68 of the leg 70 of the patient in the directions of the arrow 256 in FIG. 25. It is contemplated that a drive assembly could be connected with the support surface 332 to rotate the support surfaces about a vertical axis. The drive assembly may include a rack and pinion drive arrangement or a worm and wheel drive arrangement. By rotating the support surface 332 about a vertical axis relative to the piston and cylinder assembly 334, movement of the lower portion 68 of the leg 70 in the directions of the arrow 258 in FIG. 25 would be facilitated.

Percutaneous Instrumentation Mounting

In accordance with another feature of the invention, it is contemplated that the size of the incision 114 may be reduced by connecting one or more of the guide members with one or more bones through the skin of the patient. For example, the anterior resection guide 138 (FIGS. 10 and 11), distal resection guide 186 (FIG. 16), femoral cutting guide 210 (FIGS. 19 and 20), and/or tibial resection guide 218 (FIG. 21) could be mounted on the outside of the leg 70 and connected with bone in either the upper portion 72 or the lower portion 68 of the leg 70 of the patient. This would minimize or even eliminate the necessity of moving the guide through the incision 114 into engagement with the bone. It would also minimize or even eliminate the necessity of sizing the incision 114 so as to accommodate the guide.

Figure 31:
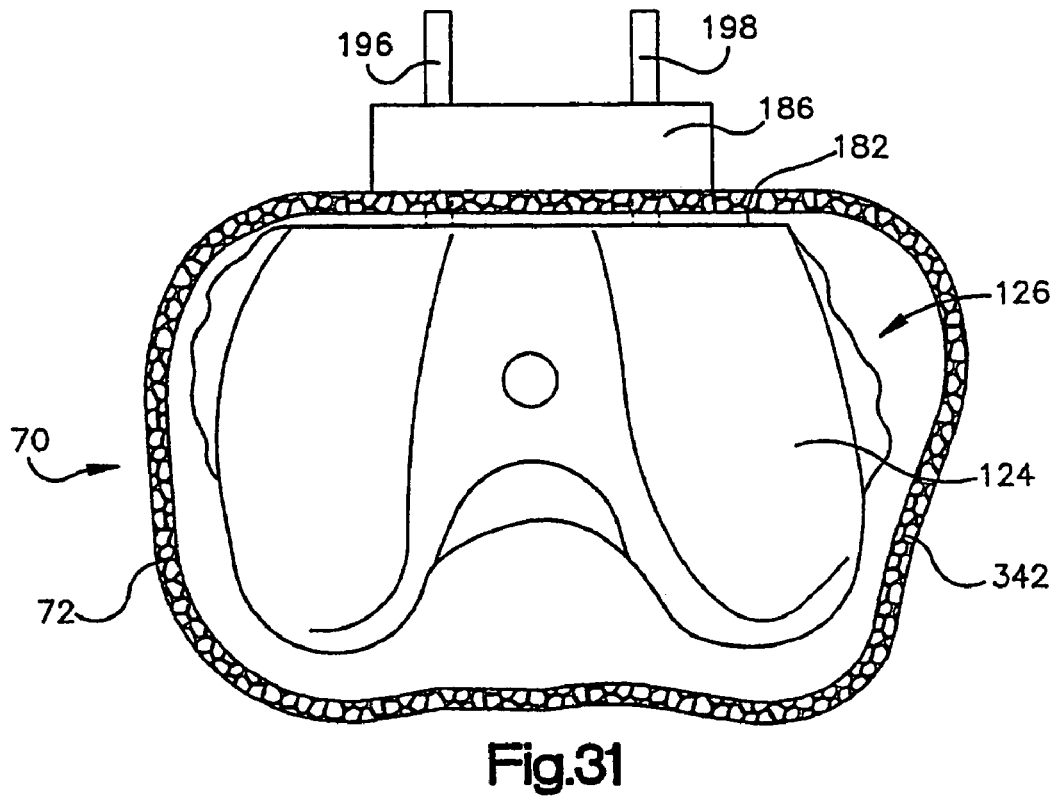
FIG. 31 is a schematic illustration depicting the manner in which a distal resection guide is connected with a patient's femur by pins which extend through the guide and through skin in the upper portion of the patient's leg into the femur with the leg of the patient in the position illustrated in FIGS. 2 and 3.

For example, the distal resection guide 186 (FIGS. 16-18) is illustrated schematically in FIG. 31 as being mounted outside of the upper portion 72 of the leg 70 of the patient. The distal resection guide 186 is illustrated in FIG. 31 as being disposed in engagement with an outer surface of skin 342 which encloses the distal end portion 124 of the femur 126. The distal resection guide 186 is mounted directly outward of the flat anterior cut surface 182 formed on the distal end portion 124 of the femur 126. The skin 342 and other body tissue extends between the distal resection guide 186 and the distal end portion 124 of the femur 126.

The distal resection guide 186 is connected with the femur 126 by the pins 196 and 198. The pins 196 and 198 extend through the distal resection guide 186 and the skin 342 into the femur 126. The pins 196 and 198 extend through the flat anterior cut surface 182 into the femur 126 and hold the distal resection guide 186 against movement relative to the femur 126.

Although a distal resection guide 186 has been illustrated in FIG. 31, it is contemplated that an anterior resection guide, corresponding to the anterior resection guide 138 of FIG. 11 could be mounted in a similar manner. If this were done, the anterior resection guide 138 would have a generally L-shaped configuration with a body portion which would extend along the outer surface of the skin 342 (FIG. 31). Pins, corresponding to the pins 196 and 198 of FIG. 31, would extend through the relatively long body portion of the generally L-shaped anterior resection guide 138, through the skin 342 and into the femur 126.

The short leg of the L-shaped anterior resection guide 138 would be positioned adjacent to the distal end portion 124 of the femur 126. The short leg of the anterior resection guide would have a guide surface aligned with the distal end portion 124 of the femur 126 at a location corresponding to the location where the flat anterior cut surface 182 is to be formed. This guide surface could be of the slot or capture type illustrated in FIG. 14. Alternatively, the guide surface could be formed on a flat end face of the anterior resection guide. This would result in elimination of the slot commonly utilized to capture a saw blade or other cutting instrument. By having a portion of the anterior resection guide disposed outside of the incision 114 and connected with the femur 126 through the skin 342, the size of the incision 114 tends to be minimized.

In addition to the aforementioned guides associated with the femur 126, it is contemplated that a guide associated with the tibia 214 (FIG. 21) could be connected with the tibia by pins extending through the skin 342. For example, the tibial resection guide 218 could be placed in abutting engagement with skin which overlies the proximal end portion 212 of the tibia 214. Suitable pins would extend through the tibial resection guide 218 (FIG. 21) and through the skin 342 (FIG. 31) into engagement with the distal end portion 212 of the tibia. Although it may be preferred to provide a tibial guide surface 242 of the slot type illustrated in FIG. 22, it is contemplated that only a single guide surface could be provided on a flat end portion of the tibial resection guide if desired.

Inspection

It is contemplated that at various times during the performance of the foregoing procedures, it may be desired to inspect locations remote from the incision 114. Thus, it may be desired to visually ascertain the condition of soft tissue in the posterior of the knee portion 76. In addition, it may be desired to visually check the condition of the collateral ligaments or soft tissue adjacent to the ligaments. The inspections may be conducted before or after the making of femoral and tibial cuts, before or after trials, and/or before or after installation of the implants 286, 290 and 294.

In accordance with another feature of the invention, locations remote from the limited incision may be visually inspected. To inspect locations remote from the incision 114, a leading end portion 350 (FIG. 32) of an endoscope 352 can be inserted through the incision 114 and moved to the posterior of the knee portion 76. Alternatively, the leading end portion 350 of the endoscope 352 can be inserted through a smaller stab wound incision. A camera 354 transmits an image to a monitor 356. The surgeon 106 can then view images of the posterior of the knee portion 76 transmitted through the endoscope 352. The upper portion 72 of the leg 70 is supported by the leg support 80. The leg 70 is shown in FIG. 32 in the same position illustrated in FIGS. 2 and 3.

In order to provide the surgeon 106 with information as to how the femoral and tibial implants 286, 290 and 294 interact with tissues in the knee portion 76, the leg 70 of the patient may be bent between the flexed condition of FIG. 32 and the extended condition of FIG. 33. In addition, the lower portion 68 of the leg 70 may be rotated about its longitudinal central axis, in the manner indicated by the arrow 258 in FIG. 25. During bending of the knee portion 76, the surgeon views images of the posterior knee portion transmitted through the endoscope 352 to the monitor 356. This enables the surgeon to detect any present or potential interference of tissue in the knee portion 76 with the full range of motion of the knee portion. During relative movement between the femur 126 and tibia 214, the surgeon can view the manner in which the femoral and tibial implants interact with each other and the tissue in the joint capsule.

It is contemplated that the end portion 350 of the endoscope 352 will be moved so as to enable the surgeon 106 to view the collateral ligaments, particularly the ligament on the lateral side of the knee portion 76, during bending of the knee portion. Although the endoscope 352 is illustrated in FIGS. 32 and 33 as being utilized after the femoral and tibial implants 286, 290 and 294 have been connected with the femur 126 and tibia 214, it is contemplated that the endiscope will be utilized prior to cutting of the femur and tibia, after cutting of the femur and tibia and prior to trials, after trials, and/or during trials.

It is contemplated that the endoscope 352 may be inserted into the knee portion 76 of the patient at a location other than through the incision 114. Thus, if desired, a separate, very small portal or puncture type incision could be formed in the knee portion 76 of the leg of the patient at a location adjacent to a location where it is desired to visually inspect the knee portion of the patient. Although it is believed that it will be desired to inspect the knee portion 76 of the patient while there is relative movement between the femur 126 and tibia 214, it should be understood that the endoscope 352 could be utilized to inspect the knee portion 76 while the femur 126 and tibia 214 are stationary relative to each other.

Although an endoscope 352 is illustrated in FIGS. 32 and 33, it is contemplated that other known devices could be utilized to inspect knee portion 76. Thus any desired fiber optic type instruments may be utilized to inspect the knee portion 76. For example any of the known instruments associated with arthroscopic surgery could be utilized to inspect the knee portion 76.

Generation of Images and Robotic Device

In accordance with another feature of the invention, during performance of surgery on a knee portion 76 of a patient's leg 70 (FIG. 34), a known C-arm fluoroscope 360 or other imaging system is utilized to generate images of the knee portion 76 of the leg 70 during movement of the lower portion 68 of the leg relative to the upper portion of the leg. Images are transmitted in any fashion from the C-arm fluoroscope 360 to a control unit 362. Video images are transmitted from the control unit 362 to a video screen 364 which is viewable by the surgeon 106 during surgery on the knee portion 76 of the leg 70. A continuous display of images is projected in rapid succession on the screen illustrating the knee portion 76 of the leg 70 when the lower portion 68 of the leg is in various positions relative to the upper portion of the leg.

Thus, during flexion and/or extension of the leg 70, video images are transmitted to the screen 364 to enable a surgeon to view images of the distal end portion 124 of the femur 126 and the proximal end portion 212 of the tibia 214 during bending of the knee portion. The video display of images may be undertaken prior to forming of the incision 114 to enable the surgeon to view the manner in which components of the knee portion 76 interact prior to surgery. After the incision 114 has been made, the images provided on the video screen 364 enable the surgeon to visually determine the relationship between the distal end portion 124 of the femur 126 and the proximal end portion 212 of the tibia 214 after the patella 120 has been moved to an offset position and prior to initiating any cuts on the bones in the patient's leg 70.

After cuts have been made on the distal end portion 124 of the femur 126 and the proximal end portion 212 of the tibia 214 in the manner previously explained, the lower portion 68 of the patient's leg can be moved relative to the upper portion 72 of the patient's leg. The images provided on the video screen 364 will enable a surgeon to better understand the relationship between the femur, tibia, and ligaments in the patient's leg during preliminary checking of ligament balancing after the distal end portion 124 of the femur 126 has been cut and after the proximal end portion 212 of the tibia 214 has been cut.

During trials when trial tibial and femoral components have been temporarily connected with the femur 126 and tibia 214, the images provided at the video screen 364 will enable the surgeon to better evaluate the interaction between the trial components and body tissue in the knee portion 76 of the patient's leg 70. Once the trials have been completed and the femoral and tibial implants 286, 290 and 294 positioned on the femur 126 and tibia 214, the images provided at the video screen 364 will enable the surgeon to evaluate the relationship between the femoral and tibial implants.

During ligamentous balancing, images provided at the video screen 364 will indicate to the surgeon whether or not there is any undesired relative movement between the femoral and tibial implants. It is contemplated that the images be transmitted from the control unit 362 to the video screen 364 during movement of the lower portion 68 of the patient's leg 70 in any one or a combination of the directions indicated by the arrows 256, 258, 259 and 260 in FIG. 25. Once the surgeon, with the assistance of images provided at the video screen 364, is satisfied that the femoral and tibial implants 286, 290 and 294 have been correctly positioned in the knee portion 76 of the patient's leg 70, the incision 114 is closed.

The general construction and mode of operation of the C-arm fluoroscope 360 (FIG. 34) and control unit 362 is the same as is disclosed in U.S. Pat. Nos. 5,099,859; 5,772,594; 6,118,845 and/or 6,198,794. However, it is contemplated that other known image generating devices could be utilized in place of the fluoroscope if desired. For example, an image generating device similar to a magnetic resonance imaging unit (MRI) could be utilized.

In accordance with still another feature of the invention, a robot 370 (FIG. 34) is provided to perform cutting and/or implant placement operations on the knee portion 76 in the leg 70 of a patient. The robot 370 includes a base 372. A support column 374 is moveable vertically relative to the base 372, in a manner indicated by arrows 376 in FIG. 34. In addition, the support column 374 is rotatable about coincident longitudinal central axes of the base 372 and support column in a manner indicated schematically by arrows 378 in FIG. 32. A main arm 382 is pivotally attached to an upper end portion of the support column 374. Motors and controls 386 are connected with the main arm 382. The main arm is pivotal relative to the support column 374 in the manner indicated by arrows 388 in FIG. 34.

A secondary arm 390 is pivotally mounted on an outer end portion of the main arm 382. The secondary arm 390 is pivotal relative to the main arm 382 in the manner indicated by arrows 392. A mounting section 396 is rotatable about a longitudinal central axis of the secondary arm 390 and has a mounting flange which is rotatable about an axis which extends perpendicular to the longitudinal central axis of the secondary arm 390.

It is contemplated that a cutting tool, such as the saw 172, may be mounted on the mounting section 396. Controls for the robot 370 effect movement of the saw relative to the distal end portion 124 of the femur 126 to form the anterior cut surface 182 on the femur and to form a distal end cut on the femur. In addition, the robot 370 moves the saw to form chamfer cuts on the distal end portion 124 of the femur 126.

The robot 370 may also be utilized to move the saw to make the cuts to form the proximal end portion 212 of the tibia 214. Thus, the robot may be utilized to form the proximal tibial cut surface 246 (FIG. 22).

By using the robot 370 to move the saw to form the cuts on the distal end portion 124 of the femur 126 and on the proximal end portion 212 of the tibia 214, the need for instrumentation, such as the femoral alignment guide 134 and anterior resection guide 138 of FIG. 11, the distal resection guide 186 of FIGS. 16 and 18, and the tibial resection guide 218, is eliminated. Controls for the robot 370 are connected with the C-arm fluoroscope 360 to enable the position of the saw relative to the femur and tibia to be viewed by the surgeon during an operation.

The robot 370 may have any one of many different constructions. Specifically, it is contemplated that the robot 370 may have the same construction as is disclosed in U.S. Pat. No. 5,154,717. Alternatively, the robot 370 could have the construction disclosed in U.S. patent application Ser. No. 09/789,621 filed Feb. 21, 2001 by Peter M. Bonutti. However, it should be understood that other known robots could be utilized if desired. For example, a robot similar to the known "Robo Doc"™ could be utilized.

It is contemplated that a computer navigation system may be used with the robot 370 to guide movement of a cutting tool, such as a saw or milling cutter, relative to the tibia and femur in the leg 70 of the patient. Two or more locating devices are connected with the distal end portion 124 of the femur 126. In addition, two or more locating devices are connected to the proximal end portion of the tibia 214. The locating devices cooperate with motors and computer controls 386 for the robot 370 to provide the robot with information as to the position of the mounting section 396 and cutting tool relative to the femur 126 and tibia 214.

The locating devices may be of the reflective or energy emitting type or energy receiving type. For example, three reflectors may be pinned onto the distal end portion 124 of the femur 126. Similarly, three reflectors may be pinned onto the proximal end portion 212 of the tibia 214. Light transmitted from the robot 370 to the reflectors on the femur and tibia is reflected back to photo cells on the robot to enable the robot to determine the positions of the femur and tibia. Rather than using reflectors, energy emitting devices may be pinned onto the femur 126 and tibia 214. The energy emitting devices may emit either light or radio waves.

The above-described image guided surgery system is merely intended to be representative of the type of system that can be used with the present invention. However, it should be understood that other known image guided surgery systems, both in conjunction and independent of robotic systems, could be utilized if desired. Examples of commercially available systems include systems the Z-KAT (Hollywood, Fla.) suites, the MEDIVISION system (Oberdorf, Switzerland), the STEALTH NAVIGATOR system (Louisville, Colo.), and the ORTHOPILOT System (Tuttlingen, Gemany).

It should also be understood that the robot 370 could have any one of many different constructions. It is also contemplated that the robot 370 could interact with a surgeon and patient in many different ways. For example, the robot could have a plurality of articulate arms which are controlled by the surgeon. Images provided by the fluoroscope 360 would enable the surgeon to control the articulate arms. Locating devices connected with the femur and tibia are visible to the surgeon in images provided by the fluoroscope 360. Computer controls which respond to the locating devices provide information to the surgeon about cutting tools and/or other instruments being moved by the articulate arms. The surgeon operated controls, the articulate arms, and the fluoroscope or other imaging device may cooperate in the manner disclosed in U.S. Pat. Nos. 6,063,095 and 6,102,850 if desired.

It is believed that it may be desired to use a hologram to provide a three-dimensional optical image of cuts to be made. The three-dimensional image would be projected onto the end portion 124 of the femur 126 and/or onto the end portion 212 of the tibia 214. The three-dimensional image may be lines indicating where the femur 126 and/or tibia 214 are to be cut.

The three dimensional image would allow a surgeon 106 to visually monitor operation of the robot 370 during the making of cuts. If there was even a small discrepancy, the surgeon 106 could interrupt operation of the robot and take corrective action. It is believed that the projecting of a three-dimensional image onto surfaces to be cut will be particularly advantageous when a robotic system which has surgeon operated articulate arms is utilized. The projection of a hologram generated three-dimensional image would enable a surgeon to visually determine whether or not a robotic system, similar to the system disclosed in U.S. Pat. No. 6,063,095 or 6,102,850, is being operated properly.

Patellar Resection

In the foregoing description, the patella 120 was everted or flipped from its normal position to a position in which an inner side 122 of the patella faces outward (FIG. 7). The patella 120 was then cut while it was in the everted position. A patellar implant was then mounted on the patella 120 in a known manner. The patella 120 was then returned to its normal position with the inner side of the patella facing inward toward the distal end portion 124 of the femur 126. This is a well known manner of performing surgery on a patella to install a patellar implant.

In accordance with one of the features of the present invention and as discussed above, it is contemplated that the patella 120 will be cut and an implant positioned on the patella while the patella remains in a substantially normal position relative to the femur 126. When the patella 120 is in its normal position relative to the femur 126 (FIG. 35), an inner side 122 of the patella 120 is disposed adjacent to the distal end portion 124 of the femur 126. The patella 120 is urged toward the trochlear groove 452 in the distal end portion 124 of the femur 126 by the patellar tendon 456 and the patellar ligament 458. The patellar tendon 456 connects the patella 120 with the quadriceps femoris muscle. The patellar ligament 458 connects the patella 120 with the tibia 214. The patellar tendon 456 and patellar ligament 458 may be referred to as fibrous connective tissue.

Figure 35:
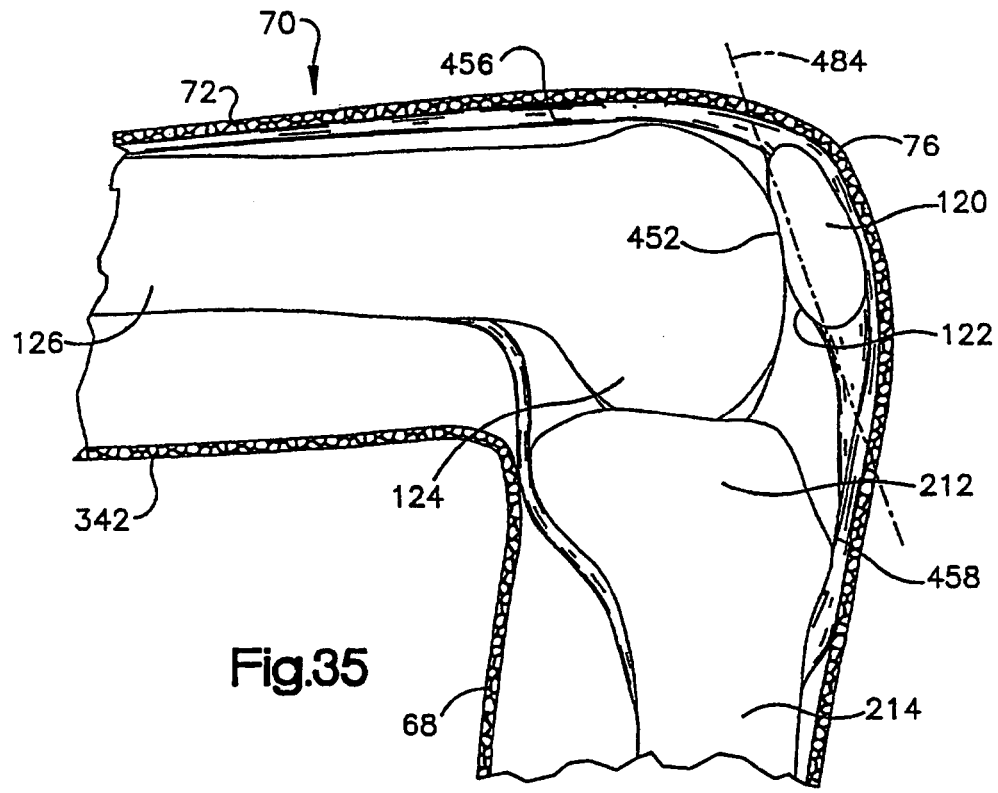
FIG. 35 is a schematic illustration depicting the relationship of a cut line to a patella in a knee of the leg of the patient with the leg in the position illustrated in FIGS. 2 and 3 and with the patella in the normal position.

While the patella 120 is in the normal position illustrated in FIG. 35, a guide assembly 464 (FIG. 36) is positioned relative to the patella. The guide assembly 464 includes a main section 466 (FIG. 36) with a slot 468 having guide surfaces along which a blade 170 of a saw 172 is moved. The main section 466 of the guide assembly 464 is positioned relative to the patella 120 by a pair of parallel arms 474 and 476.

The arm 474 extends through the medially offset incision 114 and under the superior aspect 480 of the in situ patella 120. The arm 476 extends through the incision 114 and under the inferior aspect 482 of the in situ patella 120. By positioning the arm 474 under the upper end portion 480 of the patella and the arm 476 under the lower end portion 482 of the patella 120, the guide surfaces in the slot 468 are accurately aligned with the patella 120 while the patella is in its normal position relative to the femur 126 and tibia 214 (FIG. 35).

While the in situ patella 120 is urged toward the distal end portion 124 of the femur 126 by the patellar tendon 456 and the patellar ligament 458 (fibrous connective tissue), the saw 170 or other cutting tool cuts along a plane 484 (FIG. 35) to form a flat surface on the inside of the patella 120. A relatively thin layer on which the inner side 122 of the patella is disposed, is then removed from the patella 120. A patellar prosthesis or implant is then mounted on the cut surface on the inside of the patella while the patella remains in its normal position. A suitable cement can be utilized to connect the implant with the patella. In addition, one or more projections may be provided on the inside of the implant to interconnect the implant and the patella in a known manner.

The guide assembly 464 can include inflatable bladders as an adjunct or replacement for arms 474 and 476. These bladders would elevate the patella 120 to obtain access to inner side 122. In this regard, U.S. Pat. No. 5,163,949 and progeny, such as U.S. Pat. Nos. 6,358,266 B1, 6,277,136 B1, and 6,187,023 B1, discloses various embodiments of retractors and method of dissecting tissue. These embodiments include fluid operated retractors, mechanical retractors, and combinations thereof. The retractors and methods disclosed in this line of patents, which is incorporated herein by reference, can be used for patella procedures and/or visualization while the patella is maintained in a substantially non-everted, anatomic position.

If desired, the patella 120 may be repaired before making cuts on the femur 126 and tibia 214. Thus, immediately after making the incision 114, the patella 120 may be cut while it is disposed in its normal position. An implant may then be mounted on the patella 120. The surgically repaired patella 120 may then be moved to the offset position of FIG. 8. The femoral and tibial cuts may then be made in the manner previously explained in association with FIGS. 8-25 and the tibial and femoral implants 286, 290 and 294 mounted on the femur 126 and tibia 214 (FIGS. 27-29) while the previously repaired patella is in the offset position.

Extramedullary Tibial Instrumentation

When a tibial resection guide 500 (FIGS. 37 and 38) or the tibial resection guide 218 (FIG. 21) is to be positioned relative to the proximal end portion 212 of the tibia 214, an external tibial alignment guide 504 (FIG. 37) may be used to position the tibial resection guide relative to the tibia 214. The external tibial alignment guide 504 is disposed outside of the patient's leg 70 and extends along the lower portion 68 of the patient's leg. If desired, the patient's leg can be in the position illustrated in FIGS. 2, 3, and 25.

The external tibial alignment guide 504 (FIG. 37) includes a hollow distal shaft 508. A proximal shaft 510 is telescopically received in the distal shaft 508. When the proximal shaft 510 has been extended for a desired distance from the distal shaft 508, a vertical adjustment knob 514 is tightened to hold the proximal shaft 510 against movement relative to the distal shaft 508.

The foot or lower end portion of the hollow distal shaft 508 is connected with the mid-point between the palpable medial and lateral malleoli by a spring clamp 518. The spring clamp 518 is aligned with the second metatarsal and grips the outside of the ankle portion 86 (FIG. 25) of the patient's leg 70. The proximal shaft 510 (FIG. 37) of the external tibial alignment guide 504 is aligned with the medial third of the tibial tubercle. This results in the external tibial alignment guide 504 being positioned along the outside of the patient's leg with the longitudinal axis of the external tibial alignment guide 504 extending parallel to a longitudinal central axis of the tibia 214.

A stylus 522 (FIG. 38) is mounted on the tibial resection guide 500. The stylus 522 engages the proximal end portion 212 of the tibia to position the tibial resection guide 500 relative to the tibia. The tibial resection guide 500 is connected to the proximal end portion 212 of the tibia by a single pin 524 (FIG. 38) which extends through the tibial resection guide 500 into engagement with the proximal end portion 212 of the tibia 214. The external tibial alignment guide 504 and the stylus 522 cooperate with the tibial resection guide 500 and pin 524 to hold the tibial resection guide against rotation.

Although the tibial resection guide 500 has been shown in FIG. 38 as being connected directly to the proximal end portion 212 of the tibia 214, the tibial resection guide could be connected with proximal end portion 212 of the tibia 214 in different manner. Thus, in FIG. 38, the posterior facing side of the tibial resection guide 500 is disposed in abutting engagement with the proximal end portion 212 of the tibia 214. However, the posterior facing side of the tibial resection guide 500 could be positioned in engagement with skin which encloses the proximal end portion 212 of the tibia 214 in order to minimize the overall length of the incision 114. This would result in the pin 524 extending through the tibial resection guide and through the skin and other tissue overlying the proximal end portion 212 of the tibia 214 into engagement with the proximal end portion of the tibia. The manner in which the tibial resection guide would be mounted on the tibia, would be similar to that disclosed in FIG. 31 for the distal resection guide 186. However, the tibial resection guide 500 is secured in place by a single pin 524, by the external tibial alignment guide 504, and, to some extent at least, the stylus 522.

The tibial resection guide 500 is medially offset from the external tibial alignment guide 504. This is because the incision 114 (FIG. 6) is disposed adjacent to the medial edge portion of the patella 120. If desired, the incision 114 could be disposed adjacent to the lateral side of the patella 120. If this was done, the tibial resection guide 500 would be laterally offset from the external tibial alignment guide 504. Regardless of which direction the tibial resection guide 500 is offset, a portion of the tibial resection guide may be disposed beneath body tissue to minimize the size of the incision 114.

In accordance with a feature of the apparatus of FIGS. 37 and 38, the external tibial alignment guide 504 is maintained in position on the tibia 214 during cutting of the proximal end portion 212 of the tibia 214 in a manner similar to that illustrated in FIG. 21. Maintaining the tibial alignment guide 504 in place during cutting of the proximal end portion 212 of the tibia 214, enables the tibial alignment guide to be utilized to position the tibial resection guide 500 relative to the tibia 214. This enables the tibial resection guide 500 to be connected to the tibia 214 by only the single pin 524. In the past, a plurality of pins have been utilized to connect the tibial resection guide 500 with the tibia 214 in a manner similar to the disclosures in U.S. Pat. Nos. 5,234,433 and 5,643,272. It should be understood that the tibial alignment guide 504 and a tibial resection guide, similar to the tibial resection guide 500, may be utilized during performance of a partial knee replacement in the manner disclosed in the aforementioned U.S. Pat. No. 5,234,433.

Since, the external tibial alignment guide 504 is maintained in position during cutting of the tibia, the saw blade 170 or other cutting tool must be angled around the proximal shaft 510 of the external tibial alignment guide 504 as the proximal end portion 212 of the tibia 214 is cut. During movement of the saw blade 170 (FIGS. 13 and 21) along the guide surface 530 (FIG. 38), only an initial portion of the cut in the proximal end portion 212 of the tibia is made. This is because the proximal shaft 510 of the external tibial alignment guide 504 partially blocks the saw blade 170. In addition, the tibial resection guide 500 is down sized.

Opposite ends 534 and 536 of the tibial resection guide 500 are space apart by a distance less than two thirds (⅔) of the distance between tips of lateral and medial epicondyles 236 and 238 (FIG. 38) on the proximal end portion 212 of the tibia 214. Therefore, after an initial portion of the cut across the proximal end portion 212 of the tibia 214 has been made while moving the saw blade 170 along the guide surface 530, the tibial resection guide 500 and external tibial alignment guide 504 are disconnected from the tibia 214. The tibial cut is then completed.

During completion of the tibial cut, the guide surface 530 on the resection guide 500 is not in position to guide the saw blade 170. Therefore, cut surfaces formed during the making of the initial portions of the tibial cut are utilized to guide the saw blade. When the tibial cut is to be completed the saw blade 170 is inserted into a slot or kerf formed in the distal end portion 212 of the tibia 214 by the saw blade 170 as it moved along the guide surface 530 and made the initial portion of the tibial cut. During completion of the tibial cut, the cut surfaces which were formed on the proximal end portion 212 of the tibia 214 during the initial portion of the tibial cut are used to guide movement of the saw blade.

The tibial resection guide 218 of FIG. 21 has a guide surface 242 formed by a closed ended slot. The tibial resection guide 500 of FIG. 38 has a guide surface 530 formed by an open ended slot. Thus, the tibial resection guide 500 includes a slot 540 which has an open end 542. The open end 542 of the slot 540 facilitates movement of the saw blade 170 along the slot and angling of the saw blade relative to the slot to maximize the extent of the initial portion of the tibial cut. Thus, the extent of the tibial cut formed during movement of the saw blade along the guide surface 530 on the tibial resection guide 500 is maximized by forming the slot 540 with the open end 542 so that the saw blade can be angled at the open end 542 of the slot.

The tibial resection guide 500 may be used with a first cutting tool during making of the initial portion of the tibial cut. A second cutting tool may be used to complete the tibial cut. For example, a relatively small blade 170 of an oscillating saw 172 may be used to make the initial portion of the tibial cut. A relatively long blade of a reciprocating saw may be used to complete the tibial cut. If desired, a chisel and/or milling cutter could be used to make the initial portion and/or final portion of the tibial cut.

It is contemplated that it may be desired to set the tibial resection guide 500 (FIG. 37) for any one of a plurality of different resection levels. Thus, the tibial resection guide 500 could be set to make a tibial cut at a distance of two millimeters from a location on the proximal end portion 212 of the tibia 214 which is engaged by the stylus 522. Alternatively, the tibial resection guide 500 could be utilized to make a cut at a distance of eight millimeters from the location where the stylus 522 engages the proximal end portion 212 of the tibia 214. Of course, the greater the distance at which the tibial cut is made from the location where the stylus 522 engages the proximal end portion 212 of the tibia 214, the greater will be the thickness of a layer of bone removed from the distal end portion 212 of the tibia 214.

To facilitate movement of the tibial resection guide 500 between various depths, the stylus 522 includes a drive assembly 548 (FIG. 38). The drive assembly 548 is actuated by rotating a knob 550 on the stylus. Rotation of the knob 550 through a predetermined distance, that is, one complete revolution, will cause the drive assembly 548 to move the tibial resection guide 500 for a predetermined distance along the proximal shaft 510 of the external tibial alignment guide 504. Thus, rotation of the knob 550 for one complete revolution in a clockwise direction, viewed from above, is effective to move the tibial resection guide 500 through a distance of two millimeters downwards along the proximal shaft 510 of the external tibial alignment guide. Of course, this would increase the depth of the tibial cut by a distance of two millimeters. Similarly, rotating the knob 550 through two complete revolutions is effective to actuate the drive assembly 548 to move the tibial resection guide 500 downward (as viewed in FIG. 39) along the proximal shaft 510 of the external tibial alignment guide 504 through a distance of four millimeters.

The drive assembly 548 includes an externally threaded member which is connected with the knob 550. An internally threaded member is connected with the tibial resection guide 500. The internally threaded member engages the externally threaded member and is held against axial and rotational movement relative to the tibial resection guide 500.

After the tibial resection guide 500 has been moved to a desired position relative to the proximal end portion 212 of the tibia 214, a locking knob 556 is rotated to actuate a lock screw to hold the tibial resection guide 500 against movement along the proximal shaft 510 of the external tibial alignment guide 504. The pin 524 is then inserted through the tibial resection guide 500 into the proximal end portion 212 of the tibia 214.

Rather than moving the tibial resection guide 500 along the proximal shaft 510 of the external alignment guide 504 under the influence of force transmitted from the knob 550 through the drive assembly 548 to the tibial resection guide, the drive assembly could be connected with the knob 556. For example, the knob 556 could be connected with a pinion gear of a rack and pinion drive arrangement. The rack portion of the drive arrangement could be mounted on the proximal shaft 510. If this was done, rotation of the knob 556 would cause the rack and pinion gear set to move the tibial resection guide along the proximal shaft 510 through a distance which is a function of the extent of rotation of the knob 556. The stylus 552 would be connected to the tibial resection guide 500 and would engage the proximal end of the tibia 214 to indicate when the tibial resection guide 500 had moved to a desired position relative to proximal end portion 212 of the tibia.

It is contemplated that the stylus 522 could be eliminated if desired. The tibial resection guide 500 could be positioned by sliding a thin member, such as a blade, beneath tissue overlying the proximal end portion 212 of the femur 214. A reference surface on the tibial resection guide 500 would then be moved into engagement with the blade or other thin member. The reference surface may be disposed on the upper (as viewed in FIG. 38) end of the tibial resection guide 500 or may be disposed in a slot in the tibial resection guide. The reference surface may also be utilized to guide movement of a saw or other cutting tool.

If desired a hook or sickle shaped locating member could be extended from the tibial resection guide 500 to position the tibial resection guide relative to the proximal end portion 212 of the tibia 214. When the incision 114 and tibial resection guide 500 are medially offset relative to the tibia 214, the locating member would extend along the medial side of the proximal end portion 212 of the tibia. This would enable the stylus 522 to be eliminated.

It is contemplated that retractors may be mounted on the proximal shaft 510 of the external tibial alignment guide 504. The retractors engage opposite sides of the incision. The retractors are effective to expand the incision 114 and/or maintain the incision in a desired position relative to the proximal end portion 212 of the tibia 214.

Cannula

Figure 39:
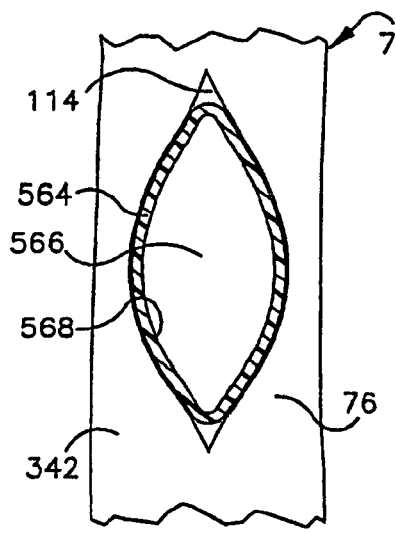
FIG. 39 is a schematic illustration depicting the relationship between an expandable cannula and an incision in the knee portion of one leg of the patient with the leg of the patient in the position illustrated in FIGS. 2 and 3.

In accordance with another feature of the invention, access to the interior of the knee portion 76 of the leg 70 may be obtained through a cannula 564 (FIG. 39). The cannula 564 is inserted into the incision 114. If desired, the patient's leg 70 can be in the position shown in FIGS. 2, 3 and 25. The upper portion of the patient's leg is supported by the leg support 80.

The incision 114 is formed with a relatively short length in the manner previously described herein. The cannula 564 has an initial size, illustrated in FIG. 39, which stretches the viscoelastic material of tissues forming the knee portion 76 of the leg 70. Therefore, initial insertion of the cannula 564 into the incision 114 is effective to expand the incision.

Compact cutting tools, similar to those utilized for arthroscopic, endoscopic, or fiber optic assisted surgery may be at least partially moved through a passage 566 (FIG. 39) formed by an inner side 568 of the cannula 564. The cutting tools may have a construction similar to the construction illustrated in U.S. Pat. No. 5,540,695 or 5,609,603. Alternatively, the cutting tools may have a construction similar to the construction disclosed in U.S. patent application Ser. No. 09/483,676 filed Jan. 14, 2000 by Peter M. Bonutti and having a disclosure which corresponds to U.S. Pat. No. 5,269,785.

The cannula 564 is advantageously expandable to further stretch the viscoelastic tissue of the knee portion 76. Of course, expanding the cannula 564 increases the size of the passage 566 to enable a relatively large object to pass through the passage. Thus, the cannula 564 may be expanded to facilitate movement of the implants 286, 290 and 294 through the cannula. The leg 70 is in the position shown in FIGS. 2, 3 and 24 during expansion of the cannula and movement of objects through the passage 566.

It is contemplated that the expandable cannula 564 may have many different known constructions. The illustrated cannula 564 is formed of elastomeric material and has the same construction as is disclosed in U.S. patent application Ser. No. 08/470,142 filed Jun. 6, 1995 by Peter M. Bonutti, et al. and having a disclosure which corresponds to the disclosure in U.S. Pat. No. 5,961,499. It should be understood that the cannula 564 could have a different construction, for example, a construction similar to the constructions disclosed in U.S. Pat. No. 3,811,449 or 5,183,464.

The cannula 564 can be expanded in many different ways other than under the influence of force transmitted directly to the cannula from an object moving through the cannula. For example, the cannula may be expanded by force transmitted from an implant 286, 290 and/or 294 to the cannula. The cannula 564 may be expanded by inserting tubular members into the cannula. Alternatively, fluid pressure could be used to expand the cannula 564 in the manner disclosed in the aforementioned Bonutti, et al. patent application Ser. No. 08/470, 142 filed Jun. 6, 1995.

Rather than being expanded by inserting the expandable cannula 564 into the incision 114, the incision may be expanded by utilizing pneumatic retractors. The pneumatic retractors may have a construction similar to the construction disclosed in U.S. Pat. No. 5,163,949. By utilizing the expandable cannula 564 or the expandable pneumatic retractors, force can be applied against opposite sides of the incision 114 to stretch the viscoelastic material disposed adjacent to opposite sides of the incision. This will result in the relatively small incision 114 being expanded to accommodate relatively large surgical instruments and/or implants.

Although a single incision 114 is illustrated in FIG. 39, it is contemplated that a plurality of incisions could be provided. Thus, a small incision may be spaced from the incision 114 to enable a cutting tool to be moved into the knee portion 76 along a path which is spaced from and may be transverse to a path along which a cutting tool is moved through the incision 114. A second cannula, which is smaller than the cannula 564, may be utilized with the second incision.

Implant with Interconnectable Portions

Figure 40:
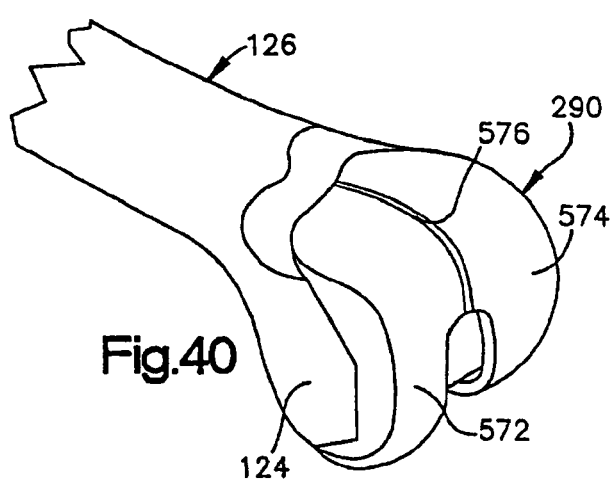
FIG. 40 is a schematic illustration depicting the relationship between two separate portions of an implant which are interconnected within the patient's body.

In order to enable surgery on a knee portion 76 of a patient's leg 70 to be conducted through an incision 114 of relatively small size, the implant may advantageously be formed in two or more portions (FIG. 40). The portions of the implant are sequentially moved through the incision 114 into engagement with the distal end portion 124 of the femur 126 and/or the proximal end portion 212 of the tibia 214. It is believed that having the implant formed as two or more portions will facilitate movement of the implant through the cannula 564 (FIG. 39).

As the portions of the implant are sequentially moved through the incision 114, they are positioned in engagement with one or more of the bones, that is, the femur 126 and/or the tibia 214 in the leg 70 of a patient. After the plurality of portions of the implant have been moved through the incision 114 and positioned in engagement with the femur 126 and/or tibia 214, the portions of the implant are interconnected to form a unitary implant. If desired, the portions of the implant are moved through the incision 114 and interconnected while the leg of the patient is in the position illustrated in FIGS. 2, 3 and 25.

It is contemplated that the portions of the implant may be interconnected, while they are disposed in the patient's body and in engagement with either the femur 126 and/or tibia 214, in many different ways. For example, the portions of the implant may be bonded together to form a one piece implant. The portions of the implant may be bonded together by the application of energy in anyone of many different forms to a joint between portions of the implant. For example, ultrasonic energy could be applied to the implant. Alternatively, heat could be directly applied to the implant. If desired, a laser could be utilized to effect bonding of separate portions of the implant together.

It is also contemplated that the separate portions of the implant could be mechanically interconnected. This could be done with a fastener which extends between portions of the implant. Alternatively, a retainer member such as a rod or bar could extend between portions of the implant. Regardless of how the portions of the implant are interconnected, the portions of the implant are interconnected after they have been moved into the patient's body.

In the embodiment of the invention illustrated in FIG. 40, the femoral component 290 of an implant is formed as two separate portions 572 and 574. The portion 572 of the implant 290 is moved through the incision 114 into engagement with the distal end portion 124 of the femur 126. Thereafter, the portion 574 of the implant 290 is moved through the incision 114 into engagement with the distal end portion 124 of the femur 126. After the two portions 572 and 574 of the femoral component 290 of the implant have been positioned in abutting engagement with the femur 126, the two portions of the implant are interconnected at a joint 576 between the two portions of the implant. If desired, the portions 572 and 574 of the femoral component 290 of the implant may be moved through the cannula 564 of FIG. 39.

The specific implant 290 illustrated in FIG. 40 has portions formed of a polymeric material which may be either a polymer or a co-polymer. The material of the two portions 572 and 574 of the implant 290 are heated at the joint 576 while the two portions of the implant are disposed in the patient's body in engagement with the femur 126. As this occurs, the material forming the two portions 572 and 574 of the implant 290 is heated to a temperature within its transition temperature range and becomes tacky without changing its overall configuration. The two portions 572 and 574 of the implant 290 may be heated by the direct or indirect application of heat. The indirect application of heat may include applying ultrasonic energy to the implant.

The heated material of the two portions 572 and 574 of the implant 290 are then pressed together at the joint 576 to form a bond between the two portions of the implant. As this occurs, there is a fusing of the material of the portion 572 of the implant 290 with the material 574 of the implant. This fusing together of the two portions 572 and 574 occur in the patient's body and results in the formation of a one-piece unitary implant 290.

Rather than being formed of a polymeric material, it is contemplated that the two portions 572 and 574 of the implant could be formed of metal and have a polymeric layer on a side of the metal toward the femur 126. This would result in the layer of polymeric material being disposed in engagement with the distal end portion 124 of the femur 126 and the metal forming the femoral component 290 facing toward the tibia 214 for engagement with the tibial bearing insert 294 (FIG. 32). With such a construction, the application of energy to the two portions 572 and 574 of the implant would result in a heating of the layer of polymeric material on the inside of the layer of metal. The heated polymeric materials on the two portions 572 and 574 bond together at the joint 576 in a manner previously described.

When the two portions 572 and 574 of the femoral implant 290 are to be interconnected by fusing together sections of polymeric material which form the portions 572 and 574 of the implant or sections of polymeric material which are disposed on layers of metal forming part of the portions 572 and 574 of the implant 290 to be interconnected, it is contemplated that they may be interconnected in many different ways. One way in which polymeric material on the portions 572 and 574 of the femoral implant 290 may be interconnected is the same as is disclosed in U.S. patent application Ser. No. 09/737,380 filed Dec. 15, 2000 by Peter M. Bonutti, et al. This patent application contains a disclosure which corresponds to the disclosure in U.S. Pat. No. 6,059,817.

The two portions 572 and 574 of the implant 290 (FIG. 40) may be formed of only metal. If this is done, the two portions 572 and 574 of the implant may be mechanically interconnected. For example, a screw could extend from the portion 574 of the implant 270 to the portion 572 of the implant while the two implants are in engagement with the distal end portion 124 of the femur 126. Alternatively, a snap type joint 576 could be provided between the portions 572 and 574 of the implant. Although the two portions 572 and 574 of the implant 290 are positioned in engagement with the femur 126 and interconnected while the leg 70 of the patient is in the position illustrated in FIGS. 2, 3 and 25, the two portions of the implant could be positioned in engagement with the femur 126 while the leg 70 is straight (extended).

The implant 290 is connected with the femur 126. However, it is contemplated that a tibial implant could be formed as a plurality of separate portions which are interconnected when they are in the knee portion 76 of the patient's leg 70. It should be understood that the implant 290 could be formed of more than two portions. For example the implant could be formed with four separate portions which are interconnected in the patient's body. Although the implant 290 is to be used in a knee portion of a patient's body, it is contemplated that implants used at other portions of a patient's body could be interconnected in the patient's body.

In the embodiment of the invention illustrated in FIG. 40, the separate portions 572 and 574 of the implant 290 are positioned in engagement with the same bone, that is, femur 126 and interconnected. However, it is contemplated that one position of an implant could be positioned in engagement with a first bone and another portion of the implant positioned in engagement with a second bone. However, the two portions of the implant would be interconnected in the patient's body. The two portions of the implant may be interconnected after they have been positioned in engagement with bones in the patient's body. Alternatively, the two portions of the implant could be interconnected in the patient's body, before one or both portions of the implant have been positioned in engagement with a bone.

For example, a first component of an implant may be connected with a femur 126 in a patient's body. A second component may be connected with a tibia 214 in the patient's body. The two components are interconnected, in the patient's body, after they have been connected with the femur and tibia.

Transducer for Ligament Balancing

After the femoral component 290 and tibial components 286 and 294 of the implant had been positioned in the knee portion 76 of the patient's leg 70, the ligaments are balanced in flexion, extension, and rotation in the manner previously described. It should be understood that even though the implants have not been shown in FIGS. 41 and 42, ligament balancing may be undertaken before and/or after the implants been positioned in engagement with the femur 126 and tibia 214. However, it is contemplated that ligament balancing could be undertaken during surgical procedures which do not require cutting of the femur 126 and tibia 214 and/or implants.

In accordance with one of the features of the invention, during ligament balancing, tension forces in fibrous connective tissue such as collateral ligaments 590 and 592 (FIGS. 41 and 42) are compared. If the forces in one of the ligaments 590 or 592 are excessive, the ligament in which the excessive force is present may be released. Similarly, if one of the ligaments is too loose, the ligament may be tightened.

In accordance with another one of the features of the invention, transducers are positioned between one or more bones in the knee portion 76 of the leg 70 of the patient. The transducers enable tension forces in ligaments 590 and 592 to be compared. The transducers may be used to determine the magnitude of the tension forces in the ligaments 590 and 592.

Thus, a first or lateral transducer 596 (FIGS. 41 and 42) is positioned between a lateral side of the distal end portion 124 of the femur 126 and a lateral side of the proximal end portion 212 of the tibia 214. Similarly, a second or medial transducer 598 is positioned between a medial side of the distal end portion 124 of the femur 126 and a medial side of the proximal end portion of the tibia 214. The transducers 596 and 598 are connected with a computer 600 (FIG. 41) or other processor.

The computer 600 (FIG. 41) has a display area 601 at which the output from the lateral transducer 596 is displayed. Similarly, the computer 600 has a display area 602 at which the output from the medial transducer 598 is displayed. By comparing the outputs at the display areas 601 and 602, a surgeon can determine the relationship between the tension in the ligament 590 and the tension in the ligament 592. In addition, the surgeon can determine the magnitude of the tension in the ligaments 590 and 592.

Figure 34:
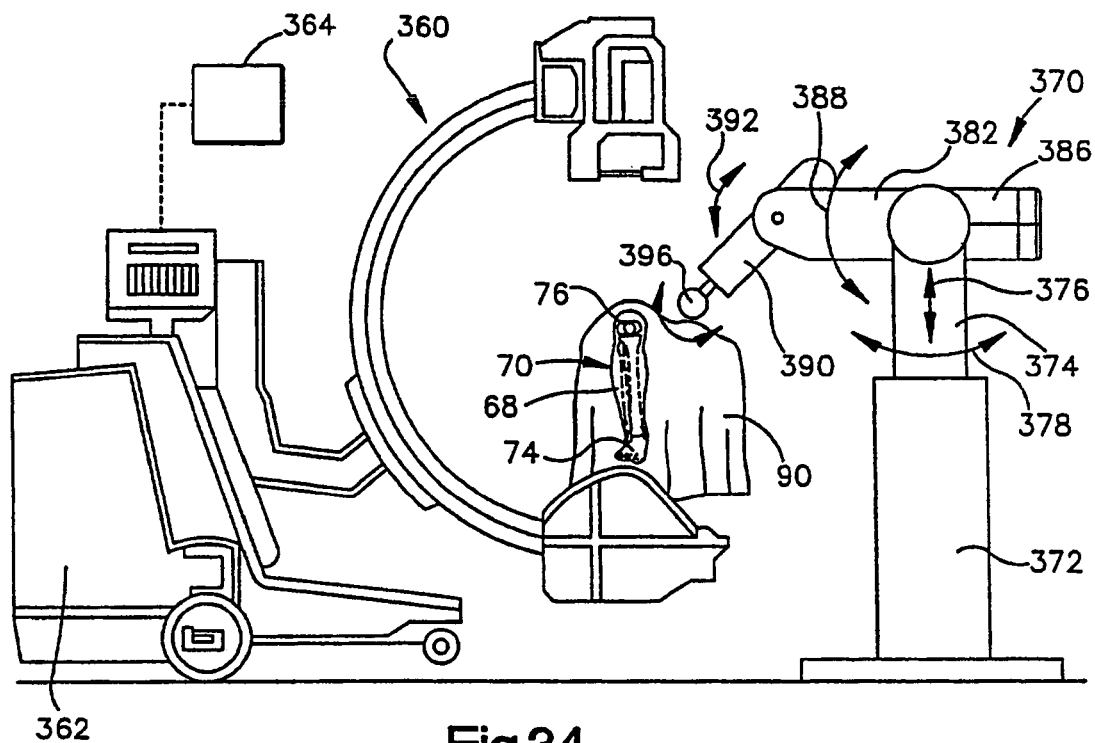
FIG. 34 is a schematic illustration depicting the manner in which an imaging apparatus may be utilized to generate images of a portion of the patient's leg and the manner in which a robot may be utilized to position cutting tools or other devices relative to the patient's leg with the patient's leg in the position illustrated in FIGS. 2 and 3.

It is contemplated that the leg 70 of the patient will be moved between the flexed condition of FIGS. 2, 3, 25 and 41 and an extended position or straight condition (FIGS. 4 and 42), while the output from the transducers 596 and 598 is viewed at the display areas 601 and 602 of the computer 600. This will provide the surgeon with a clear indication of the manner in which tension forces in the ligaments 590 and 592 varies during bending of the knee portion 76 of the leg 70 of a patient. If an image generating device, similar to the C-arm fluoroscope 360 of FIG. 34, is used in association with the transducers 596 and 598, the surgeon can see how components of the knee joint are interacting as the tension in the ligaments varies.

In addition to checking the tension in the ligaments 590 and 592 during movement of the leg 70 of the patient between flexed and extended conditions, it is contemplated that the tension in the ligaments 590 and 592 will be compared during the application of rotational forces to the lower portion 68 of the knee of the patient. Thus, forces tending to rotate the lower portion 68 of the leg of the patient in the direction of the arrow 258 in FIG. 25 are applied to the lower portion 68 of the leg 70. As these rotational forces are applied, the outputs from the transducers 596 and 598 (FIG. 41) are displayed for review by a surgeon to determine whether or not the ligaments 590 and 592 are rotationally balanced. The transducers 596 and 598 may be utilized to provide outputs corresponding to forces resulting from a combination of flexion/extension movement and rotational movement of the lower portion 68 of the patient's leg 70. It should be understood that the transducers 596 and 598 may be utilized throughout the entire ligament balancing process previously described herein in order to enable a surgeon to compare tension forces in the ligaments 590 and 592 throughout the ligament balancing process.

Figure 41:
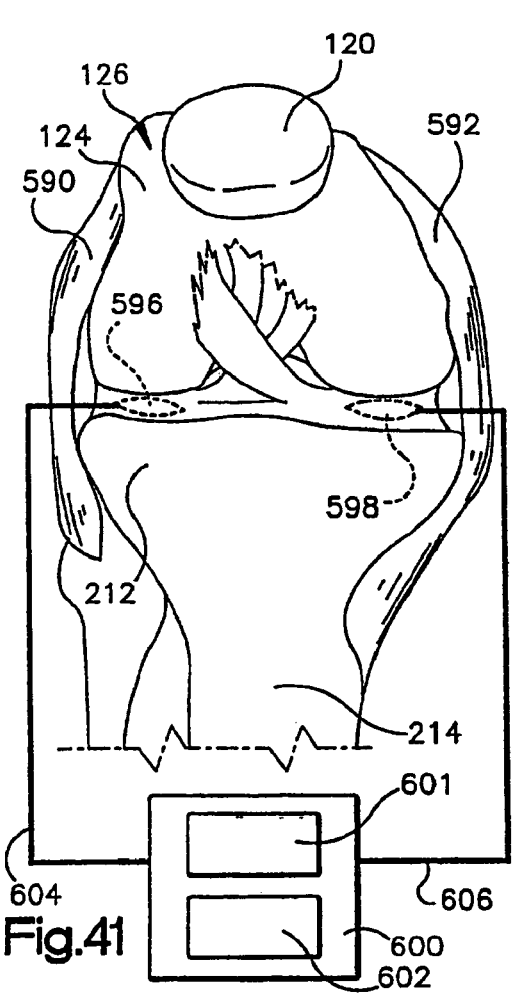
FIG. 41 is a schematic illustration depicting the relationship of transducers to a flexed knee joint of a patient when the leg of the patient is in the position illustrated in FIGS. 2 and 3.
Figure 42:
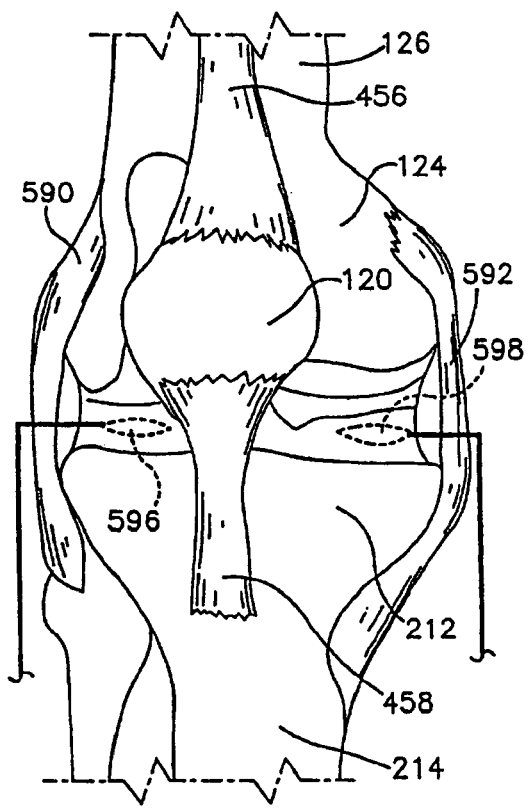
FIG. 42 is a schematic illustration, generally similar to FIG. 41, illustrating the relationship of the transducers to the knee joint when the leg of the patient is extended.

Although the transducers 596 and 598 have been illustrated schematically in FIGS. 41 and 42 as being associated with the end portions of the femur 126 and tibia 214, it should be understood that the transducers 596 and 598 could be associated with other joints if desired. For example, the transducers 596 and 598 could be positioned between vertebrae in a patient's spine. If this was done, the patient's spine could be bent in either anterior or lateral flexion and extension. The output at the display areas 601 and 602 would indicate the manner in which forces transmitted between the vertebrae vary during bending of the spine.

It is contemplated that the transducers 596 and 598 could have many different constructions. However, in the illustrated embodiment of the invention, the transducers 596 and 598 are pneumatic transducers. Thus, the lateral transducer 596 (FIG. 42) includes a container or bladder having a chamber which is filled with fluid. It is contemplated that the chamber could be filled with either a gas or a liquid. In the embodiment of the invention illustrated in FIGS. 41 and 42, the transducers 596 and 598 have the same construction and are of pneumatic type. Therefore, the chamber is filled with air. However, the chamber could be filled with a liquid, for example, saline solution, if desired.

The transducers 596 and 598 are disposed between the femur 126 and the tibia 214. Although it should be understood that the femoral implant 290 and tibial tray 286 and bearing 294 have not been illustrated in FIGS. 41 and 42, the implants may or may not be present when the transducers are positioned between the femur 126 and tibia 214. Depending upon the location of the transducers 596 and 598 they may or may not be disposed in engagement with a portion of either the femoral or tibial implant. With a partial knee replacement, one of the transducers 596 or 598, is disposed between femoral and tibial implants. The other transducer is disposed between surfaces on the femur 126 and the tibia 214.

A conductor 604 is provided to transmit an output signal from the lateral transducer 596 to the computer display 601 (FIG. 42). The conductor 604 could be constructed so as to conduct either fluid pressure from the transducer 596 to the computer 600 or to conduct an electrical signal from a fluid pressure transducer exposed to the fluid pressure in the transducer 596. The medial transducer 598 is connected with the display 602 by a conductor 606.

It is contemplated that the transducers 596 and 598 could have many different constructions including any one of the constructions disclosed in U.S. Pat. No. 5,667,520 or in U.S. patent application Ser. No. 09/483,676 filed Jan. 14, 2000 by Peter M. Bonutti and having a disclosure corresponding to the disclosure in U.S. Pat. No. 5,269,785. The transducers 596 and 598 may be formed of a material which is biodegradable or a material which is non-biodegradable.

Although the illustrated transducers 596 and 598 (FIGS. 41 and 42) are of the pneumatic type, it is contemplated that a different type of transducer could be utilized if desired. For example, the transducers 596 and 598 could be solid state devices, such as piezoelectric load cells. Alternatively, the transducers could include deformable members to which strain gauges are attached.

It should be understood that the transducers 596 and 598 could be used to measure and/or compare tension in the ligaments 590 and 592 immediately after making the incision 114. In addition or alternatively, the transducers 596 and 598 could be used to measure and/or compare tension in the ligaments 590 and 592 during trials with provisional components. Of course, the transducers 596 and 598 can be used to measure and/or compare tension in the ligaments after the implants 286, 290 and 294 have been mounted in the knee portion 76.

In the embodiment of this invention illustrated in FIGS. 41 and 42, the transducers 596 and 598 are disposed between end portions of the femur 216 and tibia 214. Therefore, the transducers 596 and 598 only indirectly respond to variations in tension in the collateral ligaments 590 and 592. It is contemplated that the transducers 596 and 598 could be positioned so as to directly respond to variations in the tension in the collateral ligaments 590 and 592.

For example, the transducer 596 could be positioned between the ligament 590 and lateral sides of the femur 126 and/or tibia 214. Similarly, the transducer 598 could be positioned between the ligament 592 and medial sides of the femur 126 and/or tibia 214.

It is contemplated that transducers, similar to the transducers 596 and 598, could be utilized to determine variations in tension in ligaments and/or tendons other than the ligaments 590 and 592. For example, transducers could be utilized to determine the tension in the patellar tendon 456 (FIG. 42) and/or the patellar ligament 458. If desired, transducers, similar to the transducers 596 and 598, could be positioned so as to respond to variations in tension in the posterior cruciate ligament 250 and/or the anterior cruciate ligament. It is contemplated that a plurality of transducers, similar to the transducers 596 and 598, may be positioned so as to respond to variations in tension in various combinations of ligaments and/or tendons.

In addition to providing outputs which are a function of variations in tension in ligaments and/or tendons, the transducers 596 and 598 may be utilized to apply force against the femur 126 and tibia 214. When this is to be done, fluid under pressure is conducted to either or both of the transducers 596 and/or 598. An increase in fluid pressure conducted to the transducers 596 and 598 is effective to expand containers or bladders in the transducers.

The fluid pressure force applied against the transducers 596 and/or 598 is transmitted to the femur 126 and tibia 214. This force may be used to stretch the collateral ligaments 590 and 592 and/or other body tissue. If it is desired to stretch one of the ligaments 590 or 592 to a greater extent the other ligament, the fluid pressure transmitted to one of the transducers 596 or 598 would be greater than the fluid pressure transmitted to the other transducer. The force transmitted to the femur 126 and tibia 214 is indicated at the displays 61 and 601.

It is contemplated that the transducers 596 and 598 will be removed before the limited incision 114 is closed. However, if it is desired, the transducers 596 and 598 may be left in place and utilized after the incision 114 is closed. When this is to be done, the transducers 596 and 598 may advantageously be formed of biodegradable material. By leaving the transducers 596 and 598 in place after the incision 114 is closed, the tension in the ligaments 590 and 592 may be compared during therapy. If desired, one or both ligaments 596 and/or 598 could be conducting fluid pressure to one or both transducers 596 and/or 598 during therapy.

Inlaid Implant—Femur

In the embodiment of the invention illustrated in FIGS. 8-28, articular surfaces on the distal end portion 124 of the femur 126 and the proximal end portion 212 of the tibia 214 are cut away using a saw or other cutting tool. This results in areas on the distal end portion 124 of the femur 126 and the proximal end portion 212 of the tibia 214, where articular surfaces were previously disposed, being cut to have a flat planar configuration. Thus, an anterior skim cut, a distal end cut, and chamfer cuts are made on the distal end portion 124 of the femur 126 while a proximal end cut is made on the proximal end portion 212 of the tibia 214. After the cuts have been made, the femoral implant extends across or encloses the cuts on the distal end portion 124 of the femur 126 and the tibial implant extends across the cut on the tibial end portion 212 of the tibia 214.

It is contemplated that rather than enclosing the end portions of the femur and tibia with implants, the implants could be inlaid into the end portion of the femur and/or tibia. When an implant is to be inlaid into the distal end portion 124 of the femur 126 (FIG. 43), a recess 610 is formed in the distal end portion 124 of the femur 126. To form the recess 610, a cutting tool, such as a milling cutter 614 (FIG. 44), is utilized to cut away a defective portion of an articular surface on the distal end portion 124 of the femur 126. The milling cutter 614 is rotated about its longitudinal central axis and has cutting edges disposed in a cylindrical array about the periphery of the milling cutter. The extent of the defective portion of the articular surface determines the extent to which the milling cutter 614 cuts away the articular surface.

A guide 620 (FIG. 44) is provided for the milling cutter or other cutting tool. The guide 620 is effective to limit the extent of axial movement of the milling cutter 614 into the distal end portion 124 of the femur 126 to thereby limit the depth of the recess 610. The guide 620 limits side wise, that is, radial movement of the milling cutter 614 to an area corresponding to the desired configuration of the recess 610. This results in the recess 610 being formed with a uniform depth throughout the extent of the recess and with a desired configuration. The construction of the guide 620 in the manner in which it cooperates with the milling cutter 614 may be similar to that disclosed in U.S. Pat. Nos. 5,344,423; 5,769,855; and/or 5,860,981.

Figure 43:
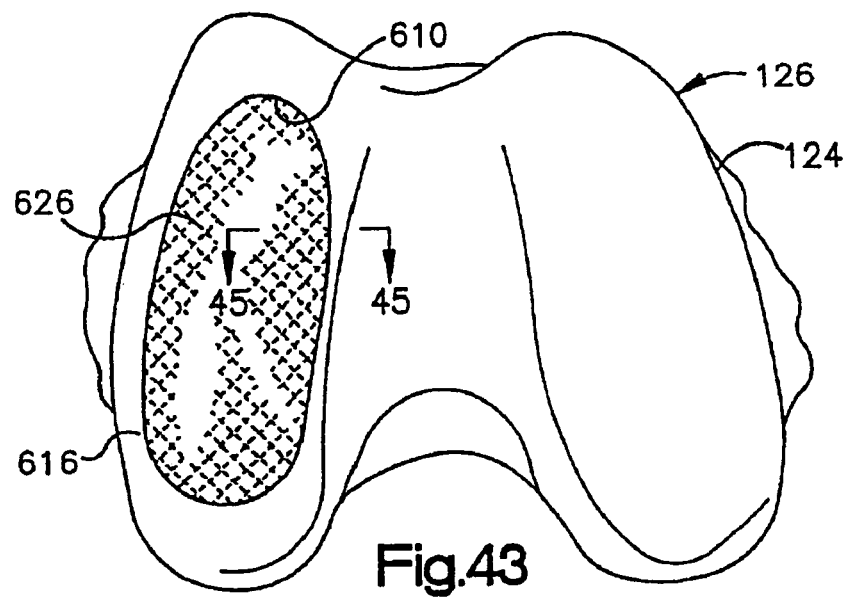
FIG. 43 is a schematic illustration of a distal end portion of a femur in a leg of a patient with the leg in the position illustrated in FIGS. 2 and 3 and illustrating the relationship of an implant to a recess in the end portion of the femur.
Figure 44:
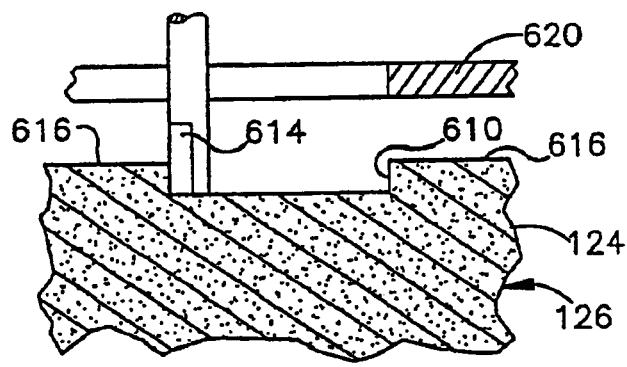
FIG. 44 is a schematic sectional view depicting the manner in which a cutting tool is used to form a recess in the end portion of the femur of FIG. 43 with the leg of the patient in the position illustrated in FIGS. 2 and 3.

Once the recess 610 has been formed using the milling cutter 614 in the manner illustrated schematically in FIG. 44, an implant 626 (FIGS. 43 and 45) is positioned in the recess. The implant 626 fills the recess 610 and has an outer surface 628 (FIG. 45) which forms a continuation of the naturally occurring articular surface 616 formed by the distal end portion 124 of the femur 126. The outer surface 628 of the implant 626 replaces defective articular surface area removed by the milling cutter 614 from the distal end portion 124 of the femur 126.

The outer surface 628 on the implant 626 cooperates with an articular surface on a tibia 214 in the same general manner as the original articular surface area removed by the milling cutter 614. Of course, the outer surface 628 of the implant 626 is free of defects that made it necessary to replace the corresponding area on the articular surface 616 of the distal end portion 124 of the femur 126. The outer surface 628 of the implant 626 may engage an articular surface formed by the boney material of the tibia 214. Alternatively, the outer surface 628 of the implant 626 may engage the surface of an implant disposed on the tibia 214.

During recovery of the patient, the naturally occurring surface 616 on the femur 126 and the implant 626 may both be load bearing. By having the implant 626 surrounded by load bearing natural bone, the implant is held in place on the distal end portion 124 of the femur 26. In addition, the magnitude of the load which must be transmitted through the implant 626 is minimized.

The implant 626 could have any desired construction. Thus, the implant could be formed of a polymeric material or it could be formed of a metallic material. However, in accordance with one of the features of the invention, the implant 626 is formed of a material which promotes biological resurfacing and the growth of bone from the distal end portion 124 of the femur 126 into the implant to fill the recess 610 with new bone growth. The implant 626 may also be at least partially formed of material which promotes the growth of cartilage or other tissue over the implant.

The implant 626 may be formed with a non-living three dimensional scaffold or framework structure on which bone growth promoting materials, such as bone morphogenetic proteins, are disposed. The three dimensional framework or platform on which the bone growth promoting materials are disposed may be formed of either a biodegradable or a non-biodegradable material. When the scaffold or framework structure is formed of a non-biodegradable material, the bone from the distal end portion 124 will grow through the scaffold so that the scaffold becomes embedded in new bone growth. The scaffold may be formed of a porous metal or ceramic material. When the scaffold is formed of a bio-degradable material, the scaffold will eventually degrade and be absorbed by body tissue.

The scaffold may be formed of a mesh or a felt-like material, or a porous material similar to coral. The scaffold forms a growth supporting matrix to support cellular migration from the boney material of the distal end portion 124 of the femur 126 into the implant 626. If the scaffold or platform is made of a bio-degradable material, then the scaffold or platform degrades and disappears after a period of time. It is contemplated that the scaffold could be formed of a bio-degradable material such as polyglycolic acid or polylactic acid. If desired, the scaffold or framework could be formed of fibrous connective materials such as portions of ligaments, tendons and/or bones obtained from human and/or animal sources. The scaffold could be formed of collagen. The scaffold may be formed of submucosal tissue.

The scaffold holds bone growth inducing materials and may include bone fragments to which tri-calcium phosphate, an antibiotic, hydroxyapatiate, allografts, autografts, and/or any other polymeric has been added. It is believed that it will be particularly advantageous to provide a bone growth morphogenetics protein in the implant 626 to promote the growth of bone into the implant. The scaffold may hold cultured and/or noncultured cells which promote biological resurfacing.

The matrix or scaffold for the implant 626 may contain tissue inductive factors and/or cells. The cells may be mesenchymal cells which are introduced into the scaffold in the operating room. Thus, the matrix or scaffold may be either biodegradable or non-biodegradable and may be constructed at a location remote from an operation. After the scaffold has been transported to the operating room the mesenchymal cells may be introduced into the scaffold.

It is contemplated that the matrix or scaffold for the implant 626 may contain stem cells and/or fetal cells. The stem cells and/or fetal cells may be introduced into either a biodegradable or non-biodegradable matrix or scaffold in the operating room. It is contemplated that tissue inductive factors may be provided in the matrix or scaffold along with any desired type of precursor cells.

The matrix or scaffold for the implant 626 may contain osteoinductive materials. The implant 626 may contain osteoblasts or osteoclast cells or their precursors. The implant 626 may also contain platlet matrix centrifuged from blood in a manner similar to that described in U.S. patent application Ser. No. 09/483,676, filed Jan. 14, 2000 by Peter M. Bonutti.

The matrix or scaffold for the implant 626 may be formed of allograft bone or collagen. Cartilage may be used to form the scaffold or matrix. The scaffold or matrix for the implant 626 may have a layered construction with the layers being formed of different materials. Each of the layers of the scaffold or matrix forming the implant 626 may be impregnated with a different material. For example, precursor cells may be provided in one layer and bone morphogentic protein may be provided in another layer.

It is contemplated that submucosal tissue may be used to form the scaffold for one or more of the layers of the implant 626. The submucosal tissue may be prepared in a manner similar to the manner disclosed in U.S. Pat. No. 5,755,791. The various layers of the implant 626 may be assembled in the operating room.

The implant 626 may be formed of multiple tissue fragments. Thus, a tissue press, similar to the tissue presses disclosed in U.S. patent application Ser. No. 09/602,743 filed Jun. 23, 2000, by Peter M. Bonutti and having a disclosure which corresponds to the disclosure in U.S. Pat. No. 5,662,710 may be utilized to shape the implant to a desired configuration.

The implant 626 may be formed to have any one of a plurality of different sizes and configurations. The implant may be shaped to the desired configuration at a location remote from an operating room and transported to the operating room. Alternatively, the implant 626 could be cut to the desired shape in the operating room.

By providing a substantial number of implants of different sizes in the operating room and/or by cutting an implant to obtain a desired configuration, it is possible for a surgeon to make a recess 610 to a shape which corresponds to a defective area on a portion of the femur 126. An implant 626 having the configuration of the particular recess can then be provided. This enables the surgeon to remove a relatively small defective area of the bone forming the articular surface on the femur 126 and to minimize the size of the implant 626.

It is believed that it will be desired to provide a series of implants of different sizes ranging from a relatively small size to a relatively large size. In addition, it is believed that it will be desired to provide a plurality of guides 620. The guides 620 will have surfaces to guide movement of the milling cutter 614 or other cutting tool to form a recess 610 of a size corresponding to any one of the sizes of the implants in the series of implants. Thus, the plurality of guides 620 would be provided with each guide having guide surfaces corresponding to the configuration of an implant of a different size.

The scaffold or base of the implant 626 may be formed of a porous bio-degradable material. The porous bio-degradable material provides a matrix for demineralized bone, collagen, bone morphogenetic protein, growth factors, and autogenous bone marrow. In addition, progenitor cells, stem cells and/or fetal cells may be disposed on the scaffold. Some non-tissue-derived components may include coralline-based HA (ProOsteon), antibiotics, calcium sulfate, calcium and phosphorus oxide rich amorphous glass, anti-inflammatories, and bovine fibrillar collagen. The resulting material will have osteoinductive and osteoconductive qualities. Cortical cancellous bone chips which are freeze dried may be provided in the implant 626. In addition, demineralized bone matrix may be provided in the implant 626.

The implant 626 may be secured in the recess 610 with a suitable adhesive. There are many different known adhesives which may be used. Fibrin can be used as an adhesive, either in a natural state or after being compressed, to hold material together and to hold the implant 626 in the recess 610.

It is contemplated that the patient's leg 70 may be in the position illustrated in FIGS. 2, 3 and 25 during forming of the recess 610 and positioning of the implant 626 in the recess. The upper portion 72 of the patient's leg 70 may be supported above the support surface 64 by the leg support 80. The limited incision 114 (FIG. 6) may be formed in the knee portion 76 of the patient's leg. The patella 120 may be in the offset position of FIG. 8 during forming of the recess 610.

The drapery system 100 of FIGS. 4 and 5 may advantageously be utilized to provide a sterile field. Although it may be desired to use a milling cutter as the cutting tool 614 (FIG. 44), other known cutting tools could be used if desired. For example, a laser or ultrasonic cutting tool could be used to form the recess 610.

Although it is believed that it will be preferred to have the patient's leg 70 in the position illustrated in FIGS. 2, 3 and 25, to support the patient's leg 70 with the leg support 80, to offset the patella 120, and to use the drapery system 100, the implant 626 may be positioned in a patient's leg 70 without using any one or any combination of these features. Thus, the implant 626 could be positioned in a patient's leg 70 with the leg in the position shown in FIG. 1 with any known drapery system. The patella may be everted (FIG. 7) rather than offset.

The foregoing description of the implant 626 has assumed that the implant is to be positioned in the femur 126 in a leg of a patient. However, the implant 626 could be positioned in any desired bone in a patient's body. The implant 626 could be positioned at a location remote from an articular surface of a bone. The implant 626 may be positioned on a bone in ways other than positioning the implant in a recess similar to the recess 610.

Inlaid Implant—Tibia

The implant 626 is illustrated in FIG. 43 in association with a femur 126 in a patient's body. It is contemplated that a similar implant 640 (FIG. 46) may be provided in the proximal end portion 212 of the tibia 214 in a leg 70 of the patient. The implant 640 is disposed in a recess 642. The recess 642 may have any desired configuration. It is contemplated that the configuration of the recess 642 would be a function of the configuration of defective portions of the bone in the proximal end portion 212 of the tibia 214.

Figure 46:
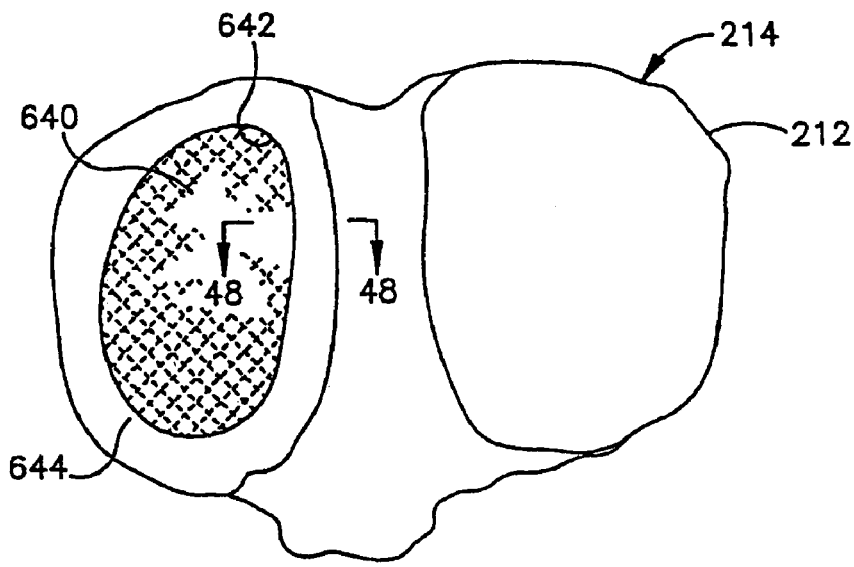
FIG. 46 is a schematic end view of a proximal end portion of a tibia in a leg of a patient, with the leg in the position illustrated in FIGS. 2 and 3, illustrating the relationship of an implant to a recess in the end portion of the tibia.

The recess 642 is surrounded by an articular surface 644 of naturally occurring bone. Thus, the articular surface 644 is not defective and extends around the recess 642. It should be understood that the extent of the articular surface 644 around the recess 642 could be substantially greater than is illustrated in FIG. 46 relative to the size of the implant 640. This is because the implant 640 is sized and has a configuration which is a function of the size and configuration of an area which was previously defective bone on the proximal end portion 212 of the tibia 214. The articular surface 644 is load bearing and functions to transmit forces between the tibia 214 and the femur 126 in the leg 70 of the patient.

Figure 45:
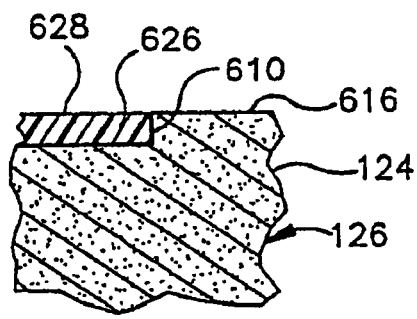
FIG. 45 is a schematic sectional view, taken generally along the line 45-45 of FIG. 43 further illustrating the relationship of the implant to the recess.
Figure 47:
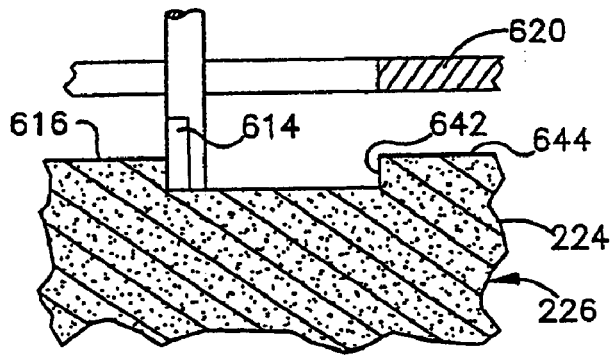
FIG. 47 is a schematic sectional view depicting the manner in which a cutting tool is used to form the recess in the end portion of the tibia of FIG. 46.

The recess 642 is formed with the milling cutter 614 (FIG. 47). A guide 620 is provided to control the depth to which the milling cutter 614 removes bone from the proximal end portion 212 of the tibia 214 in the manner previously explained in conjunction with femur 126 (FIGS. 43-45). The guide 620 and milling cutter 614 are utilized to form the recess 642 in a manner which is similar to that disclosed in U.S. Pat. No. 5,908,424. Rather than being formed by the use of a milling cutter 614 and guide 620, it is contemplated that the recess 642 in the proximal end portion 212 of the tibia 214 and/or the recess 610 in the distal end portion 124 of the femur 126 could be formed by a robot having a construction similar to the construction of the robot 370 of FIG. 33.

Figure 48:
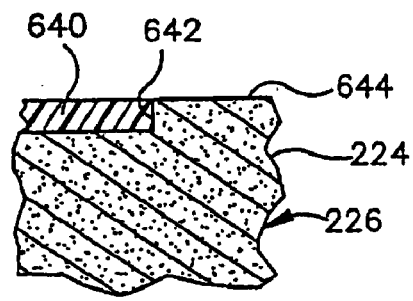
FIG. 48 is a schematic sectional view, taken generally along the line 48-48 of FIG. 46, further illustrating the relationship of the implant to the recess.

The implant 640 (FIGS. 46 and 48) may be formed of metal or a hard polymeric material. Alternatively, the implant 626 may be of a layered construction with a layer of metal backed by polymeric material. The surface of the implant forms a portion of the overall articular surface on the proximal end portion 212 of the tibia 214.

Of course, the articular surface area on the proximal end portion 212 of the tibia 214 cooperates with articular surface areas on the distal end portion 124 of the femur 126 (FIG. 43). It is contemplated that the implant 626 in the femur 126 and the implant 640 in the tibia 214 (FIG. 46) could be disposed in engagement with each other. Alternatively, the implant 626 in the distal end portion 124 of the femur 126 (FIG. 43) could be engaged by a naturally occurring articular surface on the proximal end portion 212 of the tibia 214 (FIG. 46). Similarly, the implant 640 in the proximal end portion 212 of the tibia 214 may engage a naturally occurring articular surface area on the distal end portion 124 of the femur 126.

It is contemplated that it may be preferred that the implant 640 contain bone growth promoting materials and/or materials which promote biological resurfacing. These bone growth promoting materials would promote growth of bone from the proximal end portion 212 of the tibia 214 into the recess 642. This would result in the recess 642 being filled with new bone growth. The biological resurfacing materials would promote the growth of naturally occurring tissues on the implant 640.

The implant 640 may include a three dimensional scaffold or framework structure formed of either a biodegradable material or a non-biodegradable material. Osteoinductive and/or osteoconductive materials may be disposed on this framework or platform. The scaffold may be formed of cortical bone, cartilage submucosal tissue, or other materials.

The matrix or scaffold for the implant 640 has interstitial spaces which contain material which promotes the growth of bone from the proximal end portion 212 of the tibia 214 into the matrix or scaffold. The bone growth materials may include bone morphogenic protein, factors that stimulate migration of cells, anti-inflamatories and/or immuno suppressants. Collagen, fibrin, osteoindctive materials, progenitor cells, and/or tissue inductive factors may be disposed on the platform. The implant 640 may contain cortical cancellous bone chips or demineralized bone matrix. It may be preferred to form the outer surface of the implant 640 of materials which promote biological resurfacing.

When the implant 640 is formed with a biodegradable three dimensional scaffold or matrix, it is contemplated that there will be cellular migration and growth of bone from the proximal end portion 212 of the tibia 214 into the scaffold or matrix. The scaffold or matrix will then degrade and disappear as material of the scaffold or platform hydrolyzes. However, if the matrix or scaffold is made of a non-biodegradable material, it is contemplated that the scaffold will become embedded in the bone growth from the proximal end portion 212 of the tibia 214 into the recess 614. The scaffold, whether biodegradable or non-biodegradable, may be impregnated with mesenchymal cells.

The implant 640 on the tibia has the same construction as the implant 626 on the femur. However, the implant 640 on the tibia could have a construction which is different than the construction of the implant 626 on the femur.

It is contemplated that the patient's leg will be in the position illustrated in FIGS. 2, 3 and 25 during forming of the recess 642 and positioning of the implant 640 in the recess. The upper portion 72 of the patient's leg 70 will be supported above the support surface 64 by the leg support 80. The limited incision 114 (FIG. 6) will be formed in the knee portion 76 of the patient's leg. The patella 120 will be in the offset position of FIG. 8 during forming of the recess 642. The drapery system of FIGS. 4 and 5 may advantageously be utilized to provide a sterile field. Although it may be desired to use a milling cutter as the cutting tool, other known cutting tools could be used if desired.

Layered Implant

Figure 49:
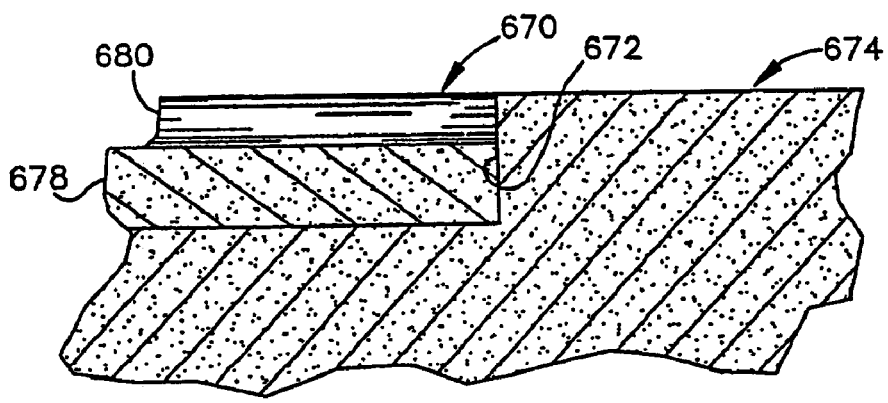
FIG. 49 is a schematic sectional view illustrating the relationship of another implant to a recess in a bone in a patient's body.

A multi layered inlaid implant 670 for use in biological resurfacing is schematically illustrated in FIG. 49. The implant 670 is disposed in a recess 672 formed in a bone 674. The recess 672 is formed in the same manner as is illustrated in FIGS. 44 and 47 for forming the recess 610 and the recess 642. The recess 672 may be disposed in a defective portion of an articular surface on the distal end portion 124 of a femur 126, as illustrated in FIG. 43, or may be located at a defective portion of an articular surface on the proximal end portion 212 of a tibia 214 as illustrated in FIG. 46. However, it is contemplated that the implant 670 may be disposed in the bone 674 at many different locations. At least some of these locations would be spaced from an articular surface on the bone. The bone may be located in many different portions of a patient's body, for example, a shoulder, spine, arm, hand, hip or foot.

The implant 670 is formed by a plurality of layers. The specific implant 670 illustrated in FIG. 49 has a base layer 678 and an outer layer 680. It should be understood that more than two layers could be provided if desired. For example, an intermediate layer could be disposed between the base layer 678 and outer layer 680 if desired. Each of the layers 678 and 680 of the implant 670 could be formed with its own separate platform or scaffold made of biodegradable materials. Alternatively, a single biodegradable scaffold or matrix could extend between the two layers 678 and 680.

The inner or base layer 678 is disposed in engagement with the bone 674. The inner layer 678 may be formed of bone growth promoting materials which promote migration of bone cells from the bone 674 to the base layer 678. New bone growth into the base layer 678 will interconnect the base layer and the bone 674. The base layer 678 may contain cortical cancellous bone power or chips and/or demineralized bone matrix, bone morphogenic protein, anti-inflammatories and/or immuno suppressants may be disposed in the base layer 678. An antibiotic, hydroxyapatiate, tricalcium phosphate and/or polymers and copolymers may also be included in the base layer 678.

The outer layer 680 may be formed of cartilage. Embryonal cells, fetal cells, and/or stem cells may be provided in the outer layer 680. The outer layer 680 may be formed of submucosal tissue. The outer layer 680 promotes biological resurfacing of a portion of the bone 674 where the implant 670 is disposed.

It is contemplated that the recess 672 may be formed in the bone 674 at a location where there is a defect in an articular surface on the bone. However, it is also contemplated that the recess 672 in a position in a portion of the bone 674 where there is no articular surface.

It is contemplated that the patient's leg will be in the position illustrated in FIGS. 2, 3 and 25 during forming of the recess 672 and positioning of the implant 670 in the recess. The upper portion 72 of the patient's leg 70 will be supported above the support surface 64 by the leg support 80. The limited incision 114 (FIG. 6) will be formed in the knee portion 76 of the patient's leg. The patella 120 will be in the offset position of FIG. 8 during forming of the recess 672. The drapery system of FIGS. 4 and 5 may advantageously be utilized to provide a sterile field. Although it may be desired to use a milling cutter as the cutting tool, other known cutting tools could be used if desired.

Implant

Figure 50:
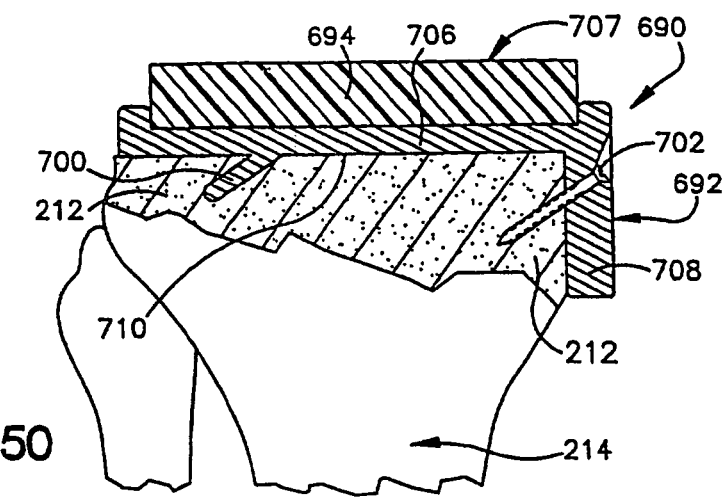
FIG. 50 is a schematic illustration depicting the relationship between a tibial implant and a tibia in the leg of the patient.

An improved implant 690 is illustrated in FIG. 50. The implant 690 may be utilized in association with either a full or partial knee replacement. Alternatively, the implant 690 could be utilized in association with a repair of a glenoid joint, an elbow, an ankle, a spine or any desired joint in a patient's body. Implant 690 includes a base 692 and an articular layer 694. The base 692 has been illustrated in FIG. 50 as being connected with the proximal end portion 212 of a tibia 214. The implant 690 is intended for use in association with either a partial or full knee replacement. However, it should be understood that an implant having a construction corresponding to the construction of the implant 690 could be utilized in association with any desired joint in a patient's body.

The base 692 (FIG. 50) is connected with the tibia 214 by projection 700 and a fastener 702. The projection 700 has a generally cylindrical configuration and extends from a main section 706 of base 692. The projection 700 extends at an acute angle to the main section 706 in a direction away from the fastener 702.

When the implant 690 is positioned on the proximal end portion 212 of the tibia 214, the implant is moved along a path which extends parallel to a longitudinal central axis of the projection 700. The path of movement of the implant 690 onto the proximal end portion 212 of the tibia 214 is indicated by an arrow 707 in FIG. 50. The arrow 707 is skewed at an acute angle to a longitudinal central axis of the tibia 214. This results in the projection 700 being forced into the bone of the proximal end portion 212 of the tibia 214. Deformation of the bone occurs adjacent to a leading end of the projection 700. There is no significant deformation of the adjacent to a longitudinally extending outer side surface of the generally cylindrical projection 700.

As the implant 690 is moved into position on the proximal end portion 212 of the tibia 214, a downwardly extending flange 708 connected with the main section 706 moves into engagement with an outer side surface area on the tibia 214 as the main section 706 of the implant 690 moves into engagement with flat proximal end surface 710 on the tibia 214. Once the inner side of the main section 706 has been pressed firmly against the flat end surface 710 on the tibia 214 and the projection 700 is moved to the position illustrated in FIG. 50, the fastener 702 is inserted through the flange 708. The fastener 702 is a screw and engages the proximal end portion 212 of the tibia 214 to securely connect the implant 690 with the tibia. A longitudinal central axis of the fastener 702 extends generally parallel to a longitudinal central axis of the projection 700. Therefore, as the fastener 702 is tightened to press the flange 708 against the outer side of the tibia 214, the projection 700 is cammed or forced inward to press the main section 706 against the end surface 710 on the tibia.

It is contemplated that the base 692 of the implant 690 may be formed of metal. For example, the base 692 may be formed of porous tantalum. Of course, the base 692 could be formed of a different material if desired. Thus, the base 692 could be formed of a polymer or copolymer if desired. The articular layer 694 is formed of a smooth polymeric material which engages in articular surface on a femur.

It is contemplated that the patient's leg will be in the position illustrated in FIGS. 2, 3 and 25 during positioning of the implant 690 on the proximal end portion of the tibia 214. The upper portion of the patient's leg 70 will be supported above the support surface 64 (FIG. 2) by the leg support 80. The limited incision 114 (FIG. 6) will be formed in the knee portion 76 of the patient's leg 70. The patella 120 will be in the offset position of FIG. 8 during positioning of the implant 690. The drapery system 100 (FIGS. 4 and 5) will provide a sterile field. The tibial resection guide 218 (FIG. 21) may be used during forming of the flat end surface 710 on the tibia 214.

Expandable Devices

In accordance with another feature of the invention, one or more expandable devices 720 and 722 (FIG. 51) may be utilized to move, stretch, or separate body tissue. The expandable devices 720 and 722 may be utilized at any time during a full or partial knee replacement. Thus, the expandable devices 720 and 722 may be utilized to separate body tissue from the distal end portion 124 of a femur 214 before a femoral component or implant 290 is connected with the femur and before the tibial tray 286 and tibial bearing insert 294 are connected with the proximal end portion 212 of the tibia 214.

The expandable devices 720 and 722 may be inserted into the knee portion 76 of the patient's leg 70 one or more days before either a partial or full knee replacement operation is to be undertaken. Before the surgery is initiated, the expandable device 720 may be expanded to stretch skin 342, the joint capsule, and other tissue in the anterior of the knee portion 76. The viscoelastic body tissue is resiliently stretched by the expandable device 720 in the general area where the limited incision 114 (FIG. 6) is to be formed.

The incision 114 is subsequently made in the body tissue which has been resiliently stretched by the expandable device 720. After the surgery on the patient's leg 70 has been completed, for example, after a full or partial knee replacement in accordance with FIGS. 8-29, the incision 114 in the stretched tissue is closed. The body tissue which was previously resiliently stretched by the expandable device 720 can, after closing of the incision 114, return to its normal or unstretched condition. As this occurs, the length of any scar resulting from the incision 114 decreases. By making the incision 114 in body tissue which has previously been resiliently stretched by the expandable device 720, the overall effective length of the incision 114 is reduced.

The expandable devices 720 and 722 may be resilient balloons which are inflated by a gas, such as air, or resilient bladders which are expanded under the influence of a liquid, such as saline solution. The resilient expandable devices 720 and 722 may be formed of a biodegradable material or a non-biodegradable material. It is contemplated that if the expandable devices 720 and 722 are to be left in the patient's body, they may advantageously be formed of a biodegradable material. However, if it is contemplated that when the expandable devices are to be removed from the patient's body during or after surgery, the expandable devices may be formed of a non-biodegradable material.

Rather than being inserted into the knee portion 76 prior to formation of the incision 114, the expandable devices 720 and 722 (FIG. 51) may be inserted into the knee portion immediately after making the incision. The expandable devices 720 and 722 may then be expanded to separate body tissue in the knee portion 76. The expandable devices 720 and 722 are inserted into the knee portion 76 in a collapsed condition. The expandable devices are expanded after being inserted into the knee portion.

For example, the expandable device 720 may be resiliently expanded to stretch the patellar ligament 458 (FIG. 51) and move the patella 120 away from the distal end portion 124 of the femur 126. Alternatively, the expandable device 720 may be positioned between the femur 126 and the patellar tendon 456. Expansion of the expandable device 720 would then result in movement of the patellar tendon 456 and patella 120 away from the distal end portion 124 of the femur 126. Of course, if expandable devices were provided between the distal end portion 124 of the femur and both the patellar tendon 456 and patellar ligament 458, the patella tendon and ligament would both be moved by expansion of the expandable devices. Positioning of the expandable device 720 between the patellar ligament and/or tendon facilitates subsequent movement of the patella 120 to offset position of FIG. 8. As previously noted, expandable device 720 can be used to access the inner surface of the patella 120.

The expandable device 722 (FIG. 51) is disposed in the posterior portion of the knee portion 76 of the leg 70. Expansion of the expandable device 722 in the posterior portion of the patient's knee is effective to move the joint capsule and fibrous connective tissue away from the distal end portion 124 of the femur 126 and the proximal end portion 212 of the tibia 214. The expandable device 722 may be expanded immediately after the incision 114 is formed to effect releases of body tissue from the distal end portion 124 of the femur 126 and/or the proximal end portion 212 of the tibia 214.

Expansion of the expandable device 722 is effective to move arteries, nerves and veins in the posterior of the knee portion 76 away from the distal end portion 124 of the femur 126 and proximal end portion 212 of the tibia 214 prior to making of the femoral and/or tibial cuts (FIGS. 8-29). If desired, the expandable device 722 may be maintained in the expanded condition during making of one or more of the femoral and/or tibial cuts. If desired, the expandable device 722 may be provided with a tough surface which would protect arteries, nerves and/or veins during the making of one or more of the femoral and tibial cuts.

Figure 51:
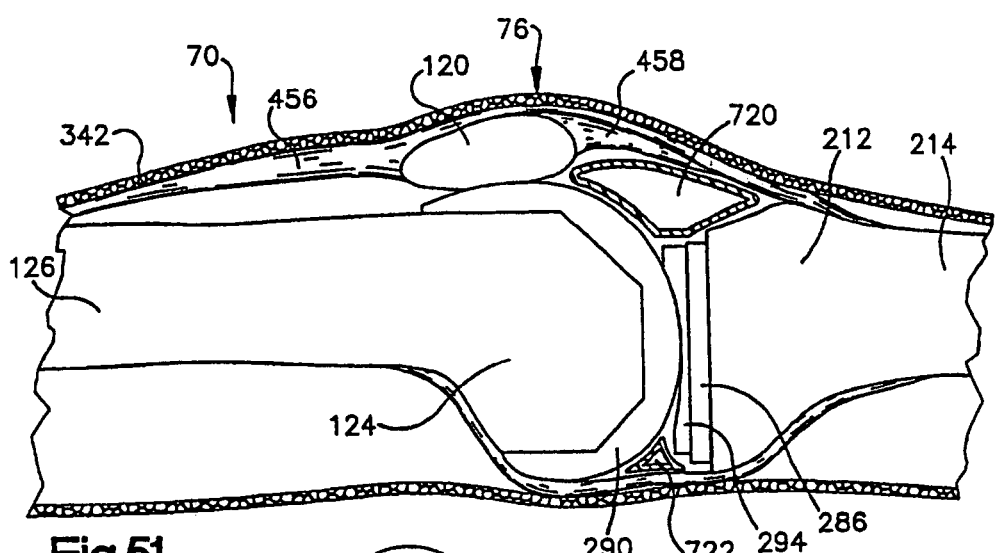
FIG. 51 is a schematic illustration depicting the relationship of expandable devices to the knee portion of a patient's leg.

It should be understood that the expandable device 722 may have a configuration which is different from the configuration illustrated in FIG. 51. For example, the expandable device 722 may extend for a greater distance along the posterior of the femur 126 and tibia 214 if desired. Although the implants 286, 290 and 294 have been illustrated in FIG. 51, it should be understood that the expandable devices 720 and 722 may be used before and/or after installation of the implants. The expandable devices 720 and 722 may be positioned in the knee portion 76 of the patient's leg 70 with the leg in the flexed condition of FIGS. 2 and 3 or with the leg in the extended condition of FIG. 51.

After the femoral component 290 and tibial tray 286 and tibial bearing insert 294 have been positioned in the knee portion 726 of the patient's leg 70, the expandable devices 720 and 722 may be utilized to assist the surgeon during ligament balancing. The expandable devices 720 and 722 will also assist the surgeon in obtaining a full range of motion of the knee portion 76. Thus, the expandable devices 720 and 722 may be expanded, under the influence of fluid pressure, to effect ligament releases or to move tissue out of an interfering relationship with relative movement between the femur 126 and tibia 214.

The expandable devices 720 and 722 may be resiliently expanded under the influence of fluid pressure conducted through conduits to the expandable devices. If the expandable devices 720 and 722 are inserted after the incision 114 is formed in the knee portion 76 of the patient's leg 70, the conduits for conducting fluid to and from the expandable devices 720 and 722 may extend through the incision. However, if the expandable devices 720 and 722 are inserted prior to making of the incision 114, the conduits for conducting fluid to and from the expandable devices may extend through small portals or stab wounds formed in the knee portion of the patient's leg. It should be understood that the conduits for conducting fluid to and from the expandable devices 720 and 722 may extend through small secondary incisions spaced from the main incision 114 even though the expandable devices 720 and 722 are positioned in the knee portion 76 after making the main incision.

The small portals or stab wounds which form secondary incisions are spaced from the location where the main incision 114 is formed. Thus, the conduit for conducting fluid to and from the expandable device 722 may extend through a portal or stab wound formed in the posterior portion of the knee portion 76 of the patient's leg 70. Before they are expanded, the contracted expandable devices 720 and 722, are very small and flexible. The contracted expandable devices 720 and 722 have an appearance similar to a collapsed balloon. The contracted expandable devices are easily moved through the small secondary incisions.

It is contemplated that the expandable devices 720 and 722 may be left in the knee portion 76 of a patient's leg 70 after the incision 114 has been closed. If this is done, the expandable devices 720 and 722 may be utilized to obtain a full range of motion of the patient's knee 76 during therapy and/or recovery of the patient after the incision has been closed. If the expandable devices 720 and 722 are formed of a non-biodegradable material, it may be desirable to remove the expandable devices after the incision 114 has been closed. If the expandable devices 720 and 722 are formed of a biodegradable material, they do not have to be removed after the incision has been closed. It is contemplated that the expandable devices 720 and 722 may be contracted by piercing the skin 342 and puncturing the expandable devices.

It is contemplated that it may be desired to form the expandable devices 720 and 722 (and/or the conduits for inflating expandable devices 720 and 722) of a biodegradable material which is absorbable by the patient's body. If this is done, the expandable devices 720 and 722 may be formed of polyglycolic acid, polylactic acid, or combinations of these materials. It is contemplated that the expandable devices 720 and 722 could be formed of materials which include hyaluronic acid, catgut material, gelatin, cellulose, nitrocellulose, collagen or other naturally occurring biodegradable materials. Although it is believed that it would be preferred to form the expandable devices 720 and 722 of biodegradable materials so that they can be left in the patient's body and hydrolyzed so as to be absorbed by the patient's body, it is contemplated that the expandable devices 720 and 722 could be made of a non-biodegradable material if desired. The resiliently expandable devices 720 and 722 may have any of the constructions disclosed in U.S. Pat. Nos. 5,163,949; 5,454,365 and 5,514,153. Of course, the resiliently expandable devices 720 and 722 could have a different construction if desired.

Obtaining Range of Motion

Figure 52:
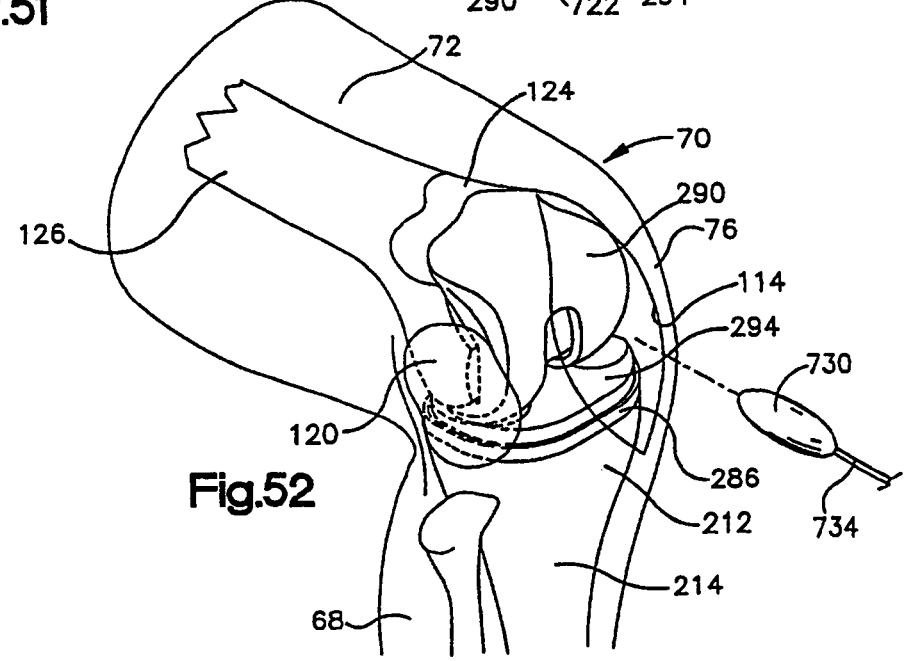
FIG. 52 is a schematic illustration depicting the manner in which an expandable device may be positioned relative to a knee portion of a patient's leg with the patient's leg in the position illustrated in FIGS. 2 and 3.

After the implants 286, 290 and 294 have been positioned on the femur 126 and tibia 214 in the manner illustrated schematically in FIG. 52, it is contemplated that the range of motion of the knee portion 76 will be checked. During the check of the range of motion of the knee portion 76, it may be found that the range is unduly limited due to interference between body tissue in the posterior of the knee portion 76 and the implants. The range of motion of the knee portion 76 may be limited by tightness of tendons, ligaments and/or other tissue in the knee portion 76.

Although it is believed that the expandable devices 720 and 722 of FIG. 51 may be utilized to alleviate these conditions, it may be preferred to use an expandable device 730 (FIG. 52) which is inserted between the tibial bearing insert 294 and the trochlear groove in the femur 126. Thus, once the implants 286, 290 and 294 have been positioned in the knee portion 76 of the patient's leg 70, the expandable device 730 may be moved through the incision 114. The expandable device 730 is then moved between the distal end portion 124 of the femur 126 and the proximal end portion 212 of the tibia 214.

The expandable device 730 may be a balloon or bladder which is made of resilient material. When fluid pressure in the expandable device 730 is increased, the expandable device is expanded from a collapsed condition to an extended condition. The resilient material of the expandable device 730 may or may not be stretched when the expandable device 730 is expanded.

The expandable device 730 may be moved posteriorly of the implants 286, 290 and 294 so as to engage tissue in the posterior portion of the patient's knee. Alternatively, the expandable device 730 may be positioned between the distal end portion 124 of the femur 126 and the proximal end portion 212 of the tibia 214. It is contemplated that the patient's leg 70 will be in the position illustrated in FIGS. 2 and 3 with the patella 120 (FIG. 52) offset when the expandable device 730 is positioned in the knee portion 76.

When the expandable device 730 is moved to the posterior of the patient's knee portion 76, expansion of the expandable device 730 applies pressure against tissue in the posterior portion of the patient's knee. This results in movement of body tissue away from the implants 286, 290 and 294. Assuming that body tissue in the posterior of the patient's knee portion 76 is interfering with the range of relative movement between the implants 286, 290 and 294, applying pressure against the body tissue in the posterior of knee portion will move the body tissue away from the implants to enable the range of motion to be increased.

Expansion of the expandable device 730 is effective to move and stretch body tissue, such as the joint capsule, ligaments, tendons, skin or other tissue associated with the posterior portion of the patient's knee. Space is established between the distal end portion 120 of the femur 126 and body tissue. Space is also established between the proximal end portion 212 of the tibia 214 and body tissue. Since the body tissue is moved and stretched by expansion of the expandable device 730, a portion of the space tends to remain even though the viscoelastic body tissue retracts when fluid is conducted from the expandable device 730 and the size of the device decreases.

The expandable device 730 may be left in place in the posterior of the patient's knee portion 76 after the incision 114 is closed. A conduit 734 connected with the expandable device 730 would extend through the closed incision 114 to enable fluid to be conducted to and from the expandable device 730. Therefore, after the incision 114 has been closed, the expandable device 730 can be expanded to increase the range of movement of the knee portion 76 of the patient's leg 70. After fluid has been conducted from the expandable device through the conduit 734, the size of the expandable device is reduced by exhausting fluid through the conduit. The reduced size of the expandable device enables the conduit 734 to be pulled outward, away from the knee portion 76, to pull the expandable device 730 through a very small opening in the closed incision.

If desired, the expandable device 730 could be formed of a biodegradable material and left in the posterior of the knee portion 76. The conduit 734 could be formed of a non-biodegradable material and pulled from the opening in the incision after the expandable device 730 has at least started to degrade. Of course, the conduit 734 could also be biodegradable.

Rather than applying force against body tissue at the posterior of the knee portion 76, the expandable device 734 may be utilized to apply force against the distal end portion 124 of the femur 126 and against the proximal end portion 212 of the tibia 214. This force would tend to stretch or release ligaments or other fibrous connective tissue connected with the femur 126 and tibia 214. This force would also stretch the joint capsule, collateral ligaments 590 and 592 (FIG. 41), and other tissues around the distal end portion 124 of the femur 126 and the proximal end portion 212 of the tibia 214.

When this is to be done, the expandable device 730 (FIG. 52) is moved to a position midway between posterior and anterior portions of the implants 286, 290 and 294. The expandable device 730 is then expanded under the influence of fluid pressure conducted through the conduit 734. As the expandable device expands, it acts as a joint jack to apply force against the femur 126 and tibia 214. This force will tend to stretch the collateral ligaments and other ligaments and tendons connected with the femur 126 and tibia 214.

Once the expandable device 730 has been utilized to apply an upwardly directed force (as viewed in FIG. 52) against the distal end portion 120 of the femur 126 and a downwardly directed force (as viewed in FIG. 52) against the proximal end portion 212 of the tibia 214, the expandable device 730 is contracted by conducting a flow of fluid from the expandable device through the conduit 734. The surgeon can then check ligament balancing and/or the range of motion of the knee portion 76. If the ligament balancing check and/or range of motion check indicates that it would be beneficial, the expandable device 730 can again be utilized to apply force against the femur 126 and tibia 214. Fluid pressure would again connected through the conduit 734 to the expandable device 730. Expansion and contraction of the expandable device 730 can be repeated as many times as necessary to obtain the desired ligament balancing and/or range of motion of the knee portion 76.

In FIG. 52, the leg 70 of the patient is in the position indicated in FIGS. 2, 3 and 25. However, the leg 70 of the patient could be moved from the flexed position of FIG. 52 to the extended condition of FIG. 51 with the expandable device in position between the distal end portion 120 of the femur 126 and the proximal end portion 212 of the tibia 214. It should be understood that the expandable devices 720, 722 and 730 of FIGS. 51 and 52 may be utilized with the leg 70 of the patient in either the extended orientation of FIG. 51 or the flexed orientation of FIG. 52. The leg 70 of the patient may be maintained stationary after insertion of the expandable devices 720, 722 and/or 730. Alternatively, the patient's leg 70 may be moved in any one or a combination of the directions indicated by the arrows 256, 258, 259 and 260 in FIG. 25 after insertion of the expandable devices 720, 722 and/or 730.

Although a single expandable device 730 is illustrated in FIG. 52, it should be understood that a plurality of expandable devices 730 could be inserted into the knee portion 76 of the patient's leg. A first one of the expandable devices 730 may be inserted into the posterior of the knee portion 76. A second expandable devices 730 may be positioned between the lateral portions of the femur 126 and tibia, that is, in a position similar to the position of the transducer 596 in FIG. 41. A third expandable device 730 may be positioned between medial portions of the femur 126 and tibia 214, that is, in a position similar to the position of the transducer 598 in FIG. 41.

It is contemplated that different pressures may be conducted to the expandable devices in different positions in the knee portion 76. For example, a relatively low fluid pressure may be conducted to the first expandable device 730 in the posterior of the knee portion 76 to move and/or stretch body tissue with a limited force. A relatively high fluid pressure may be conducted to the second and third expandable devices 730 disposed between the femur 126 and tibia 214 to effect relative movement between the femur and tibia.

If desired, a higher fluid pressure could be conducted to one of the expandable devices 730 disposed between the femur 126 and tibia 214 than the other expandable device. For example, a higher fluid pressure may be conducted to the second expandable device 730 disposed between lateral portions of the femur 126 and tibia 214 than to the third expandable device 730 disposed between the medial portions of the femur and tibia. Alternatively, a higher fluid pressure may be conducted to the third expandable device 730 disposed between medial portions of the femur 126 and tibia 214 than to the second expandable device 730 disposed between lateral portions of the femur 126 and tibia 214.

When a plurality of expandable devices 730 are used, the expandable devices may be made of the same material or different materials. For example, the first expandable device 730 in the posterior of the knee portion may be formed of a biodegradable material. The second and third expandable devices 730, located between the femur 126 and tibia 214, may be formed of a non-biodegradable material. Alternatively, the expandable devices 730 may all be formed of the same biodegradable material as the expandable devices 720 and 722.

It is contemplated that the expandable devices 720, 722 and/or 730 of FIGS. 51 and 52 may be utilized in association with many different joints in a patient's body. For example, the expandable devices may be utilized in association with surgery on a glenoid joint. Alternatively, the expandable devices may be used in association with surgery on a patient's spine. During spinal surgery, the expandable devices 720, 722 and/or 730 may be utilized to move one vertebra relative to an adjacent vertebra during replacement of an intravertebral disc between the vertebrae. If desired, the expandable devices 720, 722 and 730 could be positioned between articular processes on vertebrae. When the expandable devices 720, 722 and 730 are formed of a biodegradable material, they may be positioned relative to a patient's vertebral column during surgery and left in place after the surgery. This would allow at least partial healing after the surgery with the expandable devices being effective to transmit force between components of the patient's vertebral column.

The manner in which the expandable devices 720, 722 and 730 may be utilized in association with any one of many joints in the patient's body is similar to that disclosed in U.S. patent application Ser. No. 09/526,949 filed on Mar. 16, 2000. The manner in which an expandable device similar to the expandable devices 720, 722 and 730 may be placed within a shoulder joint is similar to the disclosure in the aforementioned application Ser. No. 09/526,949 of which this application is a continuation-in-part. The expandable devices 720, 722 and 730 may be utilized during carpal tunnel surgery in the manner disclosed in the aforementioned application Ser. No. 09/526,949. It is believed that it will be particularly advantageous to make the expandable devices 720, 722 and 730 of biodegradable material so that they may be left in a patient's body at the end of the surgery.

As previously mentioned, the expandable devices 720, 722 and 730 may be utilized during therapy after surgery to stretch body tissue in the knee portion 76 of the patient's leg 70 and/or to increase the range of motion of the knee portion. It is contemplated that an orthosis may be utilized to stretch tissue that limits joint movement. The orthosis may have a construction similar to the construction disclosed in U.S. Pat. No. 5,611,764. The orthosis may be utilized to affect static progressive stretching of tissue in the knee portion 76 of the patient's leg 70. In addition, the orthosis may be utilized during progressive stress reduction. The orthosis may be utilized in conjunction with one or more expandable devices corresponding to the expandable devices 720, 722 and 730 in the patient's knee portion. Alternatively, the orthosis may be utilized without providing expandable devices in the patient's knee portion.

It is contemplated that, during restoration of the range of motion of the knee portion 76, a constant passive motion device may be connected with the patient's leg. The constant passive motion device may include one or more load or force limiting devices similar to those disclosed in U.S. Pat. No. 5,456,268. The constant passive motion device may have a construction similar to that illustrated in U.S. Pat. No. 5,285,773. Of course, the constant passive motion device may have a different construction if desired. It is contemplated that a pulsatile stocking may be utilized to reduce the possibility of blood clots while a constant passive motion machine is utilized to increase the range of motion of the knee portion of a patient's leg.

It is contemplated that a laminar spreader may be used in association with the knee portion 76 during ligament balancing and/or gap balancing with the implants 286, 290 and 294. Alternatively, a distraction device which is spring loaded may be utilized on a medial, lateral or both sides of the knee portion 56 rather than the expandable elements 720, 722 and 730 to increase range of motion and/or provide a desired ligament balancing. Insol's technique may be utilized in establishing a desire range of motion of the knee portion 76 of the patient's leg 70.

Surgical Procedure

In the foregoing description of a specific surgical procedure which may be utilized in association with a knee portion 76 of a patient's leg, the femoral and tibial cuts are made, the patella is repaired and implants are installed in the knee portion 76 of the leg 70. However, it is contemplated that the various steps in this surgical operation may be performed in a different order if desired.

Immediately after the limited incision 114 (FIG. 6) is made in the knee portion 76 in the manner previously explained, repair of the patella 120 may be undertaken. During repair of the patella 120, the patient's leg 70 is in the position illustrated in FIGS. 2 and 3. The patella 120 is cut in situ with the guide assembly 464 (FIG. 36). After a flat surface has been cut along the plane 484 (FIG. 35) to form a flat surface on the inside of the patella, a layer on which the inner side 122 of the patella is disposed is removed. This decreases the thickness of the patella.

After the patellar cut has been made, in the manner previously explained and before installation of the patellar implant, the tibial cut is undertaken. During the tibial cut, the patient's leg 70 is in the position illustrated in FIGS. 2 and 3. The proximal end portion 212 of the tibia 214 is cut, in the manner illustrated schematically in FIG. 21.

While the tibial cut is being made, the patella 120 is offset from its normal position with the flat cut surface, previously formed on the inner side of the patella, facing toward the distal end portion 124 of the femur 126. Since the patellar cut has already been made, the patella 120 is relatively thin and provides minimal stretching of the skin 342 and other tissues in the knee portion 76 when the patella is in the offset position of FIG. 21 during the making of the tibial cut.

After the tibial cut has been made, the femoral cuts are made. Making of the femoral cuts after making of the tibial cut and after making of the patellar cut maximizes the space which is available for the making of the femoral cuts. During the making of the femoral cuts, the patient's leg 70 is in the position illustrated in FIGS. 2 and 3. After the tibial cut has been made, a layer is removed from the tibia and the cut surface 246 (FIGS. 22 and 23) on the proximal end portion 212 of the tibia is spaced from the distal end portion 124 of the femur 126. In addition, the patellar cut has been made so that the patella 120 is relatively thin and provides minimal interference. The femoral cuts are made in the manner previously explained in conjunction with FIGS. 8-20.

Figure 27:
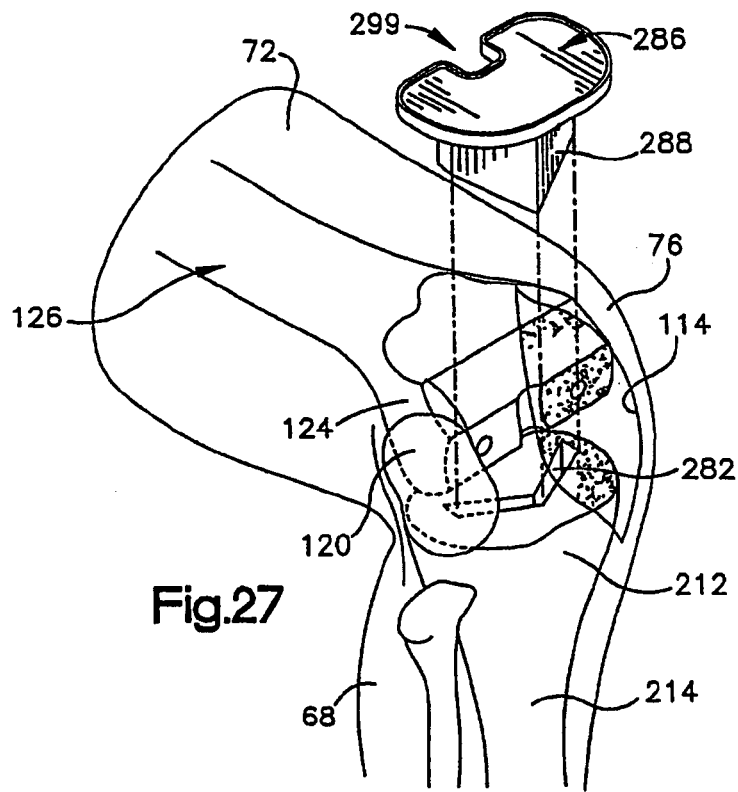
FIG. 27 is a schematic illustration depicting completed preparation of the tibia for a tibial tray implant with the leg of the patient in the position illustrated in FIGS. 2 and 3.
Figure 28:
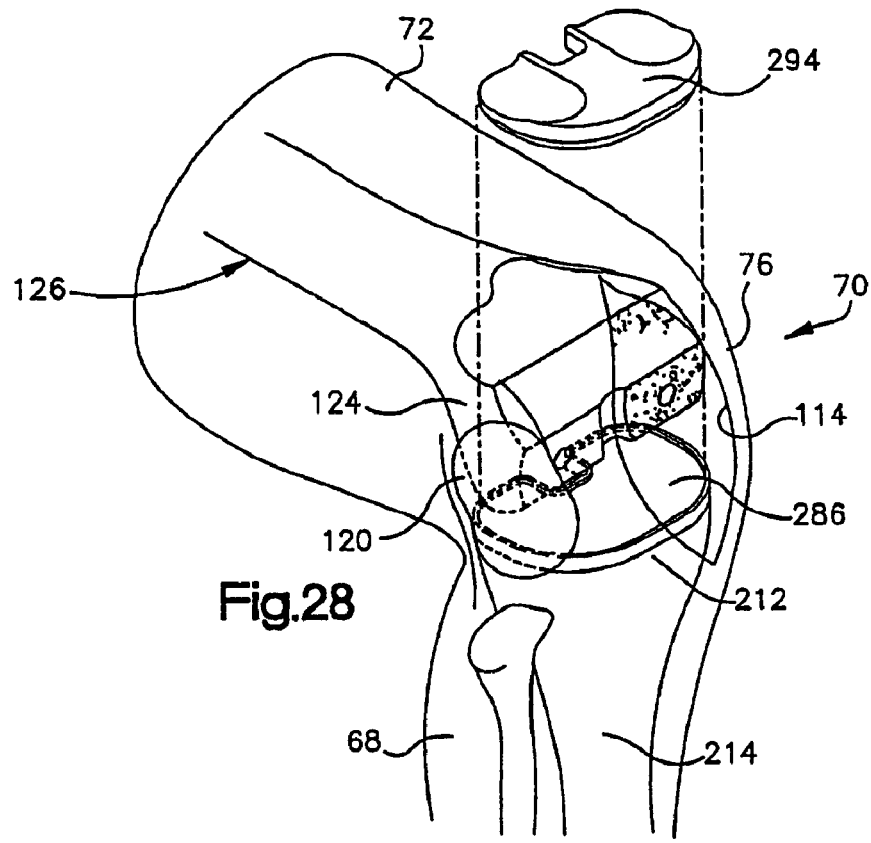
FIG. 28 is a schematic illustration depicting positioning of a tibial bearing insert in the tibial tray of FIG. 27 with the leg of the patient in the position illustrated in FIGS. 2 and 3.

After the femoral cuts have been made, the tibial tray 286 is positioned on the distal end portion 212 of the tibia 214 in the manner illustrated schematically in FIGS. 27 and 28. After the tibial tray 286 has been positioned on the tibia 214, the femoral implant 290 (FIG. 29) is positioned on the distal end portion 124 of the femur 126. After the femoral implant 290 has been positioned on the distal end portion 124 of the femur 126, the tibial bearing insert 294 (FIG. 29) is positioned on the tibial tray 286 in the manner previously explained.

Once the tibial and femoral implants 286, 290 and 294 have been positioned, the patellar implant is mounted on the cut surface of the patella 120. The patellar implant is positioned on the cut surface of the patella 120 while the patella is in the medially offset position illustrated in FIG. 29. By applying force to the patella pulling it outward away from the distal end portion 124 of the femur 126, a patellar implant can be moved between the patella 120 and the femoral implant 290 (FIG. 29) and mounted on the patella 120. When the patella 120 has been moved back to the normal or initial position illustrated in FIG. 6, the implant on the patella is aligned with the distal end portion 124 of the femur 126.

By making the patellar cut before making of the tibial cut and the femoral cuts, the available space for the tibial cut and femoral cuts is maximized. Maximization of the space for the tibial cut and femoral cuts and for the insertion of the femoral implant 290 and tibial implants 286 and 294 is maximized by mounting the patellar implant after the femoral and tibial implants have been mounted.

It should be understood that the foregoing procedure is performed with the patient's leg in the position illustrated in FIGS. 2, 3 and 25. Thus, the upper portion 72 of the patient's leg is supported above the support surface 64 by the leg support 80. The lower portion 68 of the patient's leg is suspended from the upper portion 72 of the patient's leg. The foot 74 is disposed below the support surface 64.

Femoral Cutting Guide

A femoral cutting guide 750 (FIG. 53) has cutting guide slots 752 and 754 with open ends 756 and 758. The guide slot 752 has parallel guide surfaces 762. Similarly, the guide slot 754 has parallel guide surfaces 764.

The guide surfaces 762 for the guide slot 752 are skewed at an acute angle of forty-five degrees to a major side surface 766 of the femoral cutting guide 750. Similarly, the guide surfaces 764 are skewed at an angle of forty-five degrees to the major side surface 756 of the femoral cutting guide 750. The guide surfaces 762 extend perpendicular to the guide surfaces 764. The guide surface 762 guide a saw blade during the making of an anterior chamfer resection on the distal end portion 124 of the femur 126. Similarly, the guide surfaces 764 guide a saw blade during the making of a posterior chamfer cut on the distal end portion 124 of the femur 126.

The femoral cutting guide 750 has an anterior guide surface 770 which guides movement of a saw blade during the making of an anterior resection on the distal end portion 124 of the femur 126. Anterior guide surface 770 extends across the femoral cutting guide 750 between the lateral end portion 774 and a medial end portion 776 of the femoral cutting guide 750. The anterior guide surface 750 extends perpendicular to the major side surface 766 of the femoral cutting guide 750.

A posterior guide surface 780 guides movement of a saw blade during the making of a posterior resection on the distal end portion 124 of the femur 126. The posterior guide surface 780 extends between the lateral end portion 774 and the medial end portion 776 of the femoral cutting guide 770. The posterior guide surface 780 extends perpendicular to the major side surface 766 and extends parallel to the anterior guide surface 770. The anterior guide surface 770 and the posterior guide surface 780 extend transverse to the guide surfaces 762 and 764 of the guide slots 752 and 754.

The femoral cutting guide 750 is disposed on the distal end of the femur 126. The femoral cutting guide 750 is connected with the distal end of the femur 126 by a pair of pins 784 and 786. The pins 784 and 786 have longitudinal central axes which extend perpendicular to the major side surface 766 of the femoral cutting guide 750 and extend generally parallel to a longitudinal central axis of the femur 126.

When the femoral cuts are to be made on the distal end portion 124 of the femur 126, the femoral cutting guide 750 is connected to the distal end of the femur. Initial portions of the various femoral cuts are then made by moving the saw blade along the guide surfaces 762, 764, 770 and 780 on the femoral cutting guide 750. Since the femoral cutting guide 750 extends only part way across the distal end portion 124 of the femur 126, the femoral cutting guide is disconnected from the femur and the femoral cuts are completed.

After the femoral cutting guide 750 has been disconnected from the femur 126, cut surfaces during formation of the initial portion of the anterior femoral cut are utilized to guide the saw blade during completion of the anterior femoral cut. Similarly, cut surfaces formed during the initial portion of the posterior femoral cut are utilized to guide the saw blade during completion of the posterior femoral cut. Cut surfaces formed during the making of anterior chamfer cut are utilized to guide the saw blade during completion of the anterior chamfer cut. Similarly, cut surfaces formed during making of the initial portion of the posterior chamfer cut are utilized to guide the saw blade during completion of the posterior chamfer cut.

The cutting tool which is used to form the femoral cuts, tibial cuts, and patellar cut may have any desired construction. Although a saw 172 and blade 170 have been disclosed herein as making the various cuts, many known types of cutting tools may be used if desired. For example, laser cutters, milling cutters, and/or ultrasonic cutters may be utilized. When one or more features of the present invention are utilized to perform knee joint revisions, an ultrasonic cutter may advantageously be utilized to cut cement previously used in association with an implant.

Side Cutting Guide

Figure 53:
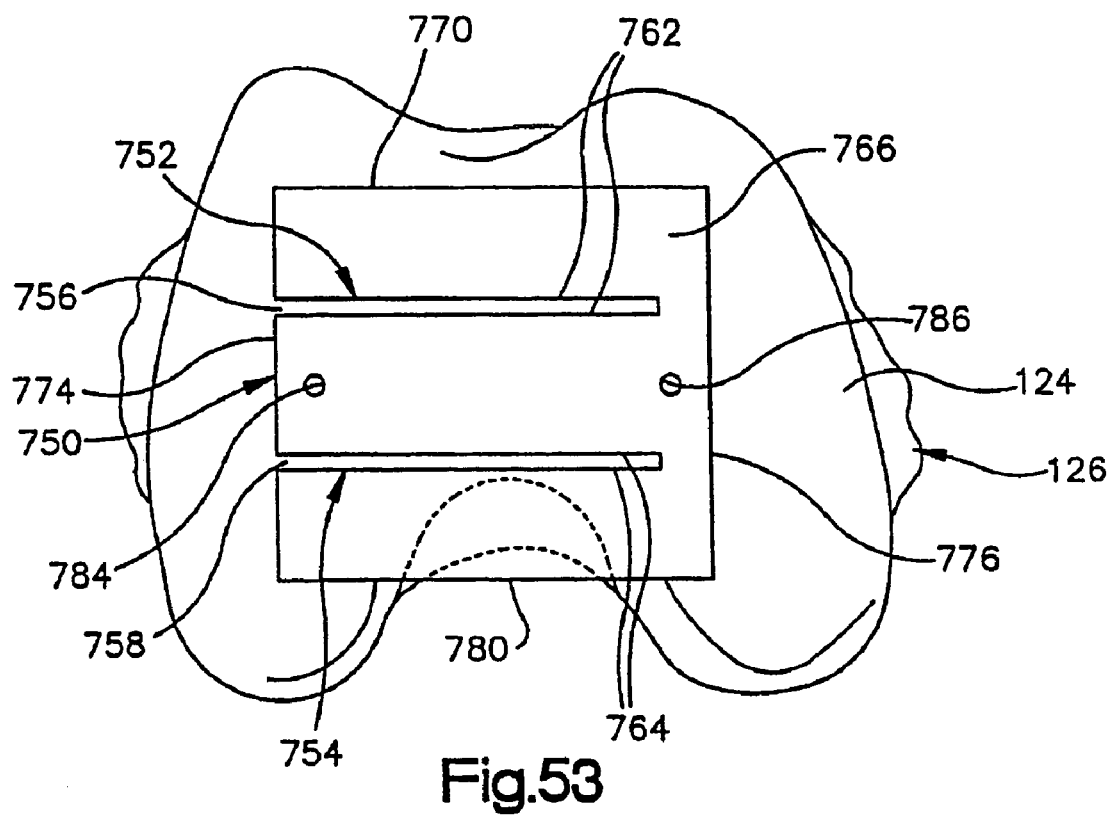
FIG. 53 is a schematic illustration depicting the manner in which a femoral cutting guide may be mounted on a distal end of a femur in a patient's leg with the patient's leg in the position illustrated in FIGS. 2 and 3.

Using the femoral cutting guide 210 of FIG. 19 or the femoral cutting guide 750 of FIG. 53, the femoral cuts are made by moving a saw blade from a distal end of the femur 126 toward a proximal end of the femur. However, it is contemplated that the femoral cuts could be made by moving a saw blade between opposite sides of the femur in a direction extending generally perpendicular to a longitudinal central axis of the femur. Thus, the saw blade is moved along a path which extends between lateral and medial surfaces on the distal end portion 124 of the femur 126.

Figure 54:
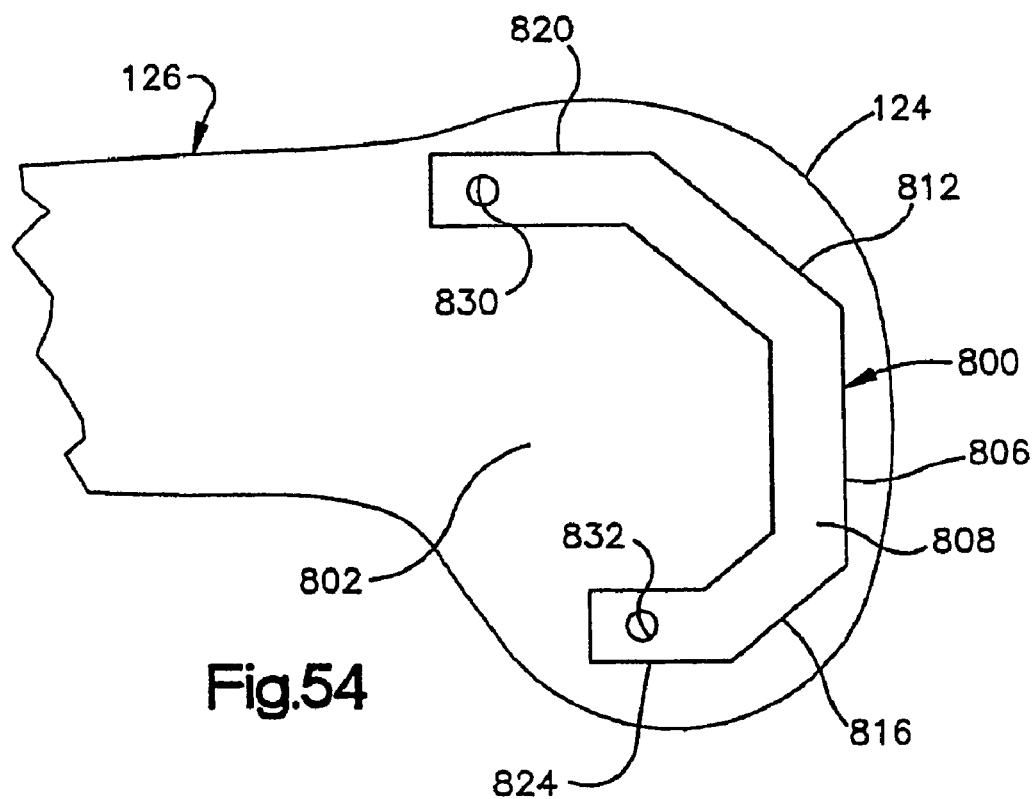
FIG. 54 is a schematic illustration of the manner in which a femoral cutting guide may be mounted on a side surface of a femur in a patient's leg with the patient's leg in the position illustrated in FIGS. 2 and 3.

A femoral cutting guide 800 is illustrated in FIG. 54 as being mounted on a lateral surface 802 of the femur 126. However, the femoral cutting guide 800 could be mounted on the medial surface of the femur 126 if desired. When the cutting guide 800 is mounted on the lateral surface 802 of the femur 126, the incision 114 (FIG. 6) is laterally offset. Similarly, when the cutting guide 800 is mounted on a medial surface of the femur 126, the incision 114 is medially offset.

The femoral cutting guide 800 has a distal guide surface 806. The distal guide surface 806 is disposed in a plane which extends perpendicular to a longitudinal central axis of the femur 126 and extends through the lateral and medial condyles. The distal guide surface 806 extends perpendicular to a major side surface 808 of the femoral cutting guide 800.

An anterior chamfer guide surface 812 extends between opposite major sides of the femoral cutting guide 800. The anterior chamfer guide surface 812 is disposed in a plane which extends at an acute angle of forty-five degrees to a plane containing the distal guide surface 806. The anterior chamfer guide surface 812 extends perpendicular to the major side surface 808 of the femoral cutting guide 800. Similarly, a posterior chamfer guide surface 816 extends between opposite major sides of the femoral cutting guide 800. The posterior chamfer guide surface 816 is disposed in a plane which extends at an acute angle of forty-five degrees to a plane containing the distal guide surface 806. The plane containing the posterior chamfer guide surface 816 extends perpendicular to the plane containing the anterior chamfer guide surface 812.

An anterior guide surface 820 is disposed on the femoral cutting guide 800. The anterior guide surface 820 extends between opposite major sides of the femoral cutting guide 800. The anterior guide surface 820 is disposed in a plane which extends perpendicular to a plane containing the distal guide surface 806. The plane containing the anterior guide surface 820 extends generally parallel to a longitudinal central axis of the femur 126.

Similarly, the femoral cutting guide 800 includes a posterior guide surface 824. The posterior guide surface 824 extends between opposite major sides of the femoral cutting guide 800. The posterior guide surface 824 is disposed in a plane which extends parallel to a plane containing the anterior guide surface 820 and perpendicular to a plane containing the distal guide surface 806.

The femoral guide 800 is formed of one piece of metal and has parallel opposite major side surfaces 808. The femoral cutting guide 800 is connected with the lateral side 802 of the distal end portion 124 of the femur 126 by a pair of pins 830 and 832. The lateral side 802 of the femur may be cut to form a flat surface which is abuttingly engaged by a major side surface of the femoral cutting guide 800.

When the femoral cuts are to be made, the lateral side of the femur is cut to form a flat side surface on which the femoral cutting guide 800 is mounted by the pins 830 and 832. A saw blade or other cutting tool is then moved from the lateral side to the medial side of the distal end portion 124 of the femur 126 while the saw blade or other cutting tool is guided by the distal guide surface 806 on the femoral cutting guide 800. The distal guide surface 806 has an extent which is less than the extent of the distal end cut to be formed on the distal end portion 124 of the femur 126. Therefore, after an initial portion of the distal end cut has been made utilizing the guide surface 806 to guide movement of a saw blade or other cutting tool, the cut surfaces are utilized to guide movement of the cutting tool during completion of the distal end cut.

Once the distal end cut has been completed, the saw blade or other cutting tool is moved from the lateral side of the femur 126 to the medial side of the femur along the anterior chamfer guide surface 812. The cutting tool is then moved from the lateral side of the femur 126 to the medial side of the femur along the posterior chamfer guide surface 816. Since the anterior chamfer guide surface 812 and posterior chamfer guide surface 816 have lengths which are less than the length of the anterior chamfer cut and posterior chamfer cut, only the initial portions of the chamfer cuts are made utilizing the guide surfaces 812 and 816 on the femoral cutting guide 800. The cuts are completed by guiding movement of the saw blade or other cutting tool with the previously cut surfaces.

The anterior guide surface 820 is then utilized to guide movement of the saw blade during an initial portion of an anterior cut. During making of the anterior cut, the saw blade or other cutting tool is moved from the lateral side to the medial side of the distal end portion 124 of the femur 126. Since the anterior guide surface 820 is smaller than the anterior cut, surfaces formed during making of an initial portion of the anterior cut are utilized to guide the saw blade or other cutting tool during a final portion of the anterior cut.

Similarly, the posterior guide surface 824 on the femoral cutting guide 800 is utilized to guide the saw blade or other cutting tool during making of a posterior cut. During the making of an initial portion of the posterior cut, the saw blade is moved along the posterior guide surface 824 from the lateral side 802 of the distal end portion 124 of the femur 126 to the medial side. The posterior guide surface 824 is shorter than the posterior cut. Therefore, cut surfaces formed during an initial portion of the posterior cut are utilized to guide the saw blade during completion of the posterior cut.

The femoral cutting guide 800 remains connected with the femur 126 during the initial portion of each of the femoral cuts and during completion of the femoral cuts. The femoral cutting guide 800 is not of the capture type. Therefore, a saw blade is free to move past the guide surfaces 806, 812, 816, 820 and 824 during completion of the femoral cuts. If the guide surfaces 806, 812, 816, 820 and 824 were formed by slots, the femoral cutting guide 800 would have to be disconnected from the femur before the femoral cuts could be completed.

The femoral cutting guide 800 has been illustrated in FIG. 54 as being mounted on the lateral side 802 of the femur 126. However, it is contemplated that the femoral cutting guide could be mounted on the medial side of the femur if desired. The distal cuts, chamfer cuts, anterior cuts and posterior cuts were set forth as being performed in that order. However, there is no critical order as to the sequence of the cuts. It is contemplated that the cuts may be formed in any desired sequence.

During use of the femoral cutting guide 800, the patient's leg 70 can be in the orientation illustrated in FIGS. 2, 3 and 25. The drapery system 100 can be utilized to maintain a sterile field during the operation on the patient's leg.

Optical Systems

Rather than using the guide members illustrated in FIGS. 9-21, it is contemplated that an optically created guide could be utilized. The optically created guide may be a three dimensional image created by projecting a hologram onto an end portion of a bone which is to be cut. For example, a hologram may be used in projecting a three dimensional image of any one of the guides 138 (FIG. 11), 186 (FIG. 17), 210 (FIG. 20), and 218 (FIG. 21) onto a femur 126 or tibia 214 in a patient's body. Alternatively, one or more beams of coherent or non-coherent light may be projected onto the bone which is to be cut to provide a two dimensional cutting guide.

Figure 55:
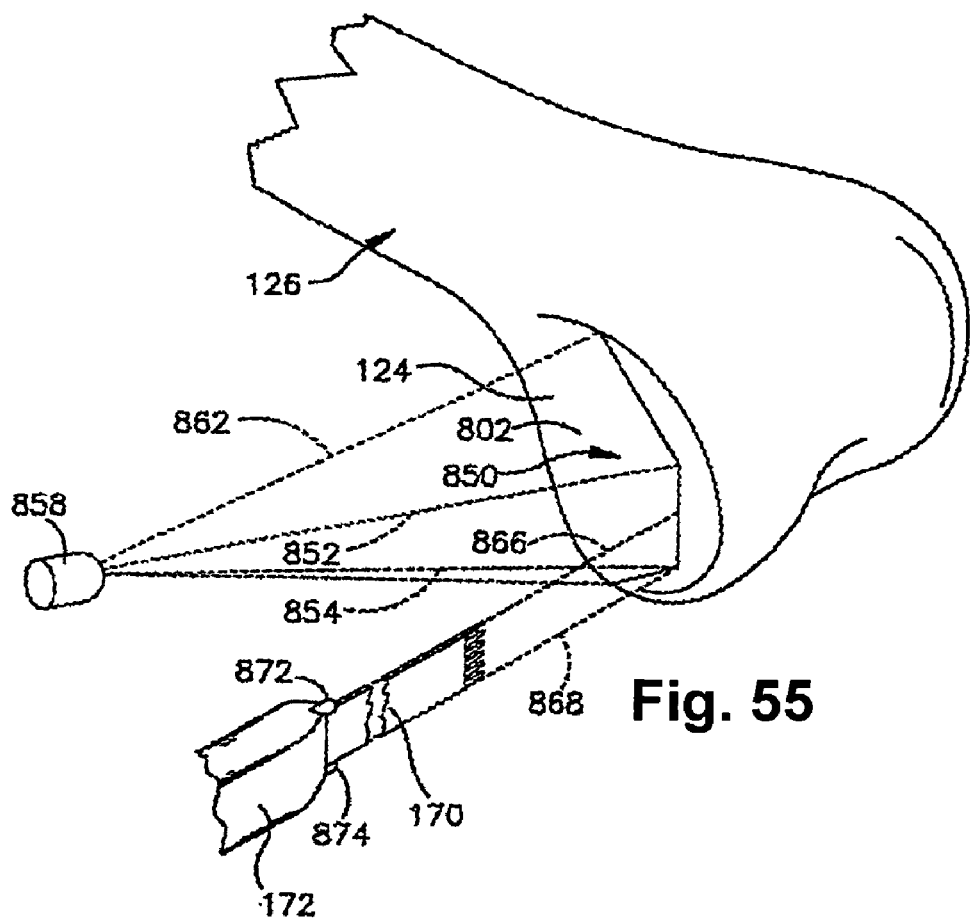
FIG. 55 is a schematic illustration depicting the manner in which light is directed onto a distal end portion of a femur with the patient's leg in the position illustrated in FIGS. 2 and 3.

Utilizing pre-operative templating based on images of one or more bones in a patient's body, for example, a distal end portion 124 (FIG. 55) of a femur 126, a hologram may be developed. The hologram is utilized with a projector 858 to create a three dimensional image 850. The illustrated three dimensional image is of a pattern of cuts to be made on the distal end portion of the femur 126. In FIG. 55, the three dimensional image 850 is visible to the surgeon 106 and is utilized to replace the femoral cutting guide 800 of FIG. 54. Rather than replacing the femoral cutting guide 800 with a pattern of cuts as shown in FIG. 55, the three dimensional image 850 may be an image of the femoral cutting guide 800.

Although a hologram may be used to produce the three dimensional image 850 which is visible to the surgeon 106, the image may be created in other ways if desired. When the visible image 850 is to be projected onto a flat surface cut on the distal end portion 124 of the femur 126, a two dimensional image may be utilized if desired. The two dimensional image 850 may be accurately projected on to the flat surface on the end portion 124 of the femur 126 utilizing either coherent or non-coherent light and known image projection techniques.

The three dimensional image 850 has visible light beams 852 and 854 which define opposite ends of a sight line for guidance of a saw 172 or other cutting tool. If desired, light may be projected with a plane of colored light which extends between the light beams 852 and 854. The colored light plane extending between the light beams 852 and 854 is visible and provides a guide for alignment of a blade 170 in a desired spatial orientation relative to the side surface 802 on the femur 126.

The surgeon 106 moves the saw blade 170 along the colored plane of light extending between the light beams 852 and 854. The colored plane of light extending between the light beams 852 and 854 indicates to the surgeon the desired spatial orientation of the saw blade 170 during the making of a cut. A sensor connected with the saw 172 enables a computer connected with a source 858 of the image 850 to have the plane of light extend along each of the desired saw cuts during the making of the saw cut. Thus, during the making of the femoral cut which extends between the light beams 852 and 854, a plane of colored light extends between the light beams. This enables the surgeon to determine when the saw blade is properly aligned with the side surface 802 of the femur 126. When a different cut is to be made, for example, a cut between the light beam 852 and a light beam 862, a plane of colored light extends between the light beams 852 and 862. The plane of light is visible and indicates to the surgeon the desired spatial orientation of the blade 170 of the saw 172 relative to the femur 126.

In addition, locating laser light beams 866 and 868 are projected from laser light sources 872 and 874 mounted on the saw 172. The locating laser light beams 866 and 868 are visible to the surgeon 106 and are of a different color than the plane of light extending between the light beams 852 and 854 of the image 850. Therefore, a surgeon can visually determine when the locating laser light beams 866 and 868 are aligned with the plane of light extending between the light beams 852 and 854 of the image 850.

When the locating laser light beams 866 and 868 are disposed in the plane of light extending between the light beams 852 and 854, the saw blade 170 is accurately aligned with the portion of the femoral cut to be made between the light beams 852 and 854 of the image 850. If the locating laser light beams 866 and 868 are not disposed in the plane of light extending the light beams 852 and 854, the saw blade 170 is not in alignment with the desired location for the femoral cut.

In addition to the visual indication provided by alignment of the locating laser light beams 866 and 868 with the plane of light between the light beams 852 and 854, audible and/or visual signals may be provided to the surgeon indicating whether or not the locating laser light beams 866 and 868 are in alignment with the plane of colored light extending between the light beams 852 and 854. For example, a green light may be illuminated when the locating laser light beams 866 and 868 are in the same plane as the light beams 852 and 854 of the image 850. A red light may be illuminated when either or both of the locating laser light beams 866 and 868 are not located in the plane of colored light extending between the light beam 852 and the light beam 854. In addition, a warning sound, that is, an alarm, may be sounded when either one of the locating laser light beams 866 or 868 is offset from the plane of colored light extending between the light beams 852 and 854.

Once the femoral cut extending between the light beams 852 and 854 has been completed, the saw 172 and saw blade 170 are moved into alignment with a plane of colored light extending between the light beam 852 and 862. A second femoral cut is then made in the same manner as previously described in conjunction with the light beams 852 and 854. This process is repeated until the desired number of femoral cuts have been made.

In the embodiment illustrated in FIG. 55, the image 850 is projected onto a side surface 802 of the femur 26. If desired, a three dimensional image may be projected onto all sides of the distal end portion 124 of the femur 126. If this is done, the image may advantageously be a three dimensional image formed by lines which define the cuts to be made. As the saw blade 170 moves along lines of the three dimensional image, the saw blade 170 is moved to orientations corresponding to the orientations of the saw blade when making the femoral cuts illustrated in FIGS. 12-23. However, rather than using the cutting guides illustrated in FIGS. 12-23, the three dimensional image, corresponding to the image 850 of FIG. 55, is projected onto the entire distal end portion 124 of the femur 126. Locating laser light beams would be projected from the saw 172 to indicate to a surgeon when a saw was in the desired orientation relative to light planes forming portions of the image projected onto the distal end 874. This enables the saw blade 170 to be located relative to the distal end 874 of the femur 126 in the same manner as previously explained in conjunction with the side surface 802 of the femur.

As was previously mentioned, the three dimensional image 850 may be an image of anyone of the guides 138, 186, 210, 500, 750 or 800. The saw blade 170 would be moved along the image of a guide surface on the three dimensional image of the guide. The locating laser light beams 866 and 868 would indicate to the surgeon the orientation of the saw blade 170 relative to the three dimensional image of a guide surface on the three dimensional image of any one of the guides 138, 186, 210, 218, 500, 750 or 800. This would eliminate the heavy metal guides which have previously been used. When the size of any one of the three dimensional images of one of the guides 138, 186, 210, 218, 500, 750 or 800 is to be changed, it is merely necessary to have a computer controlling the projection of the three dimensional image to change a hologram being used to project the image or to effect a change in optics through which the image is projected.

Once the femoral cuts have been completed, an optical measuring device, such as an interferometer, may scan the cuts to determine if they have the desired configuration. Scanning the cuts with an optical measuring device may be used to eliminate the necessity of performing trials with provisional components. Eliminating the necessity of utilizing provisional components substantially reduces the amount of equipment required during a partial or total knee replacement.

The cut surfaces on the distal end portion 124 of the femur 126 and the proximal end portion 212 of the tibia 214 are illustrated in FIGS. 22 and 23. Rather than performing trials with provisional implants, the cut surfaces on the femur 126 and tibia 214 are measured using known optical measuring devices. A computer, connected with the optical measuring device, is utilized to compare the measurement of the cut surfaces on the femur 216 and the tibia 214 with desired measurements for the specific implants 286, 290 and 294 to be mounted on the femur and tibia. The computer also compares optically determined orientations of the cut surfaces on the femur 126 and tibia 214 relative to desired orientations of the cut surfaces.

The optical measuring device may have any one of many known constructions. For example, the optical measuring device may have the construction illustrated in U.S. Pat. No. 6,185,315 or 6,195,168 if desired. If an optical measuring device or other measuring device indicates that the cut surfaces are incorrect, a computer connected with the source 858 (FIG. 55) of the image 850 will change the hologram to correspond to a next smaller size of implant. When a surgeon determines that the femur 126 should be cut for the next smaller size implant, the surgeon manually enters data into the computer. In response to this data, the computer causes the projector 858 of the image 850 to project an image corresponding to a next smaller size image. The saw 172 is then utilized to cut the femur along the lines indicated by the next smaller size image. This will allow the next smaller size implant to be mounted on the femur.

It is contemplated that the projector 858 could have any desired construction. For example, the projector 858 could have a construction which is generally similar to the construction of apparatus disclosed in U.S. Pat. No. 6,211,976. It is contemplated that the laser light sources 872 and 874 could have a construction similar to the construction of devices disclosed in U.S. Pat. No. 5,425,355. The laser light sources 872 and 874 may have a construction which is similar to the construction of devices which are commercially available from Laserscope, Inc. of San Jose, Calif.

It is contemplated that the patient's leg 70 will be in the position illustrated in FIGS. 2 and 3 when either the two dimensional or the three dimensional image is projected onto the end portion 124 of the femur 126. The relatively small incision 114 may be resiliently expanded and/or moved relative to the distal end portion 124 of the femur 126 to allow the image 850 to be sequentially projected onto various areas on the distal end portion 124 of the femur 126. A three dimensional image may be generated by any one of several known methods, including the method disclosed in U.S. Pat. No. 5,379,133.

It is contemplated that the three dimensional image 850 may be used with procedures other than cutting of one or more bones in a patient's leg 70. For example, a three dimensional image of cuts to be made on a vertebra in a patient's back may be projected onto the vertebra. The three dimensional image may be used in surgery involving soft tissue in a patient's body. For example, the three dimensional image may be projected to a location in a patient's body where a vascular anastomosis or an intestinal anastomosis is to be undertaken. The three dimensional image may correspond to a pattern of stitches to be made between portions of soft body tissue. By projecting the three dimensional image into a patient's body at any desired location where surgery of any type is to be undertaken, a guide is provided in the patient's body to assist the surgeon.

The locating laser light beams 852 and 854 may be used with surgical instruments other than the saw 172. For example, the locating laser light beams 852 and/or 854 could be utilized to indicate the position of a bovie, or a needle, or forceps relative to body tissue. The locating laser light beams may have an intensity which is sufficient to shine through body tissue and enable a surgeon on one side of body tissue to visually determine the position of a surgical instrument on the opposite side of the body tissue.

Unicompartmental Knee Replacement

The drawings associated with the foregoing description have illustrated a full knee replacement rather than a partial knee replacement. However, it is contemplated that the previously described features of the present invention may be utilized with either a partial knee replacement or a full knee replacement. A femur 126 is illustrated schematically in FIG. 56 and has a distal end portion 124 with a pair of condyles 890 and 892. When a partial knee replacement is to be made, only one of the two condyles, that is the condyle 892, is cut. A saw 172 having a blade 170 is used to cut the condyle 892 along a line indicated at 896 in FIG. 56.

The saw 172 is provided with laser light sources 902 and 904. The laser light sources 902 and 904 project visible locating laser light beams 906 and 908 which extend along opposite longitudinal edges of the saw blade 170. The locating laser light beams 906 and 908 impinge against the condyle 892. The locating light beams are of colored coherent light which is visible to a surgeon to indicate the orientation of the saw blade 170 relative to the condyle 892.

It is contemplated that the saw 172 and blade 170 may be utilized in association with a guide member which is connected with the femur 126. Alternatively, a two or three dimensional image, corresponding to the image 850 of FIG. 55, may be projected onto the distal end portion of the femur 126. Another alternative would be to make a line 896 on the condyle 892 with a marking instrument.

Rather than using a saw blade 170 to make the cut in the condyle 892, it should be understood that a different type of cutting tool could be utilized if desired. For example, a milling cutter could be used to cut along a line 896 in FIG. 56. If a full knee replacement, rather than a partial knee replacement, is desired, both condyles 890 and 892 may be cut with the saw 172 and blade 170 using the laser light sources 902 and 904 to indicate the position of the saw blade relative to the distal end portion 124 of the femur 126. Once the femoral cuts have been made, an optical measuring device may be utilized to determine whether or not the cuts are of the proper size.

Multiple Incisions

A single incision 114 is illustrated in FIGS. 6-8 to provide access to the knee portion 76 of the patient's leg 70. As has been previously explained herein, the length of the incision 114 is minimized. However, it is contemplated that the length of the incision 114 could be further reduced by providing one or more very small incisions 920 (FIG. 57) in the knee portion 76 of a patient's leg 70 in association with the incision 114. The incision 920 is a small stab wound which forms a portal through the skin 342. The blade 170 of the saw 172 or other cutting tool may be moved through the small incision 920 to make one or more femoral cuts.

After the femoral cuts have been made through the small incision 920 and the larger or main incision 114, femoral and/or tibial implants are moved through the main incision. By providing the small incision 920 in association with the larger main incision 114, the overall length of the main incision may be minimized.

During making of the incisions 114 and 970, the patient's leg 70 is in the position illustrated in FIGS. 2 and 3. During making of the tibial and femoral cuts and insertion of the implants, the patient's leg 70 is also in the position illustrated in FIGS. 2 and 3. If desired, one or more expandable devices, corresponding to the expandable devices of FIGS. 51 and 52, may be inserted through one or more small incisions 920 and/or the main incision 114.

Figure 56:
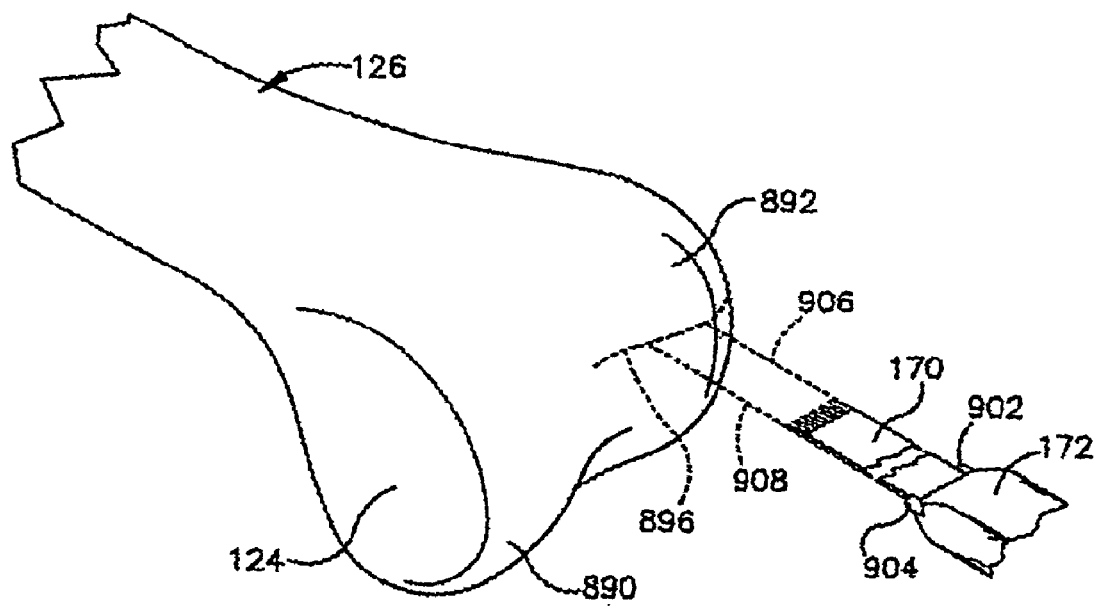
FIG. 56 is a schematic illustration depicting the manner in which light is used to guide movement of a cutting tool relative to a distal end portion of a femur with the patient's leg in the position illustrated in FIGS. 2 and 3.
Figure 57:
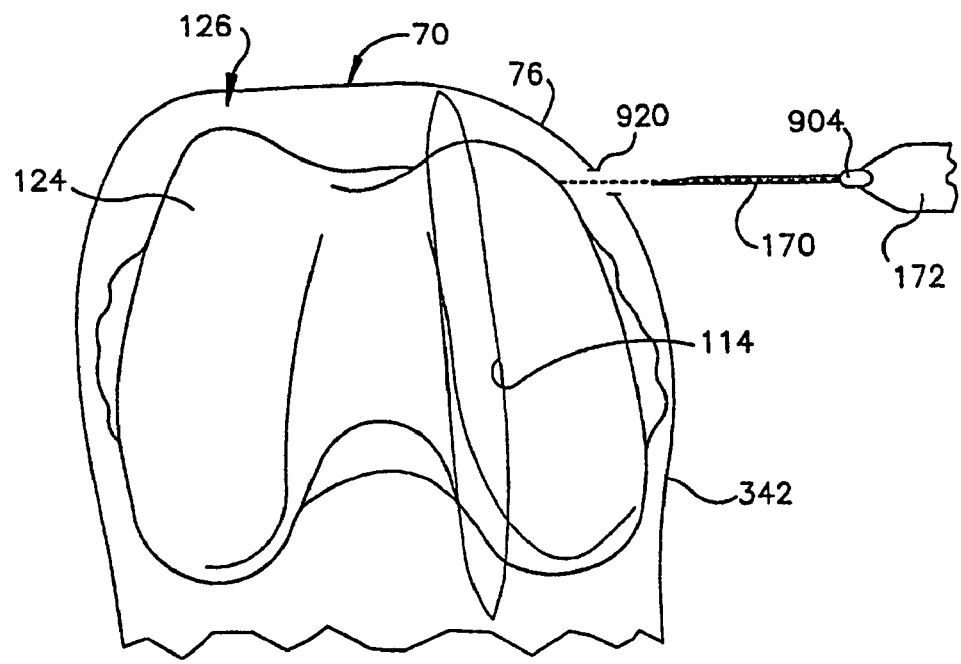
FIG. 57 is a schematic illustration depicting the manner in which a cutting tool is moved relative to a secondary incision with a knee portion of a patient's leg in the position illustrated in FIGS. 2 and 3.

In the embodiment of the invention illustrated in FIG. 57, laser light sources 902 and 904 are connected with the saw 172 in the manner illustrated schematically in FIG. 56. The laser light sources provide visible locating laser light beams, corresponding to the locating laser light beams 906 and 908 of FIG. 56.

By using more than one incision, that is, the main incision 114 and one or more small incisions 920, cutting tools can approach and move along the distal end portion 124 of the femur 126 from different directions. Thus, the saw blade 170 moves from the right to the left as viewed in FIG. 57, that is, in a lateral direction, during making of a femoral cut. A cutting tool which moves through the incision 114 may move in a superior direction along the femur 126, that is, from the distal end portion 124 of the femur 126 toward a proximal end portion of the femur. The cutting tools may be used to make cuts required for either a partial or full knee replacement.

Although it is preferred to make the incisions 114 and 920 and to cut the femur 126 with the leg 70 of the patient in the position illustrated in FIGS. 2 and 3, it should be understood that the use of a plurality of incisions during the surgery with the leg in other positions may be desired. Although the foregoing description has been in conjunction with surgery on a knee portion of a leg 70 of a patient, it is contemplated that the surgery could be performed on a different portion of the patient if desired.

Patellar Tracking

A pair of transducers 596 and 598 are illustrated in FIGS. 41 and 42 to compare tension and collateral ligaments 590 and 592. The manner in which the transducers 596 and 598 are positioned between the femur 126 and tibia 214 is illustrated schematically in FIG. 58.

In accordance with another feature of the invention, a pair of patellar transducers 930 and 932 are disposed on an inner side of the patella 120. The patellar transducers 930 and 932 are connected with a display, corresponding to the computer display areas 601 and 602 of FIG. 41. The patellar transducers 930 and 932 are disposed between the distal end portion 124 of the femur 126 and the patella 120.

The patellar transducers 930 and 932 have outputs which correspond to force transmitted between the patella 120 and the femur 126. Thus, the output from the transducer 930 corresponds to the force transmitted between the lateral side of the patella 120 and a lateral side of a trochlear groove in the femur 126. Similarly, the output from the transducer 932 corresponds to the force transmitted between a medial side of the patella 120 and a medial side of the trochlear groove in the femur 126. By comparing the output from the patellar transducers 930 and 932 during relative movement between the femur 126 and tibia 214, variations in the force transmitted between the lateral and medial portions of the patella 120 can be compared. This enables a surgeon to determine when the patella is tracking properly relative to the femur 126.

The patellar transducers 930 and 932 are resiliently expandable containers which hold fluid. As the force transmitted between the patella 120 and the femur 126 increases, the pressure of the fluid in the patellar transducers 930 and 932 increases. It is contemplated that the containers 930 and 932 may hold either a gas or a liquid. Pressure signals corresponding to the pressure in the patellar transducers 930 and 932 are conducted through conductors 934 and 936 to a display, corresponding to the computer displays 601 and 602 of FIG. 41. The patellar transducers 930 and 932 may have any desired construction which enables them to measure the force transmitted between the patella 120 and the femur 126. Thus, the transducers 930 and 932 could be of the piezoelectric type or of a strain-gauge type.

Figure 58:
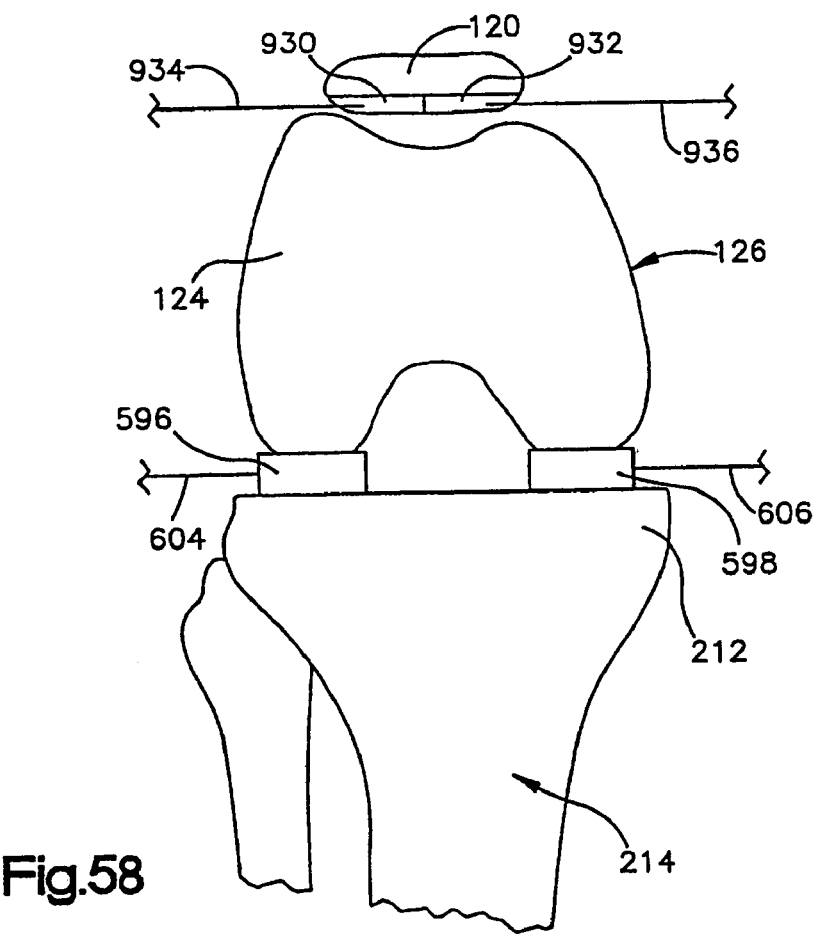
FIG. 58 is schematic illustration depicting the relationship of transducers to a patella and distal end portion of a femur with the patient's leg in the position illustrated in FIGS. 2 and 3.

During checking of patellar tracking with the transducers 930 and 932, the upper portion 72 of the leg 70 of the patient is supported above the support surface 64 by the leg holder 80 (FIG. 2). The leg 70 is moved between the flexed condition of FIGS. 2 and 3 and the extended condition of FIG. 4. During movement of the leg 70 between the flexed and extended conditions, there is relative movement between the end portion 124 of the femur 126 and the patella 120 (FIG. 58). During relative movement between the femur 126 and patella 120, the output from the patellar transducers 930 and 932 indicates the manner in which force transmitted between the patella and femur varies. This enables a surgeon to detect any defects in tracking of the patella 120 relative to the femur 126.

The patellar transducers 930 and 932 are mounted on the patella 120 after the patellar implant has been mounted on the patella. This enables the patellar transducers 930 and 932 to be utilized to detect any irregularities in the manner in which the patellar implant cooperates with the femoral implant 290 (FIG. 29). However, it is contemplated that the patellar transducers may be mounted on the patella 120 before the patellar implant is mounted on the patella. When this is to be done, the transducers 930 and 932 may be mounted in a body having a size and configuration corresponding to the intended size and configuration of the patellar implant.

In the embodiment of FIG. 58, the patellar transducers 930 and 932 extend across the patella 120 between lateral and medial edges of the patella. However, it is contemplated that the transducers 930 and 932 may extend only part way across the patella. If desired, more than the two illustrated patellar transducers 930 and 932 may be provided on the patella 120.

The transducers 596 and 598 can be utilized in combination with the patellar transducers 930 and 932 (FIG. 58). This enables the surgeon to determine the manner in which tension varies in the collateral ligaments 590 and 592 (FIGS. 41 and 42) with variations in force transmitted between the patella 120 (FIG. 58) and the femur 126. However, the patellar transducers 930 and 932 may be utilized without the transducers 596 and 598.

When it is determined that the patella 120 is not tracking properly, corrective action may be taken by increasing the fluid pressure in either or both of the patellar transducers 930 and 932. If the transducers 596 and 598 are utilized, the corrective action may include increasing the fluid pressure in either or both of the transducers 596 and 598. The transducers 596 and 598 and the patella transducers 930 and 932 are formed of resilient material which can be expanded under the influence of fluid pressure.

Although the patellar transducers 930 and 932 are utilized to measure force transmitted between lateral and medial portions of the patella 120 and the femur 126, the patellar transducers can be utilized to stretch or move body tissue in the same manner as the expandable devices 720, 722 and 730 (FIGS. 51 and 52). By increasing the fluid pressure conducted to the patellar transducer 930 (FIG. 58), the patellar transducer expands to stretch fibrous connective body tissue connected with the lateral side of the patella 120. Similarly, increasing the fluid pressure conducted to the patellar transducer 932 expands the patellar transducer 932 to stretch fibrous connective body tissue connected with the medial side of the patella 120. Increasing the fluid pressure conducted to both patellar transducers 930 and 932 is effective to expand both transducers and stretch fibrous connective body tissue with both sides of the patella 120.

The patellar transducers 930 and 932 may be formed of either a biodegradable material or a non-biodegradable material. When the patellar transducers 930 and 932 are to be left in the knee portion 76, the patellar transducers may be formed of a biodegradable material which is eventually absorbed by the patient's body. When the patellar transducers 930 and 932 are to be removed from the knee portion 76, the patella transducers may be formed of a non-biodegradable material. If the patellar transducers 930 and 932 are formed of a biodegradable material and are left in the knee portion 76 after closing of the incision 114, the patellar transducers may be expanded during therapy to stretch body tissue connected with the patella 120.

Movable Implant

The implant 690 of FIG. 50 is fixedly secured to the proximal end portion 212 of a tibia 214 by the projection 700 and fastener 702. In the embodiment of the invention illustrated in FIG. 59, a moveable implant 950 is provided between the distal end portion 124 of a femur 126 and a proximal end portion 212 of a tibia 214. In accordance with a feature of this embodiment of the invention, the implant 950 is freely moveable relative to both the femur 126 and the tibia 214.

The moveable implant 950 has a smooth upper (as viewed in FIG. 59) surface 952 which is engaged by a medial portion of the distal end portion 124 of the femur. Similarly, the moveable implant 950 has a smooth lower (as viewed in FIG. 59) surface 954 which is engaged by a medial portion of the proximal end portion 212 of the tibia 214. This smooth upper and lower end surfaces 952 and 954 compensate for defects in the existing surfaces on the distal end portion 124 of the femur 126 and the proximal end portion 212 of the tibia 214. By providing the moveable implant 950 between the distal end portion 124 of the femur 126 and the proximal end portion 212 of the tibia 214, pain which results from engagement of a surface 958 on the distal end portion 124 of the femur 126 with a surface 960 on the proximal end portion 212 of the tibia 214 is eliminated or at least substantially reduced.

During bending of the knee portion 76 of the patient's leg 70, the implant 950 may move relative to both the femur 126 and the tibia 214. The implant 950 can move in either a lateral or medial direction relative to the femur 126 and tibia 214. In addition, the implant 950 can move in either a posterior or anterior direction relative to the femur 126 and tibia 214.

By having a three hundred and sixty degree (360°) range of movement relative to both the femur 126 and tibia 214, the moveable implant 950 accommodates relative movement between the femur and tibia with minimal pain. This is because relative movement will occur between the implant 950, femur 126 and tibia 214 at locations where frictional forces due to irregularities on the surfaces of the femur 126 and tibia 214 are minimal. In addition, the implant 950 can shift relative to the femur 126 and tibia 214 during bending of the knee portion 76 to accommodate irregularities in the existing surfaces 958 and 960 on the distal end portion 124 of the femur and the proximal end portion 212 of the tibia.

The range of movement of the implant 950 relative to the distal end portion 124 of the femur 126 and the proximal end portion 212 of the tibia 214 is limited by engagement of the moveable implant 950 with soft tissue in the knee portion 76 of the patient's leg 70. Therefore, even though the implant 950 can move relative to the distal end portion 124 of the femur 126 and the proximal end portion 212 of the tibia 214, the implant is held against excessive movement relative to the femur and tibia by soft tissues associated with the femur and tibia.

For example, engagement of the implant 950 with cartilage or other soft tissue which is located at the peripheral aspect of the knee joint between the femur 126 and tibia 214 retains the implant 950 within a desired range of movement. The cartilage may be articular cartilage and/or fibrocartilage. The cartilage is engaged by peripheral surfaces on the moveable implant 952 and retains the implant in a desired position relative to the femur 126 and tibia 214. In addition, fibrous connective tissue extending between the femur 126 and tibia 214 limits movement of the implant 950 relative to the femur and tibia.

The joint capsule in the knee portion 76 of the patient's leg may be engaged by the periphery of the implant 950 to retain the implant in a desired position. By using cartilaginous, ligamentous, or other tissues to limit the range of movement of the moveable implant 950, the implant can freely shift relative to the femur 126 and tibia 214 through a limited range of movement during bending of the knee portion 76 of the patient's leg 70. If desired, growth of the tissues used to limit the range of movement of the implant may be promoted.

Figure 59:
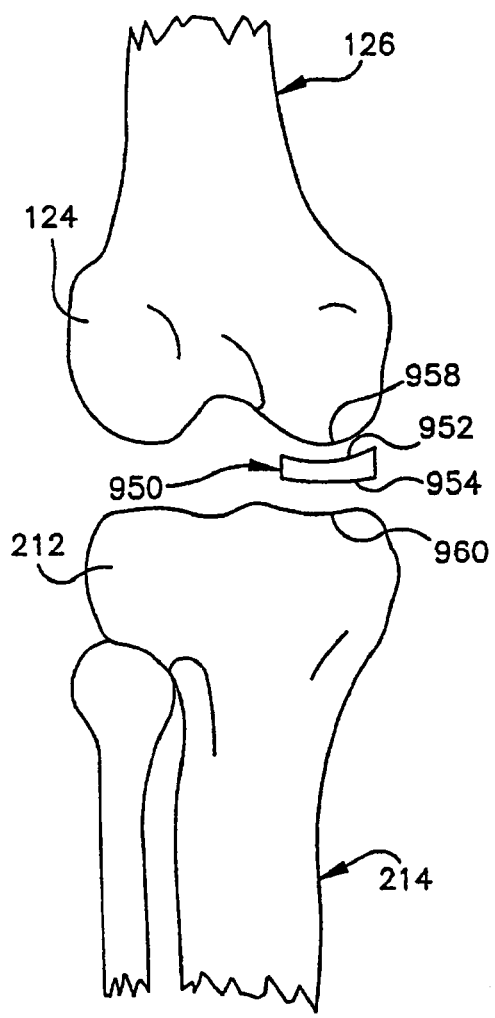
FIG. 59 is a schematic illustration depicting the relationship between a movable implant, a distal end portion of a femur, and a proximal end portion of a tibia in a knee portion of a leg of a patient.

The moveable implant 950 is sized so as to fit the surfaces 958 and 960 on the distal end portion 124 and proximal end portion 212 of the femur 126 and tibia 214 (FIG. 59). The sizing is accomplished by imaging the knee portion 76 of the patient's leg. The moveable implant 950 may be one of a series of implants of different sizes. After the patient's knee portion 76 has been imaged, a moveable implant is selected from the series of moveable implants of different sizes. The size of the selected moveable implant closely approximates the size of the space between the surfaces 958 and 960 on the distal end portion 124 and proximal end portion 212 of the femur 126 and tibia 214.

Thus, for a relatively large individual, a moveable implant 950 having a relatively large size is selected from the series of moveable implants. Similarly, for an individual having a relatively small size, a moveable implant 950 having a relatively small size is selected from the series of moveable implants. The selected implant has a size which corresponds to the general size of the space between the surfaces 958 and 960.

As a result of imaging of the knee portion 76 of the patient's leg 70, the actual configurations of the existing surfaces 958 and 960 on the femur 126 and tibia 214 can be accommodated by shaping the upper surface 952 of the moveable implant 958 to have a configuration corresponding to the surface 958 on the femur 126. Similarly, the lower surface 954 on the moveable implant 950 can be shaped to have a configuration corresponding to the configuration of the surface 960 on the tibia 214. Of course, the configuration of the periphery of the moveable implant can be changed to correspond to the configuration of the periphery of the space between the surfaces 958 and 960 into which the moveable implant 950 is to be placed.

It is contemplated that the imaging of the knee portion 76 of the patient's leg 70 may be done preoperatively, on an outpatient basis. The moveable implant 950 may then be selected from the series of available moveable implants and shaped to have a configuration which corresponds to the configuration of the space between the surfaces 958 and 960. The implant 950, which has been shaped to conform to the space between the surfaces 958 and 960, may then be moved to an operating room for insertion into a patient during the surgical procedure. Alternatively, the imaging of the knee portion 76 and shaping of the moveable implant 950 to the desired configuration may be performed in the operating room as part of the surgical procedure.

When the moveable implant 950 is to be positioned in the knee portion 76 of the patient's leg 70, in the manner indicated schematically in FIG. 59, a limited incision is made in the knee portion of the patient's leg. The limited incision is made while the patient's leg 70 is supported in the position shown in FIGS. 2, 3 and 25. The upper portion of the patient's leg is supported by the leg support 80.

The incision may have a limited length, corresponding to the limited length of the incision 114 of FIG. 7 and be located adjacent to an edge of the patella 120. When the implant 950 is to be positioned adjacent to a medial portion of the femur 126 and a medial portion of the tibia 214, in the manner illustrated schematically in FIG. 59, the incision 114 would be located adjacent to a medial edge of the patella 120, in the manner illustrated in FIG. 6. However, it should be understood that if the implant 950 is to be located adjacent to a lateral portion of the femur 126 and a lateral portion of the tibia 214, the incision 114 could be formed adjacent to a lateral edge of the patella 120.

Once the limited incision 114 has been formed in the manner previously described in conjunction with FIGS. 6 and 7 herein, the patella 120 may be moved to the offset position of FIG. 8 with the inner side 122 of the patella facing inward to facilitate utilization of an incision 114 having a limited length. Once the limited incision 114 has been formed, locations in the knee portion 76 of the patient's leg 70 may be inspected utilizing an optical device similar to the endoscope 352 of FIGS. 32 and 33. It is believed that the surgeon will bend the leg 70 of the patient between the flexed condition of FIG. 32 and the extended condition of FIG. 33 and will rotate the lower portion of the leg about it longitudinal central axis, in the manner indicated by the arrow 258 in FIG. 25 prior to positioning of the implant 950 in the knee portion 76 of the leg 70. This will enable the surgeon to detect any present or potential interference between the implant 950 and tissue in the knee portion 76 of the patient's leg 70.

Once this has been done, the surgeon may or may not decide to cut tissue in the knee portion 76 of the patient's leg 70 before inserting the moveable implant 950. If the surgeon elects to cut tissue in the knee portion 76 before insertion of the implant, this cutting will be relatively minor and will not involve the femoral and tibial cuts depicted in FIGS. 13-23 herein. This is because the moveable implant 950 is to be positioned between surfaces 958 and 960 which are in their existing condition. Of course, eliminating the major femoral and tibial cuts illustrated in FIGS. 13-23 herein will reduce the patient's post-operative recovery time. In addition, elimination of the major femoral and tibial cuts illustrated in FIGS. 13-23 enables the size of the incision 114 to be reduced.

Once the moveable implant 950 has been positioned between the existing surfaces 958 and 960 on the femur 126 and tibia 214, the patella 120 is moved from the offset position of FIG. 8 back to its normal position relative to the distal end portion 124 of the femur 126 and the proximal end portion 212 of the tibia 214. While the lower portion of the leg 70 is suspended from the upper portion of the leg and while the upper portion of the leg is held above the support surface 64 by the leg support 80 (FIG. 2), the incision 114 is closed in a normal manner. Prior to closing of the incision, an imaging apparatus can be utilized to generate images of the knee portion 76 during bending of the leg 70 between the flexed and extended conditions of FIGS. 32 and 33.

Any known imaging apparatus may utilized to image the knee portion 76 of the patient's leg 70. For example, the known C-arm fluoroscope 360 of FIG. 34 may be utilized to generate images of the knee portion 76 of the patient's leg 70. These images will enable the surgeon to determine the manner in which the implant 950 will move relative to the femur 126 and tibia 214 during bending of the patient's leg. Prior to closing of the incision 114, any corrective action which the surgeon may believe is necessary can be taken to make certain that the moveable implant 950 is in the desired relationship with the femur 126 and tibia 214.

Rather than forming the incision 114 in the mariner illustrated schematically in FIG. 6, the incision may be formed with an even shorter length and a cannula, corresponding to the cannula 364 of FIG. 39, inserted into the incision. The implant 950 may be moved through the resiliently expandable cannula into the space between the existing surfaces 958 and 960 (FIG. 59) on the femur 126 and tibia 214. The cannula would stretch the viscoelastic material of tissues in which the very limited incision is formed to resiliently expand the extent of the incision 114 to enable the implant 950 to be moved through the incision even though the moveable implant 950 is larger than the incision.

The cannula 564 (FIG. 39) through which the implant 950 (FIG. 59) is moved into the space between the surfaces 958 and 960 is advantageously expandable to accommodate the implant 950. The cannula may have any one of the constructions previously described in conjunction with FIG. 39 herein. If desired, multiple incisions, corresponding to the incisions 114 and 920 of FIG. 57 may be utilized during positioning of the implant 950. An expandable cannula may be associated with either or both of the incisions. Fiberoptic devices, such as an endoscope or arthroscope, may be inserted through a very small incision, corresponding to the incision 920 of FIG. 57, to facilitate positioning of the implant 950. By utilizing an expandable cannula and/or arthroscopic and endoscopic surgical procedures, the size of the incision 114 through which the implant 950 is moved can be minimized.

The moveable implant 950 is flexible so that force transmitted between the femur 126 and tibia 214 deflects the moveable implant 950. This results in the moveable implant 950 being shaped by the surfaces 958 and 960 on the femur 126 and tibia 214. By shaping the upper surface 952 on the moveable implant 950 with the surface 958 on the femur 126, smooth sliding engagement is provided between the surface 958 on the femur 126 and the upper surface 952 on the moveable implant 950. Similarly, the lower surface 954 on the implant 950 is shaped by the surface 960 on the tibia 214. By shaping the lower surface 954 on the implant 950 with the surface 960 on the tibia 214, smooth sliding engagement is provided between the surface 960 on the tibia 214 and the lower surface 954 on the moveable implant 950 during bending of the knee portion 76.

Shaping of the surfaces 952 and 954 on the moveable implant 950 may be accomplished in any one of many different ways. For example, the implant 950 may be formed of a material which is resiliently deflected by the surfaces 958 and 960 on the femur 126 and tibia 214. This results in the upper surface 952 and lower surface 954 and the moveable implant 950 being resiliently deflected to have a configuration corresponding to the configuration of the portions of the surfaces 958 and 960 which are engaged by the moveable implant during bending of the knee portion 76. During bending of the knee portion 76, the moveable implant 950 shifts or moves relative to the surfaces 958 and 960 on the femur 126 and tibia 214. During this shifting movement, the configuration of the upper surface 952 and the lower surface 954 of the moveable implant 950 is resiliently changed by forces transmitted between the femur 126 and tibia 214 through the moveable implant 950.

Rather than having the moveable implant 950 resiliently deflected by force transmitted between the femur 126 and tibia 214, the moveable implant 950 may be plastically deformed by the force transmitted between the femur and the tibia. Thus, the surface 958 on the femur 126 may plastically deform the upper surface 952 on the moveable implant 950 so that it retains a configuration corresponding to the configuration of the surface 958 on the femur 126. Similarly, the surface 960 on the tibia 214 may be plastically deform the lower surface 954 on the moveable implant 950 so that it maintains a configuration corresponding to the configuration of the surface 960 on the tibia 214. By plastically deforming the material of the moveable implant 950 with the surfaces 958 and 960 on the femur 126 and tibia 214, smooth sliding engagement is obtained between the upper and lower surfaces 952 and 954 on the moveable implant 950 during bending of the knee portion 76.

Even though the upper and lower surfaces 952 and 954 on the moveable implant 950 are either elastically or plastically shaped by the force transmitted between the femur 126 or tibia 214, the moveable implant will, initially, be configured to have a shape corresponding to the existing space between the surfaces 958 and 960. It is contemplated that this will result in the surfaces 952 and 954 being spaced apart by different distances between different portions of the moveable implant 950.

For example, the distance between the upper surface 952 and lower surface 954 on the moveable implant 950 may be relatively large adjacent to a medial edge portion of the moveable implant 950. The distance between the upper and lower surfaces 952 and 954 on the moveable implant 950 may be relatively small adjacent to a lateral edge portion of the moveable implant. As was previously mentioned, it is contemplated that images be generated of the knee portion 76 to enable the shape of the existing space between the surfaces 958 and 960 to be determined and to enable the moveable implant 950 to be configured, outside of the patient's body, to a configuration which generally conforms to the configuration of the space between the surfaces 958 and 960. Once the moveable implant 950 has been initially shaped to a configuration corresponding to the configuration of the space between the surfaces 958 and 960, the implant is positioned between the surfaces.

It is contemplated that the moveable implant 950 may be relatively thin compared to the thickness of the moveable implant illustrated schematically in FIG. 59. This would result in the upper surface 952 of the moveable implant 950 being spaced apart from the lower surface 954 of the moveable implant by a relatively small distance. By forming the moveable implant 950 with a relatively small thickness, that is, the distance between the upper surface 952 and the lower surface 954, the implant will be relatively flexible. This enables the implant to be deflected by force transmitted between the surfaces 958 and 960 on the femur 126 and the tibia 214.

It is contemplated that a relatively flexible moveable implant 950 may be configured so as to readily fit into an existing space in the knee portion 76. This would result in a tendency for the moveable implant 950 to become seated on the proximal end portion 212 of the tibia 214. The moveable implant 950 would be seated on the proximal end portion 212 of the tibia 214 by force applied against the moveable implant by the surface 958 on the femur 126. The lower surface of the moveable implant would be permanently deflected to have a configuration corresponding to the configuration of the upper surface 960 in the tibia 214. The upper surface 952 of the moveable implant would have an overall configuration which may differ from the configuration of the surface 958 on the femur 126. However, even though the configuration of the upper surface 952 on the moveable implant 950 is different than the configuration on the surface 958 on the femur 126, there would be smooth sliding engagement between the surface 958 on the femur 126 and the upper surface 952 of the moveable implant 950. The result would be that there would be relatively little movement between the lower surface 954 of the moveable implant 950 and the surface 960 on the tibia 214 during bending of the knee portion 76. However, there would be a relatively large amount of movement between the upper surface 952 of the implant 950 and the surface 958 on the femur 126. Since the moveable implant 950 would be permanently deflected to have a configuration corresponding to the space between the existing surfaces 958 and 960 on the femur 126 and tibia 214, the existing surfaces 958 and 960 on the femur 126 and tibia 214 would cooperate with the moveable implant 950 without inducing pain in the knee portion 76 of the leg 70 of the patient.

It is contemplated that the moveable implant 950 may be formed of many different materials. For example, the moveable implant 950 may be formed of a biological material. For example, the moveable implant 950 may be formed of allograft or autograft or xenograft. Combinations of these graft materials may be utilized. These graft materials may be shaped in the manner disclosed in U.S. Pat. No. 5,888,219. The moveable implant 950 may be formed of the same materials as the implant 626 of FIGS. 43 and 45 if desired.

It is believed that it may be desired to form the moveable implant 950 of metal. For example, the moveable implant 950 could be formed of chromium, titanium, tantalum, zirconium or aluminum. The metal forming a moveable implant may or may not have a porous construction. The metal forming the moveable implant 950 would have a wettable surface which can be wetted by body fluids to provide lubricity. If the moveable implant 950 is formed of a porous metal, the metal may be impregnated with one or more polymeric materials which function as lubricants.

The moveable implant 950 may be formed of a ceramic material. The ceramic material of the moveable implant may have either a porous or non-porous construction. When the ceramic material of the moveable implant 950 has a porous construction, it is contemplated that the openings in the ceramic material will be filled with a lubricant to facilitate relative movement between the surfaces 958 and 960 on the femur 126 and tibia 214 and the surfaces 952 and 954 on the moveable implant 950.

When the moveable implant 950 is formed of a porous material, for example a porous metal or a porous ceramic, it is contemplated that the moveable implant could be impregnated with both a bone growth promoting material and a lubricant. For example, the portion of the porous moveable implant 950 adjacent to the upper surface 952 of the implant may be impregnated with a lubricant. The portion of the moveable implant 950 adjacent to the lower surface 954 may be impregnated with bone growth inductive materials.

With such a construction, the lower surface 954 of the moveable implant is configured to correspond to the configuration of the surface 960 on the tibia 214. Therefore, the moveable implant will tend to become seated on the proximal end portion 212 of the tibia 214. Once this has occurred, the bone growth promoting materials in the porous implant 950, adjacent to the lower surface 954 of the implant, will promote growth of bone into the moveable implant 950 to connect the moveable implant with the tibia 214. The lubricant in the porous material adjacent to the upper surface 952 of the moveable implant 950 will minimize friction with the surface 958 on the femur 126 so that there will be minimal tendencies for the moveable implant 950 to move relative to the tibia 214 once the moveable implant has become seated on the proximal end portion 212 of the tibia. Of course, this will facilitate the growth of bone between the surface 960 on the proximal end portion 212 of the tibia 214 and the moveable implant 950.

The moveable implant 950 may be formed of graft materials which have been shaped in the manner disclosed in U.S. Pat. No. 5,888,219. If desired, the moveable implant 950 may have a three dimensional scaffold or framework structure on which graft materials are disposed. The framework on which the graft materials are disposed may have sufficient flexibility to enable the moveable implant 950 to be flexed to correspond to the configuration of the surface 960 on the tibia 214 by force applied against the upper surface 952 of the moveable implant by the femur 126. The graft materials on the scaffold will be shaped by the surface 958 on the femur 126 to form the upper surface 952 of the implant with the configuration which corresponds to the configuration of the surface 958 on the femur.

It is contemplated that the moveable implant 950 may be formed of materials which degrade with the passage of time. Thus, after the implant 950 has been disposed in the knee portion 76 of a patient's leg 70 for a predetermined period of time, for example two years, it may be necessary to replace the moveable implant 950. Due to the limited incision required to enable the implant 950 to be positioned in the knee portion 76, it is a relatively simple operation to replace the moveable implant 950. The size of the incision and the trauma induced in the patient by replacing the moveable implant 950 may be minimized by the use of a cannula corresponding to the cannula 564 of FIG. 39. The cannula through which the implant 950 is moved into the knee portion 76 of the patient's leg may have a construction similar to the construction illustrated in U.S. Pat. Nos. 3,811,449; 5,183,464; and/or 5,961,499.

Seating of the moveable implant on the tibia 214 may be promoted by forming the moveable implant of a hydrophilic material which absorbs body fluids and expands. When the implant 950 of hydrophilic material is positioned in the space between the surfaces 958 and 960 on the femur 126 and tibia 214, the hydrophilic material of the implant will absorb body fluids and expand to fully occupy the space. This will result in the lower surface 954 of the moveable implant 950 being pressed firmly against the surface 960 on the tibia 214. Similarly, the upper surface 952 on the moveable implant 950 will be pressed against the surface 958 on the femur 126 as the moveable implant absorbs body fluids and expands. This results in the moveable implant 950 expanding in such a manner as to change the configuration of the moveable implant to the configuration of the space between the surfaces 958 and 960 on the femur 126 and tibia 214.

The hydrophilic material of the moveable implant 950 may be a polymeric material which is either a copolymer or a dipolymer. The hydrophilic material may contain petroylglupamic acid, carboxymethylcellulose, a collagen or polylactide. The hydrophilic material may be a ceramic that is found in hydroxyapatite composites with polyethylene, polylactide or polyhydroxybutyrate. Of course, the moveable implant 950 could be formed of other known hydrophilic materials which attract body liquid under the influence of molecular attraction and establishes molecular linkages with the body liquid. The hydrophilic material may be disposed on a frame work or base which is formed of a non-hydrophilic material such as a porous metal.

It should be understood that the patient's leg 70 is supported in a manner previously explained herein in conjunction with FIGS. 2 and 3. The improved drape system 100 of FIGS. 4 and 5 may be utilized during surgery in which the moveable implant 950 is positioned in the knee portion 76 of the patient's leg 70. The patient's leg 70 may be moved in the manner schematically by arrows in FIG. 25 to enable a surgeon to make certain that the moveable implant 950 cooperates with the femur 126 and tibia 214 in a desired manner. The articular surface 122 on the patella 120 may be repaired in the manner indicated schematically in FIGS. 35 and 36, contemporaneously with positioning of the moveable implant 950 in the knee portion 76. One or more expandable devices, similar to the expandable devices 720, 722 and 730 of FIGS. 51 and 52 may be utilized to facilitate positioning of the moveable implant 950 in the knee portion 76 of a patient's leg 70. It should be understood that any of the features previously described in conjunction with FIGS. 1-58 herein could be utilized, if desired, in association with the moveable implant 950.

Moveable Inlay

Figure 60:
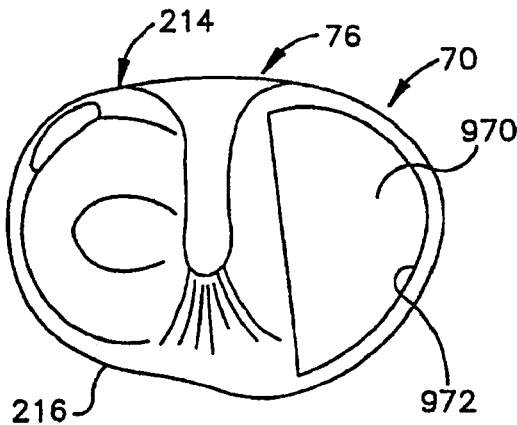
FIG. 60 is a plan view of a proximal end portion of a tibia depicting the manner in which an implant may be inlaid into a tibia.

In the embodiment of FIG. 59, the moveable implant 950 is positioned in engagement with existing surfaces 958 and 960 on the femur 126 and tibia 214. In the embodiment illustrated in FIG. 60, a moveable implant 970 is positioned in a recess 972 formed in a medial portion of the proximal end portion 212 of the tibia 214. The recess 972 may be relatively shallow and formed with a minimum or no cutting away of bone from the proximal end portion 212 of the tibia 214. The recess may be formed by cutting away cartilage and/or other material disclosed on the proximal end portion 212 of the tibia 214. Depending upon the condition of the proximal end portion 212 of the tibia 214, the bone may or may not be cut away to form the recess 972. Thus, the recess may be formed in tissues, such as fibrous tissues, associated with the end portion of the bone at the proximal end portion of the tibia 214.

The moveable implant 970 may be held in position relative to the proximal end portion 212 of the tibia 214 by engagement with the recess 972. If this is done, tissue growth promoting materials and/or materials which promote biological resurfacing may be provided in the moveable implant 970. These materials would promote the growth of tissue adjacent to the proximal end portion 212 of the tibia 214 into the moveable implant 970. The biological resurfacing materials would promote the growth of naturally occurring tissues, which were not removed to form the recess 972, into the moveable implant 970. Thus, cartilage tissues located adjacent to the peripheral aspect of the proximal end portion 212 of the tibia 214 would grow into the moveable implant 970.

It should be understood that the recess 972 may have a lower surface formed by the existing surface 960 of the tibia and side surfaces formed by fibrocartilage which extends around the periphery of the moveable implant 970. It is believed that it will be desired to position the moveable implant 970 in the recess 972 without anchoring the moveable implant to the tibia 214. However, if desired, an adhesive such as fibrin could be utilized to connect the moveable implant with the existing surface 960 on the proximal end portion 212 of the tibia. The moveable implant 970 may have any one of the constructions previously described in conjunction with the implant 640 of FIGS. 46 and 48 or the multi layered implant 670 of FIG. 49.

Multi Component Moveable Implant

The moveable implant 950 of FIG. 59 is formed as one piece. In the embodiment of the invention illustrated in FIG. 61, the moveable implant 980 is formed with a plurality of pieces. The moveable implant 980 is disposed between a medial portion of the distal end portion 124 of a femur 126 and a medial portion of the proximal end portion 212 of a tibia 214. The moveable implant 960 is positioned between an existing surface 958 on the femur 126 and an existing surface 960 on the tibia 214. The moveable implant 980 includes an upper section 982 and a lower section 984. The upper section 982 has an upper surface 988 which engages the existing surface 958 on the distal end portion 124 of the femur 126. The upper section 982 of the moveable implant 980 has a lower surface 990 which engages the lower section 984 of the moveable implant 980.

The lower section 984 of the moveable implant 980 has a lower surface 994 which engages the existing surface 960 on the proximal end portion 212 of the tibia 214. In addition, the lower section 984 of the implant 980 has an upper surface 986 which engages a lower surface 990 on the upper section 982 of the moveable implant 980.

The surfaces on the moveable implant 980 which engage existing surfaces on the femur 126 or tibia 214 are shaped to conform to the configuration of the existing surfaces on the femur and the tibia. To enable the surfaces on the moveable implant to be shaped to conform to the configuration of existing surfaces on the femur 126 and tibia 214, images of the femur and tibia are generated utilizing known imaging apparatus, such as an MRI, X-ray, or fluoroscope. These images are utilized to determine the configuration of the existing surface 958 on the femur 126 and the existing surface 960 on the tibia 214. The upper surface 988 on the upper section 982 of the moveable implant 980 is then shaped to a configuration corresponding to the configuration of the existing surface 958 on the femur 156. The lower surface 994 on the lower section 984 of the moveable implant 980 is shaped to a configuration corresponding to the configuration of the existing surface 960 on the tibia 214. By shaping the upper and lower surfaces 988 and 994 on the implant 990 to conform to the shape of the existing surfaces 958 and 960 on the femur 126 and tibia 214, the upper and lower sections 982 and 984 tend to seat themselves on the femur 126 and tibia 214. Thus, the upper surface 988 on the upper section 982 of the moveable implant 980 becomes seated against the existing surface 958 on the femur 126 under the influence of force transmitted between the existing surface 958 on the femur and the upper surface 988 on the upper section 982 of the moveable implant 980. Similarly, the lower surface 994 on the lower section 984 of the implant 980 becomes seated against the existing surface 960 on the tibia 214 under the influence of force applied to the upper surface 996 on the lower section 984 of the moveable implant 980 by the upper section 982 of the moveable implant.

The lower surface 990 on the upper section 982 of the moveable implant 980 and the upper surface 996 on the lower section 984 of the moveable implant 980 are shaped to promote the desired articulation in the knee portion 76 of the leg 70. Once the two sections 982 and 984 of the moveable implant 980 have been positioned between the existing surfaces 958 and 960 on the femur 126 and tibia 214, relative movement occurs where the lower surface 990 on the upper section 982 of the moveable implant 980 engages the upper surface 996 on the lower section 984 of the moveable implant. This tends to minimize any pain or discomfort resulting from defects in the existing surfaces 958 and 960 on the femur 126 and tibia 214 during bending of the knee portion 76.

The upper section 982 and lower section 984 may be formed of the same materials or any combination of the same materials as previously described in conjunction with the moveable implant 950 of FIG. 59. Although the upper section 982 and lower section 984 of the moveable implant 980 are formed of the same material, it is contemplated that the upper section 982 could be formed of a material which is different than the material forming the lower section 984 of the moveable implant 980.

The moveable implant 980 will be positioned in the space between the existing surfaces 958 and 960 on the femur 126 and tibia 214 in the manner previously discussed in conjunction with the embodiment of the invention illustrated in FIG. 59. Thus, the patient's leg will be supported in the orientation illustrated in FIGS. 2 and 3 during the making of a limited incision along one side of the patella 120 in the manner illustrated in FIG. 6. The patella 120 may then be offset to one side. Alternatively, the patella may remain in its initial position or be offset just slightly to provide sufficient space to insert the moveable implant 980. It is contemplated that the knee portion 76 will be inspected utilizing fiberoptic devices similar to the endoscope 352 of FIGS. 32 and 33. An expandable cannula corresponding to the cannula 364 of FIG. 39, may be inserted into the incision and the endoscope and/or the moveable implant 980 inserted into the knee portion 76 through the expandable cannula.

Moveable Implant with Anchored Section

Figure 61:
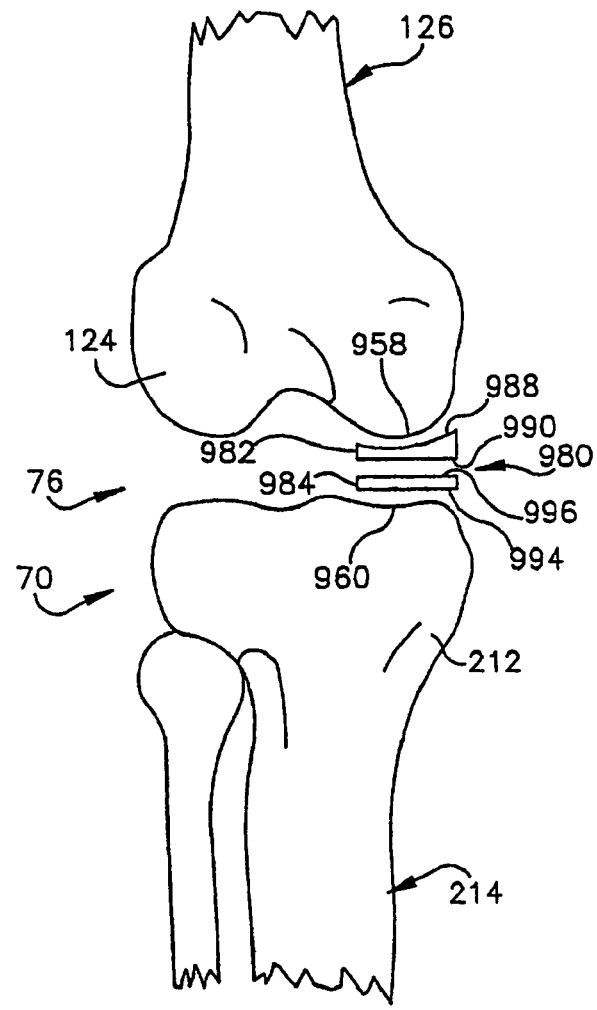
FIG. 61 is a schematic illustration, generally similar to FIG. 59, depicting the relationship between a movable implant formed by a plurality of members, a distal end portion of a femur, and a proximal end portion of a tibia in a knee portion of a leg of a patient.

In the embodiment of the invention illustrated in FIG. 61, the moveable implant 980 has upper and lower sections 982 and 984 which are moveable relative to each other and relative to the femur 126 and tibia 214. In the embodiment of the invention illustrated in FIG. 62, a moveable implant 1002 has a section which is fixedly connected with a bone in the knee portion 76 of the patient. In the embodiment of the invention illustrated in FIG. 62, the moveable implant 1002 includes an upper section 1006 and a lower section 1008. The upper section 1006 of the implant 1002 is freely moveable relative to the femur 126. The lower section 1008 of the moveable implant 1002 is anchored to the tibia 214. Thus, the upper section 1006 of the moveable implant 1002 is freely moveable relative to the existing surface 958 on a medial portion of the distal end portion 124 of the femur 126. The upper section 1006 is also freely moveable relative to the tibia 214. However, the lower section 1008 of the moveable implant 1002 is anchored to the tibia 214 by a keel or projecting section 1012. The projecting section 1012 extends through the existing surface 960 on a medial portion of the proximal end portion 212 of the tibia 214.

The upper section 1006 and lower section 1008 of the moveable implant 1002 are formed of the same material as previously discussed in conjunction with the moveable implant 950. The upper and lower sections 1006 and 1008 of the moveable implant 1002 are positioned in the space between the existing surfaces 958 and 960 through a cannula which corresponds to the cannula 564 of FIG. 39. The cannula extends into a limited incision and is resiliently expandable to stretch the viscoelastic body tissue in which the limited incision is formed to enable the moveable implant 1002 to be moved through the cannula into the space between the existing surfaces 958 and 960 on the femur 126 and tibia 214.

Figures 62, 63:
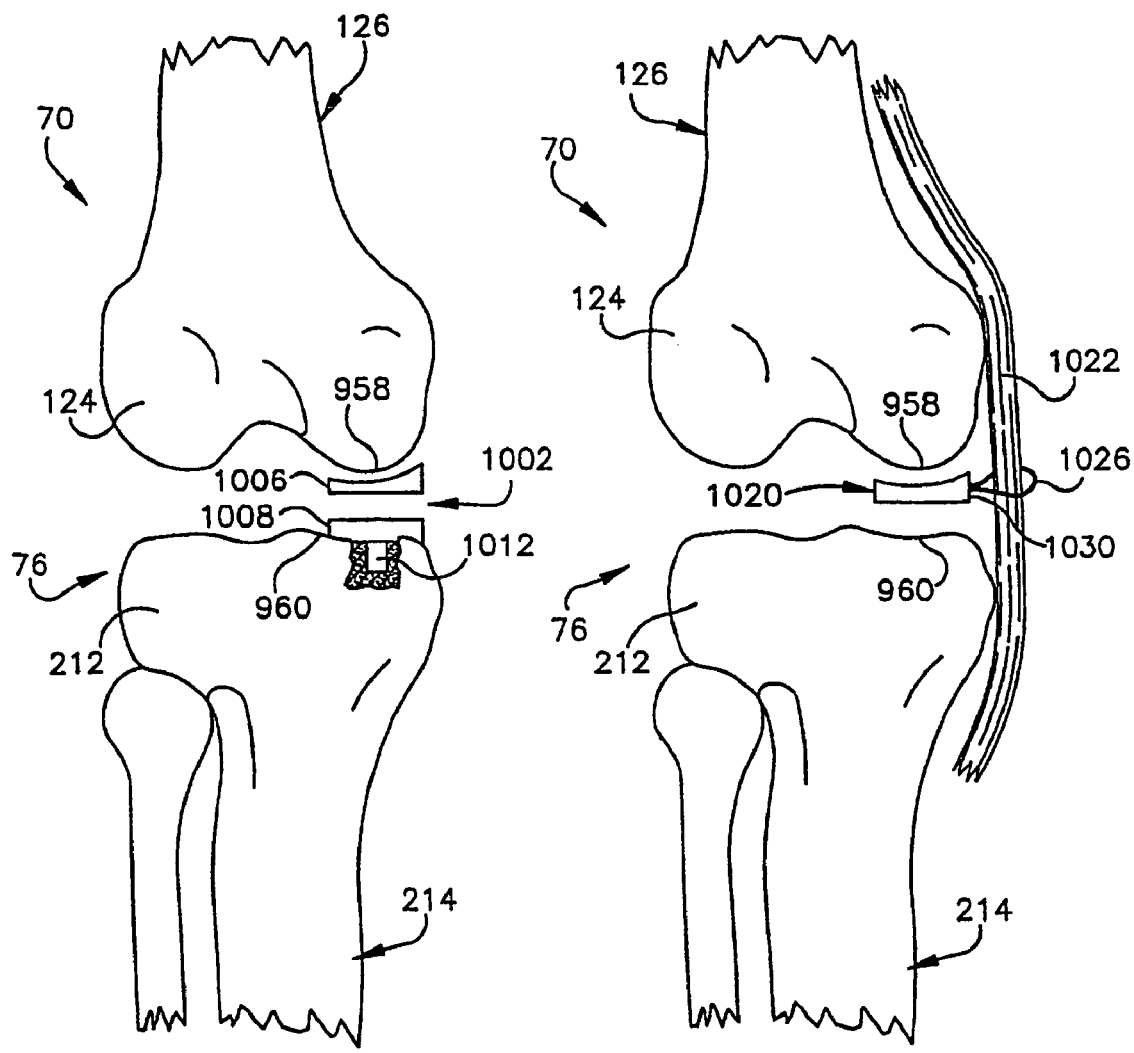
FIG. 62 is a schematic illustration, generally similar to FIGS. 59 and 61, depicting the relationship between an implant formed by a movable member and a fixed member, a distal end portion of a femur, and a proximal end portion of a tibia in a knee portion of a leg of a patient.
FIG. 63 is a schematic illustration, generally similar to FIG. 59, depicting the manner in which an implant is connected with a ligament in a knee portion of a patient's leg.

Although the lower section 1008 of the moveable implant 1002 has been illustrated in FIG. 62 as being anchored to the tibia 214 and the upper section 1006 freely moveable relative to the femur 126, this could be reversed if desired. Thus, the upper section 1006 of the moveable implant 1002 could be anchored to the femur 126. If this was done, the lower section 1008 of the moveable implant 1002 would be freely moveable relative to the tibia 214.

Securing Moveable Anchor

In the embodiment of the invention illustrated in FIG. 59, the moveable implant 950 is freely moveable relative to the existing surfaces 958 and 960 on the femur 126 and tibia 214. In the embodiment of the invention illustrated in FIG. 63, a moveable implant 1020 is connected with the medial collateral ligament 1022. Although the moveable implant 1020 is disposed between and is freely moveable relative to existing surfaces 958 and 960 on the femur 126 an the tibia 214, the connection between the moveable implant 1020 and the medial collateral ligament 1022 limits the range of movement of the moveable implant 1020 relative to the existing surface 958 on a medial portion of the distal end portion 124 of the femur 126. Similarly, the connection between the moveable implant 1020 and the medial collateral ligament 1022 limits the range of movement of the implant 1020 relative to the existing surface 960 on a medial portion of the proximal end portion 212 of the tibia 214.

The moveable implant 1020 has the same construction as the moveable implant 950 of FIG. 59. However, the moveable implant 1020 is provided with a small passage or opening which enables a suture 1026 to be used to interconnect the moveable implant 1020 and the ligament 1022. The suture 1026 extends through the opening in the moveable implant 1020 and extends around the ligament 1022. The suture 1026 holds the moveable implant 1020 in engagement with the ligament 1022. This results in a side surface 1030 on the moveable implant 1020 being held in intimate apposition with the ligament 1022. Due to engagement of the side surface 1030 on the moveable implant 1020 with the ligament 1022, tissue can grow from the ligament into the moveable implant 1020 to further interconnect the ligament and the movable implant.

It is contemplated that the moveable implant 1020 will have a construction which promotes the in growth of tissue from the ligament 1022 into the implant. Thus, the moveable implant 1020 may have a porous scaffold on which tissue growth inductive factors are disposed. For example, the moveable implant 1020 could be formed of porous tantalum. The porous tantalum scaffold could contain collagen, fibrin, progenitor cells and/or tissue inductive factors. Of course, other known materials which promote biological resurfacing could be provided on the porous metal scaffold of the moveable implant 1020 if desired.

Although one specific construction of the moveable implant 1020 has been described, it is contemplated that the moveable implant 1020 could have many different constructions. For example, the moveable implant 1020 could have any one of the constructions and be formed of any one or more of the materials previously described in conjunction with the moveable implant 950.

It is contemplated that the patient's leg 70 may be in the position illustrated in FIGS. 2 and 3 during positioning of the moveable implant 1020 in the space between the existing surfaces 958 and 960 on the femur 126 and tibia 214. The upper portion of the patient's leg 70 may be supported above the support surface 64 (FIG. 2) by the leg support 80. The drapery system 100 of FIGS. 4 and 5 may advantageously be utilized during positioning of the moveable implant 1020 to provide a sterile field.

Connection of Moveable Implant with Soft Tissue

In the embodiment of the invention illustrated in FIG. 59, the moveable implant 950 is freely moveable relative to the existing surfaces 958 and 960 on the femur 126 and tibia 214. In the embodiment of the invention illustrated in FIG. 63, the moveable implant 1020 is connected with the ligament 1022 to limit the range of movement of the moveable implant 1020. In the embodiment of the invention illustrated in FIG. 64, a moveable implant 1040 is connected with soft tissue other than the ligament 1022 of FIG. 63. Rather than being connected with the soft tissue by single suture 1026 in the manner illustrated in FIG. 63, the moveable implant 1040 is connected with soft tissue in a plurality of locations by a plurality of sutures.

Figure 64:
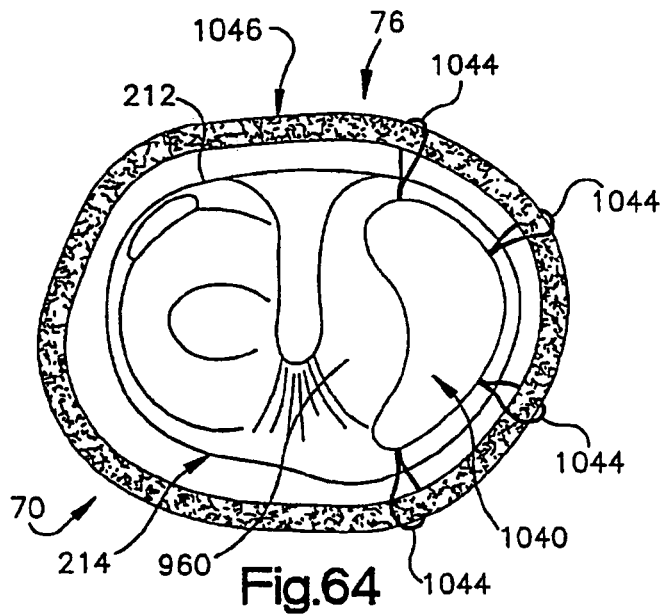
FIG. 64 is a schematic illustration, generally similar to FIG. 60, depicting the manner in which an implant is connected with a joint capsule in a knee portion of a patient's leg.

The moveable implant 1040 (FIG. 64) has the same construction as the moveable implant 950 of FIG. 59. The moveable implant 1040 is positioned between existing surfaces 958 and 960 (FIG. 59) on a femur 126 and tibia 214 in the same manner as is illustrated schematically in FIG. 59 for the moveable implant 950. The moveable implant 1040 is moved into position between the existing surfaces on a femur and a tibia in the same manner as previously explained in conjunction with the moveable implant 950 of FIG. 59. Thus, the moveable implant 1040 of FIG. 64 is moved into a position between existing surfaces 958 and 960 on a femur and tibia through a limited incision and a resiliently expandable cannula corresponding to the cannula 564 of FIG. 39.

In accordance with one of the features of this embodiment of the invention, a plurality of connections 1044 are provided between the periphery of the moveable implant 1040 and soft tissue 1046. Although many different soft tissues in the knee portion 76 of a patient's leg may be connected with the moveable implant 1040 by connections 1044, in the embodiment of the invention illustrated in FIG. 64, the moveable implant 1040 is connected with the joint capsule in the knee portion 76 of the patient's leg 70. The joint capsule extends around and encloses the knee joint. Therefore, the connections 1044 can be formed between the moveable implant 1040 and the soft tissue of the joint capsule 1046 at a plurality of locations in the manner illustrated in FIG. 64.

By providing anterior and posterior connections 1044 with the soft tissue of the joint capsule 1046, the moveable implant 1040 is held against excessive movement in either a posterior or anterior direction. Similarly, the connections 1044 between the moveable implant 1040 and the medial portion of the soft tissue or joint capsule 1046 holds the moveable implant 1040 against excessive movement in either the medial or lateral direction. The connections 1040 may initially be formed by sutures.

Although the range of movement of the moveable implant 1040 relative to the femur 126 and tibia 214 (FIG. 59) is limited by the connections 1044 (FIG. 64), the moveable implant 1040 is freely moveable relative to the existing surfaces 958 and 960 (FIG. 59) on the femur 126 and tibia 214 within the range of movement established by the connections 1044 with the soft tissue or joint capsule 1046.

Tissue inductive growth factors are provided on the moveable implant 1040. The tissue inductive growth factors promote a growth of the soft tissue onto the moveable implant 1040. It is contemplated that the moveable implant 1040 will have a porous platform in which the tissue growth inductive factors are disposed. This will promote a growth of the soft tissue or joint capsule 1046 into the moveable implant 1040 to assist the sutures at the connections 1044 in interconnecting the moveable implant 1040 and the soft tissue or joint capsule 1046.

Thus, the connections 1044 between the moveable implant 1040 and the soft tissue 1046 is initially established by sutures which extend between the moveable implant 1040 and the soft tissue or joint capsule 1046. With the passage of time, tissue grows from the soft tissue or joint capsule 1046 into the periphery of the moveable implant 1040 to further interconnect the moveable implant 1040 and the soft tissue. The sutures which initially form the connections 1044, hold the periphery of the moveable implant 1040 in engagement with the soft tissue 1046. Due to the intimate apposition of the moveable implant 1040 with the soft tissue or joint capsule 1046 and the tissue growth promoting factors in the moveable implant 1040, growth of the soft tissue or joint capsule 1046 into the periphery of the moveable implant 1040 is promoted.

Molded Implant

Figure 65:
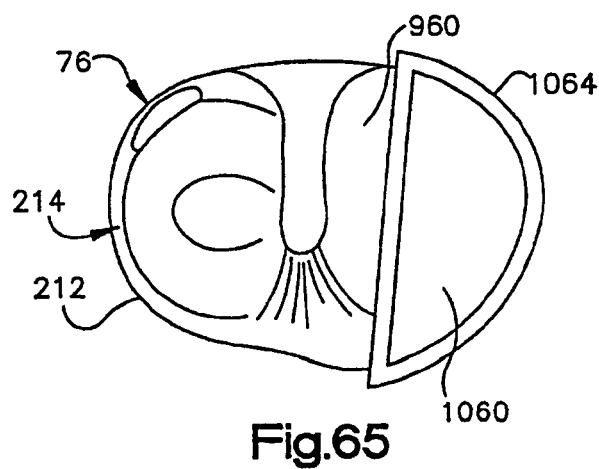
FIG. 65 is a schematic illustration, generally similar to FIG. 60, depicting the manner in which a retainer holds moldable implant material in place on a proximal end portion of a tibia in the knee portion of a leg of the patient.
Figure 66:
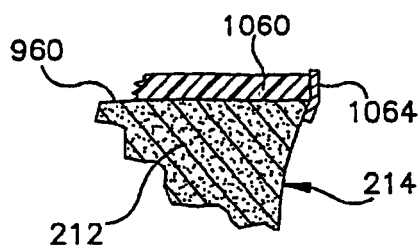
FIG. 66 is a fragmentary sectional view, taken generally along the line 66-66 of FIG. 65 further illustrating the manner in which the retainer holds moldable implant material.

In the embodiment of the invention illustrated in FIGS. 65 and 66, an implant 1060 is molded onto an existing surface 960 on the proximal end portion 212 of the tibia 214. The implant 1060 is formed of bone cement which is held in place by a retainer or dam 1064 which extends around a medial portion of the proximal end portion 212 of the tibia 214. The dam forms a compartment which is filled with the bone cement. As the bone cement hardens, the femur 126 (FIG. 59) is moved relative to the tibia 214 to impart a desired configuration to the bone cement.

Once the bone cement has hardened, the retainer or dam 1064 may be removed. The bone cement then forms an implant which is disposed on the existing surface 960 of the tibia 214. The bone cement is connected with existing surface 960 of the tibia 214 by adhesion between the implant 1060 and the existing surface 960 of the tibia 214. It is contemplated that a releasing agent could be mixed with the bone cement which is used to form the implant 1060 so that the implant would not adhere to the existing surface 960 of the tibia 214. This would result in the implant 1060 being freely moveable relative to both the tibia 214 and the femur 126 in the same manner as in which the moveable implant 950 is freely moveable relative to the femur 126 and tibia 214.

Deformity Correction

The moveable implants of FIGS. 59-66 are utilized to affect a resurfacing of joint surfaces to minimize pain resulting from defective joint surfaces. The moveable implants of FIGS. 59-66 are not particularly effective in correcting deformities in the femur 126 and/or tibia 214. Thus, the moveable implant 950 (FIG. 67) is positioned between the femur 126 and tibia 214 to compensate for defects in the existing surfaces 958 and 960 on the femur 126 and tibia 214. It is contemplated that other devices will have to be utilized to compensate for bone deformities. The devices which are utilized to compensate for bone deformities may be positioned in the femur 126 and/or tibia 214.

The devices which compensate for bone deformities may have a construction similar to the construction of any one of the devices disclosed in U.S. Pat. No. 6,086,593. Of course, other known devices could be utilized to correct bone deformities if desired.

Figure 67:
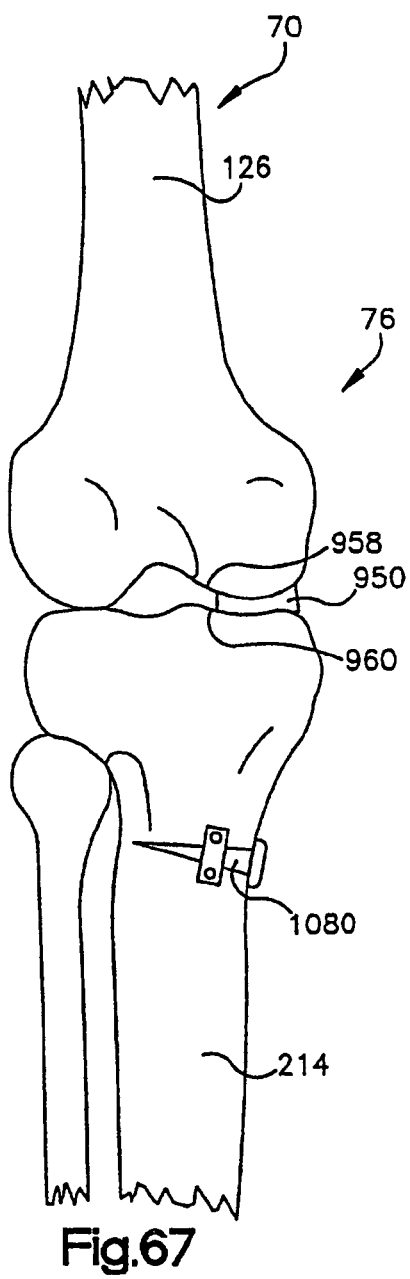
FIG. 67 is a schematic illustration depicting the manner in which an implant is provided in a knee portion of a leg of a patient to correct defects in a joint and in which an osteotomy wedge is provided to correct defects in bone alignment.

One specific device which may be utilized to correct bone deformities is a wedge member 1080 (FIG. 67). The wedge member 1080 is formed of a relatively hard rigid material. The wedge member 1080 is capable of transmitting force between upper and lower portions of a bone, such as the tibia 214. The wedge member 1080 may be hollow and have a compartment which is filled with bone growth inductive material. The wedge member may be formed of a suitable rigid material, such as tantalum or stainless steel. Alternatively, the wedge member 1080 could be formed of a biodegradable material. It is contemplated that the wedge member 1080 may be formed of human bone.

When the wedge member 1080 is to be positioned in the tibia 214, a saw cut is made to form a slot at the location where the wedge member 1080 is to be installed. The saw cut and resulting slot extend only part way through the tibia 214. The wedge member 1080 is then moved into the slot. As the wedge member is forced into the slot, the wedge member pivots an upper portion of the tibia 214 in a counter-clockwise direction (as viewed in FIG. 67) relative to a lower portion of the tibia to correct a deformity in the tibia or to compensate for a deformity in the femur 126.

Although the wedge member 1080 has been illustrated in FIG. 67 as being installed in the tibia 214, it is contemplated that the wedge member could be installed in the femur 126 if desired. Although the wedge member 1080 has been illustrated in FIG. 67 as being installed in a medial portion of the tibia 214, the wedge member 1080 could be installed in a posterior, anterior or lateral portion of the tibia if desired. The wedge member 1080 has the same construction and cooperates with the femur in the same manner as is disclosed in the aforementioned U.S. Pat. No. 6,086,593.

It is contemplated that the patient's leg 70 will be in the position illustrated in FIGS. 2 and 3 during installation of any one of the implants illustrated in FIGS. 59-66. However, the implants could be positioned in the patient's leg with the patient's leg in a different orientation if desired. Thus, any one of the implants of FIGS. 59-66 could be placed in the patient's leg with the patient's leg in either the flexed or extended orientation illustrated in FIG. 1.

The foregoing description of the moveable implants of FIGS. 59-66 has been in conjunction with the knee portion 76 of a patient's leg 70. However, it is contemplated that the implants will be used in association with other joints in a patient's body. For example, any one of the implants of FIGS. 59-66 could be utilized in association with a glenoid joint. Alternatively, any one of the implants could be used in association with an ankle, wrist or elbow joint. It is contemplated that any one of the many different features of the present invention may be utilized separately or in association with the implants illustrated in FIGS. 59-66 and that the implants may be used in association with any desired joint in a patient's body.

In-Situ Bone Removal

As previously detailed, one aspect of the present invention is the performance of all or a portion of a surgical procedure through a cannula. FIGS. 68-74 show one embodiment of this aspect as applied to the hip joint. Access to acetabulum 1100 and proximal portion of femur 1102 may be obtained through a cannula 1104. Cannula 1104 is inserted into incision 1106, which is formed with a relatively short length (generally less than 10 cm in length) in the manner previously described herein. Cannula 1104 has an initial size, illustrated in FIG. 68, which stretches the viscoelastic tissue around the hip joint. Therefore, initial insertion of cannula 1104 into incision 1106 is effective to expand the incision.

Figure 68:
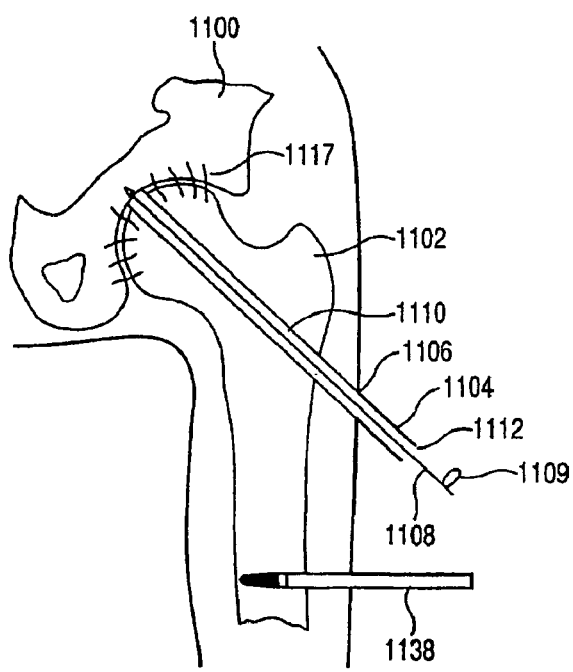
FIG. 68 is a schematic view of the hip region with a guide wire and cannula inserted.

FIG. 68 shows one manner in which guidance of the cannula (and any subsequent surgical implement going therethrough) to the desired location can be facilitated. A guide wire 1108 having a sharp tip is driven through femur 1102 and pinned to bone. Although guide wire 1108 is shown pinned to acetabulum 1100, guide wire 1108 can be pinned to femur 1102, as discussed below. Pinning guide wire 1108 to bone helps to ensure that the location of cannula 1104 remains relatively constant during the surgical procedure.

A pilot hole can be created through femur 1102 to help insert guide wire 1108. Additionally, the creation of this pilot hole and/or the insertion of guide wire 1108 can be done under imaging guidance, such as fluoroscopy. Additionally, the proximal end of guide wire 1108 or cannula 1104 (FIG. 69) can include an IR reflector 1109 for use with a computer surgical navigation system to monitor the location of guide wire 1108. As is well known, IR reflector 1109 can alternatively be an electromagnetic radiation transmitter or receiver depending on the specific computer surgical navigation system.

Cannula 1104 is advantageously expandable to further stretch the viscoelastic tissue. Of course, expanding cannula 1104 increases the size of a passage 1110 formed by an inner side 1112 of cannula 1104, thereby enabling a relatively large object to pass through the passage. Thus, cannula 1104 may be expanded to facilitate movement of surgical implements, such as implants and instruments through the cannula.

It is contemplated that expandable cannula 1104 may have many different known constructions. The illustrated cannula 1104 is formed of elastomeric material and has the same construction as disclosed in U.S. Pat. No. 6,338,730. It should be understood that cannula 1104 could have a different construction, for example, a construction similar to the constructions disclosed in U.S. Pat. No. 3,811,449 or 5,183,464.

Cannula 1104 can be expanded in many different ways other than under the influence of force transmitted directly to the cannula from an object moving through the cannula. Cannula 1104 may be expanded by inserting tubular members into the cannula. Alternatively, fluid pressure could be used to expand cannula 1104 in the manner disclosed in the aforementioned U.S. Pat. No. 6,338,730.

By utilizing expandable cannula 1104 or the expandable pneumatic retractors previously disclosed, force can be applied against opposite sides of incision 1106 to stretch the viscoelastic material disposed adjacent to opposite sides of the incision. This will result in the relatively small incision 1106 being expanded to accommodate relatively large surgical instruments and/or implants.

Once cannula 1104 is inserted, guide wire 1108 can be removed if desired. Alternatively, guide wire 1108 can be used to direct insertion of other surgical implements. Regardless of whether guide wire 1108 is removed, cannula 1104 can be moved or pivoted about incision 1106 so that its location can be varied. This is particularly useful, for example, if the area surrounding the surgical site needs to be accessed.

Although a single incision 1106 is illustrated in FIG. 68, it is contemplated that a plurality of incisions could be provided. Thus, a small incision may be spaced from the incision 1106 to enable a suctioning tool to be moved into the hip joint along a path which is spaced from and may be transverse to a path along which a cutting tool is moved through the incision 1106. A second cannula, which is smaller than the cannula 1106, may be utilized with the second incision.

If desired, tissue retractors and/or dissectors can be used to create space between the soft tissue and the bones of the hip joint. Prior art mechanical dissectors and retractors can be used. It is also contemplated that fluid operated retractors, expanders, and/or dissectors may be used to retract, expand or dissect body tissue. For example, retractors having a construction similar to any one of the constructions disclosed in U.S. Pat. No. 5,197,971 may be utilized to release tissue at locations spaced from incision 1106. When tissue is to be released at locations where there is limited accessibility from incision 1106, a device similar to any one of the devices disclosed in U.S. Pat. No. 5,295,994 may be utilized. It is believed that devices similar to those disclosed in U.S. patent application Ser. No. 09/526,949 filed Mar. 16, 2000 may be used in ways similar to those disclosed therein to move and/or release body tissue.

Figure 69:
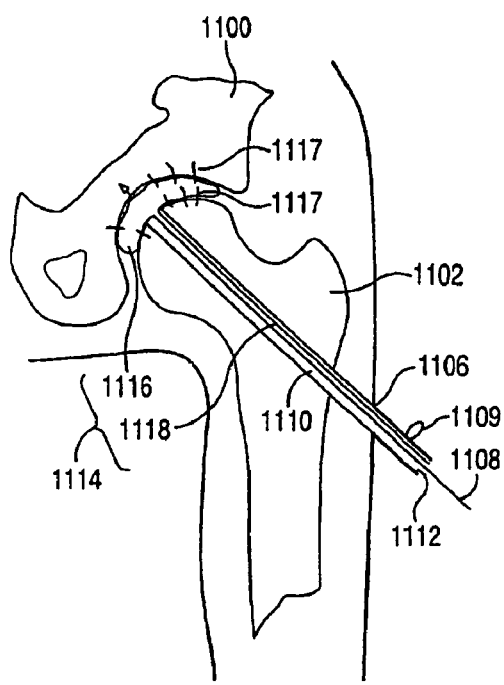
FIG. 69 is a schematic view of the hip region with an inflatable device inserted.

As shown in FIG. 69, a fluid operated device 1114 is inserted through cannula 1104 so that a bladder 1116 is placed between soft tissue 1117 and acetabulum 1100 and femur 1102. Bladder 1116 is inflated by fluid introduced via tubing 1118 to move soft tissue 1117 relative to acetabulum 1100 and femur 1102. Fluid operated device 1114 may be formed of biodegradable or non-biodegradable material. If bladder 1116 and tubing 1118 are formed of a biodegradable material, they need not be removed prior to closing of incision 1106.

In the case of a hip replacement surgery (total or partial), a reamer is typically used to create a uniform cavity for the acetabular component and/or an oscillating blade is typically used to remove a portion of the femoral head so that the femoral component can be received in the medullary canal of the femur. In this regard, compact cutting tools, similar to those utilized for arthroscopic, endoscopic, or fiber optic assisted surgery may be at least partially moved through passage 1110 to affect in situ removal of bone. The cutting tools may have a construction similar to the construction illustrated in U.S. Pat. No. 5,540,695 or 5,609,603. Alternatively, the cutting tools may have a construction similar to the construction disclosed in published U.S. Patent Application No. 2002/0055755 A1.

U.S. Pat. No. 5,269,785 also discloses a tissue removal system and method that can be used with the limited incision system according to the present invention. This patent discloses a device with a flexible shaft and a controllable tip. Furthermore, the device can be single lumen or multi-lumen, with a cannula if desired. The cutting tip can be controlled via valves, pneumatics, radio control, fiberoptic control, electric wire control, cable control, or pneumatic control. Multiple movable segments or a single movable segment can provide the flexibility. Joints can be provided between rigid sections. The flexibility and controllability are particularly useful in limited incision procedures. For example, the device can be bent over a 60-90° angle, and then selectively remove osteophytes at the edge of the tissue without damaging the associated tissue. Furthermore, the option of suction provides for tissue removal and the option of irrigation minimizes heat necrosis in the limited operative space.

The reaming of the acetabulum can be done in a single pass with a single reamer, or a plurality of progressively larger reamers can be used. Guide wire 1108 is particularly helpful with multiple reamers since the locking of guide wire 1108 with respect to acetabulum 1100 helps ensure that each reamer is reaming about the same central axis.

Figure 70A:
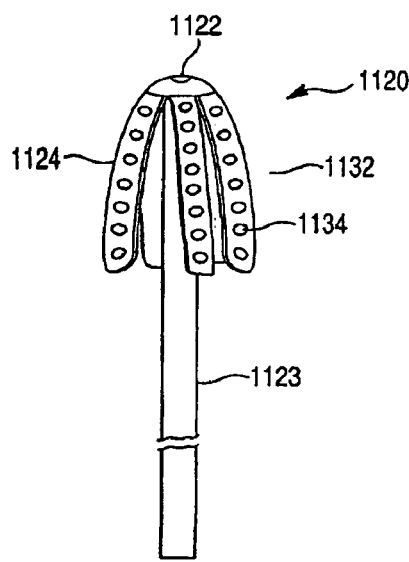
FIG. 70A is a side view of a bone removing instrument according to the present invention in a retracted state.
Figure 70B:
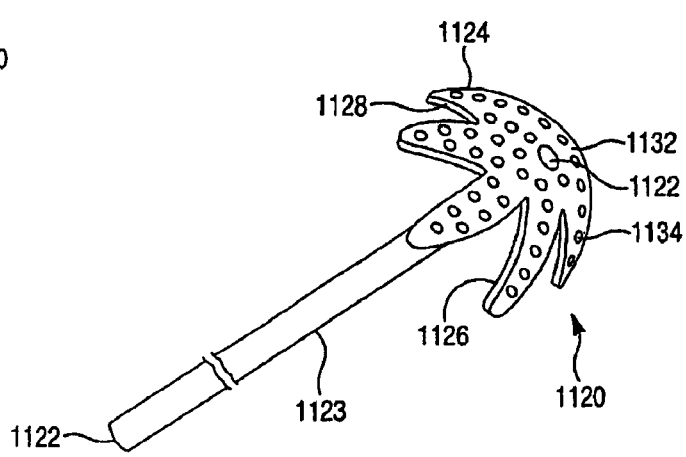
FIG. 70B is a perspective view of the bone removing instrument of FIG. 70A in an expanded state.
Figure 71:
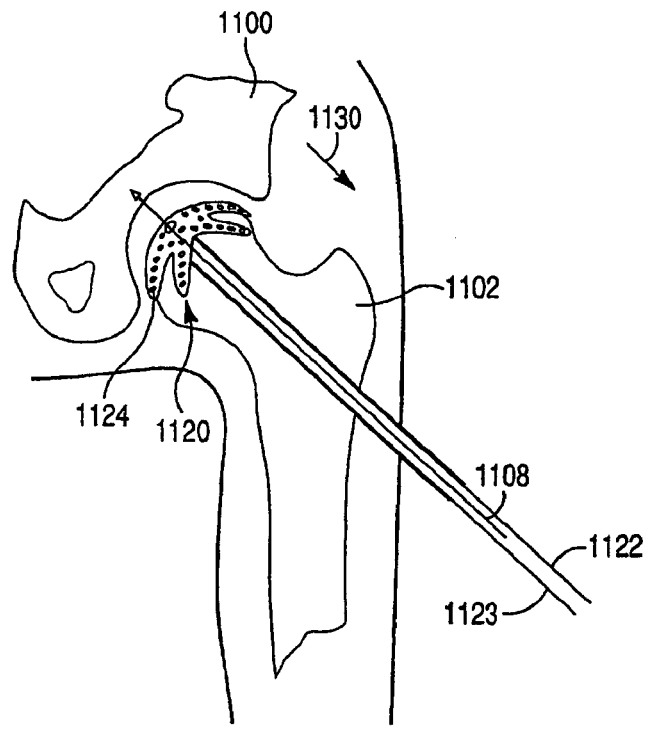
FIG. 71 is a schematic view of the hip region with the bone remover of FIG. 70B inserted and removing the femoral head.
Figure 72:
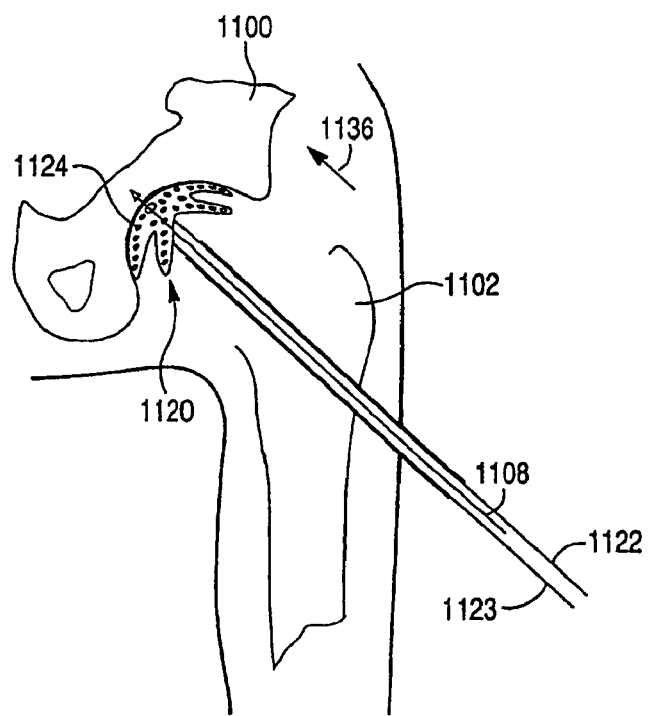
FIG. 72 is a schematic view of the hip region with the bone remover of FIG. 70B inserted and removing the acetabulum.

FIGS. 70A-70B show another embodiment of a tissue removing surgical instrument particularly useful for minimally invasive hip replacement surgeries. FIG. 70A shows tissue removing surgical instrument 1120 in a retracted position so that instrument 1120 can move freely within lumen 1110 of cannula 1104. Instrument 1120 is provided with a cannulation 1122 along a shaft 1123 so that instrument 1120 can be moved along guide wire 1108. Upon activation, distal end 1124 of instrument 1120 assumes the shape shown in FIG. 70B. Concave underside 1126 of the cup-shaped distal end 1124 has at least one cutting surface 1128 so that rotation of instrument 1120 in conjunction with retrograde movement of instrument 1120, i.e. movement in the direction of arrow 1130 (FIG. 71), causes removal of the bone forming the head of femur 1102.

Convex top side 1132 of the cup-shaped distal end 1124 has at least one cutting surface 1134 (shown in the form of gratings typical of prior art acetabular reamers) so that rotation of instrument 1120 in conjunction with antegrade movement of instrument 1120, i.e. movement in the direction of arrow 1136 (FIG. 72), causes reaming of acetabulum 1100. Instrument 1120 can be provided with irrigation and suctioning capacities, as taught in published U.S. Patent Application No. 2002/0055755 A1 to minimize heat necrosis and aid in the evacuation of the removed bone. Alternatively, a separate suctioning, and if desired, irrigation device, can be used. The separate device(s) can extend through cannula 1104 or an additional cannula.

Activation of instrument 1120 can occur in a number of different ways. For example, rotational movement of instrument 1120 alone can cause instrument 1120 to go from the retracted (FIG. 70A) to the extended position (FIG. 70B). U.S. Pat. No. 5,445,639 teaches one such rotational mechanism. Alternatively, fluid pressure, cable means, or other similar mechanisms can be used for activation.

After removal of the head of femur 1102 and reaming of acetabulum 1100, the cutting tool or tools can be withdrawn from the hip joint. In the case of instrument 1120, instrument 1120 can be pulled back through passage 1110, with distal end 1124 in the retracted position, or in the expanded position if the diameter of passage 1110 permits and the surgeon so desires. Alternatively, distal end 1124 can be separated from the rest of instrument 1120, for example by cutting off and removal through a separate incision.

It should be noted that the reaming of acetabulum 1100 and removal of the head of femur 1102 can be done with minimal, i.e. subluxation, or no dislocation of the hip joint. As previously noted, access to the joint space can be increased by movement of cannula 1104. Additionally, the joint space can be manipulated remotely. For example and as shown in FIG. 68, an elongate member 1138, such as a Schanz screw, can be inserted through a stab wound and attached to femur 1102. Elongate member 1138 can be used as a lever arm to increase the access to the hip joint. As a result of the reduction or elimination of dislocation, the interoperative strain on the soft tissue surrounding the hip joint is minimized. Any damage or cutting of soft tissue is also minimized. These features limit post-operative pain and lead to quicker surgical recovery.

Figure 73:
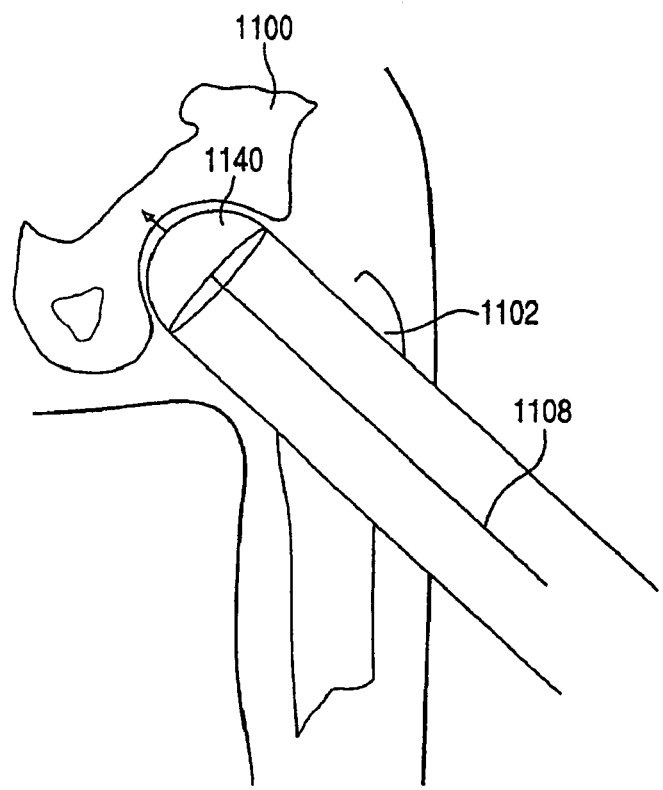
FIG. 73 is a schematic view of the hip region with a backing of an acetabular component being implanted.

The present invention also envisions insertion of some or all of the implant components through cannula 1104. This concept will be illustrated with a description of the procedure for an acetabular component. An analogous procedure for the femoral component can be used and a procedure for use with the knee has been described above. FIG. 73 shows the backing 1140 (typically made of a metal) of an acetabular component being inserted. Cannula 1104 is in an expanded state to accommodate the backing 1140. Alternatively, a larger non-expandable cannula could be used. Preferably, guide wire 1108 is the same guide wire that was used for cannula 1104 and tissue removing instrument 1120. This helps to ensure that backing 1140 is implanted at the same location that the reaming occurred.

Figure 74A:
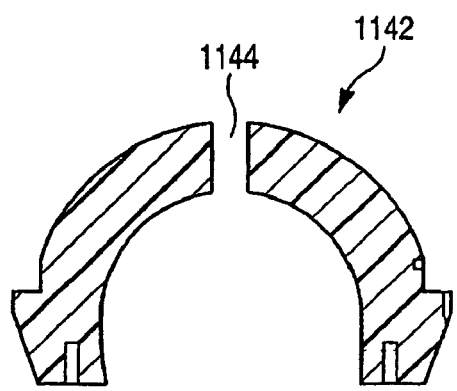
FIG. 74A is a sectional view of one embodiment of a liner for an acetabular component.
Figure 74B:
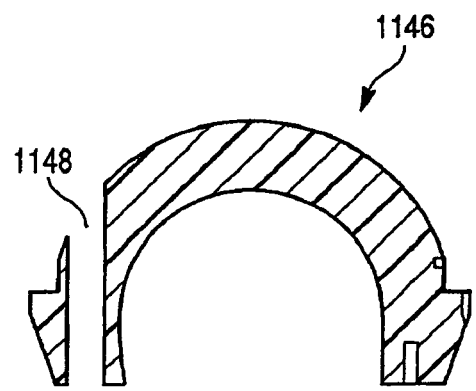
FIG. 74B is a sectional view of another embodiment of a liner for an acetabular component.

Guide wire 1108 can be removed so that a standard liner or insert (typically made of polyethylene) can be used in conjunction with backing 1140. Alternatively and as shown in FIG. 74A, an insert 1142 having a bore 1144 can be used so that insert 1142 can slide over guide wire 1108 in a manner similar to backing 1140. FIG. 74B shows another design for an insert 1146 that has a bore 1148 so that insert 1146 can slide over guide wire 1108. One different between insert 1142 and insert 1146 is the location of bore 1144 compared to bore 1148. Bore 1148 is placed in an area where no articulation with the ball of the femoral component occurs. As a result, the tolerances for the edges surrounding bore 1148 are not a significant concern for the generation of wear debris. Regardless of the location, the bore can be sealed, for example with an adhesive, to help contain any wear debris and minimize migration.

Other acetabular designs can be used. For example, the backing and liner acetabular components can be bonded together, either inside or outside of the patient. The portions may be bonded together by the application of energy in any one of many different forms, such as ultrasonic energy and heat. The present invention also envisions the application of the principles described and shown in FIGS. 68-74 to other locations in the body. Examples include the knee, the shoulder (both the glenoid and humeral components), the joints of the hand and wrist, the joints of the foot and ankle, and the spine. With respect to the spine, suitable procedures include any procedure involving the disc space and/or the vertebra, such as fusions, pedicle screw insertions, cages, or other implants.

In knee replacement procedures, in situ reaming of the patella as well as the condyles of the femur and tibia can be performed. Specifically, a guide wire is placed over the condyles and reaming occurs over this guide wire using a mill or a cutting saw. The patella could be removed in a similar fashion with a retrograde reamer directed by a guide wire. As previously described, the milling/cutting tools could be used in conjunction with jigs that allow a plurality of intersecting straight cuts or a smooth arc cut. The jig can be mounted on the medial or lateral side. If desired, the cutting of the femur and tibia can be done using a limited incision approach and the implantation of the femur, tibia, and/or patella components can be done through a larger incision.

Lateral/Medial Approach to Knee Replacement

Figure 75:
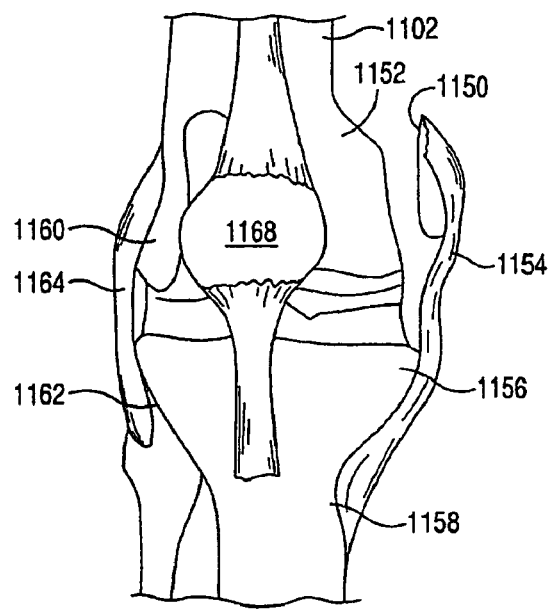
FIG. 75 is a schematic illustration of a knee joint with an osteotomy performed.
Figure 76:
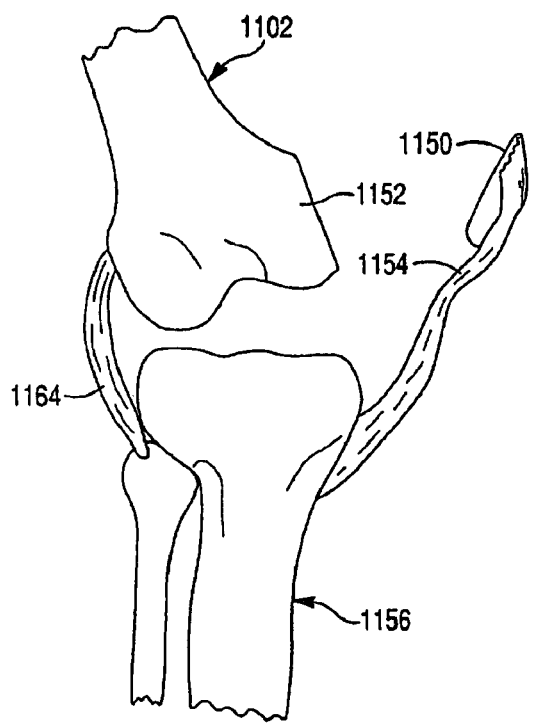
FIG. 76 is a schematic illustration of the access created by the osteotomy of the knee joint of FIG. 75 with the patella not shown for clarity.
Figure 77:
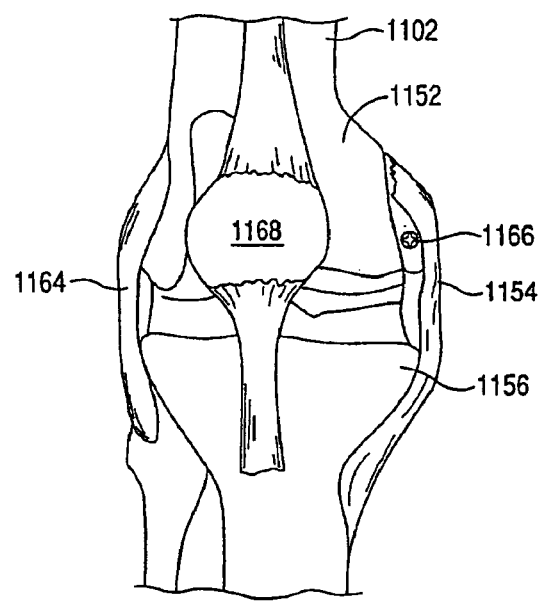
FIG. 77 is a schematic illustration of the knee joint of FIG. 75 with the osteotomy repaired.

As previously discussed (see, e.g. FIG. 54 and associated text), one aspect of the present invention includes a medial or lateral approach to joint replacement and other surgeries near a joint. FIGS. 75-77 show one embodiment of this aspect. FIG. 75 shows that femoral medial epicondyle 1150 is osteotomized or cut from distal end 1152 of femur 1102. This osteotomy removes the superior attachment point of medial collateral ligament 1154 so that the joint space between femur 1102 and tibia 1156 can be pivoted open and accessed from the medial side. As an alternative, the tibial medial epicondyle 1158 could be osteotomized to separate the inferior attachment point of medial collateral ligament 1154 so that the joint space could be accessed from the medial side. Additionally, either the femoral or tibial lateral epicondyle 1160, 1162 could be osteotomized to separate one of the attachment points of lateral collateral ligament 1164. Furthermore, medial collateral ligament 1154 or lateral collateral ligament 1164 can be cut without the need for removal of bone, if desired. However, as healing a bone/bone interface can be easier than healing a ligament/ligament interface, separate of the ligament through an osteotomy may be preferable.

In this regard, FIG. 77 shows that femoral medial epicondyle 1150 can be reattached to distal end 1152 of femur 1102 with a screw 1166 or staple. As an alternative to screw 1166, any method suitable for reattaching one piece of bone to another piece of bone can be used.

By accessing the joint space from a side medial or lateral to the centerline of the joint, the incision can be made shorter, as previously discussed. Additionally, and as previously discussed, a medial or lateral incision stretches less than a direct anterior incision. With respect to the knee joint in particular, when an incision is directly over the patella, the incision length increases 30% from 0° extension to 120° flexion. If the incision is shifted more laterally or medially, such as over the medial collateral ligament, the incision only lengthens approximately 12% from 0° extension to 120° flexion. There is less stress on the soft tissue and therefore less scarring and less postoperative pain. Also by going more medial or lateral with the incision there is less damage and less disruption of the quadriceps mechanism. Furthermore, patella 1168 tends to naturally move toward the pivot location when the joint space is hinged open from either a medial or lateral approach. The natural movement of patella 1168 allows anterior access to the joint space without the need to evert patella 1168. However, patella 1168 can be minimally subluxed and/or everted to increase the exposure of the joint space, if desired.

Figure 78:
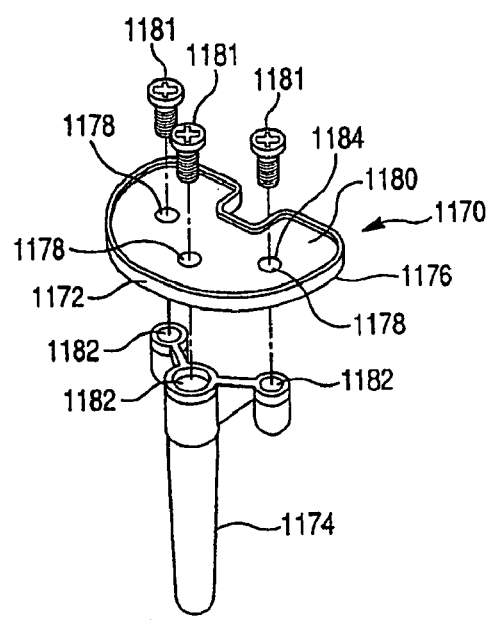
FIG. 78 is an exploded view of a modular tibial component.
Figure 79:
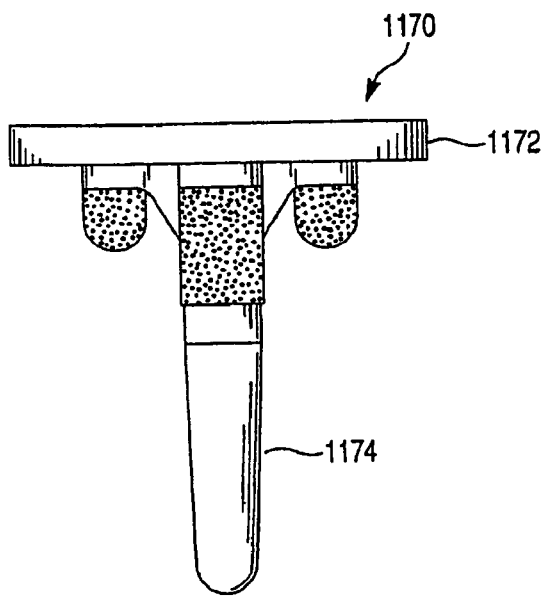
FIG. 79 is a schematic illustration of the modular tibial component of FIG. 78 assembled.

Returning to the embodiment in FIGS. 75-77, any desired procedure can be performed within any joint space. Thus, the medial or lateral approach can be applied, for example, to the hip, shoulder, the joints of the hand and wrist, the joints of the foot and ankle, and the spine. However, this embodiment is particularly useful for knee joint replacement surgeries. FIGS. 78 and 79 show one implant that can be used in this regard. In general, prior art knee prostheses for partially or totally replacing a knee joint include a femoral component for attachment to the distal end of the femur and a tibial component for attachment to the proximal end of the tibia. The tibial component typically includes a base or tray that is implanted in the tibia and an insert or meniscal plate placed on the face of the tray for articulating with the condyles of the femoral component. The tray often includes a keel or stem that inserts in the tibia to provide stability.

In contrast, tibial tray 1170 is a modular unit comprising a base 1172 and a keel 1174. An inferior surface 1176 of tibial tray 1170 is substantially flat so that tibial tray 1170 can be slid into position from the lateral or medial side onto previously cut or milled tibia 1156. A side cutting jig analogous to that shown in FIG. 54 or other side cutting or milling techniques can advantageously be used to prepare tibia 1156 for receiving tibial tray 1170. Tibial tray 1170 is provided with openings 1178 that extend from a superior surface 1180 through inferior surface 1176. Openings 1178 are sized to receive keel 1174. As shown, keel 1174 is implanted prior to implantation of tibial tray 1170. In another embodiment, tibial tray 1170 is implanted prior to implantation of keel 1174. In this embodiment, openings 1178 are sized so that once tibial tray 1170 is sitting on the tibial surface, keel 1174 can be pushed or pounded through opening 1178 to secure tibial tray 1170 to tibia 1156.

Base 1172 and keel 1174 can be provided with a locking mechanism to secure keel 1174 to base 1172. One example of such a mechanism is a locking screw 1181 that inserts through base 1172 and keel 1174. If keel 1174 is implanted after tibial tray 1170, keel 1174 can also be provided with a head 1182 or other stop mechanism that prevents further insertion of keel 1174 through openings 1178 once keel 1174 has been inserted through openings 1178 a given distance. In one embodiment, head 1182 can be made to be flush with superior surface 1180 of base 1172. In this regard, openings 1178 have a countersink 1184 for accommodating keel head 1182. In another embodiment, head 1182 extends above superior surface 1180 even after full insertion through openings 1178 (i.e. stands proud with respect to superior surface 1180). In this embodiment, keel head 1182 can cooperate with a bore or slit provided on the inferior surface of a tibial insert to serve as a centering mechanism for insertion (locking the tibial insert to base 1172 in a fixed bearing design) and/or articulation of the femoral and tibial components (in a mobile bearing design).

If tibial tray 1170 were an integral single-piece unit, it would be difficult to insert tibial tray 1170 through a minimal incision, regardless of the location of the incision. However, since tibial tray 1170 is modular, base 1172 can be readily slid in through either a lateral or medial side incision (which can be smaller than typical mid-line incisions) and, keel 1174 can be interoperatively coupled to base 1172 after base 1172 is in the desired position. Keel 1174 can be inserted through the same incision as base 1172 or through a separate incision. This separate incision can be a substantially anterior incision or an incision located on the same or opposite side as the incision for base 1172. As is well known, tibial tray 1170 can be inserted either with or without bone cement. If bone cement is used, the cement can be placed under base 1172 after it is positioned on tibia 1156 and then keel 1174 is inserted into openings 1178.

Figure 80:
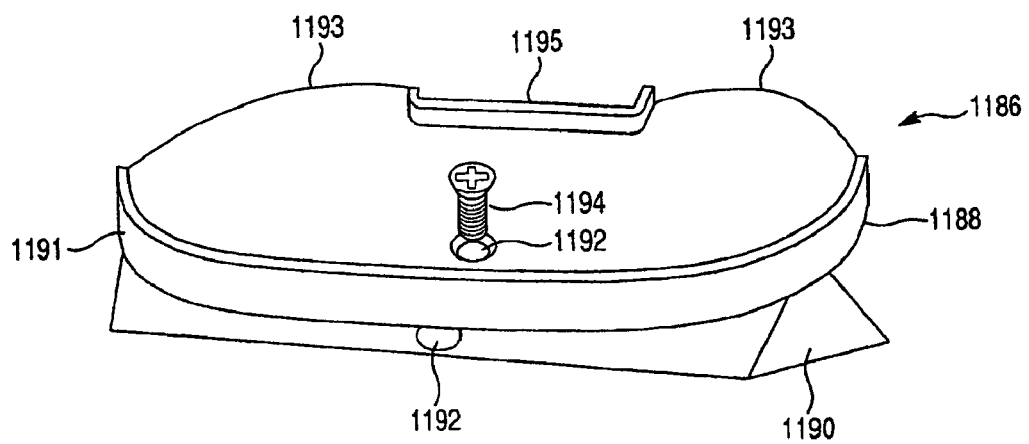
FIG. 80 is a schematic illustration of a tibial component.

FIG. 80 shows another embodiment of a tibial tray 1186 that can be used with or without a keel. An inferior surface 1188 of tibial tray 1186 includes a slot 1190 extending substantially across the entire width of inferior surface 1188. Slot 1190 provides stability for tray 1186. Like tray 1170, tray 1186 can be inserted from either the medial or lateral side. Slot 1190 and/or tibial tray 1186 can be provided with a bore 1192 (or a plurality of bores) for receiving a screw 1194 or other fastener to further secure tray 1186 to the tibia.

Tibial tray 1186 also includes another feature to assist implantation. Specifically, like prior art tibial trays, tibial tray 1186 includes a rim 1191 for retaining the tibial insert or bearing surface. However, as shown, rim 1191 does not extend around the entire perimeter of tibial tray 1186. Specifically, lateral and medial posterior regions 1193 have no rim. A centrally located section 1195 can be provided with a rim for retention of the tibial insert. The elimination of rim 1191 from posterior regions 1193, facilitates implantation of the femoral component as there is no posterior rim in lateral an medial regions 1193 to impede impaction of the femoral component. Section 1195 will not interfere with impaction of the femoral component as the femoral component has a geometry matching the natural condyles of the femur. The novel feature of eliminating the posterior rim can be applied to different tibial tray designs and is not limited to tibial tray 1186.

Figure 81:
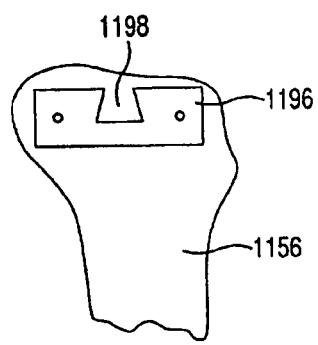
FIG. 81 is a schematic illustration of a tibial side-cutting jig for the tibial component of FIG. 80.

In order to facilitate implantation of tray 1186, a side cutting or milling jig 1196 (FIG. 81) can be provided with a groove 1198 having a shape that mates with slot 1190. Thus, when tibia 1156 is cut or milled, the tibia has a recess corresponding to the shape of slot 1190, thereby allowing tray 1186 to be readily moved into position. It should be noted that use of a jig having a groove is not necessary for implantation of tray 1186. For example, tray 1186 can be press fit into position, either by tapping in tray 1186 in a direction along the longitudinal axis of slot 1190 or by tapping tray 1186 from the superior direction. It should also be noted that although slot 1190 is shown having a substantially dove-tail shape, slot 1190 can be made to have any suitable shape that provides stability for tray 1186.

Figure 82:
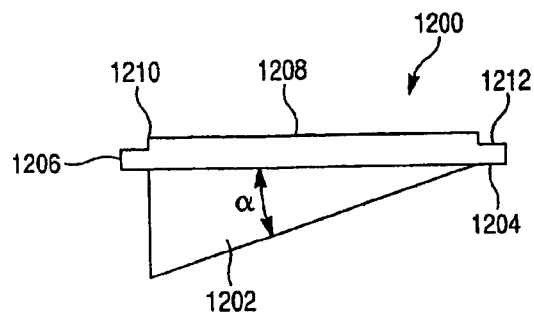
FIG. 82 is a front view of a tibial component.

FIG. 82 shows another embodiment of a tibial tray 1200 that has a novel keel design. A keel 1202 extends from an inferior surface 1204 of tibial base 1206. A superior surface 1208 is generically shown, and, as is well known, is configured and dimensioned for receiving an insert (not shown) that articulates against a femoral component (also not shown). Tibial base 1206 has lateral and medial regions 1210, 1212.

When viewed from the anterior (FIG. 82) or posterior direction, keel 1202 extends downward from inferior surface 1204 at an acute angle $\alpha$. Thus, keel 1202 extends downward toward lateral region 1210 and away from medial region 1212. This is in contrast to prior art keels, which generally extend substantially perpendicularly and symmetrically from the tibial base. Like prior art keels, keel 1202 can be tapered and can be inclined either posteriorly or anteriorly when viewed from the medial/lateral direction. Although keel 1202 is shown as connected to inferior surface 1204 centrally located with respect to both lateral and medial regions 1210, 1212, keel 1202 can be offset with respect to either lateral or medial regions 1210, 1212.

Figure 83:
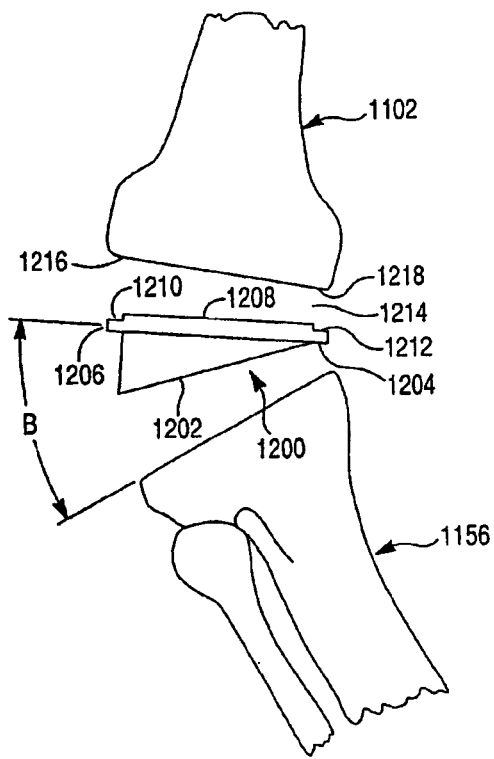
FIG. 83 is a schematic illustration of the tibial component of FIG. 82 being implanted.
Figure 84:
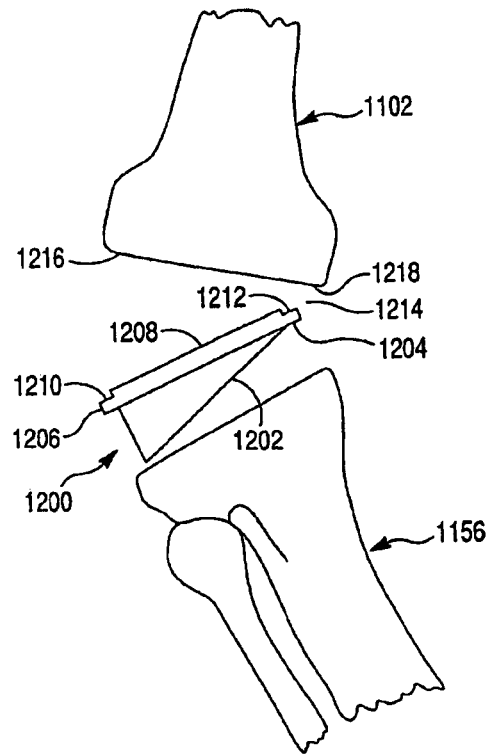
FIG. 84 is another schematic illustration of the tibial component of FIG. 82 being implanted.

FIGS. 83 and 84 show examples of surgical approaches for which tibial tray 1200 is particularly useful. Specifically, knee joint space 1214 is accessed using a lateral approach such as the procedure previously described in connection with FIGS. 75-77. Since joint space 1214 is hinged or pivoted open from a lateral aspect 1216 about a medial aspect 1218, the area of joint space 1214 that is accessible decreases from lateral aspect 1216 to medial aspect 1218. As a result, it would be difficult to insert a typical tibial tray since the length of the keel (compared to the working space of medial aspect 1216) would not permit proper implantation.

FIG. 83 shows one method of implanting tibial tray 1200. Because of the size and geometry of keel 1202, tibial tray 1200 can be inserted into joint space 1214 at an angle $\beta$ (defined by the cut surface of tibia 1156 and superior surface 1208 of tibial tray 1200). At angle $\beta$, lateral region 1210 is at the same height as medial region 1212 so that when tibial tray 1200 is initially inserted, inferior surface 1204 of medial region 1212 is in contact (or close to contact) with tibia 1156. Thus, in order to implant tibial tray 1200 in tibia 1156, lateral region 1210 is driven in tibia 1156, with essentially rotation about medial region 121 occurring.

FIG. 84 shows another method of implanting tibial tray 1200. Here, superior surface 1208 of tibial tray 1200 is substantially parallel to the cut surface of tibia 1156. As a result, the distal end of keel 1202 is substantially perpendicular to the cut surface of tibia 1156. This initial substantially perpendicular relationship facilitates insertion of keel 1202 into tibia 1156. Regardless of the method of implantation, keel 1202 can have a length so that keel 1202 does not penetrate the lateral cortex of tibia 1156 when fully inserted into tibia 1156.

Figure 85:
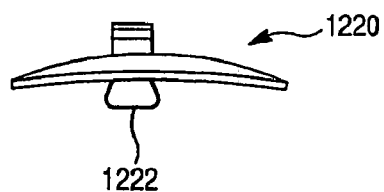
FIG. 85 is a side view of a patellar implant.

Although tibial trays 1170, 1186, and 1200 are, as the name implies, intended for use in the tibia, the concepts can be applied to the other components in partial or total knee replacement surgeries. For example, FIG. 85 shows a patellar implant 1220 having a slot 1222 that engages bone. Thus, patellar implant 1220 is analogous to tibial tray 1186. Typically, patellar implants have one or more pegs that must be driven into bone. This requires substantial working space, so that the patella needs to be everted or dislocated. In contrast, patellar implant 1220 can be slid into position without evertion and with little or no dislocation. If desired, patellar implant 1220 can be fixed into position with bone cement.

Figure 86:
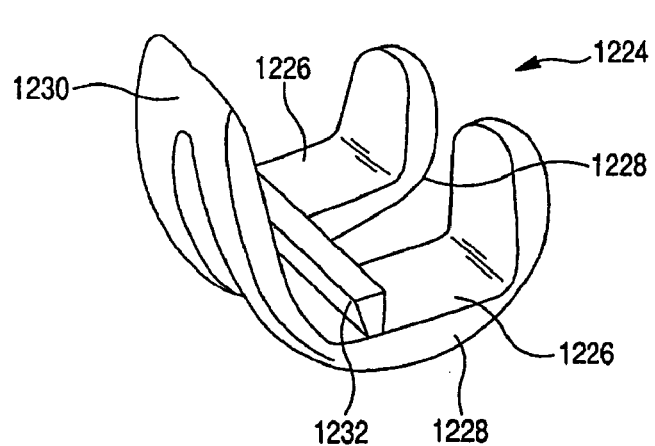
FIG. 86 is a schematic illustration of a femoral component.

FIG. 86 shows a femoral component 1224 that is also analogous to tibial tray 1186. In particular, femoral component 1224 has a pair of spaced condyle sections 1226 defining curved condyle surfaces 1228. Joining region 1230 is anterior located and connects the two condyle sections 1226. Instead of having pins for insertion into the femur, femoral component 1224 is provided with a slot 1232 for securing femoral component 1224 to the femur. Since the pins are absent, femoral component 1224 can be slid into position from the lateral or medial side. As an alternative to slot 1232 (or in addition to slot 1232), each of condyle sections 1226 can be provided with an aperture for receiving a fastener to secure femoral component 1224 to the femur. This design could be analogous to tibial tray 1170.

In order to facilitate insertion of femoral component 1224 through a minimally invasive lateral or medial incision, femoral component 1224 can be made modular. This allows femoral component 1224 to be implanted in sections through an incision that would otherwise be much longer which are then coupled in vivo. As shown, femoral component 1224 comprises an anterior femoral section 1234, and a posterior femoral section 1236. However, any desired number of sections could be used. Anterior femoral section 1234 is coupled to posterior femoral section 1236.

Figure 87:
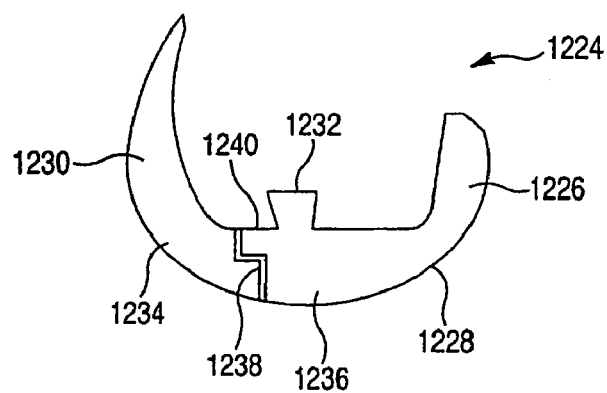
FIG. 87 is a section illustration of the femoral component of FIG. 86.

FIG. 87 shows one manner of coupling the sections. A tongue 1238 located on one section (shown as anterior femoral section 1234) mates with a groove 1240 on an adjacent section (shown as posterior femoral section 1236). The mating results in substantially smooth condyle surfaces 1228 so as to minimize the potential for generation of wear debris.

Self-Centering Mobile Bearing Implant

Figure 88:
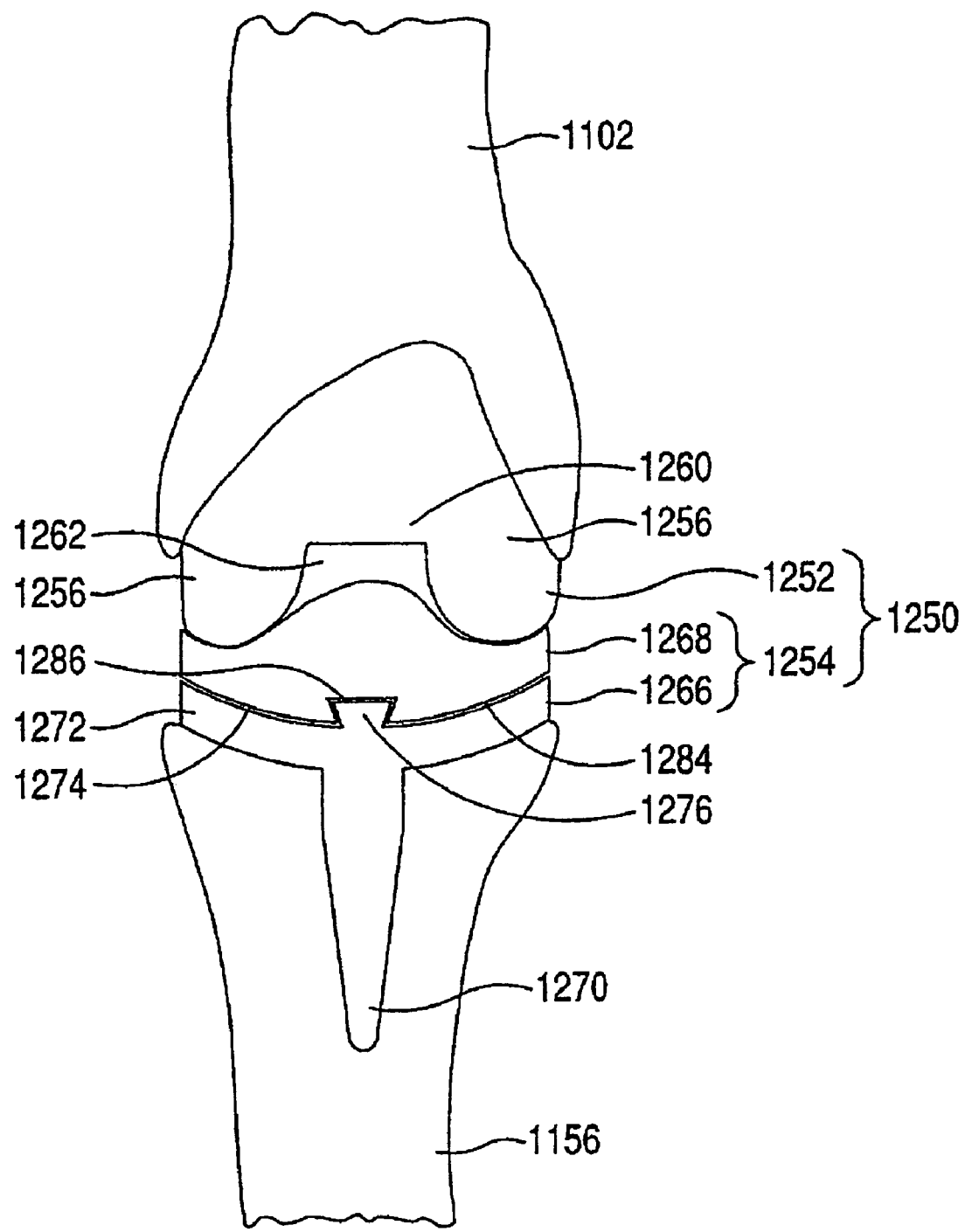
FIG. 88 is a schematic illustration of a knee implant.
Figure 89:
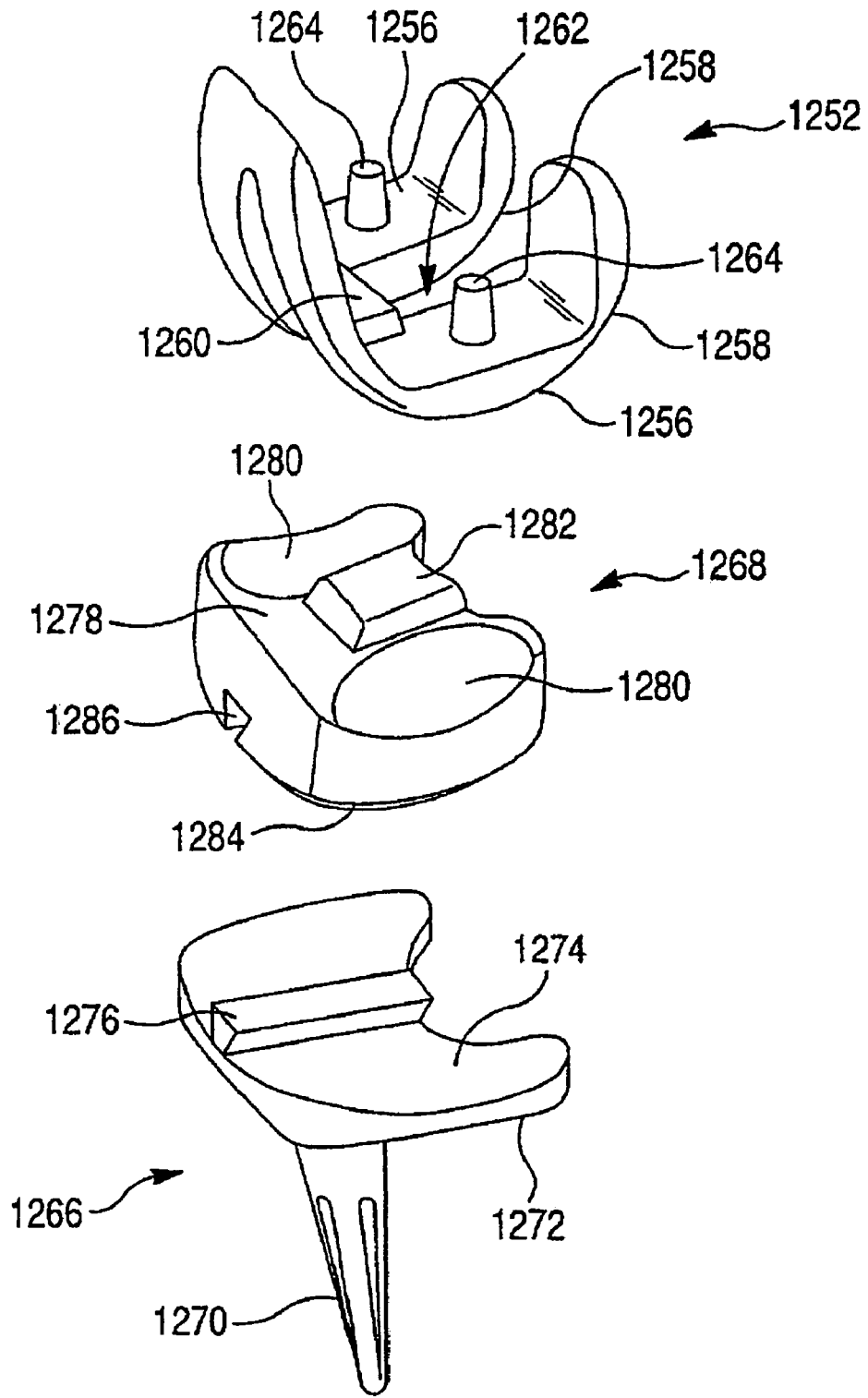
FIG. 89 is an exploded perspective illustration of the total knee implant of FIG. 88.

FIGS. 88 and 89 show one embodiment of a self-centering mobile bearing implant according to the present invention. An implant 1250, in the form of a prosthetic knee, comprises a femoral component 1252 secured to femur 1102 and a tibial component 1254 secured to tibia 1156. Femoral component 1252 includes a pair of spaced apart condyle sections 1256 defining curved condyle surfaces 1258. A joining region 1260 is anterior located and connects the two condyle sections 1256 so that a recess 1262 is defined by condyle sections 1256 and joining region 1260. The side of femoral component 1252 facing femur 1102 can include fixation pins 1264. As femoral component 1252 has a structure and function analogous to prior art femoral components, further description is not believed necessary.

Tibial component 1254 includes a tray 1266 and a bearing insert 1268. Tray 1266 is defined by a tapered keel or spike 1270 and a plate member 1272. As previously discussed with respect to other embodiments, other mechanisms for fixing tibial component 1254 can be used as an alternative to spike 1270. Plate member 1272 has a superior surface 1274 defined by a concave, spherically shaped plateau surface.

As is more fully described below, bearing insert 1268 also has a spherically shaped surface so that the interface between tibial tray 1266 and bearing insert 1268 is defined by cooperating spherically shaped, concave and convex surfaces that enable sliding motions along these surfaces. In this regard, superior surface 1274 has a mirror polish to minimize friction during relative slidable movements of bearing insert 1268. Additionally, superior surface 1274 is provided with a track 1276 that cooperates with a groove located on bearing insert 1268 so that the sliding motion occurs substantially in the anterior-posterior direction. Although a single track 1276 is shown centrally located, track 1276 can be located elsewhere along superior surface 1274 and/or more than one track can be used (e.g. two lateral symmetrically placed tracks). Also, the arrangement of the track and groove can be switched so that bearing insert 1268 is provided with the track and superior surface 1274 is provided with the groove.

Bearing insert 1268 has a superior surface 1278 that includes a pair of spaced apart curved depressions 1280 that form bearing surfaces for condyle surfaces 1258 of femoral component 1252. Condyle surfaces 1258 and depressions 1280 are shaped so that pivoting motion between femoral component 1252 and bearing insert 1268 can occur over a wide range of motion. A protrusion 1282 can be located between depressions 1280 so that extension of protrusion 1282 into recess 1262 of femoral component 1252 substantially prevents hyperextension (counterclockwise rotation beyond a certain point) of femoral component 1252. Interference between protrusion 1282 and recess 1262 also prevents relative motion in the lateral-medial direction.

Bearing insert 1268 has an inferior surface 1284 that is convex and spherically shaped and mates with concave superior surface 1274 of tibial tray 1266. A groove 1286 is located on inferior surface 1284 and is configured and dimensioned to receive track 1276.

As is evident from the foregoing, implant 1250 operates like prior art mobile bearing knee implants in the occurrence of sliding motion between bearing insert 1268 and both femoral and tibial tray 1266 components 1252. However, unlike prior art mobile bearing knee implants that rely on tracks and grooves to substantially limit the movement to the anterior-posterior direction, the articulating surfaces are not flat. Rather, superior surface 1274 of tibial tray 1266 and inferior surface 1284 of bearing insert 1268 are mating curved surfaces.

With the prior art flat surfaces, there is increased risk for dislocation and variable degrees of laxity. Additionally, ligament balancing and self-centering of the joint may be more difficult, allowing for some feelings of instability and/or ligamentous laxity. Because superior surface 1274 of tibial tray 1266 and inferior surface 1284 of bearing insert 1268 are mating curved surfaces, the curvature toward the center of the tibia encourages bearing insert 1268 to want to fall back into the center of the curvature of superior surface 1274.

In order to enhance ligament stability, tray 1266 and/or bearing insert 1268 can be made to have a thickness that increases from the center toward the edge. As shown in FIGS. 88 and 89, this increase in thickness can occur in both the anterior-posterior direction and the medial-lateral direction. Thus, as bearing insert 1268 slides, both the curvature and decrease in thickness cooperate as a self-centering mechanism that draws bearing insert 1268 back to the center of the tibia (also resisting posterior rollback), the lowest point in tibial tray 1266 when they are at rest. This enhances stability, yet allows free motion and a mobile bearing construct.

The curvature of inferior surface 1284 of bearing insert 1268 can be made to match the curvature of superior surface 1274 of tibial tray 1266. Alternatively, the curvatures can be different. For example, the curvature of inferior surface 1284 can be smaller than the curvature of superior surface 1274. Regardless of whether of curvatures match, the curvature of inferior surface 1284 and/or superior surface 1274 can be constant or have a radius which progressively varies.

Each of femoral component 1252, tibial tray 1266, and bearing insert 1268 can be made of any suitable biocompatible material. For example, femoral component 1252 and tibial tray 1266 can both be made of a metallic material such as a cobalt-chromium alloy or titanium alloy, and bearing insert 1268 can be made of a polymer such as UHMW polyethylene. This provides metal articulating against a polymer. Additionally and as previously discussed with respect to other embodiments, this can be reversed so that femoral component 1252 and tibial tray 1266 are made of a polymer and bearing insert 1268 is made of a metallic material.

Figure 90:
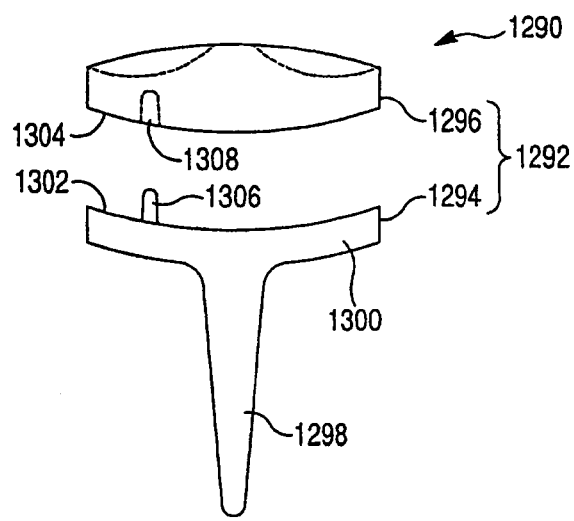
FIG. 90 is a schematic illustration of a tibial component of a knee implant.

FIG. 90 shows another embodiment of the self-centering mechanism according to the present invention. An implant 1290 in the form of a rotating platform knee implant includes a tibial component 1292 secured to the tibia and a femoral component secured to the femur. As the femoral component used with implant 1290 is analogous to femoral component 1252, reference is made to FIGS. 88 and 89 and accompanying text and further description is not believed necessary.

Tibial component 1292 includes a tray 1294 and a bearing insert 1296. Tray 1294 includes a tapered spike 1298 and a plate member 1300. As was the case for tibial component 1254, other mechanisms for fixing tibial component 1292 can be used as an alternative to spike 1298. Plate member 1300 has a superior surface 1302 defined by a concave, spherically shaped plateau surface.

Analogous to bearing insert 1268, bearing insert 1296 also has a spherically shaped inferior surface 1304 so that the interface between tibial tray 1294 and bearing insert 1296 is defined by cooperating spherically shaped, concave and convex surfaces that enable sliding motions along these surfaces. In this regard, superior surface 1302 has a mirror polish to minimize friction during relative slidable movements of bearing insert 1296. Additionally, superior surface 1302 is provided with a post 1306 that cooperates with a recess 1308 located on bearing insert 1296 to permit rotation of bearing insert 1296 with respect to tibial tray 1294. The arrangement of the post and recess can be switched so that bearing insert 1296 is provided with the post and superior surface 1302 is provided with the recess.

As is evident from the foregoing, implant 1290 operates like prior art mobile bearing knee implants in the occurrence of rotation motion between bearing insert 1296 and both femoral and tibial tray components 1292. However, unlike prior art mobile bearing knee implants that rely on a post mechanism to control the rotational movement, the articulating surfaces are not flat. Rather, superior surface 1302 of tibial tray 1294 and inferior surface 1304 of bearing insert 1296 are mating curved surfaces.

Compared to the prior art, implant 1290, like implant 1250, provides improved dislocation risk, ligament balancing, and ligament stability. In order to enhance ligament stability, tray 1294 and/or bearing insert 1296 can be made to have a thickness that increases from the center toward the edge. Thus, as bearing insert 1296 slides, both the curvature and decrease in thickness cooperate as a self-centering mechanism that draws bearing insert 1296 back to the center of post 1306 (also resisting posterior rollback), the lowest point in tibial tray 1294 when they are at rest. This enhances stability, yet allows free motion and a mobile bearing construct.

As is evident from FIG. 90, post 1306 is not located directly over spike 1298, i.e. the center of the tibia. Rather, post 1306 is offset medially toward the medial compartment of the knee. In prior art rotating platform designs, the post is substantially in line with the central keel. This design does not account for the anatomical motion of the knee, which has more motion and a greater range of motion laterally with greater anteroposterior translation laterally and less anteroposterior translation medially. Offsetting post 1306 more toward the medial compartment of the knee recreates the natural pivoting motion on the knee, with less translation medially, a more stable joint medially, and more rotational arc or more movement laterally.

Any of the above-described embodiments of self-centering mechanism can be applied to total or partial knee replacement. These embodiments could be used in any joint, such as the shoulder, ankle, wrist, as well as others.

Bicompartment Implants

As previously discussed (see, e.g. FIG. 40 and associated text), the present invention includes implants that have interconnectable portions. Another embodiment of this concept is the combination of limited incision unicompartmental knee replacement with limited incision patellofemoral replacement. This combination can be done percutaneously with limited incisions, possibly one or two smaller incisions to approach the medial aspect of the knee in the patellofemoral joint.

Arthritis typically does not involve the entire joint space. Most arthritis of the knee is medial joint, lateral joint, patellofemoral joint, or some combination of two of these three joint compartments. Usually advanced arthritis involves both the medial or lateral compartment and the patellofemoral joint. Replacement of the medial or lateral compartment through limited incision surgery and then patellofemoral replacement through the same incision or another incision will lead to faster patient rehabilitation. Additionally, limited incision replacement of these compartments that avoided everting the patellofemoral joint and reduced damage of the quadriceps mechanism would further accelerate rehabilitation.

Figure 91:
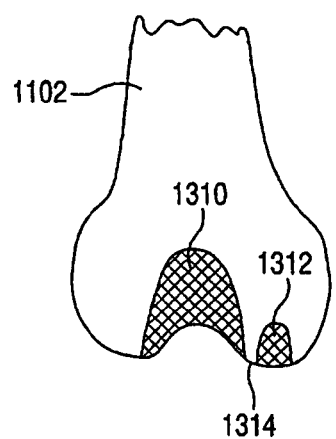
FIG. 91 is a schematic illustration of a bicompartment femoral implant.
Figure 92:
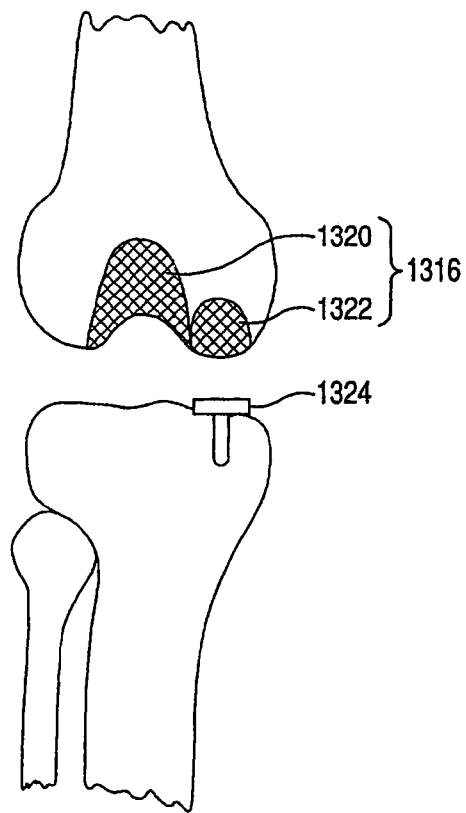
FIG. 92 is a schematic illustration of a bicompartment femoral implant and a unilateral tibial implant.

FIG. 91 shows a bicompartment arrangement that includes trochlear implant 1310 and medial implant 1312. Implants 1310 and 1312 are dimensioned and configured so that bone 1314 is located between the implants. FIG. 92 shows an embodiment of a bicompartment implant 1316 that includes trochlear section 1320 and medial section 1322. In implant 1316, there is no bone between the sections. Implant 1316 can be made so that sections 1320 and 1322 are integral. Alternatively, implant 1316 could be modular, being assembled inside the body or outside of the body prior to implantation.

In the interest of brevity, the reader is referred to FIG. 40 and associated text for different methods for coupling sections 1320 and 1322. As previously discussed, the patella and the other portions of the joint can be resurfaced to receive the implant. In this regard, the resurfacing can be with a mill, saw or robotic arm and computer navigation system. The computer navigation system could also be used to assist in aligning the unicompartmental replacement with the patellofemoral joint replacement. The patellofemoral replacement could be performed from a mid-vastus or sub-vastus approach without disrupting the quadriceps mechanism. As also previously discussed, the patella could be elevated using fluid retractors or simple mechanical retractors to minimize soft tissue damage associated with dislocating or everting the patella.

FIG. 92 shows the tibial component 1324, which articulates against medial section 1322. Each of the components can be made of any suitable biocompatible material. For example, all of the components can be made of a metallic material such as a cobalt-chromium alloy or titanium alloy. This provides metal articulating against metal. Alternative articulating surface pairs include metal/polymer, metal/ceramic, metal/composite, polymer/ceramic, polymer/polymer, polymer/composite, ceramic/ceramic, and ceramic/composite.

In order to reduce the generation of wear debris, the articulating surfaces can be magnetically charged to have the same polarity so that the surfaces are repelled from each other. Thus, the surfaces glide smoothly over each other, essentially floating with respect to one another. This would also potentially allow a replacement surface that is a strip or point contact, rather than being a full surface that matches the surface of the joint. This embodiment, which is described in more detail below, would include strips that glide along each other, as opposed to a full resurfacing of the joint so one would have strips in contact with each other rather than a full surface. The surface magnetic charges can diminish with time. Additionally, certain environments could also diminish the magnetic charges. For example, exposure to an MRI apparatus could severely alter the magnetic fields. In order to account for these possibilities, the magnetic charges of the articulating surfaces can be re-magnetized.

The present invention also envisions the application of magnetically charged articulating surfaces to other implant designs and to other locations in the body. Examples include the knee, the shoulder (both the glenoid and humeral components), the joints of the hand and wrist, the joints of the foot and ankle, and the spine. With respect to the spine, suitable procedures include any procedure involving the disc space and/or the vertebra.

Adjustable Cutting Jig

Figure 93:
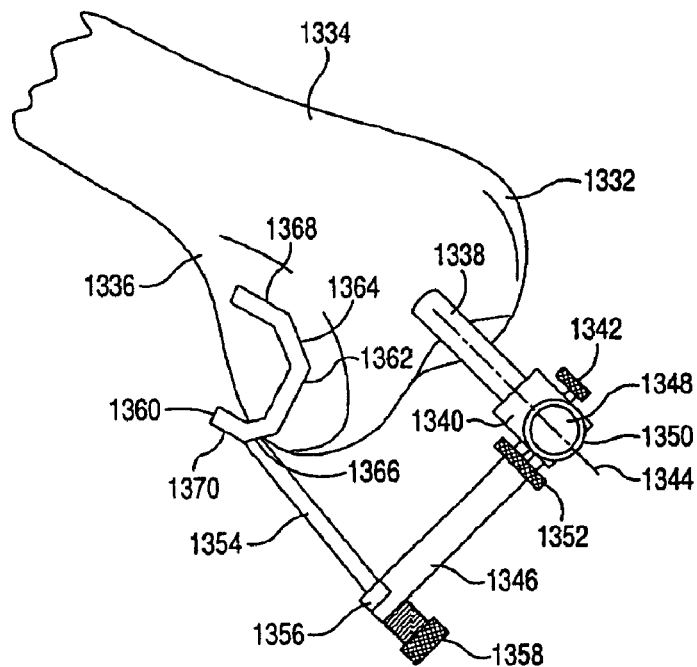
FIG. 93 is a schematic illustration depicting the manner in which an adjustable femoral cutting jig may be mounted on a distal end of a femur in a patient's leg.

As previously discussed, various embodiments of the present invention involve a lateral or medial approach to accessing a joint space. FIG. 93 shows an adjustable cutting jig 1330 that is particularly useful in such an approach. With the cutting jig 1330, the femoral cuts can be made by moving a saw blade or other cutting device, such as a miller, between opposite sides of the femur in a direction extending generally perpendicular to a longitudinal central axis of the femur. Thus, the cutting device is moved along a path which extends between lateral and medial surfaces on the distal end portion 1332 of the femur 1334.

The cutting jig 1330 is illustrated in FIG. 93 as being used on a lateral surface 1336 of the femur 1334. However, the cutting jig 1330 could be used on the medial surface of the femur 1334 if desired. When the cutting jig 1330 is mounted on the lateral surface 1336 of the femur 1334, the incision 114 (FIG. 6) is laterally offset. Similarly, when the cutting jig 1330 is mounted on a medial surface of the femur 1334, the incision 114 is medially offset.

Although either intramedullary or extramedullary instrumentation can be used to attach the cutting jig 1330 to the femur 1334, FIG. 93 shows intramedullary instrumentation. Accordingly, the cutting jig 1330 includes a shaft 1338 that can be inserted into the medullary canal of femur 1334 in any known manner, for example using a technique analogous to that previously described in connection with FIGS. 8-10. In this regard, a separate stab wound incision can be made for shaft 1338, rather than attempting to stretch the incision 114.

A length adjustment member 1340 slides along shaft 1338 so that the location of length adjustment member 1340 on shaft 1338 can be changed to accommodate different anatomies. Tightening knob 1342 can be used to lock length adjustment member 1340 at the desired location. Length adjustment member 1340 can also freely rotate about shaft axis 1344. This is useful, for example, if a medial approach is to be used.

An arm 1346 extends from length adjustment member 1340. Arm 1346 includes a head 1348 that is received in ring 1350 on length adjustment member 1340. The arm 1346 can be made as two telescoping rods or a similar configuration so that the length of the arm 1346 can be adjusted. The head 1348 can rotate within the ring 1350 to allow rotation of the arm 1346. A tightening knob 1352 locks the arm 1346 at the desired position.

An extension 1354 extends from the lateral end of arm 1346. Like the arm 1346, extension 1354 can be made as two telescoping rods or a similar configuration so that the length of the extension 1354 can be adjusted. A link 1356 is generically shown to indicate that different types of joints can be used to couple the arm 1346 and the extension 1354. For example, it may be desirable to have the extension 1354 rotate and/or pivot with respect to the arm 1346. Regardless of the specific design of the link 1356, a tightening knob 1358 is provided to lock the extension 1354 at the desired position.

A cutting guide 1360 is located on an end of the extension 1354. As was the case for link 1356, different types of joints can be used to couple the cutting guide 1360 to the extension 1354. The cutting guide 1360 includes a distal guide surface 1362, an anterior chamfer guide surface 1364, a posterior chamfer guide surface 1366, an anterior guide surface 1368, and a posterior guide surface 1370. As is readily apparent, the cutting guide 1360 has a structure substantially similar to the cutting guide 800. Furthermore, the operation and use of the cutting guide 1360 is substantially similar to that of the cutting guide 800. Accordingly, reference is made thereto.

Each of the guide surfaces 1362, 1364, 1366, 1368, and 1370 can be made to have a length less than the extent of the cut to be formed on the distal end portion 1332 of the femur 1334. Therefore, after an initial portion of the cut has been made utilizing the appropriate guide surface to guide movement of the cutting tool, the cut surfaces are utilized to guide movement of the cutting tool during completion of the cut. The cutting guide 1360 is not of the capture type. Therefore, the cutting tool is free to move past the guide surfaces 1362, 1364, 1366, 1368, and 1370 during completion of the femoral cuts. If the guide surfaces 1362, 1364, 1366, 1368, and 1370 were formed by slots, the cutting guide 1360 could be disconnected from the femur 1334 to complete the femoral cuts.

The cutting guide 1360 can be made so that one or more of the guide surfaces 1362, 1364, 1366, 1368, and 1370 have an adjustable length so that the size of the guided portion of the cuts can be adjusted depending upon the size of the bone and the implant that is to be used. Furthermore, the cutting guide 1360 is shown having a plurality of guide surfaces 1362, 1364, 1366, 1368, and 1370, with each guide surface being used to make a different cut. Other embodiments of cutting guides 1360 can be used with the cutting jig 1330.

Figure 94:
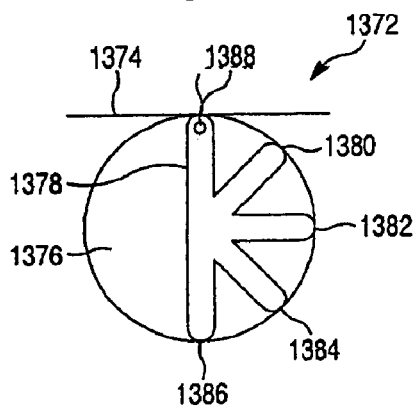
FIG. 94 is a schematic illustration of a femoral cutting guide having a single cutting guide surface.

For example, FIG. 94 shows a cutting guide 1372 that has a single guide surface 1374. As will be discussed, the guide surface 1374 is movable to make multiple guided cuts of different orientations. As the cutting guide 1372 only has one guide surface 1374, the cutting guide 1372 can be used through a smaller incision than prior art cutting blocks. The cutting guide 1372 includes a base 1376 that can be positioned on the femur using the adjustable cutting jig 1330. In other words, the cutting guide 1372 would be a substitute for the cutting guide 1360. Other intramedullary instrument could be used with the cutting guide 1372. Additionally, extramedullary instrument could be employed. If desired, the base 1376 could be pinned directly to the femur in a manner analogous to the cutting guide 800 (FIG. 54). Alternatively, the base 1376 could be positioned on the femur using a computer navigation system.

Figure 95:
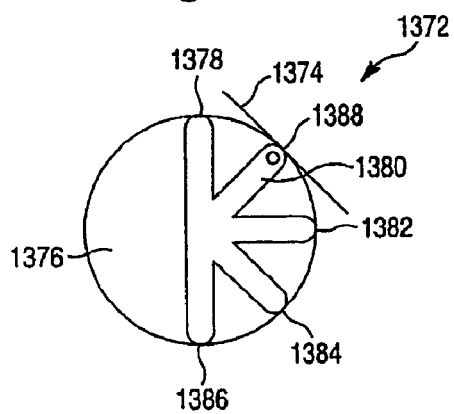
FIG. 95 is a schematic illustration of the femoral cutting guide of FIG. 94 with the cutting guide surface in a different position.

The base 1376 has a plurality of tracks 1378, 1380, 1382, 1384, and 1386. The guide surface 1374 is attached to a pin member 1388. The pin member 1388 is sized to be received in the tracks 1378, 1380, 1382, 1384, and 1386. When pin member 1388 is located in the track 1378, the guide surface 1374 is positioned on the femur for making an anterior cut, as shown in FIG. 94. When pin member 1388 is located in the track 1380, the guide surface 1374 is positioned on the femur for making an anterior chamfer cut, as shown in FIG. 95. When pin member 1388 is located in the track 1382, the guide surface 1374 is positioned on the femur for making a distal cut. When pin member 1388 is located in the track 1384, the guide surface 1374 is positioned on the femur for making a posterior chamfer cut. When pin member 1388 is located in the track 1386, the guide surface 1374 is positioned on the femur for making a posterior cut.

The pin member 1388 can be locked in the tracks 1378, 1380, 1382, 1384, and 1386 to stabilize the guide surface 1374 during making of the cuts. This can be done in any number of ways. For example, the pin member 1388 can have a threaded portion that receives a nut to secure the pin member 1388 within the track. The specific configuration of the tracks 1378, 1380, 1382, 1384, and 1386 shown in FIGS. 94 and 95 are exemplary only, as any configuration that allows movement of the guide surface 1374 with respect to the base 1376 could be used.

As was the case with the cutting guide 1360, the guide surface 1374 can be made so that the size of the guided portion of the cuts can be adjusted depending upon the size of the bone and the implant that is to be used. Furthermore, the guide surface 1374 can be made to have a length less than the extent of the cut to be formed on the distal end portion of the femur. Therefore, after initial portions of the cuts have been made utilizing the guide surface 1374 to guide movement of the cutting tool, the cut surfaces are utilized to guide movement of the cutting tool during completion of the cut. The cutting guide 1372 is not of the capture type. Therefore, the cutting tool is free to move past the guide surface 1374 during completion of the femoral cuts. If the guide surface 1374 were of the capture type (having a slot), the cutting guide 1372 could be disconnected from the femur to complete the femoral cuts.

Figure 96:
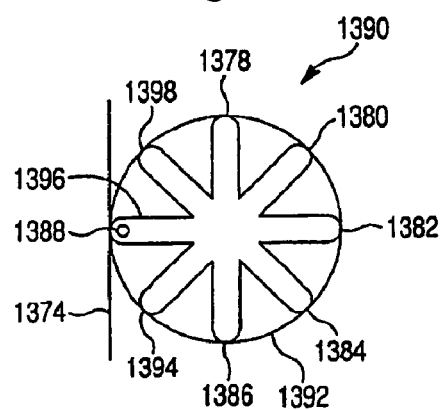
FIG. 96 is a schematic illustration of another embodiment of a femoral cutting guide having a single cutting guide surface.

The cutting guide 1372 is illustrated in FIGS. 94 and 95 for use on a lateral surface of the femur. However, the cutting guide 1372 could be used on the medial surface of the femur by either flipping or rotating the base 1376. In this regard, FIG. 96 shows a cutting guide 1390 that could be used on either the lateral or medial side of the femur. In addition to containing the tracks 1378, 1380, 1382, 1384, and 1386, a base 1392 includes tracks 1394, 1396, and 1398. As shown, the track 1396 would be used to make a distal femoral cut on the medial side of the femur.

Implants with Reduced Articulating Surfaces

As previously detailed, the present invention relates to methods, implants, and instrumentation for performing surgery through minimally invasive procedures. One aspect is the insertion of a partial or total joint replacement implant through a minimally invasive incision. For example, modular implants that are assembled after insertion in the body can typically be more easily inserted through a smaller incision than a unitary implant of the same size or a modular implant that is assembled prior to implantation. Thus, it is advantageous to have smaller implants, modular or not, in order to reduce the size of the incision that is needed for implantation.

Smaller implants will generally have a smaller articulating surface area. While prior art prosthetic components provide a low-friction articulating surface for the surface of accompanying member, interaction between the articulating component and the member can produce wear debris. Such debris may cause adverse local and systemic reactions in the body. Thus, it is advantageous to minimize the articulating surface area of one or both of a joint component.

Figure 97:
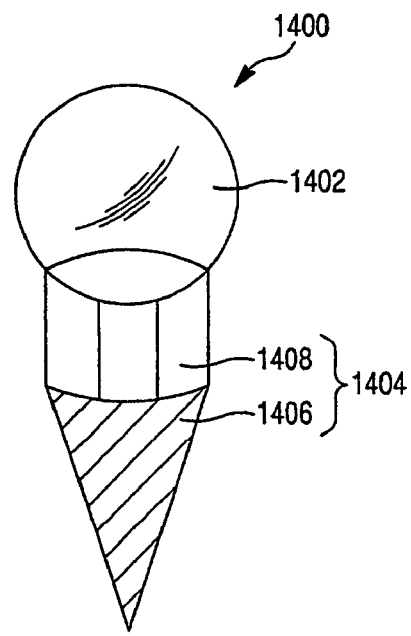
FIG. 97 is a schematic illustration of an implant having a reduced articulating surface area.
Figure 98:
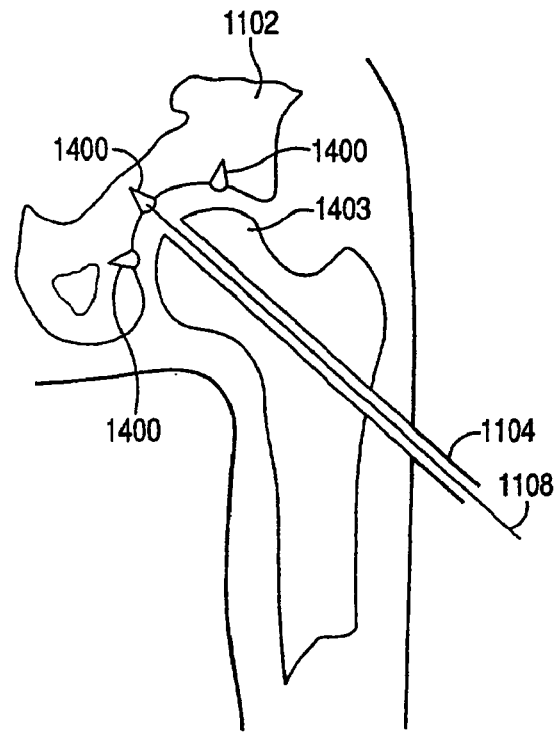
FIG. 98 is a schematic illustration showing a number of the implants of FIG. 97 implanted in an acetabulum.

FIG. 97 shows one embodiment of a joint component implant 1400 that is both small in size to facilitate implantation through a minimal incision and has a reduced articulating surface area. Specifically, implant 1400 comprises a head 1402 connected to a body 1404. In use, head 1402 articulates against the other joint component. In this regard, the other component could be an artificial component or a natural component. For example, if implant 1400 were implanted in the acetabulum 1102 as shown in FIG. 98, the other joint component 1403 could be the natural femoral head or the head of a prosthetic femoral component. Although head 1402 is shown as substantially spherical, any shape that provides a smooth bearing surface could be used.

Body 1404 includes a threaded region 1406 for fixing implant 1400 to tissue. A joining region 1408 is located between head 1402 and threaded region 1406. Joining region 1408 is provided with multiple surfaces so that an inserter or other tool can be used to thread implant 1400 into tissue. By providing an area separate from head 1402 that is used for insertion, the risk of scratching or otherwise damaging the bearing surface is reduced.

Threaded region 1406 can be eliminated and other mechanisms for attaching implant 1400 can be used. For example, implant 1400 could simply be driven into the tissue. Bone cement or an adhesive could be used to attach implant 1400. Alternatively, body 1404 could have a rivet type means, an expandable portion, or some other known fixation means.

Implant 1400 can be made from any biocompatible material that will undergo articulating movement with a corresponding natural or prosthetic member. For example, the bearing component could be formed from a variety of metals, polymers, ceramics, or composite materials. In the event that polymers are chosen, a high density polyethylene may be used, although numerous types of polymers may be suitable so long as the material provides both strength and a low-friction articulation surface for the corresponding joint face. If desired, head 1402 and body 1404 can be made of different materials. It may also be advantageous to include some type of known tissue in-growth promoting features on at least a portion of body 1404. Such features include a porous or textured surface, a porous body (for example so-called "foam metals"), and osteoinductive or osteoconductive materials or factors.

FIG. 98 shows a number of implants 1400 located in the acetabulum 1102 for articulation against femoral head 1403. As shown, implants 1400 can be implanted through cannula 1104 and can be cannulated so that they can be inserted over guide wire 1108, without the need to dislocate the joint or with only slight dislocation. Implants 1400 also present a small surface area against which femoral component 1403 articulates. The bearing surface minimizes available surface area of articulation for the component and the production of wear debris. If desired, implants 1400 can be used without the need to ream acetabulum 1102, thereby saving bone stock. Alternatively, acetabulum could be partially reamed to ensure a surface free of asperities. Because of the overall reduction in size and bearing surface of implants 1400, a larger femoral component 1403 can be used without the risk of significant increase of wear debris. The larger femoral component 1403 may enhance joint stability.

Although any number of implants 1400 can be used for a given application, the use of three implants 1400 for acetabulum 1102 may be preferable as three implants serve as a centering mechanism for femoral component 1403. In this regard, the number and location of implants 1400 can be selected to suit a particular application. The size of implants 1400, and in particular head 1402, can also be varied. In acetabulum 1102, smaller heads 3-6 mm in diameter or larger heads 10-15 mm in diameter may be desirable.

Although FIG. 98 shows implants 1400 used in acetabulum 1102, implants 1400 could be used in any joint component including, a glenoid, patellar, femoral, humoral, tibial, ulnar, radial, wrist, and/or ankle component for a prosthetic joint assembly.

Figure 99:
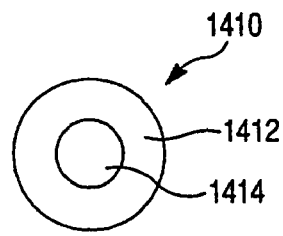
FIG. 99 is a schematic illustration of another implant having a reduced articulating surface area.

FIG. 99 shows another embodiment of a reduced articulating surface area implant 1410. Implant 1410 has a substantially annular shape with a curved surface 1412. When implanted, surface 1412 serves as the bearing surface against which the other joint component articulates. Surface 1412 can be provided with a beveled bearing surface, if desired. The annular shape of implant 1410 defines an interior region 1414. If implant 1410 were to be used on the femur, implant 1410 would be placed around the femoral head with interior region 1414 in contact with bone. If implant 1410 were to be used on the acetabulum, implant 1410 could be fixed to the bone or freely float within the acetabulum with no fixation. As was the case for implant 1400, implant 1410 can be used in other joints.

Figure 100:
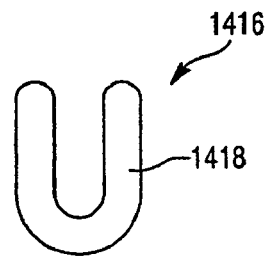
FIG. 100 is a schematic illustration of another implant having a reduced articulating surface area.

FIG. 100 shows another embodiment of a reduced articulating surface area implant 1416. Like implant 1410, implant 1416 is a unitary implant that can be implanted through a minimal incision, has a reduced articulating surface area, and does not require extensive removal of bone. Rather than having a ring shape, implant 1410 has a U-shaped body with curved surface 1418 that serves as the bearing surface.

Disposable Trial Implants, Instruments, and Other Surgical Implements

As previously discussed throughout this specification, the present invention includes disposable surgical implants and instruments. Currently for hip, knee, shoulder, and other joint replacement surgeries (partial or total), there can be six or more trays of instruments and trial implants. Each tray has to be re-sterilized for each procedure. In the case of knee replacement surgeries, one tray may contain femoral trials, one may contain tibial trials, one may contain polyethylene spacer blocks, one may contain tibial cutting instruments, and one tray may contain femoral cutting instruments.

This is cumbersome and unnecessary as only a few of these instruments and trial implants need to be made of surgical grade metal and alloys that are rigid and reusable. There is a significant expense in the multiple tray setups. One company, for example, spends over $150 million just to have instruments in the field. Additionally, shipping charges and re-sterilization costs can be significant. The delay due to the shipping and re-sterilization also adds hidden costs and time. Obviously, money and time can be saved if the number of trays for each procedure were reduced.

Also, as a company modifies implant systems or instruments, representatives of the company need to update their inventories accordingly. Frequently, companies are unable to charge for the new instruments as an incentive to promote a new system. Although these costs cannot be recovered, they ultimately add to the cost of joint replacement surgeries.

These issues can be addressed by a disposable trialing system. For example, the tibial trial base plate 270 (FIG. 26) and other trial components can be made of a light-weight low cost material such as aluminum, injection molded plastic, composite material, and the like. There would be a series of these disposable trial implants in various sizes for the implant system the surgeon intended to use. Each would come prepackaged in a sterile state. Alternatively, each sterile package could include different components of the same size. In the case of a knee replacement procedure, each sterile package could include a femoral trial, a tibial trial, a patellar trial, and a spacer trial. Preoperatively, the surgeon could obtain an estimate of the needed size from x-rays and other clinical information. Based upon this estimate, one or more sizes of the trial implants would be brought to the operating room or surgical suite.

The use of disposable trial implants would reduce the number of trays needed for a given procedure. The use of disposable cutting blocks would further reduce the number of trays. In this regard, the disposable cutting blocks could be made of a material that has color or some other chemical or physical property that would allow the detection of trace amounts of the cutting blocks. This is particularly useful if the cutting blocks are inadvertently scratched so that any debris could be detected and removed. The instruments and trials could have changeable lugs, changeable stems, or similar modularity to allow modification of the position and the rotation.

If desired, some or all of the instruments and other disposables could be packaged in a single sterile unit. Some items that could be included in the unit include the instruments, draping, cement, cement mixer, pulsatile lavage, retractors, drill bits, pins, and guide wires. This would save significant time for the operating personnel as they open this unit and it has all the cutting blocks.

One advantage of the disposable system is that the disposable cutting blocks could easily be modified for new or updated instrumentation or for customized instrumentation. The disposable system saves the cost and time of cleaning and re-sterilization. Also, the disposable system would improve the sterile technique in the operating room and since these are single use and sterilized there is no risk of cross-contamination going from one patient to another patient.

If desired, only a portion of the trial implants or instrumentation could be disposable. For example, the intramedullary rod for distal femoral cutting blocks could be reusable, however, the actual cutting surface, such as the captured guide 4 in 1 block, the mill cut, etc., could be disposable.

Program for Learning Minimally Invasive Surgical Techniques

As the minimally invasive surgical instruments, implants, systems, and methods disclosed herein represent a significant deviation from those used in open surgical procedures, the present invention includes a program for training surgeons and other health care professionals. The program is a sequential approach in which the trainee starts the training process using an incision of standard length and progressively decreases the incision size as milestones are achieved.

The program is sequential learning, analogous to returning to residency or a mini-fellowship. The program can involve a series of visits to a dedicated training sites and/or remote linking, for example via videoconferences or the Internet, to certain training programs. The goal of the program is to allow the trainee to progress from: working with a standard incision, traditionally to learn anatomy; working through a smaller incision, with a combination of prior art instruments and implants and the downsized instruments and implants according to the present invention; and working through a minimally invasive incision to use the instruments, implants, systems, and techniques according to the present invention. As previously discussed, these techniques include minimizing or avoiding joint dislocation, video and fluoroscopic or other radiographic guidance, computer assisted surgical procedures, cannulated instruments and implants, and downsized instruments and implants.

The program can include the following training tools, in any combination: lectures and video demonstrations to understand the instruments, both intra and extramedullary, implants, systems, and methods; observation and discussion of live broadcast surgeries; practice using saw bones; practice with cadavers, animal models, or plastic models that have artificial skin, muscle, tissue, ligaments, and bones; virtual reality evaluations; and practice with minimal incisions.

Once proficiency with some or all of the training tools have be achieved, which can be determined by grading based on examination, the trainee can be assigned a mentor, a previously certified health care professional. The trainee can be required to visit and observe the mentor during surgery. Additionally, the mentor could visit the trainee at the trainee's practice and supervise or otherwise monitor the trainee's techniques.

Even after the initial visits between the mentor and trainee, the mentor could be available for consultation by the trainee. The trainee could start probationary work at his practice by initially using an incision that is only slightly smaller than standard incisions. The x-rays, inter-operative pictures or videos, and other case data could be reviewed and graded by the mentor or other certified instructor. Advancement to the next level would only be allowed if the review were satisfactory. The next level could involve a return to some or all of the training tools to practice working through a smaller incision, with a combination of prior art instruments and implants and the downsized instruments and implants according to the present invention. After the training tools are mastered, probationary work by the trainee at this level would be followed by review and grading by the mentor or other certified instructor. Once again, advancement to the next level would only be allowed if the review were satisfactory. The process is repeated for the final level.

The program could be implemented so that the trainee must meet given standards in order to receive instrumentation and implants to allow the trainee to perform the procedures independently without supervision. Furthermore, achieving these standards could be required prior to being allowed to promote or advertise proficiency in the techniques. The standards could be coordinated with hospital Institutional Review Boards.

The program could be offered through a professional society, such as the American Academy of Orthopaedic Surgeons and the Hip and Knee Society, a commercial entity, or some combination thereof. Continuing Medical Education (CME) credits and grades could be provided. The instructors and preceptors could be certified, with the certification process through a professional society.

The trainees could pay a portion of the costs of the program. Trainees would offset the costs of the program from the added revenue from the procedures and possible lower insurance premiums. The costs of the program may be subsidized by governmental agencies and commercial entities, which would benefit from sales and leasing of instruments and implants. Costs could be subsidized by insurers, which would benefit from the lower costs of the procedures compared to traditional open procedures. Finally, costs could also be subsidized by surgical centers, which would benefit from having trained personnel and added revenue from the procedures.

In additional to the educational benefits of the program, the program also provides some legal protection to the trainees. Perhaps more importantly, the program affords protection to the patient by ensuring adequately trained medical personnel.

CONCLUSION

In view of the foregoing description, it is apparent that the present invention relates to a new and improved method and apparatus for use in performing any desired type of surgery on a joint in a patient's body. The joint may advantageously be a joint in a knee portion 76 of a patient's leg 70. However, the method and apparatus may be used in association with surgery on other joints in a patient's body. There are many different features of the present invention which may used either together or separately in association with many different types of surgery. Although features of the present invention may be used with many different surgical procedures, the invention is described herein in conjunction with surgery on a joint in a patient's body.

One of the features of the present invention relates to the making of a limited incision 114. The limited incision 114 may be in any desired portion of a patient's body. For example, the limited incision 114 may be in a knee portion 76 of a leg 70 of a patient. The limited incision 114 may be made while a lower portion 68 of the leg 70 of the patient is extending downward from the upper portion 72 of the leg of the patient. At this time, a foot 74 connected with the lower portion 68 of the leg of the patient may be below a surface 64 on which the patient is supported. The limited incision 114 may be made while the lower portion 68 of the leg 70 of the patient is suspended from the upper portion of the leg or while the lower portion of the leg and/or the foot 74 of the patient are held by a support device. After the incision 114 has been made, any one of many surgical procedures may be undertaken.

It is believed that in certain circumstances, it may be desired to have a main incision 114 of limited length and a secondary incision 920 of even smaller length. The secondary incision 920 may be a portal or stab wound. A cutting tool 170 may be moved through the secondary incision 920. An implant 286, 290 and/or 294 may be moved through the main incision 114.

Once the incision 114 has been made, a patella 120 in the knee portion 76 of the patient may be offset to one side of its normal position. When the patella 120 is offset, an inner side 122 of the patella faces inward toward the end portions 124 and 212 of a femur 126 and tibia 214.

Although any one of many known surgical procedures may be undertaken through the limited incision 114, down sized instrumentation 134, 138, 186, 210 and/or 218 for use in the making of cuts in a femur 126 and/or tibia 214 may be moved through or part way through the incision. The down sized instrumentation may be smaller than implants 286, 290 and/or 294 to be positioned in the knee portion 76 of the patient. The down sized instrumentation 286, 290 and/or 294 may have opposite ends which are spaced apart by a distance which is less than the distance between lateral and medial epicondyles on a femur or tibia in the leg of the patient.

It is contemplated that the down sized instrumentation 134, 138, 186, 210 and/or 218 may have cutting tool guide surfaces of reduced length. The length of the cutting tool guide surfaces may be less than the length of a cut to be made on a bone. A cut on a bone in the patient may be completed using previously cut surfaces as a guide for the cutting tool.

It is contemplated that at least some, if not all, cuts on a bone may be made using light directed onto the bone as a guide. The light directed onto the bone may be in the form of a three dimensional image 850. The light directed onto the bone may be a beam 866 or 868 along which a cutting tool 170 is moved into engagement with the bone.

There are several different orders in which cuts may be made on bones in the knee portion of the leg of the patient. It is believed that it may be advantageous to make the patellar and tibial cuts before making the femoral cuts.

There are many different reasons to check ligament balancing in a knee portion 76 of the leg of a patient. Ligament balancing may be checked while the knee portion 76 of the leg 70 of the patient is flexed and the foot 74 of the patient is below the support surface 64 on which the patient is disposed. Flexion and extension balancing of ligaments may be checked by varying the extent of flexion of the knee portion 76 of the leg 70 of the patient. In addition, rotational stability of the ligaments may be checked by rotating the lower portion of the leg of the patient about its central axis. Balancing of ligaments may also be checked by moving the foot 74 of the patient sideways, rotating the lower portion 68 of the leg 70 of the patient, and/or moving the foot anteriorly or posteriorly.

It is believed that it may be advantageous to utilize an endoscope 352 or a similar apparatus to examine portions of the patient's body which are spaced from the incision 114. It is also contemplated that images of the knee portion of the patient's leg may be obtained by using any one of many known image generating devices other than an endoscope 352. The images may be obtained while the patient's leg 70 is stationary or in motion. The images may be obtained to assist a surgeon in conducting any desired type of surgery.

Balancing of the ligaments in the knee portion 76 of a patient's leg 70 may be facilitated by the positioning of one or more transducers 596 and/or 598 between tendons, ligaments, and/or bones in the knee portion. One transducer 598 may be positioned relative to a medial side of a knee joint. Another transducer 596 may be positioned relative to a lateral side of the knee joint. During bending of the knee joint, the output from the transducers 596 and 598 will vary as a function of variations in tension forces in the ligaments. This enables the tension forces in ligaments in opposite sides of the knee portion to be compared to facilitate balancing of the ligaments.

Patellar tracking may be checked by the positioning of one or more transducers 930 and/or 932 between the patella 120 and the distal end portion 124 of the femur 126. If desired, one transducer 932 may be placed between a medial portion of the patella 120 and the distal end portion 124 of the femur 126. A second transducer 930 may be placed between a lateral portion of the patella 120 and the distal end portion 124 of the femur 126. Output signals from a transducer 930 will vary as a function of variations in force transmitted between the patella 120 and femur 126 during bending of the leg.

The articular surface 122 on the patella 120 may be repaired. The defective original articular surface 122 on the patella 120 may be removed by cutting the patella while an inner side of the patella faces toward a distal end portion 124 of a femur 126. The step of cutting the patella may be performed while the patella is disposed in situ and is urged toward the distal end portion of the femur by connective tissue. An implant may then be positioned on the patella 120.

It is contemplated that the size of the incision 114 in the knee or other portion of the patient may be minimized by conducting surgery through a cannula 564. The cannula 564 may be expandable. To facilitate moving of an implant 286, 290 and/or 294 through the cannula 564, the implant may be formed in two or more portions 572 and 574. The portions of the implant 286, 290 and/or 294 may be interconnected when the portions of the implant have been positioned in the patient's body. Although the implants disclosed herein are associated with a patient's knee, it should be understood that the implants may be positioned at any desired location in a patient's body.

An implant 626, 640 or 670 may be positioned in a recess 610, 642 or 672 formed in a bone 126 or 214 in a patient. The implant 626, 640 or 670 may contain biological resurfacing and/or bone growth promoting materials. The implant 626, 640 and/or 670 may contain mesenchymal cells and/or tissue inductive factors. Alternatively, the implant 626 or 640 may be formed of one or more materials which do not enable bone to grow into the implant.

In accordance with one of the features of the present invention, body tissue may be moved or stretched by a device 720, 722 and/or 730 which is expandable. The expandable device 720, 722 and/or 730 may be biodegradable so that it can be left in a patient's body. The expandable device 720, 722 and/or 730 may be expanded to move and/or stretch body tissue and increase a range of motion of a joint. The expandable device may be used to stretch body tissue in which an incision is to be made.

An improved drape system 100 is provided to maintain a sterile field between a surgeon 106 and a patient during movement of the surgeon relative to the patient. The improved drape system 100 includes a drape 102 which extends between the surgeon and a drape 90 for the patient. During surgery on a knee portion 76 of a leg 70 of a patient, the drape system 100 extends beneath the foot portion 74 of the leg 70 of a patient. It is contemplated that the drape system 100 will be utilized during many different types of operations other than surgery on a leg of a patient.

An implant 950, 970, 980, 1002, 1020, 1040 or 1060 may be movable relative to both a femur 126 and a tibia 214 in a leg of a patient during bending of the leg. The implant may include a single member (FIGS. 59, 60, 63, 64 and 65) which is disposed between and engage by end portions of the femur and tibia. Alternatively, the implant may include a plurality of members (FIGS. 61 and 62) which are disposed in engagement with each other. If desired one of the members of the plurality of members may be secured to a bone and engaged by a member which is not secured to a bone. The implant may be secured to soft tissue in the knee portion of the patient's leg (FIGS. 63 and 64).

There are many different features to the present invention. It is contemplated that these features may be used together or separately. It is also contemplated that the features may be utilized in association with joints in a patient's body other than a knee joint. For example, features of the present invention may be used in association with surgery on vertebral joints or glenoid joints. However, it is believed that many of the features may be advantageously utilized together during the performance of surgery on a patient's knee. However, the invention should not be limited to any particular combination of features or to surgery on any particular joint in a patient's body. It is contemplated that features of the present invention will be used in association with surgery which is not performed on a joint in a patient's body.

Thus, while various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of performing total knee arthroplasty through a primary incision having a length of less than thirteen (13) centimeters, comprising:

making a primary incision of less than thirteen (13) centimeters near the knee joint of a leg of a patient;

cutting medial and lateral condyles, and the trochlear groove of the femur of the leg to create at least one femoral cut surface;

moving a femoral component of a total knee implant operative to replace at least the entire articulating surface of at least one of the medial condyle, lateral condyle, or the trochlear groove, through the primary incision;

moving remaining femoral components through the primary incision; and positioning the femoral component with respect to the at least one femoral cut surface.

2. The method according to claim 1, wherein the primary incision is located on a side surface of the knee joint, the side surface being one of medial and lateral relative to the centerline of the patient.

3. The method according to claim 2, further comprising cutting a tibia of the leg to create at least one tibial cut surface, moving a tibial component of the total knee implant through the primary incision, and positioning the tibial component with respect to the at least one tibial cut surface.

4. The method according to claim 3, further comprising displacing the patella of the leg to an offset position without everting the patella so that the inner side of the patella remains in a position facing the femur.

5. The method according to claim 4, further comprising cutting a portion of the patella to create a patellar cut surface, moving a patellar component of the total knee implant through the primary incision, and positioning the patellar component with respect to the patellar cut surface.

6. The method according to claim 1, wherein the primary incision is made when the knee joint of the leg is flexed.

7. The method according to claim 6, wherein a lower portion of the leg is suspended relative to an upper portion of the leg.

8. The method according to claim 7, wherein the upper portion of the leg is supported by a leg support.

9. The method according to claim 1, further comprising moving a guide member through the primary incision and positioning the guide member against the femur, the guide member having a guide surface.

10. The method according to claim 9, wherein cutting the medial and lateral condyles and the trochlear groove of the femur includes positioning a cutting tool in association with the guide surface of the guide member to form the at least one femoral cut surface.

11. The method according to claim 10, further comprising removing the guide member from the femur.

12. The method according to claim 11, further comprising continuing the cut of the medial and lateral condyles of the femur while guiding the cutting tool along the at least one femoral cut surface.

13. The method according to claim 9, wherein the guide member has opposite ends with a transverse dimension which is less than a distance between medial and lateral condyles of the femur.

14. The method according to claim 9, wherein the guide member has ends which are spaced apart by a distance less than two thirds of a distance between the medial and lateral condyles of the femur.

15. The method according to claim 1, wherein the length of the primary incision is less than ten (10) centimeters.

16. The method according to claim 1, wherein the length of the primary incision is about seven (7) centimeters.

17. The method according to claim 1, further comprising making a secondary incision near the knee joint of the leg, the secondary incision having a length less than the length of the primary incision.

18. The method according to claim 17, further comprising moving at least a portion of a cutting tool through the secondary incision and wherein cutting the medial and lateral condyles of the femur is performed with the cutting tool.

19. The method according to claim 17, further comprising moving an imaging device through the secondary incision.

20. The method according to claim 19, wherein the imaging device is an endoscope.

21. The method according to claim 1, wherein the femoral component comprises a plurality of portions passable through the primary incision and assembleable within the body, each portion sized substantially smaller than the assembled femoral component.

22. The method of claim 1, wherein in said moving step, a femoral component of a total knee implant operative to replace the articulating surfaces of both condyles and the trochlear groove is moved through the primary incision.

23. A method of performing total knee arthroplasty through a primary incision having a length of less than thirteen (13) centimeters, comprising the steps of:

making a primary incision of less than thirteen (13) centimeters near the knee joint of a leg of a patient, and carrying out the further steps, through the primary incision, of cutting medial and lateral condyles, and the trochlear groove of the femur of the leg to create at least one femoral cut surface;

moving a single femoral component of a total knee implant operative to replace the entire articulating surfaces of the medial and lateral condyles and the trochlear groove, through the primary incision; and positioning the femoral component with respect to the at least one femoral cut surface.

24. A method of performing total knee arthroplasty on a patient through a primary incision, comprising:

making a primary incision sized not larger than approximately twice the length of the patient's patella;

cutting medial and lateral condyles, and the trochlear groove of the femur of the leg of the patient to create at least one femoral cut surface;

stretching the primary incision to create an opening sufficiently wide for passing at least one component of a total knee arthroplasty into the body, the at least one component operative to replace at least the entire articulating surface of at least one of the medial condyle, lateral condyle, or the trochlear groove;

passing at least one femoral component, including the at least one component of a total knee implant, and such other femoral components as are required to replace the articulating surfaces of both condyles and the trochlear groove, through the primary incision;

positioning the at least one passed femoral components with respect to the at least one femoral cut surface.

25. The method of claim 24, wherein the primary incision is not longer than a distance between the proximal end of the tibia and the epicondylar notch.

26. The method of claim 24, wherein the primary incision is sized smaller than the smallest implant portion.

27. The method of claim 24, wherein the primary incision has a configuration corresponding to the lateral or medial edge of the patella.

28. The method of claim 24, wherein the primary incision is stretched with at least one mechanical or pneumatic retractor.

29. The method of claim 24, wherein the retractor is a balloon which is expanded to increase a width of the primary incision.

30. The method of claim 24, wherein the retractor is formed with a malleable polymeric material, whereupon the shape of the retractor may be changed.

31. The method of claim 24, wherein the skin proximate the primary incision is moved to facilitate moving femoral components through the primary incision.

32. The method of claim 24, wherein the patella is moved medially or laterally, maintaining the inner side surface of the patella in a normal, non-everted orientation, facing the femur.

\* \* \* \* \*

(12) INTER PARTES REVIEW CERTIFICATE (31st)
United States Patent
Bonutti

(10) Number: US 7,749,229 K1
(45) Certificate Issued: Sep. 23, 2014

(54) TOTAL KNEE ARTHROPLASTY THROUGH SHORTENED INCISION

(75) Inventor: Peter M. Bonutti

(73) Assignee: Bonutti Skeletal Innovations LLC

Trial Number:

IPR2013-00605 filed Sep. 25, 2013

Petitioner: Smith & Nephew, Inc.

Patent Owner: Bonutti Skeletal Innovations LLC

Inter Partes Review Certificate for:

Patent No.: 7,749,229
Issued: Jul. 6, 2010
Appl. No.: 11/170,969
Filed: Jun. 30, 2005

The results of IPR2013-00605 are reflected in this inter partes review certificate under 35 U.S.C. 318(b).

INTER PARTES REVIEW CERTIFICATE
U.S. Patent 7,749,229 K1
Trial No. IPR2013-00605
Certificate Issued Sep. 23, 2014

AS A RESULT OF THE INTER PARTES REVIEW PROCEEDING, IT HAS BEEN DETERMINED THAT:

Claim 23 is disclaimed.

\* \* \* \* \*